(12) United States Patent
Bhujade et al.

(10) Patent No.: US 11,286,242 B2
(45) Date of Patent: Mar. 29, 2022

(54) OXADIAZOLES FOR USE IN CONTROLLING PHYTOPATHOGENIC FUNGI

(71) Applicant: PI INDUSTRIES LTD., Udaipur Rajasthan (IN)

(72) Inventors: Paras Raybhan Bhujade, Ahmadnagar-Maharashtra (IN); Rajesh Pawar, Betul-MP (IN); Maruti N. Naik, Karnataka (IN); Rajender Kumar Potlapally, Miyapur-Hyderabad (IN); Nitin Ramesh Tembhare, Maharashtra (IN); Santosh Shridhar Autkar, Akola-Maharashtra (IN); Ruchi Garg, Varanasi-UP (IN); Hagalavadi M. Venkatesha, Bengaluru-Karnataka (IN); Alexander G. M. Klausener, Pulheim (DE); Visannagari Ramakrishna, Rangareddy-Telangana (IN); Nilesh Bharat Adhav, Ahmednagar-Maharashtra (IN); Pooja Trivedi, Pratapgarh-Rajshthan (IN)

(73) Assignee: PI INDUSTRIES LTD., Udaipur Rajasthan (IN)

(*) Notice: Subject to any disclaimer, the term of this patent is extended or adjusted under 35 U.S.C. 154(b) by 0 days.

(21) Appl. No.: 15/733,437

(22) PCT Filed: Jan. 21, 2019

(86) PCT No.: PCT/IB2019/050469
§ 371 (c)(1),
(2) Date: Jul. 30, 2020

(87) PCT Pub. No.: WO2019/150219
PCT Pub. Date: Aug. 8, 2019

(65) Prior Publication Data
US 2020/0354326 A1 Nov. 12, 2020

(30) Foreign Application Priority Data
Jan. 30, 2018 (IN) .............................. 201811003534

(51) Int. Cl.
*C07D 271/06* (2006.01)
*A01N 43/82* (2006.01)

(52) U.S. Cl.
CPC ........... *C07D 271/06* (2013.01); *A01N 43/82* (2013.01)

(58) Field of Classification Search
CPC .................... C07D 271/06; A01N 43/82
See application file for complete search history.

(56) References Cited

U.S. PATENT DOCUMENTS

| 3,296,272 A | 1/1967 | Johnston |
| 3,325,503 A | 6/1967 | Bimber |
| 4,488,897 A | 12/1984 | Rusay |
| 2021/0002232 A1* | 1/2021 | Adhav ................ A01N 43/653 |

FOREIGN PATENT DOCUMENTS

| DE | 196 50 197 A1 | 6/1998 |
| DE | 100 21 412 A1 | 6/2001 |
| DE | 10 2005 009 458 A1 | 9/2006 |
| EP | 0 141 317 A2 | 5/1985 |
| EP | 0 152 031 A2 | 8/1985 |
| EP | 0 226 917 A1 | 7/1987 |
| EP | 0 243 970 A1 | 11/1987 |
| EP | 0 256 503 A2 | 2/1988 |
| EP | 0 374 753 A2 | 6/1990 |
| EP | 0 392 225 A2 | 10/1990 |
| EP | 0 427 529 A1 | 5/1991 |
| EP | 0 428 941 A1 | 5/1991 |
| EP | 0 451 878 A1 | 10/1991 |
| EP | 0 532 022 A1 | 3/1993 |
| EP | 1 028 125 A1 | 8/2000 |
| EP | 1 035 122 A1 | 9/2000 |
| EP | 1 122 244 A1 | 8/2001 |
| EP | 1 201 648 A1 | 5/2002 |
| EP | 3 165 093 A1 | 5/2017 |
| EP | 3 165 094 A1 | 5/2017 |
| EP | 3 167 716 A1 | 5/2017 |
| JP | S56-65881 A | 6/1981 |
| JP | S60-51188 A | 3/1985 |
| JP | S60-61573 A | 4/1985 |
| JP | S62-96480 A | 5/1987 |

(Continued)

OTHER PUBLICATIONS

Richard W. Heintzelman et al, "Sulfoximines. 2. New method for the preparation of N-arylsulfoximines", Journal of Organic Chemistry,vol. 41, No. 12, Jun. 1, 1976 (Jun. 1, 1976), p. 2207-2209.
Peter K. Claus et al, "Conformational preference of the sulfimide functionality in cyclic sulfimides", Journal of Organic Chemistry,vol. 44, No. 16, Aug. 1, 1979 (Aug. 1, 1979), p. 2863-2871.
Peter K. Claus et al, "Alkyl- and arylsulfenanilides by cycloelimination of propene from N-aryl-S-isopropyl-sulfimiden", Monatshefte Für Chemie = Chemical Monthly,vol. 116, No. 6-7, Jan. 1, 1985 (Jan. 1, 1985), p. 841-850.

(Continued)

*Primary Examiner* — Yong L Chu
(74) *Attorney, Agent, or Firm* — Fay Sharpe LLP

(57) ABSTRACT

The present invention relates to novel oxadiazoles of Formula I.

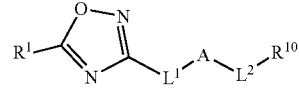

Formula 1 wherein, $R^1$, $L^1$, A, $L^2$ and $R^{10}$ are as defined in the detailed description.

13 Claims, No Drawings

(56) References Cited

FOREIGN PATENT DOCUMENTS

| | | |
|---|---|---|
| JP | S63-162680 A | 7/1988 |
| JP | 2002-316902 A | 10/2002 |
| JP | 2005-336101 A | 12/2005 |
| JP | 2017-190296 A | 10/2017 |
| WO | 93/07278 A1 | 4/1993 |
| WO | 95/34656 A1 | 12/1995 |
| WO | 98/46608 A1 | 10/1998 |
| WO | 99/14187 A1 | 3/1999 |
| WO | 99/24413 A2 | 5/1999 |
| WO | 99/27783 A1 | 6/1999 |
| WO | 00/29404 A1 | 5/2000 |
| WO | 00/46148 A1 | 8/2000 |
| WO | 00/65913 A1 | 11/2000 |
| WO | 01/54501 A2 | 8/2001 |
| WO | 01/56358 A2 | 8/2001 |
| WO | 02/15701 A2 | 2/2002 |
| WO | 02/22583 A2 | 3/2002 |
| WO | 02/40431 A2 | 5/2002 |
| WO | 03/010149 A1 | 2/2003 |
| WO | 03/011853 A1 | 2/2003 |
| WO | 03/014103 A1 | 2/2003 |
| WO | 03/016286 A1 | 2/2003 |
| WO | 03/016303 A1 | 2/2003 |
| WO | 03/018810 A2 | 3/2003 |
| WO | 03/052073 A2 | 6/2003 |
| WO | 03/053145 A1 | 7/2003 |
| WO | 03/061388 A1 | 7/2003 |
| WO | 03/066609 A1 | 8/2003 |
| WO | 03/074491 A1 | 9/2003 |
| WO | 2004/049804 A2 | 6/2004 |
| WO | 2004/083193 A1 | 9/2004 |
| WO | 2005/051932 A1 | 6/2005 |
| WO | 2005/063721 A1 | 7/2005 |
| WO | 2005/087772 A1 | 9/2005 |
| WO | 2005/087773 A1 | 9/2005 |
| WO | 2005/120234 A2 | 12/2005 |
| WO | 2005/123689 A1 | 12/2005 |
| WO | 2005/123690 A1 | 12/2005 |
| WO | 2006/015866 A1 | 2/2006 |
| WO | 2006/087325 A1 | 8/2006 |
| WO | 2006/087343 A1 | 8/2006 |
| WO | 2007/006670 A1 | 1/2007 |
| WO | 2007/082098 A2 | 7/2007 |
| WO | 2007/090624 A2 | 8/2007 |
| WO | 2009/090181 A2 | 7/2009 |
| WO | 2010/069882 A1 | 6/2010 |
| WO | 2011/028657 A1 | 3/2011 |
| WO | 2011/077514 A1 | 6/2011 |
| WO | 2011/135833 A1 | 11/2011 |
| WO | 2012/168188 A1 | 12/2012 |
| WO | 2013/007767 A1 | 1/2013 |
| WO | 2013/010862 A1 | 1/2013 |
| WO | 2013/024009 A1 | 2/2013 |
| WO | 2013/024010 A1 | 2/2013 |
| WO | 2013/047441 A1 | 4/2013 |
| WO | 2013/047749 A1 | 4/2013 |
| WO | 2013/092224 A1 | 6/2013 |
| WO | 2013/124238 A1 | 8/2013 |
| WO | 2013/127704 A1 | 9/2013 |
| WO | 2013/162072 A1 | 10/2013 |
| WO | 2015/185485 A1 | 12/2015 |
| WO | 2017/055469 A1 | 4/2017 |
| WO | 2017/055473 A1 | 4/2017 |
| WO | 2017/072247 A1 | 5/2017 |
| WO | 2017/076739 A1 | 5/2017 |
| WO | 2017/076740 A1 | 5/2017 |
| WO | 2017/076742 A1 | 5/2017 |
| WO | 2017/076757 A1 | 5/2017 |
| WO | 2017/076935 A1 | 5/2017 |
| WO | 2017/081309 A1 | 5/2017 |
| WO | 2017/081310 A1 | 5/2017 |
| WO | 2017/081311 A1 | 5/2017 |
| WO | 2017/081312 A1 | 5/2017 |
| WO | 2017/085098 A1 | 5/2017 |
| WO | 2017/085100 A1 | 5/2017 |
| WO | 2017/093019 A1 | 6/2017 |
| WO | 2017/093348 A1 | 6/2017 |
| WO | 2017/102006 A1 | 6/2017 |
| WO | 2017/103219 A1 | 6/2017 |
| WO | 2017/103223 A1 | 6/2017 |
| WO | 2017/109044 A1 | 6/2017 |
| WO | 2017/110861 A1 | 6/2017 |
| WO | 2017/110862 A1 | 6/2017 |
| WO | 2017/110863 A1 | 6/2017 |
| WO | 2017/110864 A1 | 6/2017 |
| WO | 2017/110865 A1 | 6/2017 |
| WO | 2017/111152 A1 | 6/2017 |
| WO | 2017/118689 A1 | 7/2017 |
| WO | 2017/148797 A1 | 9/2017 |
| WO | 2017/157962 A1 | 9/2017 |
| WO | 2017/162868 A1 | 9/2017 |
| WO | 2017/169893 A1 | 10/2017 |
| WO | 2017/174158 A1 | 10/2017 |
| WO | 2017/178549 A1 | 10/2017 |
| WO | 2017/198852 A1 | 11/2017 |
| WO | 2017/207757 A1 | 12/2017 |
| WO | 2017/211649 A1 | 12/2017 |
| WO | 2017/211650 A1 | 12/2017 |
| WO | 2017/211652 A1 | 12/2017 |
| WO | 2017/213252 A1 | 12/2017 |
| WO | 2017/220485 A1 | 12/2017 |
| WO | 2018/015447 A1 | 1/2018 |
| WO | 2018/015449 A1 | 1/2018 |
| WO | 2018/015458 A1 | 1/2018 |
| WO | 2018/029242 A1 | 2/2018 |
| WO | 2018/030460 A1 | 2/2018 |
| WO | 2018/055135 A1 | 3/2018 |
| WO | 2018/056340 A1 | 3/2018 |
| WO | 2018/065414 A1 | 4/2018 |
| WO | 2018/080859 A1 | 5/2018 |
| WO | 2018/114393 A1 | 6/2018 |
| WO | 2018/117034 A1 | 6/2018 |
| WO | 2018/118781 A1 | 6/2018 |
| WO | 2018/153730 A1 | 8/2018 |
| WO | 2018/158365 A1 | 9/2018 |
| WO | 2018/162643 A1 | 9/2018 |
| WO | 2018/184970 A1 | 10/2018 |
| WO | 2018/184982 A1 | 10/2018 |
| WO | 2018/184984 A1 | 10/2018 |
| WO | 2018/184985 A1 | 10/2018 |
| WO | 2018/184986 A1 | 10/2018 |
| WO | 2018/184987 A1 | 10/2018 |
| WO | 2018/184988 A1 | 10/2018 |
| WO | 2018/185013 A1 | 10/2018 |
| WO | 2018/185211 A1 | 10/2018 |
| WO | 2018/187553 A1 | 10/2018 |
| WO | 2018/202491 A1 | 11/2018 |

OTHER PUBLICATIONS

Anguo Hou et al, "Copper-catalyzed preparation of N-aroylated sulfoximines from methylarenes", Synthetic Communications, vol. 47, No. 13, Jul. 3, 2017 (Jul. 3, 2017), p. 1201-1208.

Long Wang et al, "Copper-Catalyzed Oxidative Cross-Coupling of Sulfoximines and Alkynes", Angewandte Chemie, International Edition, vol. 52, No. 12, Mar. 18, 2013 (Mar. 18, 2013), p. 3478-3480.

Goldberg Frederick W et al, "General synthetic strategies towardsN-alkyl sulfoximine building blocks for medicinal chemistry and the use of dimethylsulfoximine as a versatile precursor", Tetrahedron, Elsevier Science Publishers, Amsterdam, NL, vol. 70, No. 37, Jul. 3, 2014 (Jul. 3, 2014), p. 6613-6622.

Claus P K et al, "N-Aryl sulfinimides", Tetrahedron, Elsevier Science Publishers, Amsterdam, NL, vol. 31, No. 6, Jan. 1, 1975 (Jan. 1, 1975), p. 505-510.

* cited by examiner

OXADIAZOLES FOR USE IN CONTROLLING PHYTOPATHOGENIC FUNGI

This application is a National Stage Entry of International Application No. PCT/IB2019/050469, filed Jan. 21, 2019, and entitled "OXADIAZOLES FOR USE IN CONTROLLING PHYTOPATHOGENIC FUNGI"; which claims priority to Indian Application No. 201811003534, filed Jan. 30, 2018, and entitled "OXADIAZOLES FOR USE IN CONTROLLING PHYTOPATHOGENIC FUNGI", the contents of which are incorporated by reference herein.

FIELD OF THE INVENTION

The present invention relates to novel oxadiazoles, N-oxides, metal complexes, isomers, polymorphs or the agriculturally acceptable salts thereof and plurality of processes for preparing the same. Further, the present invention relates to a combination and a composition comprising novel oxadiazoles of the present invention. Still further, the present invention relates to a use of novel oxadiazoles of the present invention for controlling or preventing phytopathogenic fungi and to a method for controlling or preventing phytopathogenic harmful fungi.

BACKGROUND

Oxadiazoles have already been disclosed in the literature. For example in JP56065881, JP63162680, JPS6061573, JPS6296480, JPS6051188, JP2005336101, WO2005051932, EP3165093, EP3165094, EP3167716, EP3165093, JP2017190296, U.S. Pat. No. 4,488,897, WO2015185485, WO2017055469, WO2017055473, WO2017076739, WO2017076740, WO2017081311, WO2017085098, WO2017085100, WO2017093019, WO2017093348, WO2017102006, WO2017103219, WO2017103223, WO2017109044, WO2017110861, WO2017110862, WO2017110863, WO2017110864, WO2017110865, WO2017111152, WO2017118689, WO2017148797, WO2017157962, WO2017162868, WO2017169893, WO2017174158, WO2017178549, WO2017198852, WO2017207757, WO2017211649, WO2017211650, WO2017211652, WO2017213252, WO2017220485, WO201772247, WO201776742, WO201776757, WO201776935, WO201781309, WO201781310, WO201781312, WO2018015447, WO2018015449, WO2018015458, WO2018029242, WO2018030460, WO2018056340, WO2018055135, WO2018065414, WO2018080859, WO2018118781, WO2018117034, WO2018114393, WO2018153730, WO2018158365, WO2018162643, WO2018184970, WO2018184982, WO2018184984, WO2018184985, WO2018184986, WO2018184987, WO2018184988, WO2018185013, WO2018185211, WO2018187553 and WO2018202491 various oxadiazoles have be disclosed.

The oxadiazole compounds reported in the above literature have disadvantages in certain aspects, such as that they exhibit a narrow spectrum of application or they do not have satisfactory fungicidal activity, particularly at low application rates.

Therefore, it is an object of the present invention to provide compound/s having improved/enhanced activity and/or a broader activity spectrum against phytopathogenic fungi.

This objective is achieved by the using oxadiazoles of the present invention for controlling or preventing phytopathogenic fungi.

SUMMARY

The present invention relates to novel oxadiazoles of Formula I.

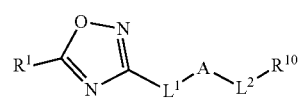

Formula 1 wherein, $R^1$, $L^1$, A, $L^2$ and $R^{10}$ are as defined in the detailed description.

The compounds of formula I have now been found to be advantages over the compounds reported in the literature in either of improved fungicidal activity, broader spectrum biological activity, lower application rates, biological or environmental properties, or enhanced plant compatibility.

The present invention further relates to a combination comprising novel oxadiazoles of the present invention and at least one further pesticidally active substance for effectively controlling or preventing phytopathogenic fungi which are difficult to control or prevent.

The present invention still further relates to a composition comprising novel oxadizoles or novel oxadiazloes in combination with further pesticidally active substance.

The present invention still further relates to a method and use of novel oxadizoles, combinations or compositions thereof for controlling and or preventing plant diseases, particularly phtopathogenic fungi.

DETAILED DESCRIPTION OF THE INVENTION

Definitions

The definitions provided herein for the terminologies used in the present disclosure are for illustrative purpose only and in no manner limit the scope of the present invention disclosed in the present disclosure.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Further, unless expressly stated to the contrary, "or" refers to an inclusive "or" and not to an exclusive "or". For example, a condition A "or" B is satisfied by any one of the following: A is true (or present) and B is false (or not present), A is false (or not present) and B is true (or present), and both A and B are true (or present).

Also, the indefinite articles "a" and "an" preceding an element or component of the present invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous nematodes (Nematoda), flukes (Tematoda), acanthocephala and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from an invertebrate parasitic pest by administering a parasiticidally effective (i.e. biologically effective) amount of a compound of the present invention, typically in the form of a composition formulated for veterinary use, to the animal to be protected. As referred to in the present disclosure and claims, the terms "parasiticidal" and "parasiticidally" refers to observable effects on an invertebrate parasite pest to provide protection of an animal from the pest. Parasiticidal effects typically relate to diminishing the occurrence or activity of the target invertebrate parasitic pest. Such effects on the pest include necrosis, death, retarded growth, diminished mobility or lessened ability to remain on or in the host animal, reduced feeding and inhibition of reproduction. These effects on invertebrate parasite pests provide control (including prevention, reduction or elimination) of parasitic infestation or infection of the animal.

The compounds of the present disclosure may be present either in pure form or as mixtures of different possible isomeric forms such as stereoisomers or constitutional isomers. The various stereoisomers include enantiomers, diastereomers, chiral isomers, atropisomers, conformers, rotamers, tautomers, optical isomers, polymorphs, and geometric isomers. Any desired mixtures of these isomers fall within the scope of the claims of the present disclosure. One skilled in the art will appreciate that one stereoisomer may be more active and/or may exhibit beneficial effects when enriched relative to the other isomer(s) or when separated from the other isomer(s). Additionally, the person skilled in the art knows processes or methods or technology to separate, enrich, and/or to selectively prepare said isomers.

The meaning of various terms used in the description shall now be illustrated.

The term "alkyl", used either alone or in compound words such as "alkylthio" or "haloalkyl" or —N(alkyl) or alkylcarbonylalkyl or alkylsuphonylamino includes straight-chain or branched $C_1$ to $C_2$ alkyl, preferably $C_1$ to $C_{15}$ alkyl, more preferably $C_1$ to $C_{10}$ alkyl, most preferably $C_1$ to $C_6$ alkyl. Non limiting examples of alkyl include methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl or the different isomers. If the alkyl is at the end of a composite substituent, as, for example, in alkylcycloalkyl, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, carbonyl, carbonyloxy and the like, are at the end.

The term "alkenyl", used either alone or in compound words includes straight-chain or branched $C_2$ to $C_{24}$ alkenes, preferably $C_2$ to $C_{15}$ alkenes, more preferably $C_2$ to $C_{10}$ alkenes, most preferably $C_2$ to $C_6$ alkenes. Non limiting examples of alkenes include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2- butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl and the different isomers. "Alkenyl" also includes polyenes such as 1,2-propadienyl and 2,4-hexadienyl. This definition also applies to alkenyl as a part of a composite substituent, for example haloalkenyl and the like, unless defined specifically elsewhere.

Non limiting examples of alkynes include ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl and the different isomers. This definition also applies to alkynyl as a part of a composite substituent, for example haloalkynyl etc., unless specifically defined elsewhere. The term "Alkynyl" can also include moieties comprised of multiple triple bonds such as 2,5-hexadiynyl.

The term "cycloalkyl" means alkyl closed to form a ring. Non limiting examples include cyclopropyl, cyclopentyl and cyclohexyl. This definition also applies to cycloalkyl as a part of a composite substituent, for example cycloalkylalkyl etc., unless specifically defined elsewhere.

The term "cycloalkenyl" means alkenyl closed to form a ring including monocyclic, partially unsaturated hydrocarbyl groups. Non limiting examples include cyclopropenyl, cyclopentenyl and cyclohexenyl. This definition also applies to cycloalkenyl as a part of a composite substituent, for example cycloalkenylalkyl etc., unless specifically defined elsewhere.

The term "cycloalkynyl" means alkynyl closed to form a ring including monocyclic, partially unsaturated groups. Non limiting examples include cyclopropynyl, cyclopentynyl and cyclohexynyl.

This definition also applies to cycloalkynyl as a part of a composite substituent, for example cycloalkynylalkyl etc., unless specifically defined elsewhere.

The terms "cycloalkoxy", "cycloalkenyloxy" and the like are defined analogously. Non limiting examples of cycloalkoxy include cyclopropyloxy, cyclopentyloxy and cyclohexyloxy. This definition also applies to cycloalkoxy as a part of a composite substituent, for example cycloalkoxy alkyl etc., unless specifically defined elsewhere.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Non-limiting Examples of "haloalkyl" include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 1,1-dichloro-2,2,2-trifluoroethyl, and 1,1,1-trifluoroprop-2-yl. This definition also applies to haloalkyl as a part of a composite substituent, for example haloalkylaminoalkyl etc., unless specifically defined elsewhere.

The terms "haloalkenyl", "haloalkynyl" are defined analogously except that, instead of alkyl groups, alkenyl and alkynyl groups are present as a part of the substituent.

The term "haloalkoxy" means straight-chain or branched alkoxy groups where some or all of the hydrogen atoms in these groups may be replaced by halogen atoms as specified above. Non-limiting examples of haloalkoxy include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy. This definition also applies to haloalkoxy as a part of a composite substituent, for example haloalkoxyalkyl etc., unless specifically defined elsewhere.

The term "haloalkylthio" means straight-chain or branched alkylthio groups where some or all of the hydrogen atoms in these groups may be replaced by halogen atoms as specified above. Non-limiting examples of haloalkylthio include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio. This definition also applies to haloalkylthio as a part of a composite substituent, for example haloalkylthioalkyl etc., unless specifically defined elsewhere.

Non limiting examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$.

The term "hydroxy" means —OH, Amino means —NRR, wherein R can be H or any possible substituent such as alkyl. Carbonyl means —C(O)—, carbonyloxy means —OC(O)—, sulfinyl means SO, sulfonyl means $S(O)_2$.

The term "alkoxy" used either alone or in compound words included $C_1$ to $C_{24}$ alkoxy, preferably $C_1$ to $C_{15}$ alkoxy, more preferably $C_1$ to $C_{10}$ alkoxy, most preferably $C_1$ to $C_6$ alkoxy. Examples of alkoxy include methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy and the different isomers. This definition also applies to alkoxy as a part of a composite substituent, for example haloalkoxy, alkynylalkoxy, etc., unless specifically defined elsewhere.

The term "alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$.

The term "alkoxyalkoxy" denotes alkoxy substitution on alkoxy.

The term "alkylthio" includes branched or straight-chain alkylthio moieties such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio and the different isomers.

The terms Halocycloalkyl, halocycloalkenyl, alkylcycloalkyl, cycloalkylalkyl, cycloalkoxyalkyl, alkylsulfinylalkyl, alkylsulfonylalkyl, haloalkylcarbonyl, cycloalkylcarbonyl, haloalkoxyalkyl, and the like, are defined analogously to the above examples.

The term "alkylthioalkyl" denotes alkylthio substitution on alkyl. Non limiting examples of "alkylthioalkyl" include —CH$_2$SCH$_3$, —CH$_2$SCH$_2$CH$_3$, CH$_3$CH$_2$SCH$_2$, CH$_3$CH$_2$CH$_2$SCH$_2$ and CH$_3$CH$_2$SCH$_2$CH$_2$. "Alkylthioalkoxy" denotes alkylthio substitution on alkoxy. The term "cycloalkylalkylamino" denotes cycloalkyl substitution on alkyl amino.

The terms alkoxyalkoxyalkyl, alkylaminoalkyl, dialkylaminoalkyl, cycloalkylaminoalkyl, cycloalkylaminocarbonyl and the like, are defined analogously to "alkylthioalkyl" or cycloalkylalkylamino.

The term "alkoxycarbonyl" is an alkoxy group bonded to a skeleton via a carbonyl group (—CO—). This definition also applies to alkoxycarbonyl as a part of a composite substituent, for example cycloalkylalkoxycarbonyl and the like, unless specifically defined elsewhere.

The term "alkoxycarbonylalkylamino" denotes alkoxy carbonyl substitution on alkyl amino. "Alkylcarbonylalkylamino" denotes alkyl carbonyl substitution on alkyl amino. The terms alkylthioalkoxycarbonyl, cycloalkylalkylaminoalkyl and the like are defined analogously.

Non limiting examples of "alkylsulfinyl" include methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl and the different isomers. The term "arylsulfinyl" includes Ar—S(O), wherein Ar can be any carbocyle or heterocylcle. This definition also applies to alkylsulphinyl as a part of a composite substituent, for example haloalkylsulphinyl etc., unless specifically defined elsewhere.

Non limiting examples of "alkylsulfonyl" include methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl and the different isomers. The term "arylsulfonyl" includes Ar—S(O)$_2$, wherein Ar can be any carbocyle or heterocylcle. This definition also applies to alkylsulphonyl as a part of a composite substituent, for example alkylsulphonylalkyl etc., unless defined elsewhere.

The term "alkylamino", "dialkylamino", and the like, are defined analogously to the above examples.

The term "carbocycle" includes "aromatic carbocyclic ring system" and "nonaromatic carbocylic ring system" or polycyclic or bicyclic (spiro, fused, bridged, nonfused) ring compounds in which ring may be aromatic or non-aromatic (where aromatic indicates that the Huckel rule is satisfied and non-aromatic indicates that the Huckel rule is not statisfied).

The term "hetero" in connection with rings refers to a ring in which at least one ring atom is not carbon and which can contain 1 to 4 heteroatoms independently selected from the group consisting of nitrogen, oxygen and sulfur, provided that each ring contains no more than 4 nitrogens, no more than 2 oxygens and no more than 2 sulfurs.

The term "heteroaryl" or "aromatic heterocyclic" means 5 or 6-membered, fully unsaturated monocyclic ring system containing one to four heteroatoms from the group of oxygen, nitrogen and sulphur; if the ring contains more than one oxygen atom, they are not directly adjacent; 5-membered heteroaryl containing one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, 1,3,4-oxadiazolyl, 1,3,4-thiadiazolyl, 1,3,4-triazolyl, tetrazolyl; nitrogen-bonded 5-membered heteroaryl containing one to four nitrogen atoms, or benzofused nitrogen-bonded 5-membered heteroaryl containing one to three nitrogen atoms: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited to) 1-pyrrolyl, 1-pyrazolyl, 1,2,4-triazol-1-yl, 1-imidazolyl, 1,2,3-triazol-1-yl and 1,3,4-triazol-1-yl.

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4- triazin-3-yl and 1,2,4,5-tetrazin-3-yl; benzofused 5-membered heteroaryl containing one to three nitrogen atoms or one nitrogen atom and one oxygen or sulphur atom: for example (but not limited to) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl; benzofused 6-membered heteroaryl which contains one to three nitrogen atoms: for example (but not limited to) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl.

This definition also applies to heteroaryl as a part of a composite substituent, for example heteroarylalkyl etc., unless specifically defined elsewhere.

The term "aromatic" indicates that the Huckel rule is satisfied and the term "non-aromatic" indicates that the Huckel rule is not satisfied.

The term "heterocycle" or "heterocyclic" includes "aromatic heterocycle" or "heteroaryl ring system" and "non-aromatic heterocycle ring system" or polycyclic or bicyclic (spiro, fused, bridged, non-fused) ring compounds in which ring may be aromatic or non-aromatic, wherein the heterocycle ring contains at least one heteroatom selected from N, O, $S(O)_{0-2}$, and or C ring member of the heterocycle may be replaced by $C(=O)$, $C(=S)$, $C(=CR^*R^*)$ and $C=NR^*$, * indicates integers.

The term "non-aromatic heterocycle" or "non-aromatic heterocyclic" means three- to fifteen-membered, preferably three- to twelve-membered, saturated or partially unsaturated heterocycle containing one to four heteroatoms from the group of oxygen, nitrogen and sulphur: mono, bi- or tricyclic heterocycles which contain, in addition to carbon ring members, one to three nitrogen atoms and/or one oxygen or sulphur atom or one or two oxygen and/or sulphur atoms; if the ring contains more than one oxygen atom, they are not directly adjacent; for example (but not limited to) oxetanyl, oxiranyl, aziridinyl, 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-1-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, pyrrolinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, piperidinyl, 2-piperidinyl, 3-piperidinyl, 4-piperidinyl, pyrazynyl, morpholinyl, thiomorphlinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl, 1,2,4-hexahydrotriazin-3-yl, cycloserines, 2,3,4,5-tetrahydro[1H]azepin-1- or -2- or -3- or -4- or -5- or -6- or -7-yl, 3,4,5,6-tetra-hydro[2H]azepin-2- or -3- or -4- or -5- or -6- or -7-yl, 2,3,4,7-tetrahydro[1H] azepin-1- or -2- or -3- or -4- or -5- or -6- or -7-yl, 2,3,6,7-tetrahydro[1H]azepin-1- or -2- or -3- or -4- or -5- or -6- or -7-yl, hexahydroazepin-1- or -2- or -3- or -4-yl, tetra- and hexahydrooxepinyl such as 2,3,4,5-tetrahydro[H]oxepin-2- or -3- or -4- or -5- or -6- or -7-yl, 2,3,4,7-tetrahydro[1H] oxepin-2- or -3- or -4- or -5- or -6- or -7-yl, 2,3,6,7-tetrahydro[1H]oxepin-2- or -3- or -4- or -5- or -6- or -7-yl, hexahydroazepin-1- or -2- or -3- or -4-yl, tetra- and hexahydro-1,3-diazepinyl, tetra- and hexahydro-1,4-diazepinyl, tetra- and hexahydro-1,3-oxazepinyl, tetra- and hexahydro-1,4-oxazepinyl, tetra- and hexahydro-1,3-dioxepinyl, tetra- and hexahydro-1,4-dioxepinyl. This definition also applies to heterocyclyl as a part of a composite substituent, for example heterocyclylalkyl etc., unless specifically defined elsewhere.

The term "trialkylsilyl" includes 3 branched and/or straight-chain alkyl radicals attached to and linked through a silicon atom such as trimethylsilyl, triethylsilyl and t-butyl-dimethylsilyl. The term "halotrialkylsilyl" denotes at least one of the three alkyl radicals is partially or fully substituted with halogen atoms which may be the same or different. The term "alkoxytrialkylsilyl" denotes at least one of the three alkyl radicals is substituted with one or more alkoxy radicals which may be the same or different. The term "trialkylsilyloxy" denotes a trialkylsilyl moiety attached through oxygen.

Non limiting examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Non limiting examples of "dialkylaminocarbonyl" include $(CH_3)_2NC(=O)$, $(CH_3CH_2)_2NC(=O)$, $CH_3CH_2(CH_3)NC(=O)$, $CH_3CH_2CH_2(CH_3)NC(=O)$ and $(CH_3)_2CHN(CH_3)C(=O)$. Examples of "alkoxyalkylcarbonyl" include $CH_3OCH_2C(=O)$, $CH_3OCH_2CH_2C(=O)$, $CH_3CH_2OCH_2C(=O)$, $CH_3CH_2CH_2OCH_2C(=O)$ and $CH_3CH_2OCH_2CH_2C(=O)$. Non limiting examples of "alkylthioalkylcarbonyl" include $CH_3SCH_2C(=O)$, $CH_3SCH_2CH_2C(=O)$, $CH_3CH_2SCH_2C(=O)$, $CH_3CH_2CH_2CH_2SCH_2C(=O)$ and $CH_3CH_2SCH_2CH_2C(=O)$. The term haloalkylsufonylaminocarbonyl, alkylsulfonylaminocarbonyl, alkylthioalkoxycarbonyl, alkoxycarbonylalkyl amino and the like are defined analogously Non limiting examples of "alkylaminoalkylcarbonyl" include $CH_3NHCH_2C(=O)$, $CH_3NHCH_2CH_2C(=O)$, $CH_3CH_2NHCH_2C(=O)$, $CH_3CH_2CH_2CH_2NHCH_2C(=O)$ and $CH_3CH_2NHCH_2CH_2C(=O)$.

The term "amide" means A-R'C=ONR"—B, wherein R' and R" indicates substituents and A and B indicate any group.

The term "thioamide" means A-R'C=SNR"—B, wherein R' and R" indicates substituents and A and B indicate any group.

The total number of carbon atoms in a substituent group is indicated by the "$C_i$-$C_j$" prefix where i and j are numbers from 1 to 21. For example, $C_1$-$C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript m in $(R)_m$ indicates an integer ranging from for example 0 to 4 then the number of substituents may be selected from the integers between 0 and 4 inclusive.

When a group contains a substituent which can be hydrogen, then, when this substituent is taken as hydrogen, it is recognized that said group is being un-substituted.

The embodiments herein and the various features and advantageous details thereof are explained with reference to the non-limiting embodiments in the description. Descriptions of well-known components and processing techniques are omitted so as to not unnecessarily obscure the embodiments herein. The examples used herein are intended merely to facilitate an understanding of ways in which the embodiments herein may be practiced and to further enable those of skilled in the art to practice the embodiments herein. Accordingly, the examples should not be construed as limiting the scope of the embodiments herein.

The description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Any discussion of documents, acts, materials, devices, articles and the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned in the description and the description/claims though might form a critical part of the present invention of the present invention, any deviation from such numerical values shall still fall within the scope of the present invention if that deviation follows the same scientific principle as that of the present invention disclosed in the present invention. The inventive compounds of the present invention may, if appropriate, be present as mixtures of different possible isomeric forms, especially of stereoisomers, for example E and Z, threo and erythro, and also optical isomers, but if appropriate also of tautomers. Both the E and the Z isomers, and also the threo and erythro isomers, and the optical isomers, any desired mixtures of these isomers and the possible tautomeric forms are disclosed and claimed.

The term "pest" for the purpose of the present disclosure includes but is not limited to fungi, stramenopiles (oomycetes), bacteria, nematodes, mites, ticks, insects and rodents.

The term "plant" is understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights.

For the purpose of the present disclosure the term "plant" includes a living organism of the kind exemplified by trees, shrubs, herbs, grasses, ferns, and mosses, typically growing in a site, absorbing water and required substances through its roots, and synthesizing nutrients in its leaves by photosynthesis.

Examples of "plant" for the purpose of the present invention include but are not limited to agricultural crops such as wheat, rye, barley, triticale, oats or rice; beet, e.g. sugar beet or fodder beet; fruits and fruit trees, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit and citrus trees, such as oranges, lemons, grapefruits or mandarins; any horticultural plants, vegetables, such as spinach, lettuce, asparagus, cabbages, carrots, onions, tomatoes, potatoes, cucurbits or paprika; lauraceous plants, such as avocados, cinnamon or camphor; *cucurbitaceae*; oleaginous plants; energy and raw material plants, such as cereals, corn, soybean, other leguminous plants, rape, sugar cane or oil palm; tobacco; nuts; coffee; tea; cacao; bananas; peppers; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Preferably, the plant for the purpose of the present invention include but is not limited to cereals, corn, rice, soybean and other leguminous plants, fruits and fruit trees, grapes, nuts and nut trees, citrus and citrus trees, any horticultural plants, *cucurbitaceae*, oleaginous plants, tobacco, coffee, tea, cacao, sugar beet, sugar cane, cotton, potato, tomato, onions, peppers and vegetables, ornamentals, any floricultural plants and other plants for use of human and animals.

The term "plant parts" is understood to mean all parts and organs of plants above and below the ground. For the purpose of the present disclosure the term plant parts includes but is not limited to cuttings, leaves, twigs, tubers, flowers, seeds, branches, roots including taproots, lateral roots, root hairs, root apex, root cap, rhizomes, slips, shoots, fruits, fruit bodies, bark, stem, buds, auxillary buds, meristems, nodes and internodes.

The term "locus thereof" includes soil, surroundings of plant or plant parts and equipment or tools used before, during or after sowing/planting a plant or a plant part.

Application of the compounds of the present disclosure or the compound of the present disclosure in a composition optionally comprising other compatible compounds to a plant or a plant material or locus thereof include application by a technique known to a person skilled in the art which include but is not limited to spraying, coating, dipping, fumigating, impregnating, injecting and dusting.

The term "applied" means adhered to a plant or plant part either physically or chemically including impregnation.

Accordingly, novel oxadizole compounds of the present invention are represent by Formula I, N-oxides, metal complexes, isomers, polymorphs or the agriculturally acceptable salts thereof;

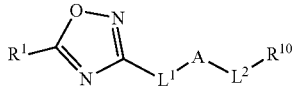

Formula 1 wherein:
$R^1$ is $C_1$-$C_2$-haloalkyl;
$L^1$ is a direct bond, —$CR^2R^3$—, —C(=O)—, —O—, —S(=O)$_{0-2}$—, —$NR^4$—, —$CR^2R^3C$(=O)—, —S(=O)$_{0-2}$(—$NR^4$)—, —$SR^5$(=O)$_{0-1}$(=N)—, —S(=O)$_{0-1}$(=$NR^4$)—, —$SR^5$(=O)$_{0-1}$(=N)—$CR^2R^3$—, wherein, an expression "-" at the start and the end of the group indicates the point of attachment to either oxadiazole ring or A;
A is an aromatic or non-aromatic carbocyclic ring, wherein the ring members of the non-aromatic carbocyclic ring are selected from C, C(=O), C(=S), C(=$CR^{2a}R^{3a}$) and C=$NR^6$; or
A is an aromatic or non-aromatic heterocyclic ring; wherein the heteroatom of the aromatic heterocyclic ring is selected from N, O and S; wherein heteroatom of the non-aromatic heterocyclic ring is selected from N, O, S(=O)$_{0-2}$, and S(=O)$_{0-1}$(=$NR^6$) and one or more C atoms of the non-aromatic heterocyclic ring may be optionally replaced by C(=O), C(=S), C(=$CR^{2a}R^{3a}$) and C=$NR^6$; and
wherein, A is unsubstituted or is substituted with one or more identical or different $R^A$ groups,
wherein, $R^A$ is selected from the group consisting of hydrogen, halogen, cyano, nitro, amino, hydroxy, $SF_5$, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxy-$C_1$-$C_4$-alkyl, $C_1$-$C_6$-hydroxyalkyl, $C_2$-$C_6$-haloalkenyl, $C_2$-$C_6$-haloalkynyl, $C_3$-$C_8$-halocycloalkyl, $C_1$-$C_6$-alkoxy, $C_1$-$C_6$-haloalkoxy, $C_1$-$C_6$-haloalkoxycarbonyl, $C_1$-$C_6$-alkylthio, $C_1$-$C_6$-haloalkylthio, $C_1$-$C_6$-haloalkylsulfinyl, $C_1$-$C_6$-haloalkylsulfonyl, $C_1$-$C_6$-alkylsulfinyl, $C_1$-$C_6$-alkylsulfonyl, $C_1$-$C_6$-alkylamino, $C_1$-$C_6$-dialkylamino, $C_3$-$C_8$-cycloalkylamino, $C_1$-$C_6$-alkyl-$C_3$-$C_8$-cycloalkylamino, $C_1$-$C_6$-alkylcarbonyl, $C_1$-$C_6$-alkoxycarbonyl, $C_1$-$C_6$-alkylaminocarbonyl, $C_1$-$C_6$-dialkylaminocarbonyl, $C_1$-$C_6$-alkoxycarbonyloxy, $C_1$-$C_6$-alkylaminocarbonyloxy, or $C_1$-$C_6$-dialkylaminocarbonyloxy, 5- to 11-membered spirocyclic ring, and 3- to 6-membered carbocyclic or heterocyclic ring,
wherein, $R^A$ may be optionally substituted with one or more identical or different $R^a$ selected from halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_1$-$C_6$-alkoxy-$C_1$-$C_4$-alkyl, $C_3$-$C_8$-halocycloalkyl, $C_1$-$C_6$-alkylamino, di-$C_1$-$C_6$-alkylamino or $C_3$-$C_8$-cycloalkylamino;
wherein, 5- to 11-membered spirocyclic ring, 3- to 6-membered carbocyclic or heterocyclic ring may be optionally substituted with one or more identical or different substituents selected from halogen, cyano, nitro, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxyalkyl, $C_1$-$C_6$-hydroxyalkyl, $C_2$-$C_6$-haloalkenyl, $C_2$-$C_6$-haloalkynyl, $C_3$-$C_6$-halocycloalkyl, $C_1$-$C_6$-alkoxy, $C_1$-$C_6$-alkylthio, $C_1$-$C_6$-haloalkylthio, $C_1$-$C_6$-haloalkylsulfinyl, $C_1$-$C_6$-haloalkylsulfonyl, $C_1$-$C_6$-alkylsulfinyl, $C_1$-$C_6$-alkylsulfonyl, $C_1$-$C_6$-alkylamino, di-$C_1$-$C_6$-alkylamino, $C_3$-$C_6$-cycloalkylamino, $C_1$-$C_6$-alkyl-$C_3$-$C_6$-cycloalkylamino, $C_1$-$C_6$ alkylcarbonyl, $C_1$-$C_6$-alkoxycarbonyl, $C_1$-$C_6$-alkylaminocarbonyl, di-$C_1$-$C_6$-alkylaminocarbonyl, $C_1$-$C_6$-alkoxycarbonyloxy, $C_1$-$C_6$-alkylaminocarbonyloxy, or di-$C_1$-$C_6$-alkylaminocarbonyloxy, or
two $R^A$ together with the atoms to which they are attached may form a 3- to 10-membered aromatic or non-aromatic carbocyclic ring or ring system, or aromatic or non-aromatic heterocyclic ring or ring system which may be optionally substituted with one or more identical or different $R^a$,
wherein, the C atom of the non-aromatic carbocyclic ring may be optionally replaced by C(=O), C(=S), C(=$CR^{2b}R^{3b}$) and C=$NR^{6a}$ or,
wherein, the heteroatom of the aromatic heterocyclic ring is selected from N, O and S; wherein heteroatom of the non-aromatic heterocyclic ring is selected from N, O, S(=O)$_{0-2}$, and S(=O)$_{0-1}$(=$NR^{6a}$) and one or more C atoms of the non-aromatic heterocyclic ring may be optionally replaced by C(=O), C(=S), C(=$CR^{2b}R^{3b}$) and C=$NR^{6a}$;
$R^4$, $R^6$, $R^{6a}$, $R^{6b}$, and $R^{6c}$ are independently selected from the group of hydrogen, cyano, hydroxy, $NR^bR^c$, (C=O)—$R^d$, $S(O)_{0-2}R^e$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, tri-$C_1$-$C_6$-alkylamino or $C_3$-$C_8$-cycloalkyl;
$R^b$ and $R^c$ represent hydrogen, hydroxyl, cyano, $C_1$-$C_4$-alkyl, $C_1$-$C_4$-haloalkyl, $C_1$-$C_4$-alkoxy, $C_3$-$C_8$-cycloalkyl or $C_3$-$C_8$-halocycloalkyl, $R^d$ represents hydrogen, hydroxy, halogen, $NR^bR^c$, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl or $C_3$-$C_8$-halocycloalkyl, and $R^e$ represents hydrogen, halogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl or $C_3$-$C_8$-halocycloalkyl, $L^2$ is a fragment selected from the group of

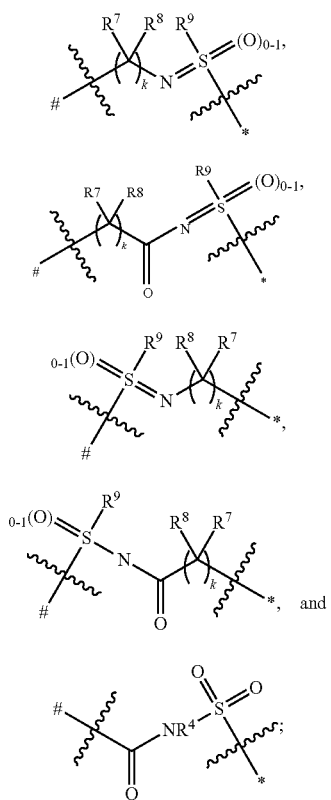

$L^{2a}$ $L^{2b}$ $L^{2c}$ $L^{2d}$ $L^{2e}$ wherein, k is an integer ranging from 0 to 4; an expression "#" on the left side indicates the point of attachment to A, and an expression "*" on the right side indicates the point of attachment to $R^{10}$;

wherein, in Formula I when $R^1$ is $CF_3$; A is phenyl ring or $C_3$-$C_7$ carbocyclic ring or 5- to 6-membered heterocyclic ring; $L^2$ is $L^{2c}$ and k=0 then $R^{10}$ is not hydrogen, cyano, nitro, $C_1$-$C_3$alkyl, $C_1$-$C_3$ haloalkyl;

wherein, in Formula I when $R^1$ is $CF_3$; A is phenyl ring or 5- to 6-membered heteroaromatic ring $L^2$ is $L^{2d}$ and k=0 to 4 then $R^1$ is not cyano, nitro, $R^{11}$ and $OR^{11}$;

wherein, $R^{11}$ is hydrogen, $C_1$-$C_6$-alkyl optionally substituted with a group selected from halogen, cyano, nitro, $C_1$-$C_6$-alkoxy, $C_1$-$C_6$-haloalkoxy, $C_1$-$C_6$-alkylthio, $C_1$-$C_6$-haloalkylthio, and phenyl ring optionally substituted with $C_1$-$C_6$-alkyl, $C_1$-$C_6$-haloalkyl, $C_1$-$C_6$-alkoxy and $C_1$-$C_6$-haloalkoxy, $R^2$, $R^3$, $R^{2a}$, $R^{3a}$, $R^{2b}$, $R^{3b}$, $R^{2c}$, $R^{3c}$, $R^{2d}$, $R^{3d}$, $R^{2e}$, $R^{3e}$, $R^7$ and $R^8$ are independently selected from hydrogen, halogen, cyano, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_3$-$C_6$-halocycloalkyl, $C_1$-$C_4$-alkoxy or $C_1$-$C_4$-haloalkoxy, or $R^2$ and $R^3$; $R^{2a}$ and $R^{3a}$; $R^{2b}$ and $R^{3b}$; $R^{2c}$ and $R^{3c}$; $R^{2d}$ and $R^{3d}$; $R^{2e}$ and $R^{3e}$; and or $R^7$ and $R^8$ together with the atoms to which they are attached may form 3- to 5-membered non-aromatic carbocyclic ring or heterocyclic ring which may be optionally substituted with halogen, $C_1$-$C_2$-alkyl, $C_1$-$C_2$-haloalkyl or $C_1$-$C_2$-alkoxy;

$R^9$ is independently selected from the group consisting of hydrogen; $NR^gR^h$, wherein, $R^g$ and $R^h$ independently represent hydrogen, hydroxyl, cyano, $C_1$-$C_4$-alkyl, $C_1$-$C_4$-haloalkyl, $C_1$-$C_4$-alkoxy or $C_3$-$C_8$-cycloalkyl; (C=O)—$R^i$, wherein, $R^i$ represents hydrogen, halogen, cyano, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_3$-$C_6$-halocycloalkyl, $C_1$-$C_4$-alkoxy, and $C_1$-$C_4$-haloalkoxy; $C_1$-s-alkyl-$S(O)_{0-2}R^j$, wherein $R^j$ represents hydrogen, halogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl; $C_1$-$C_6$-alkyl-(C=O)—$R^i$, $CR^i$=$NR^g$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxy, $C_1$-$C_6$-haloalkoxy, $C_3$-$C_8$-cycloalkyl, $C_4$-$C_8$-cycloalkenyl, $C_5$-$C_8$-cycloalkynyl, $C_7$-$C_{19}$-aralkyl, bicyclic $C_5$-$C_{12}$-alkyl, $C_7$-$C_{12}$-alkenyl, fused or non-fused or bicyclic $C_3$-$C_{18}$-carbocyclic; wherein one or more carbon atoms in cyclic ring system may be replaced by N, O, $S(=O)_{0-2}$, $S(=O)_{0-1}(=NR^{6c})$, $C(=O)$, $C(=S)$, $C(=CR^{2e}R^{3e})$ and $C=NR^{6c}$, wherein, $R^9$ may optionally be substituted with one or more identical or different substituents selected from hydrogen, halogen, cyano, nitro, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxy-$C_1$-$C_4$-alkyl, $C_1$-$C_6$-hydroxyalkyl, $C_2$-$C_6$-haloalkenyl, $C_2$-$C_6$-haloalkynyl, $C_3$-$C_8$-halocycloalkyl, $C_1$-$C_6$-alkoxy, $C_1$-$C_6$-haloalkoxy, $C_1$-$C_6$-haloalkoxycarbonyl, $C_1$-$C_6$-alkylthio, $C_1$-$C_6$-haloalkylthio, $C_1$-$C_6$-haloalkylsulfinyl, $C_1$-$C_6$-haloalkylsulfonyl, $C_1$-$C_6$-alkylsulfinyl, $C_1$-$C_6$-alkylsulfonyl, $C_1$-$C_6$-alkylamino, di-$C_1$-$C_6$-alkylamino, $C_3$-$C_8$-cycloalkylamino, $C_1$-$C_6$-alkyl-$C_3$-$C_8$-cycloalkylamino, $C_1$-$C_6$-alkylcarbonyl, $C_1$-$C_6$-alkoxycarbonyl, $C_1$-$C_6$-alkylaminocarbonyl, di-$C_1$-$C_6$-alkylaminocarbonyl, $C_1$-$C_6$-alkoxycarbonyloxy, $C_1$-$C_6$-alkylaminocarbonyloxy, or di $C_1$-$C_6$-alkylaminocarbonyloxy, 5- to 11-membered spirocyclic ring, 3- to 6-membered carbocyclic or heterocyclic ring;

$R^{10}$ is selected from the group of hydrogen, halogen, hydroxy, cyano, —$OR^{12}$, —$NR^{13}R^{14}$, nitro, —SH, —SCN, —$COR^{15}$, —$C(=O)OR^{12}$, —$C(=O)NR^{13}R^{14}$, —$NR^{13}C(=O)R^{15}$, —$O(C=O)R^{15}$, —$O(C=O)NR^{13}R^{14}$, —$C(=NOR^{13})R^{15}$, —$NR^{13}SO_2R^{16}$, —$CSR^{16}$, —$C(=S)OR^{12}$, —$C(=S)NR^{13}R^{14}$, —$NR^{13}C(=S)R^{15}$, —$O(C=S)R^{15}$, —$O(C=S)NR^{13}R^{14}$, —$O(C=S)SR^{16}$, —N=$C(R^{15})_2$, —NHCN, —$SO_2NHCN$, —$C(=O)NHCN$, —$C(=S)NHCN$, —$C(=S(O))NHCN$, —$SO_2NR^{12}R^{13}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_3$-$C_8$-cycloalkyl-$C_1$-$C_6$-alkyl, $C_3$-$C_8$-cycloalkyl-$C_3$-$C_8$-cycloalkyl, $C_3$-$C_8$-halocycloalkyl-$C_1$-$C_6$-alkyl, $C_1$-$C_6$-alkyl-$C_3$-$C_8$-cycloalkyl-$C_1$-$C_6$-alkyl, $C_3$-$C_8$-cycloalkenyl, $C_3$-$C_8$-halocycloalkenyl, $C_1$-$C_6$-alkoxy-$C_1$-$C_6$-alkyl, $C_3$-$C_8$-cycloalkoxy-$C_1$-$C_6$-alkyl, $C_1$-$C_6$-alkoxy-$C_1$-$C_6$-alkoxy-$C_1$-$C_6$-alkyl, $C_1$-$C_6$-alkyl-$C_1$-$C_6$-thioalkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylamino, di-$C_1$-$C_6$-alkylamino, $C_1$-$C_6$-alkylamino-$C_1$-$C_6$-alkyl, di-$C_1$-$C_6$-alkylamino-$C_1$-$C_6$-alkyl, $C_1$-$C_6$-haloalkylamino-$C_1$-$C_6$-alkyl, $C_3$-$C_8$-cycloalkylamino, $C_3$-$C_8$-cycloalkylamino-$C_1$-$C_6$-alkyl, $C_1$-$C_6$-alkylcarbonyl, $C_1$-$C_6$-haloalkoxy-$C_1$-$C_6$-alkyl, $C_1$-$C_6$-hydroxyalkyl, $C_2$-$C_6$- hydroxyalkenyl, $C_2$-$C_6$-hydroxyalkynyl, $C_3$-$C_8$-halocycloalkoxy, $C_3$-$C_8$-cycloalkyl-$C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkoxy, $C_1$-$C_6$-alkylcarbonylalkoxy, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl, tri-$C_1$-$C_6$-alkylsilyl, $C_1$-$C_6$-alkylsulfonylamino, $C_1$-$C_6$-haloalkylsulfonylamino, $C_1$-$C_6$-alkylcarbonylthio, $C_1$-$C_6$-alkylsulfonyloxy, $C_1$-$C_6$-alkylsulfinyloxy, $C_6$-$C_{10}$-arylsulfonyloxy, $C_6$-$C_{10}$-arylsulfinyloxy, $C_6$-$C_{10}$-arylsulfonyl, $C_6$-$C_{10}$-arylsulfinyl, $C_6$-$C_{10}$-arylthio, $C_1$-$C_6$-cyanoalkyl, $C_2$-$C_6$-alkenylcarbonyloxy, $C_1$-$C_6$-alkoxy-$C_1$-$C_6$-alkylthio, $C_1$-$C_6$-alkylthio-$C_1$-$C_6$-alkoxy, $C_2$-$C_6$-haloalkenylcarbonyloxy, $C_1$-$C_6$-alkoxycarbonyl-$C_1$-$C_6$-alkyl, $C_1$-$C_6$-alkoxy-$C_2$-$C_6$-alkynyl, $C_2$-$C_6$-alkynylthio, $C_3$-$C_8$-halocycloalkylcarbonyloxy, $C_2$-$C_6$-alkenylamino, $C_2$-$C_6$-alkynylamino, $C_1$-$C_6$-haloalkylamino, $C_3$-$C_8$-cycloalkyl-$C_1$-$C_6$-alkylamino, $C_1$-$C_6$-alkoxyamino, $C_1$-$C_6$-haloalkoxyamino, $C_1$-$C_6$-alkoxycarbonylamino, $C_1$-$C_6$-alkylcarbonyl-$C_1$-$C_6$-alkylamino, $C_1$-$C_6$-haloalkylcarbonyl-$C_1$-$C_6$-alkylamino, $C_1$-$C_6$-alkoxycarbonyl-$C_1$-$C_6$-alkylamino, $C_2$-$C_6$-alkenylthio, $C_1$-$C_6$-alkoxy-$C_1$-$C_6$-alkylcarbonyl, $C_1$-$C_6$-haloalkoxycarbonylamino, di($C_1$-$C_6$-haloalkyl) amino-$C_1$-$C_6$-alkyl, $C_3$-$C_8$-halocycloalkenyloxy-$C_1$-$C_6$-alkyl, $C_1$-$C_6$-alkoxy($C_1$-$C_6$-alkyl)aminocarbonyl, $C_1$-$C_6$-haloalkylsulfonylaminocarbonyl, $C_1$-$C_6$-alkylsulfonylaminocarbonyl, $C_1$-$C_6$-alkoxycarbonylalkoxy, $C_1$-$C_6$-alkylaminothiocarbonylamino, $C_3$-$C_8$-cycloalkyl-$C_1$-$C_6$-alkylamino-$C_1$-$C_6$-alkyl, $C_1$-$C_6$-alkylthiocarbonyl, $C_3$-$C_8$-cycloalkenyloxy-$C_1$-$C_6$-alkyl, $C_1$-$C_6$-alkoxy-$C_1$-$C_6$-alkoxycarbonyl, di-$C_1$-$C_6$-alkylaminothiocarbonylamino, $C_1$-$C_6$-haloalkoxy-$C_1$-$C_6$-haloalkoxy, $C_1$-$C_6$-alkoxy-$C_1$-$C_6$-haloalkoxy, $C_3$-$C_8$-halocycloalkoxy-$C_1$-$C_6$-alkyl, di-$C_1$-$C_6$-alkylaminocarbonylamino, $C_1$-$C_6$-alkoxy-$C_2$-$C_6$-alkenyl, $C_1$-$C_6$-alkylthiocarbonyloxy, $C_1$-$C_6$-haloalkoxy-$C_1$-$C_6$-alkoxy, $C_1$-$C_6$-haloalkylsulfonyloxy, $C_1$-$C_6$-alkoxy-$C_1$-$C_6$-haloalkyl, di($C_1$-$C_6$-haloalkyl)amino, di-$C_1$-$C_6$-alkoxy-$C_1$-$C_6$-alkyl, $C_1$-$C_6$-alkylaminocarbonylamino, $C_1$-$C_6$-haloalkoxy-$C_1$-$C_6$-haloalkyl, $C_1$-$C_6$-alkylaminocarbonyl-$C_1$-$C_6$-alkylamino, tri-$C_1$-$C_6$-alkylsilyl-$C_2$-$C_6$-alkynyloxy, tri-$C_1$-$C_6$-alkylsilyloxy, tri-$C_1$-$C_6$-alkylsilyl-$C_2$-$C_6$-alkynyl, cyano($C_1$-$C_6$-alkoxy)-$C_1$-$C_6$-alkyl, di-$C_1$-$C_6$-alkylthio-$C_1$-$C_6$-alkyl, $C_1$-$C_6$-alkoxysulfonyl, $C_3$-$C_8$-halocycloalkoxycarbonyl, $C_1$-$C_6$-alkyl-$C_3$-$C_8$-cycloalkylcarbonyl, $C_3$-$C_8$-halocycloalkylcarbonyl, $C_2$-$C_6$-alkenyloxycarbonyl, $C_2$-$C_6$-alkynyloxycarbonyl, $C_1$-$C_6$-cyanoalkoxycarbonyl, $C_1$-$C_6$-alkylthio-$C_1$-$C_6$-alkoxycarbonyl, $C_2$-$C_6$-alkynylcarbonyloxy, $C_2$-$C_6$-haloalkynylcarbonyloxy, cyanocarbonyloxy, $C_1$-$C_6$-cyanoalkylcarbonyloxy, $C_3$-$C_8$-cycloalkylsulphonyloxy, $C_3$-$C_8$-cycloalkyl-$C_1$-$C_6$-alkylsulphonyloxy, $C_3$-$C_8$-halocycloalkylsulphonyloxy, $C_2$-$C_6$-alkenylsulphonyloxy, $C_2$-$C_6$-alkynylsulphonyloxy, $C_1$-$C_6$-cyanoalkylsulphonyloxy, $C_2$-$C_6$-haloalkenylsulphonyloxy, $C_2$-$C_6$-haloalkynylsulphonyloxy, $C_2$-$C_6$-alkynylcycloalkyloxy, $C_2$-$C_6$-cyanoalkenyloxy, $C_2$-$C_6$-cyanoalkynyloxy, $C_1$-$C_6$-alkoxycarbonyloxy, $C_2$-$C_6$-alkenyloxycarbonyloxy, $C_2$-$C_6$-alkynyloxycarbonyloxy, $C_1$-$C_6$-alkoxy-$C_1$-$C_6$-alkylcarbonyloxy, sulfilimines, sulfoximines, $SF_5$ or $Z^1Q^1$;

$Z^1$ and $Z^2$ are independently a direct bond, $CR^{2d}R^{3d}$, N, O, C(O), C(S), C(=$CR^{2d}R^{3d}$) or S(O)$_{0-2}$;

$Q^1$ and $Q^2$ are independently selected from phenyl, benzyl, naphthalenyl, a 5- or 6-membered aromatic ring, an 8- to 11-membered aromatic multi-cyclic ring system, an 8- to 11-membered aromatic fused ring system, a 5- or 6-membered heteroaromatic ring, an 8- to 11-membered heteroaromatic multi-cyclic ring system or an 8- to 11-membered heteroaromatic fused ring system; wherein the heteroatom of the heteroaromatic rings is selected from N, O or S, and each ring or ring system may be optionally substituted with one or more substituents independently selected from $R^{17}$; or $Q^1$ and $Q^2$ are independently selected from a 3- to 7-membered non-aromatic carbocyclic ring, a 4-, 5-, 6- or 7-membered non-aromatic heterocyclic ring, an 8- to 15-membered non-aromatic multi-cyclic ring system, an 5- to 15 membered spirocyclic ring system, or an 8- to 15-membered non-aromatic fused ring system, wherein, the heteroatom of the non-aromatic rings is selected from N, O or S(O)$_{0-2}$, and C ring member of the non-aromatic carbocylic or non-aromatic heterocyclic rings or ring systems may be replaced with C(O), C(S), C(=$CR^{2c}R^{3c}$) or C(=$NR^6$), and each ring or ring system may be optionally substituted with one or more substituents independently selected from $R^{17}$;

wherein, $R^{17}$ is selected from hydrogen, halogen, hydroxy, cyano, —$OR^{12}$, —$NR^{13}R^{14}$, nitro, —SH, —SCN, —$COR^1$, —C(=O)$OR^{12}$, —C(=O)$NR^{13}R^{14}$, —$NR^{13}$C(=O)R, —O(C=O)$R^5$, —O(C=O)$NR^{13}R^{14}$, —C(=$NOR^{13}$)$R^{15}$, —$NR^{13}SO_2R^{16}$, —$CSR^{16}$, —C(=S)$OR^2$, —C(=S) $NR^{13}R^{14}$, —$NR^{13}$C(=S)$R^1$, —O(C=S)$R^{15}$, —O(C=S) $NR^{13}R^{14}$, —O(C=S)$SR^{16}$, —N=C($R^{15}$)$_2$, —NHCN, —$SO_2$NHCN, —C(=O)NHCN, —C(=S)NHCN, —C(=S(O))NHCN, —$SO_2NR^{12}R^{13}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_3$-$C_8$-cycloalkyl-$C_1$-$C_6$-alkyl, $C_3$-$C_8$-cycloalkyl-$C_3$-$C_8$-cycloalkyl, $C_3$-$C_8$-halocycloalkyl-$C_1$-$C_6$-alkyl, $C_1$-$C_6$-alkyl-$C_3$-$C_8$-cycloalkyl-$C_1$-$C_6$-alkyl, $C_3$-$C_8$-cycloalkenyl, $C_3$-$C_8$-halocycloalkenyl, $C_1$-$C_6$-alkoxy-$C_1$-$C_6$-alkyl, $C_3$-$C_8$-cycloalkoxy-$C_1$-$C_6$-alkyl, $C_1$-$C_6$-alkoxy-$C_1$-$C_6$-alkoxy-$C_1$-$C_6$-alkyl, $C_1$-$C_6$-alkyl-$C_1$-$C_6$-thioalkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylamino, di-$C_1$-$C_6$-alkylamino, $C_1$-$C_6$-alkylamino-$C_1$-$C_6$-alkyl, di-$C_1$-$C_6$-alkylamino-$C_1$-$C_6$-alkyl, $C_1$-$C_6$-haloalkylamino-$C_1$-$C_6$-alkyl, $C_3$-$C_8$-cycloalkylamino, $C_3$-$C_8$-cycloalkylamino-$C_1$-$C_6$-alkyl, $C_1$-$C_6$-alkylcarbonyl, $C_1$-$C_6$-haloalkoxy-$C_1$-$C_6$-alkyl, $C_1$-$C_6$-hydroxyalkyl, $C_2$-$C_6$-hydroxyalkenyl, $C_2$-$C_6$-hydroxyalkynyl, $C_3$-$C_8$-halocycloalkoxy, $C_3$-$C_8$-cycloalkyl-$C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkoxy, $C_1$-$C_6$-alkylcarbonylalkoxy, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl, tri-$C_1$-$C_6$-alkylsilyl, $C_1$-$C_6$-alkylsulfonylamino, $C_1$-$C_6$-haloalkylsulfonylamino, $C_1$-$C_6$-alkylcarbonylthio, $C_1$-$C_6$-alkylsulfonyloxy, $C_1$-$C_6$-alkylsulfinyloxy, $C_6$-$C_{10}$-arylsulfonyloxy, $C_6$-$C_{10}$-arylsulfinyloxy, $C_6$-$C_{10}$-arylsulfonyl, $C_6$-$C_{10}$-arylsulfinyl, $C_6$-$C_{10}$-arylthio, $C_1$-$C_6$-cyanoalkyl, $C_2$-$C_6$-alkenylcarbonyloxy, $C_1$-$C_6$-alkoxy-$C_1$-$C_6$-alkylthio, $C_1$-$C_6$-alkylthio-$C_1$-$C_6$-alkoxy, $C_2$-$C_6$-haloalkenylcarbonyloxy, $C_1$-$C_6$-alkoxycarbonyl-$C_1$-$C_6$-alkyl, $C_1$-$C_6$-alkoxy-$C_2$-$C_6$-alkynyl, $C_2$-$C_6$-alkynylthio, $C_3$-$C_8$-halocycloalkylcarbonyloxy, $C_2$-$C_6$-alkenylamino, $C_2$-$C_6$-alkynylamino, $C_1$-$C_6$-haloalkylamino, $C_3$-$C_8$-cycloalkyl-$C_1$-$C_6$-alkylamino, $C_1$-$C_6$-alkoxyamino, $C_1$-$C_6$-haloalkoxyamino, $C_1$-$C_6$-alkoxycarbonylamino, $C_1$-$C_6$-alkylcarbonyl-$C_1$-$C_6$-alkylamino, $C_1$-$C_6$-haloalkylcarbonyl-$C_1$-$C_6$-alkylamino, $C_1$-$C_6$-alkoxycarbonyl-$C_1$-$C_6$-alkylamino, $C_2$-$C_6$-alkenylthio, $C_1$-$C_6$-alkoxy-$C_1$-$C_6$-alkylcarbonyl, $C_1$-$C_6$-haloalkoxycarbonylamino, di($C_1$-$C_6$-haloalkyl)

amino-$C_1$-$C_6$-alkyl, $C_3$-$C_8$-halocycloalkenyloxy-$C_1$-$C_6$-alkyl, $C_1$-$C_6$-alkoxy($C_1$-$C_6$-alkyl)aminocarbonyl, $C_1$-$C_6$-haloalkylsulfonylaminocarbonyl, $C_1$-$C_6$-alkylsulfonylaminocarbonyl, $C_1$-$C_6$-alkoxycarbonylalkoxy, $C_1$-$C_6$-alkylaminothiocarbonylamino, $C_3$-$C_8$-cycloalkyl-$C_1$-$C_6$-alkylamino-$C_1$-$C_6$-alkyl, $C_1$-$C_6$-alkylthiocarbonyl, $C_3$-$C_8$-cycloalkenyloxy-$C_1$-$C_6$-alkyl, $C_1$-$C_6$-alkoxy-$C_1$-$C_6$-alkoxycarbonyl, di-$C_1$-$C_6$-alkylaminothiocarbonylamino, $C_1$-$C_6$-haloalkoxy-$C_1$-$C_6$-haloalkoxy, $C_1$-$C_1$-alkoxy-$C_1$-$C_6$-haloalkoxy, $C_3$-$C_8$-halocycloalkoxy-$C_1$-$C_6$-alkyl, di-$C_1$-$C_6$-alkylaminocarbonylamino, $C_1$-$C_6$-alkoxy-$C_2$-$C_6$-alkenyl, $C_1$-$C_6$-alkylthiocarbonyloxy, $C_1$-$C_6$-haloalkoxy-$C_1$-$C_6$-alkoxy, $C_1$-$C_6$-haloalkylsulfonyloxy, $C_1$-$C_6$-alkoxy-$C_1$-$C_6$-haloalkyl, di($C_1$-$C_6$-haloalkyl)amino, di-$C_1$-$C_6$-alkoxy-$C_1$-$C_6$-alkyl, $C_1$-$C_6$-alkylaminocarbonylamino, $C_1$-$C_6$-haloalkoxy-$C_1$-$C_6$-haloalkyl, $C_1$-$C_6$-alkylaminocarbonyl-$C_1$-$C_6$-alkylamino, tri-$C_1$-$C_6$-alkylsilyl-$C_2$-$C_6$-alkynyloxy, tri-$C_1$-$C_6$-alkylsilyloxy, tri-$C_1$-$C_6$-alkylsilyl-$C_2$-$C_6$-alkynyl, cyano($C_1$-$C_6$-alkoxy)-$C_1$-$C_6$-alkyl, di-$C_1$-$C_6$-alkylthio-$C_1$-$C_6$-alkyl, $C_1$-$C_6$-alkoxysulfonyl, $C_3$-$C_8$-halocycloalkoxycarbonyl, $C_1$-$C_6$-alkyl-$C_3$-$C_8$-cycloalkylcarbonyl, $C_3$-$C_8$-halocycloalkylcarbonyl, $C_2$-$C_6$-alkenyloxycarbonyl, $C_2$-$C_6$-alkynyloxycarbonyl, $C_1$-$C_6$-cyanoalkoxycarbonyl, $C_1$-$C_6$-alkylthio-$C_1$-$C_6$-alkoxycarbonyl, $C_2$-$C_6$-alkynylcarbonyloxy, $C_2$-$C_6$-haloalkynylcarbonyloxy, cyanocarbonyloxy, $C_1$-$C_6$-cyanoalkylcarbonyloxy, $C_3$-$C_8$-cycloalkylsulphonyloxy, $C_3$-$C_8$-cycloalkyl-$C_1$-$C_6$-alkylsulphonyloxy, $C_3$-$C_8$-halocycloalkylsulphonyloxy, $C_2$-$C_6$-alkenylsulphonyloxy, $C_2$-$C_6$-alkynylsulphonyloxy, $C_1$-$C_6$-cyanoalkylsulphonyloxy, $C_2$-$C_6$-haloalkenylsulphonyloxy, $C_2$-$C_6$-haloalkynylsulphonyloxy, $C_2$-$C_6$-alkynylcycloalkyloxy, $C_2$-$C_6$-cyanoalkenyloxy, $C_2$-$C_6$-cyanoalkynyloxy, $C_1$-$C_6$-alkoxycarbonyloxy, $C_2$-$C_6$-alkenyloxycarbonyloxy, $C_2$-$C_6$-alkynyloxycarbonyloxy, $C_1$-$C_6$-alkoxy-$C_1$-$C_6$-alkylcarbonyloxy, sulfilimines, sulfoximines, $SF_5$ or $Z^2Q^2$;

$R^9$ and $R^{10}$; and or $R^9$ and $R^A$ together with the atoms to which they are attached may form a 3- to 10-membered carbocyclic ring or ring system, or heterocyclic ring or ring system which may be optionally substituted with $R^{17}$;

wherein,
$R^{12}$ represents $C_1$-$C_6$-alkyl, $C_1$-$C_6$-haloalkyl, $C_3$-$C_8$-cycloalkyl, $C_3$-$C_8$-halocycloalkyl,
$R^{13}$ and $R^{14}$ independently represent hydrogen, hydroxyl, cyano, $C_1$-$C_6$-alkyl, $C_1$-$C_6$-haloalkyl, $C_1$-$C_6$-alkoxy, $C_3$-$C_8$-cycloalkyl, $C_3$-$C_8$-halocycloalkyl,
$R^{15}$ represents hydrogen, hydroxy, halogen, $NR^bR^c$, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, $C_3$-$C_8$-cycloalkyl, and
$R^{16}$ represents hydrogen, halogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, or $C_3$-$C_8$-cycloalkyl.

Particularly, α carbon atom of $R^1$ from the oxadiazole ring bears at least two fluorine atoms; and the β carbon atom of $R^1$ from the oxadiazole ring in case of $C_2$-haloalkyl bears at least one fluorine atom.

Particularly, the present invention relates a compound of Formula I, wherein:
$R^1$ is trifluoroalkyl;
$L^1$ is a direct bond;
A is a phenyl ring or pyridyl ring; wherein phenyl or pyridyl ring is unsubstituted or substituted with one or more identical or different $R^A$ groups,
wherein, $R^A$ is halogen, cyano, $C_1$-$C_6$-alkyl and $C_1$-$C_6$-alkoxy, wherein $R^A$ may be optionally substituted with one or more identical or different $R^a$ selected from halogen, cyano, and amino;

$L^2$ is a fragment selected from the group of

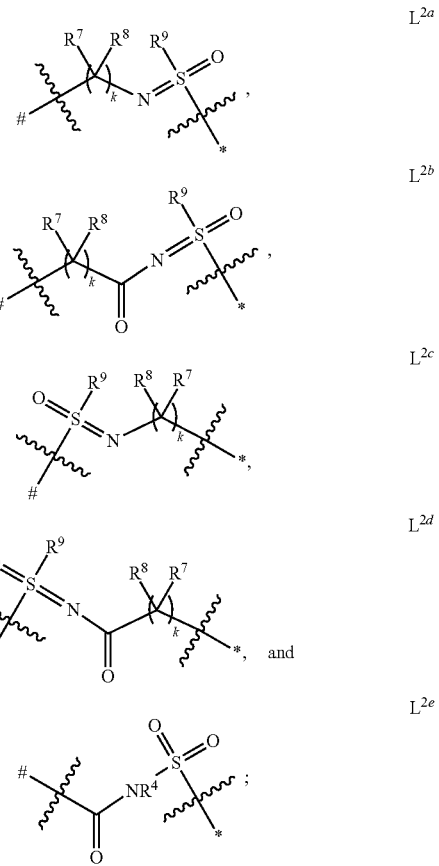

wherein, k is an integer ranging from 0 to 1; an expression "#" on the left side indicates the point of attachment to A, and an expression "*" on the right side indicates the point of attachment to $R^{10}$;

$R^7$ and $R^8$ are hydrogen, $C_1$-$C_4$-alkyl, $C_1$-$C_4$-haloalkyl, $C_3$-$C_6$-cycloalkyl, $C_3$-$C_6$-halocycloalkyl, or $C_1$-$C_4$-alkoxy;

$R^9$ is selected from the group consisting of $C_1$-$C_6$-alkyl, $C_2$-$C_6$-alkenyl, $C_1$-$C_6$-haloalkyl, $C_1$-$C_6$-alkoxy, $C_1$-$C_6$-haloalkoxy, and $C_3$-$C_8$-cycloalkyl;

$R^{10}$ is selected from the group of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_3$-$C_8$-cycloalkyl-$C_1$-$C_6$-alkyl, $C_3$-$C_8$-cycloalkyl-$C_3$-$C_8$-cycloalkyl, $C_3$-$C_8$-halocycloalkyl-$C_1$-$C_6$-alkyl, $C_1$-$C_6$-alkyl-$C_3$-$C_8$-cycloalkyl-$C_1$-$C_6$-alkyl, $C_1$-$C_6$-alkoxy-$C_1$-$C_6$-alkyl, $C_3$-$C_8$-cycloalkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_1$-$C_6$-hydroxyalkyl, $C_3$-$C_8$-halocycloalkoxy, $C_3$-$C_8$-cycloalkyl-$C_1$-$C_6$-alkoxy, $C_1$-$C_6$-alkoxy-$C_1$-$C_6$-alkoxy, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl or $Z^1Q^1$;

$Z^1$ and $Z^2$ are independently a direct bond, $CR^{2d}R^{3d}$, and O;

$Q^1$ and $Q^2$ are phenyl, benzyl, 5- or 6-membered aromatic ring, a 5- or 6-membered heteroaromatic ring; wherein the heteroatom of the heteroaromatic ring is selected from N, O and S; and each ring may be optionally substituted with one or more substituents independently selected from $R^{17}$; or wherein, $R^{17}$ is selected from halogen, cyano, —$OR^{12}$; wherein $R^{12}$ represents $C_1$-$C_6$-alkyl, $C_1$-$C_6$-haloalkyl, $C_3$-$C_8$-cycloalkyl and $C_3$-$C_8$-halocycloalkyl; $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl and $Z^2Q^2$;

$R^9$ and $R^{10}$ together with the atoms to which they are attached may form a 3- to 10-membered heterocyclic ring or ring system which may be optionally substituted with $R^{17}$; wherein the heteroatom of the heterocyclic ring or ring system is selected from N, O and S(O)-2.

More particularly, the compound of Formula I is selected from the group consisting of:

N-(methyl(oxo)(p-tolyl)-$\lambda^6$-sulfaneylidene)-4-(5-(trifluoromethyl)-1,2,4-oxadiazol-3-yl)benzamide; N-((4-cyanobenzyl)(methyl)(oxo)-$\lambda^6$-sulfaneylidene)-4-(5-(trifluoromethyl)-1,2,4-oxadiazol-3-yl)benzamide; N-((2,6-difluorobenzyl)(methyl)(oxo)-$\lambda^6$-sulfaneylidene)-4-(5-(trifluoromethyl)-1,2,4-oxadiazol-3-yl)benzamide; N-((2,3-difluorobenzyl)(methyl)(oxo)-$\lambda^6$-sulfaneylidene)-4-(5-(trifluoromethyl)-1,2,4-oxadiazol-3-yl)benzamide; N-((4-methoxybenzyl)(methyl)(oxo)-$\lambda^6$-sulfaneylidene)-4-(5-(trifluoromethyl)-1,2,4-oxadiazol-3-yl)benzamide; N-((4-bromobenzyl)(methyl)(oxo)-$\lambda^6$-sulfaneylidene)-4-(5-(trifluoromethyl)-1,2,4-oxadiazol-3-yl)benzamide; N-((2,6-difluorophenyl)(methyl)(oxo)-$\lambda^6$-sulfaneylidene)-4-(5-(trifluoromethyl)-1,2,4-oxadiazol-3-yl)benzamide; N-((2,4-difluorobenzyl)(methyl)(oxo)-$\lambda^6$-sulfaneylidene)-4-(5-(trifluoromethyl)-1,2,4-oxadiazol-3-yl)benzamide; N-((2-fluorobenzyl)(methyl)(oxo)-$\lambda^6$-sulfaneylidene)-4-(5-(trifluoromethyl)-1,2,4-oxadiazol-3-yl)benzamide; N-((3-fluorobenzyl)(methyl)(oxo)-$\lambda^6$-sulfaneylidene)-4-(5-(trifluoromethyl)-1,2,4-oxadiazol-3-yl)benzamide; N-(methyl(2-methylbenzyl)(oxo)-$\lambda^6$-sulfaneylidene)-4-(5-(trifluoromethyl)-1,2,4-oxadiazol-3-yl)benzamide; N-((3,5-dimethylphenyl)(methyl)(oxo)-$\lambda^6$-sulfaneylidene)-4-(5-(trifluoromethyl)-1,2,4-oxadiazol-3-yl)benzamide; N-((4-cyanophenyl)(methyl)(oxo)-$\lambda^6$-sulfaneylidene)-4-(5-(trifluoromethyl)-1,2,4-oxadiazol-3-yl)benzamide; N-(1-oxidotetrahydro-2H-1$\lambda^6$-thiopyran-1-ylidene)-4-(5-(trifluoromethyl)-1,2,4-oxadiazol-3-yl)benzamide; N-(methyl(oxo)(m-tolyl)-$\lambda^6$-sulfaneylidene)-4-(5-(trifluoromethyl)-1,2,4-oxadiazol-3-yl)benzamide; N-(methyl(3-methylbenzyl)(oxo)-$\lambda^6$-sulfaneylidene)-4-(5-(trifluoromethyl)-1,2,4-oxadiazol-3-yl)benzamide; N-((3-methoxyphenyl)(methyl)(oxo)-$\lambda^6$-sulfaneylidene)-4-(5-(trifluoromethyl)-1,2,4-oxadiazol-3-yl)benzamide; N-((2,4-difluorophenyl)(methyl)(oxo)-$\lambda^6$-sulfaneylidene)-4-(5-(trifluoromethyl)-1,2,4-oxadiazol-3-yl)benzamide; N-(methyl(oxo)(thiazol-2-yl)-$\lambda^6$-sulfaneylidene)-4-(5-(trifluoromethyl)-1,2,4-oxadiazol-3-yl)benzamide; N-((4-fluorobenzyl)(methyl)(oxo)-$\lambda^6$-sulfaneylidene)-4-(5-(trifluoromethyl)-1,2,4-oxadiazol-3-yl)benzamide; N-(methyl(oxo)(4-(trifluoromethyl)benzyl)-$\lambda^6$-sulfaneylidene)-4-(5-(trifluoromethyl)-1,2,4-oxadiazol-3-yl)benzamide; N-((2,6-dichlorobenzyl)(methyl)(oxo)-$\lambda^6$-sulfaneylidene)-4-(5-(trifluoromethyl)-1,2,4-oxadiazol-3-yl)benzamide; N-(methyl(oxo)(pyridin-2-ylmethyl)-$\lambda^6$-sulfaneylidene)-4-(5-(trifluoromethyl)-1,2,4-oxadiazol-3-yl)benzamide; N-(methyl(4-methylthiazol-2-yl)(oxo)-$\lambda^6$-sulfaneylidene)-4-(5-(trifluoromethyl)-1,2,4-oxadiazol-3-yl)benzamide; N-(methyl(5-methyl-1,3,4-thiadiazol-2-yl)(oxo)-$\lambda^6$-sulfaneylidene)-4-(5-(trifluoromethyl)-1,2,4-oxadiazol-3-yl)benzamide; N-((2,5-dichlorophenyl)(methyl)(oxo)-$\lambda^6$-sulfaneylidene)-4-(5-(trifluoromethyl)-1,2,4-oxadiazol-3-yl)benzamide; N-((2,4-dimethoxyphenyl)(methyl)(oxo)-$\lambda^6$-sulfaneylidene)-4-(5-(trifluoromethyl)-1,2,4-oxadiazol-3-yl)benzamide; N-((3,4-difluorophenyl)(methyl)(oxo)-$\lambda^6$-sulfaneylidene)-4-(5-(trifluoromethyl)-1,2,4-oxadiazol-3-yl)benzamide; N-(4-oxido-1,4,$\lambda^6$-oxathian-4-ylidene)-4-(5-(trifluoromethyl)-1,2,4-oxadiazol-3-yl)benzamide; N-((2-fluorophenyl)(methyl)(oxo)-$\lambda^6$-sulfaneylidene)-4-(3-(trifluoromethyl)-1,2,4-oxadiazol-5-yl)benzamide; N-(methyl(oxo)(pyridin-4-ylmethyl)-$\lambda^6$-sulfaneylidene)-4-(5-(trifluoromethyl)-1,2,4-oxadiazol-3-yl)benzamide; N-((4-chlorobenzyl)(methyl)(oxo)-$\lambda^6$-sulfaneylidene)-4-(5-(trifluoromethyl)-1,2,4-oxadiazol-3-yl)benzamide; N-((4-chloro-3-fluorobenzyl)(methyl)(oxo)-$\lambda^6$-sulfaneylidene)-4-(5-(trifluoromethyl)-1,2,4-oxadiazol-3-yl)benzamide; N-((2,5-difluorobenzyl)(methyl)(oxo)-$\lambda^6$-sulfaneylidene)-4-(5-(trifluoromethyl)-1,2,4-oxadiazol-3-yl)benzamide; N-((2-fluorophenyl)(methyl)(oxo)-$\lambda^6$-sulfaneylidene)-3-(5-(trifluoromethyl)-1,2,4-oxadiazol-3-yl)benzamide; N-(methyl(oxo)(4-(trifluoromethyl)phenyl)-$\lambda^6$-sulfaneylidene)-3-(5-(trifluoromethyl)-1,2,4-oxadiazol-3-yl)benzamide; N-((4-fluorophenyl)(methyl)(oxo)-$\lambda^6$-sulfaneylidene)-3-(5-(trifluoromethyl)-1,2,4-oxadiazol-3-yl)benzamide; N-(methyl(oxo)(pyridin-2-yl)-$\lambda^6$-sulfaneylidene)-3-(5-(trifluoromethyl)-1,2,4-oxadiazol-3-yl)benzamide; N-(methyl(oxo)(phenyl)-$\lambda^6$-sulfaneylidene)-3-(5-(trifluoromethyl)-1,2,4-oxadiazol-3-yl)benzamide; N-((2,6-difluorobenzyl)(methyl)(oxo)-$\lambda^6$-sulfaneylidene)-3-(5-(trifluoromethyl)-1,2,4-oxadiazol-3-yl)benzamide; N-((2,4-difluorobenzyl)(methyl)(oxo)-$\lambda^6$-sulfaneylidene)-3-(5-(trifluoromethyl)-1,2,4-oxadiazol-3-yl)benzamide; N-((4-methoxybenzyl)(methyl)(oxo)-$\lambda^6$-sulfaneylidene)-3-(5-(trifluoromethyl)-1,2,4-oxadiazol-3-yl)benzamide; N-((4-methoxyphenyl)(methyl)(oxo)-$\lambda^6$-sulfaneylidene)-3-(5-(trifluoromethyl)-1,2,4-oxadiazol-3-yl)benzamide; N-((2,6-difluorophenyl)(methyl)(oxo)-$\lambda^6$-sulfaneylidene)-3-(5-(trifluoromethyl)-1,2,4-oxadiazol-3-yl)benzamide; N-(methyl(oxo)(thiazol-2-yl)-$\lambda^6$-sulfaneylidene)-3-(5-(trifluoromethyl)-1,2,4-oxadiazol-3-yl)benzamide; N-(1-oxido-tetrahydro-2H-1$\lambda^6$-thiopyran-1-ylidene)-3-(5-(trifluoromethyl)-1,2,4-oxadiazol-3-yl)benzamide; N-((4-cyanobenzyl)(methyl)(oxo)-$\lambda^6$-sulfaneylidene)-3-(5-(trifluoromethyl)-1,2,4-oxadiazol-3-yl)benzamide; N-((4-fluorophenyl)(isopropyl)(oxo)-$\lambda^6$-sulfaneylidene)-4-(5-(trifluoromethyl)-1,2,4-oxadiazol-3-yl)benzamide; N-(isopropyl(4-methoxyphenyl)(oxo)-$\lambda^6$-sulfaneylidene)-4-(5-(trifluoromethyl)-1,2,4-oxadiazol-3-yl)benzamide; N-((4-chlorophenyl)(isopropyl)(oxo)-$\lambda^6$-sulfaneylidene)-4-(5-(trifluoromethyl)-1,2,4-oxadiazol-3-yl)benzamide; N-(isopropyl(oxo)(pyridin-2-yl)-$\lambda^6$-sulfaneylidene)-4-(5-(trifluoromethyl)-1,2,4-oxadiazol-3-yl)benzamide; N-(isopropyl(oxo)(phenyl)-$\lambda^6$-sulfaneylidene)-4-(5-(trifluoromethyl)-1,2,4-oxadiazol-3-yl)benzamide; 3-fluoro-N-((4-methoxyphenyl)(methyl)(oxo)-$\lambda^6$-sulfaneylidene)-4-(5-(trifluoromethyl)-1,2,4-oxadiazol-3-yl)benzamide; N-((3-bromophenyl)(ethyl)(oxo)-$\lambda^6$-sulfaneylidene)-4-(5-(trifluoromethyl)-1,2,4-oxadiazol-3-yl)benzamide;

N-(methyl(oxo)(2-phenoxyethyl)-$\lambda^6$-sulfaneylidene)-4-(5-(trifluoromethyl)-1,2,4-oxadiazol-3-yl)benzamide; (2,6-difluorophenyl)(methyl)((4-(5-(trifluoromethyl)-1,2,4-oxadiazol-3-yl)phenyl)imino)-$\lambda^6$-sulfanone; (2,6-difluorobenzyl)(methyl)((4-(5-(trifluoromethyl)-1,2,4-oxadiazol-3-yl)phenyl)imino)-$\lambda^6$-sulfanone; (2,4-difluorobenzyl)(methyl)((4-(5-(trifluoromethyl)-1,2,4-oxadiazol-3-yl)phenyl)imino)-$\lambda^6$-sulfanone; (2,3-difluorobenzyl)(methyl)((4-(5-(trifluoromethyl)-1,2,4-oxadiazol-3-yl)phenyl)imino)-$\lambda^6$-sulfanone; methyl(2-methylbenzyl)((4-(5-(trifluoromethyl)-1,2,4-oxadiazol-3-yl)phenyl)imino)-$\lambda^6$-sulfanone; (4-fluorobenzyl)(methyl)((4-(5-(trifluoromethyl)-1,2,4-oxadiazol-3-yl)phenyl)imino)-$\lambda^6$-sulfanone; methyl((4-(5-(trifluoromethyl)-1,2,4-oxadiazol-3-yl)phenyl)imino)(4-(trifluoromethyl)benzyl)-$\lambda^6$-sulfanone; (2,6-dichlorobenzyl)(methyl)((4-(5-(trifluoromethyl)-1,2,4-oxadiazol-3-yl)phenyl)imino)-$\lambda^6$-sulfanone; (4-bromobenzyl)(methyl)((4-(5-(trifluoromethyl)-1,2,4-oxadiazol-3-yl)phenyl)imino)-$\lambda^6$-sulfanone; methyl(pyridin-2-ylmethyl)((4-(5-(trifluoromethyl)-1,2,4-oxadiazol-3-yl)phenyl)imino)-$\lambda^6$-sulfanone; (2-fluorobenzyl)(methyl)((4-(5-(trifluoromethyl)-1,2,4-oxadiazol-3-yl)phenyl)imino)-$\lambda^6$-sulfanone; (3-fluorobenzyl)(methyl)((4-(5-(trifluoromethyl)-1,2,4-oxadiazol-3-yl)phenyl)imino)-$\lambda^6$-sulfanone; (2,4-dimethoxyphenyl)(methyl)((4-(5-(trifluoromethyl)-1,2,4-oxadiazol-3-yl)phenyl)imino)-$\lambda^6$-sulfanone; (3,4-difluorophenyl)(methyl)((4-(5-(trifluoromethyl)-1,2,4-oxadiazol-3-yl)phenyl)imino)-$\lambda^6$-sulfanone; (4-chlorobenzyl)(methyl)((4-(5-(trifluoromethyl)-1,2,4-oxadiazol-3-yl)phenyl)imino)-$\lambda^6$-sulfanone; (4-chloro-3-fluorobenzyl)(methyl)((4-(5-(trifluoromethyl)-1,2,4-oxadiazol-3-yl)phenyl)imino)-$\lambda^6$-sulfanone; (4-methoxyphenyl)(methyl)((3-(5-(trifluoromethyl)-1,2,4-oxadiazol-3-yl)phenyl)imino)-$\lambda^6$-sulfanone; (3-methoxyphenyl)(methyl)((3-(5-(trifluoromethyl)-1,2,4-oxadiazol-3-yl)phenyl)imino)-$\lambda^6$-sulfanone; 1-((3-(5-(trifluoromethyl)-1,2,4-oxadiazol-3-yl)phenyl)imino)hexahydro-1$\lambda^6$-thiopyran 1-oxide; (2,4-dimethoxyphenyl)(methyl)((3-(5-(trifluoromethyl)-1,2,4-oxadiazol-3-yl)phenyl)imino)-$\lambda^6$-sulfanone; (4-fluorophenyl)(methyl)((3-(5-(trifluoromethyl)-1,2,4-oxadiazol-3-yl)phenyl)imino)-$\lambda^6$-sulfanone; (2-fluorophenyl)(methyl)((3-(5-(trifluoromethyl)-1,2,4-oxadiazol-3-yl)phenyl)imino)-$\lambda^6$-sulfanone; (3-methoxyphenyl)(methyl)((4-(5-(trifluoromethyl)-1,2,4-oxadiazol-3-yl)phenyl)imino)-$\lambda^6$-sulfanone; (2,5-dichlorophenyl)(methyl)((4-(5-(trifluoromethyl)-1,2,4-oxadiazol-3-yl)phenyl)imino)-$\lambda^6$-sulfanone; (4-methoxyphenyl)(methyl)((6-(5-(trifluoromethyl)-1,2,4-oxadiazol-3-yl)pyridin-3-yl)imino)-$\lambda^6$-sulfanone; methyl(phenyl)((6-(5-(trifluoromethyl)-1,2,4-oxadiazol-3-yl)pyridin-3-yl)imino)-$\lambda^6$-sulfanone; methyl(pyridin-2-yl)((6-(5-(trifluoromethyl)-1,2,4-oxadiazol-3-yl)pyridin-3-yl)imino)-$\lambda^6$-sulfanone; (2,6-difluorobenzyl)(methyl)((6-(5-(trifluoromethyl)-1,2,4-oxadiazol-3-yl)pyridin-3-yl)imino)-$\lambda^6$-sulfanone; (4-chlorophenyl)(methyl)((3-(5-(trifluoromethyl)-1,2,4-oxadiazol-3-yl)phenyl)imino)-$\lambda^6$-sulfanone; methyl(pyridin-2-yl)((3-(5-(trifluoromethyl)-1,2,4-oxadiazol-3-yl)phenyl)imino)-$\lambda^6$-sulfanone; methyl(m-tolyl)((3-(5-(trifluoromethyl)-1,2,4-oxadiazol-3-yl)phenyl)imino)-$\lambda^6$-sulfanone; methyl(thiazol-2-yl)((3-(5-(trifluoromethyl)-1,2,4-oxadiazol-3-yl)phenyl)imino)-$\lambda^6$-sulfanone; methyl((4-(5-(trifluoromethyl)-1,2,4-oxadiazol-3-yl)pyridin-2-yl)-$\lambda^6$-sulfanone; methyl(4-methylthiazol-2-yl)((4-(5-(trifluoromethyl)-1,2,4-oxadiazol-3-yl)phenyl)imino)-$\lambda^6$-sulfanone; methyl(thiazol-2-yl)((4-(5-(trifluoromethyl)-1,2,4-oxadiazol-3-yl)phenyl)imino)-$\lambda^6$-sulfanone; (4-chlorophenyl)(methyl)((6-(5-(trifluoromethyl)-1,2,4-oxadiazol-3-yl)pyridin-3-yl)imino)-$\lambda^6$-sulfanone; (2,6-difluorophenyl)(methyl)((6-(5-(trifluoromethyl)-1,2,4-oxadiazol-3-yl)pyridin-3-yl)imino)-$\lambda^6$-sulfanone; (3,4-difluorophenyl)(methyl)((3-(5-(trifluoromethyl)-1,2,4-oxadiazol-3-yl)phenyl)imino)-$\lambda^6$-sulfanone; methyl(phenyl)((3-(5-(trifluoromethyl)-1,2,4-oxadiazol-3-yl)phenyl)imino)-$\lambda^6$-sulfanone; (4-fluorophenyl)(methyl)((6-(5-(trifluoromethyl)-1,2,4-oxadiazol-3-yl)pyridin-3-yl)imino)-$\lambda^6$-sulfanone; methyl((6-(5-(trifluoromethyl)-1,2,4-oxadiazol-3-yl)pyridin-3-yl)imino)(4-(trifluoromethyl)phenyl)-$\lambda^6$-sulfanone; (2-fluorophenyl)(methyl)((6-(5-(trifluoromethyl)-1,2,4-oxadiazol-3-yl)pyridin-3-yl)imino)-$\lambda^6$-sulfanone; (4-fluorobenzyl)(methyl)((6-(5-(trifluoromethyl)-1,2,4-oxadiazol-3-yl)pyridin-3-yl)imino)-$\lambda^6$-sulfanone; (3-methoxyphenyl)(methyl)((6-(5-(trifluoromethyl)-1,2,4-oxadiazol-3-yl)pyridin-3-yl)imino)-$\lambda^6$-sulfanone; 1-((6-(5-(trifluoromethyl)-1,2,4-oxadiazol-3-yl)pyridin-3-yl)imino)hexahydro-1$\lambda^6$-thiopyran 1-oxide; 4-((6-(5-(trifluoromethyl)-1,2,4-oxadiazol-3-yl)pyridin-3-yl)imino)-1,4$\lambda^6$-oxathiane 4-oxide; methyl(p-tolyl)((4-(5-(trifluoromethyl)-1,2,4-oxadiazol-3-yl)phenyl)imino)-$\lambda^6$-sulfanone; (2,4-difluorophenyl)(methyl)((4-(5-(trifluoromethyl)-1,2,4-oxadiazol-3-yl)phenyl)imino)-$\lambda^6$-sulfanone; methyl((4-(5-(trifluoromethyl)-1,2,4-oxadiazol-3-yl)phenyl)imino)(5-(trifluoromethyl)pyridin-2-yl)-$\lambda^6$-sulfanone; 4-((4-(5-(trifluoromethyl)-1,2,4-oxadiazol-3-yl)phenyl)imino)-1,4$\lambda^6$-oxathiane 4-oxide; 1-((4-(5-(trifluoromethyl)-1,2,4-oxadiazol-3-yl)phenyl)imino)hexahydro-1$\lambda^6$-thiopyran 1-oxide; methyl(4-(5-(trifluoromethyl)-1,2,4-oxadiazol-3-yl)phenyl)((4-(5-(trifluoromethyl)-1,2,4-oxadiazol-3-yl)phenyl)imino)-$\lambda^6$-sulfanone; methyl(4-(5-(trifluoromethyl)-1,2,4-oxadiazol-3-yl)phenyl)((3-(5-(trifluoromethyl)-1,2,4-oxadiazol-3-yl)phenyl)imino)-$\lambda^6$-sulfanone; methyl(p-tolyl)((4-(5-(trifluoromethyl)-1,2,4-oxadiazol-3-yl)benzyl)imino)-$\lambda^6$-sulfanone; methyl(phenyl)((3-(5-(trifluoromethyl)-1,2,4-oxadiazol-3-yl)benzyl)imino)-$\lambda^6$-sulfanone; (4-methoxyphenyl)(methyl)((3-(5-(trifluoromethyl)-1,2,4-oxadiazol-3-yl)benzyl)imino)-$\lambda^6$-sulfanone; (2,4-dimethoxyphenyl)(methyl)((3-(5-(trifluoromethyl)-1,2,4-oxadiazol-3-yl)benzyl)imino)-$\lambda^6$-sulfanone; (3,4-difluorophenyl)(methyl)((3-(5-(trifluoromethyl)-1,2,4-oxadiazol-3-yl)benzyl)imino)-$\lambda^6$-sulfanone; methyl((3-(5-(trifluoromethyl)-1,2,4-oxadiazol-3-yl)benzyl)imino)(4-((4-(trifluoromethyl)pyridin-2-yl)oxy)phenyl)-$\lambda^6$-sulfanone; (4-chlorophenyl)(methyl)((3-(5-(trifluoromethyl)-1,2,4-oxadiazol-3-yl)benzyl)imino)-$\lambda^6$-sulfanone; methyl(thiazol-2-yl)((3-(5-(trifluoromethyl)-1,2,4-oxadiazol-3-yl)benzyl)imino)-$\lambda^6$-sulfanone; (4-fluorophenyl)(methyl)((3-(5-(trifluoromethyl)-1,2,4-oxadiazol-3-yl)benzyl)imino)-$\lambda^6$-sulfanone; (2-bromo-5-fluorophenyl)(methyl)((3-(5-(trifluoromethyl)-1,2,4-oxadiazol-3-yl)benzyl)imino)-$\lambda^6$-sulfanone; 4-fluoro-N-(3-(5-(trifluoromethyl)-1,2,4-oxadiazol-3-yl)benzyl)benzenesulfonamide; (4-bromo-2-fluorophenyl)(methyl)((3-(5-(trifluoromethyl)-1,2,4-oxadiazol-3-yl)benzyl)imino)-$\lambda^6$-sulfanone; (2-fluorophenyl)(methyl)((3-(5-(trifluoromethyl)-1,2,4-oxadiazol-3-yl)benzyl)imino)-$\lambda^6$-sulfanone; 4-((3-(5-(trifluoromethyl)-1,2,4-oxadiazol-3-yl)benzyl)imino)-1,4$\lambda^6$-oxathiane 4-oxide; isopropyl(4-methoxyphenyl)((4-(5-(trifluoromethyl)-1,2,4-oxadiazol-3-yl)benzyl)imino)-$\lambda^6$-sulfanone; isopropyl(phenyl)((4-(5-(trifluoromethyl)-1,2,4-oxadiazol-3-yl)benzyl)imino)-$\lambda^6$-sulfanone; (4-chlorophenyl)(isopropyl)((4-(5-(trifluoromethyl)-1,2,4-oxadiazol-3-yl)benzyl)imino)-$\lambda^6$-sulfanone; N-tosyl-4-(5-(trifluoromethyl)-1,2,4-oxadiazol-3-yl)benzamide; N-((5- chloro-2-methoxyphenyl)sulfonyl)-4-(5-(trifluoromethyl)-1,2,4-oxadiazol-3-yl)benzamide; N-((2-fluorophenyl)sulfonyl)-4-(5-(trifluoromethyl)-1,2,4-oxadiazol-3-yl)benzamide; N-((2,4-dichlorophenyl)sulfonyl)-4-(5-(trifluoromethyl)-1,2,4-oxadiazol-3-yl)benzamide; N-((4-methoxyphenyl)sulfonyl)-4-(5-(trifluoromethyl)-1,2,4-oxadiazol-3-yl)benzamide; N-((3-methoxyphenyl)sulfonyl)-4-(5-(trifluoromethyl)-1,2,4-oxadiazol-3-yl)benzamide; 4-(5-(trifluoromethyl)-1,2,4-oxadiazol-3-yl)-N-((4-(trifluoromethyl)phenyl)sulfonyl)benzamide; N-(pyridin-3-ylsulfonyl)-4-(5-(trifluoromethyl)-1,2,4-oxadiazol-3-yl)benzamide; N-((2,5-difluorophenyl)sulfonyl)-4-(5-(trifluoromethyl)-1,2,4-oxadiazol-3-yl)benzamide; N-((4-bromophenyl)sulfonyl)-4-(5-(trifluoromethyl)-1,2,4-oxadiazol-3-yl)benzamide; N-((2,6-dichlorophenyl)sulfonyl)-4-(5-(trifluoromethyl)-1,2,4-oxadiazol-3-yl)benzamide; N-((3-fluorophenyl)sulfonyl)-4-(5-(trifluoromethyl)-1,2,4-oxadiazol-3-yl)benzamide; ((2-fluoro-4-(5-(trifluoromethyl)-1,2,4-oxadiazol-3-yl)phenyl)imino)(2-fluorophenyl)(methyl)-$\lambda^6$-sulfanone; ((2-fluoro-4-(5-(trifluoromethyl)-1,2,4-oxadiazol-3-yl)phenyl)imino)(methyl)(phenyl)-$\lambda^6$-sulfanone; (4-chlorophenyl)((2-fluoro-4-(5-(trifluoromethyl)-1,2,4-oxadiazol-3-yl)phenyl)imino)(methyl)-$\lambda^6$-sulfanone; ((2-fluoro-4-(5-(trifluoromethyl)-1,2,4-oxadiazol-3-yl)phenyl)imino)(methyl)(pyridin-2-yl)-$\lambda^6$-sulfanone; ((2-fluoro-4-(5-(trifluoromethyl)-1,2,4-oxadiazol-3-yl)phenyl)imino)(3-fluorophenyl)(methyl)-$\lambda^6$-sulfanone; ((2-fluoro-4-(5-(trifluoromethyl)-1,2,4-oxadiazol-3-yl)phenyl)imino)(4-fluorophenyl)(methyl)-$\lambda^6$-sulfanone; ((2-fluoro-4-(5-(trifluoromethyl)-1,2,4-oxadiazol-3-yl)phenyl)imino)(4-methoxyphenyl)(methyl)-$\lambda^6$-sulfanone; 2-fluoro-N-(methyl(oxo)(4-(5-(trifluoromethyl)-1,2,4-oxadiazol-3-yl)phenyl)-$\lambda^6$-sulfaneylidene)benzamide; 3-methoxy-N-(methyl(oxo)(4-(5-(trifluoromethyl)-1,2,4-oxadiazol-3-yl)phenyl)-$\lambda^6$-sulfaneylidene)benzamide; 3-fluoro-N-(methyl(oxo)(4-(5-(trifluoromethyl)-1,2,4-oxadiazol-3-yl)phenyl)-$\lambda^6$-sulfaneylidene)benzamide; 4-chloro-2-fluoro-N-(methyl(oxo)(4-(5-(trifluoromethyl)-1,2,4-oxadiazol-3-yl)phenyl)-$\lambda^6$-sulfaneylidene)benzamide; 2-chloro-6-fluoro-N-(methyl(oxo)(4-(5-(trifluoromethyl)-1,2,4-oxadiazol-3-yl)phenyl)-$\lambda^6$-sulfaneylidene)benzamide; N-(methyl(oxo)(4-(5-(trifluoromethyl)-1,2,4-oxadiazol-3-yl)phenyl)-$\lambda^6$-sulfaneylidene)benzamide; N-(methyl(oxo)(4-(5-(trifluoromethyl)-1,2,4-oxadiazol-3-yl)phenyl)-$\lambda^6$-sulfaneylidene)-2-phenylacetamide; 4-chloro-N-(methyl(oxo)(4-(5-(trifluoromethyl)-1,2,4-oxadiazol-3-yl)phenyl)-$\lambda^6$-sulfaneylidene)benzamide; N-(methyl(oxo)(4-(5-(trifluoromethyl)-1,2,4-oxadiazol-3-yl)phenyl)-$\lambda^6$-sulfaneylidene)pivalamide; N-(methyl(oxo)(4-(5-(trifluoromethyl)-1,2,4-oxadiazol-3-yl)phenyl)-$\lambda^6$-sulfaneylidene)cyclopropanecarboxamide; ((3-chlorobenzyl)imino)(methyl)(4-(5-(trifluoromethyl)-1,2,4-oxadiazol-3-yl)phenyl)-$\lambda^6$-sulfanone; ((4-fluorobenzyl)imino)(methyl)(4-(5-(trifluoromethyl)-1,2,4-oxadiazol-3-yl)phenyl)-$\lambda^6$-sulfanone; ((2,4-difluorobenzyl)imino)(methyl)(4-(5-(trifluoromethyl)-1,2,4-oxadiazol-3-yl)phenyl)-$\lambda^6$-sulfanone; ((3-fluorobenzyl)imino)(methyl)(4-(5-(trifluoromethyl)-1,2,4-oxadiazol-3-yl)phenyl)-$\lambda^6$-sulfanone; N-((4-fluorophenyl)(methyl)(oxo)-$\lambda^6$-sulfaneylidene)-2-(4-(5-(trifluoromethyl)-1,2,4-oxadiazol-3-yl)phenyl)acetamide; ((2,4-difluorophenyl)imino)(methyl)(4-(5-(trifluoromethyl)-1,2,4-oxadiazol-3-yl)phenyl)-$\lambda^6$-sulfanone; ((2-fluoro-4-methoxyphenyl)imino)(methyl)(4-(5-(trifluoromethyl)-1,2,4-oxadiazol-3-yl)phenyl)-$\lambda^6$-sulfanone; ((2-fluorophenyl)imino)(methyl)(4-(5-(trifluoromethyl)-1,2,4-oxadiazol-3-yl)phenyl)-$\lambda^6$-sulfanone; ((2-methoxy-4-(5-(trifluoromethyl)-1,2,4-oxadiazol-3-yl)phenyl)imino)(4-methoxyphenyl)(methyl)-$\lambda^6$-sulfanone; ((2-methoxy-4-(5-(trifluoromethyl)-1,2,4-oxadiazol-3-yl)phenyl)imino)(methyl)(phenyl)-$\lambda^6$-sulfanone; ((2-methoxy-4-(5-(trifluoromethyl)-1,2,4-oxadiazol-3-yl)phenyl)imino)(methyl)(pyridin-2-yl)-$\lambda^6$-sulfanone; ((2-methoxyphenyl)imino)(methyl)(4-(5-(trifluoromethyl)-1,2,4-oxadiazol-3-yl)phenyl)-$\lambda^6$-sulfanone; ((3-fluoro-4-(5-(trifluoromethyl)-1,2,4-oxadiazol-3-yl)phenyl)imino)(2-fluorobenzyl)(trifluoromethyl)-6-sulfanone; ((3-fluoro-4-(5-(trifluoromethyl)-1,2,4-oxadiazol-3-yl)phenyl)imino)(2-fluorophenyl)(trifluoromethyl)-$\lambda^6$-sulfanone; ((3-fluoro-4-(5-(trifluoromethyl)-1,2,4-oxadiazol-3-yl)phenyl)imino)(4-methoxyphenyl)(trifluoromethyl)-$\lambda^6$-sulfanone; ((3-fluoro-4-(5-(trifluoromethyl)-1,2,4-oxadiazol-3-yl)phenyl)imino)(phenyl)(trifluoromethyl)-$\lambda^6$-sulfanone; ((3-fluoro-4-(5-(trifluoromethyl)-1,2,4-oxadiazol-3-yl)phenyl)imino)(pyridin-2-yl)(trifluoromethyl)-$\lambda^6$-sulfanone; ((3-fluorophenyl)imino)(methyl)(4-(5-(trifluoromethyl)-1,2,4-oxadiazol-3-yl)phenyl)-$\lambda^6$-sulfanone; ((4-fluorophenyl)imino)(methyl)(4-(5-(trifluoromethyl)-1,2,4-oxadiazol-3-yl)phenyl)-$\lambda^6$-sulfanone; ((4-methoxyphenyl)imino)(methyl)(4-(5-(trifluoromethyl)-1,2,4-oxadiazol-3-yl)phenyl)-$\lambda^6$-sulfanone; ((5-methoxypyridin-2-yl)imino)(methyl)(4-(5-(trifluoromethyl)-1,2,4-oxadiazol-3-yl)phenyl)-$\lambda^6$-sulfanone; (2-(dimethylamino)ethyl)(methyl)((4-((5-(trifluoromethyl)-1,2,4-oxadiazol-3-yl)methyl)phenyl)imino)-$\lambda^6$-sulfanone; (2-(dimethylamino)ethyl)(methyl)((4-(5-(trifluoromethyl)-1,2,4-oxadiazol-3-yl)benzyl)imino)-$\lambda^6$-sulfanone; (2,4-difluorophenyl)(methyl)((4-((5-(trifluoromethyl)-1,2,4-oxadiazol-3-yl)methyl)phenyl)imino)-$\lambda^6$-sulfanone; (2-fluoro-4-methoxyphenyl)(methyl)((4-((5-(trifluoromethyl)-1,2,4-oxadiazol-3-yl)methyl)phenyl)imino)-$\lambda^6$-sulfanone; (2-fluoro-4-methoxyphenyl)(methyl)((4-(5-(trifluoromethyl)-1,2,4-oxadiazol-3-yl)benzyl)imino)-$\lambda^6$-sulfanone; (2-fluorobenzyl)((2-methoxy-4-(5-(trifluoromethyl)-1,2,4-oxadiazol-3-yl)phenyl)imino)(methyl)-$\lambda^6$-sulfanone; (2-fluorobenzyl)((3-methoxy-4-(5-(trifluoromethyl)-1,2,4-oxadiazol-3-yl)phenyl)imino)(methyl)-$\lambda^6$-sulfanone; (2-fluorobenzyl)(isopropyl)((4-(5-(trifluoromethyl)-1,2,4-oxadiazol-3-yl)phenyl)imino)-$\lambda^6$-sulfanone; (2-fluorobenzyl)(methyl)((5-(5-(trifluoromethyl)-1,2,4-oxadiazol-3-yl)pyridin-2-yl)imino)-$\lambda^6$-sulfanone; (2-fluorobenzyl)(methyl)((5-(5-(trifluoromethyl)-1,2,4-oxadiazol-3-yl)pyrimidin-2-yl)imino)-$\lambda^6$-sulfanone; (2-fluorobenzyl)(trifluoromethyl)((4-(5-(trifluoromethyl)-1,2,4-oxadiazol-3-yl)phenyl)imino)-$\lambda^6$-sulfanone; (2-fluorophenyl)((2-methoxy-4-(5-(trifluoromethyl)-1,2,4-oxadiazol-3-yl)phenyl)imino)(methyl)-$\lambda^6$-sulfanone; (2-fluorophenyl)(isopropyl)((4-(5-(trifluoromethyl)-1,2,4-oxadiazol-3-yl)phenyl)imino)-$\lambda^6$-sulfanone; (2-fluorophenyl)(methyl)((4-((5-(trifluoromethyl)-1,2,4-oxadiazol-3-yl)methyl)phenyl)imino)-$\lambda^6$-sulfanone; (2-fluorophenyl)(methyl)((5-(5-(trifluoromethyl)-1,2,4-oxadiazol-3-yl)pyridin-2-yl)imino)-$\lambda^6$-sulfanone; (2-fluorophenyl)(methyl)((5-(5-(trifluoromethyl)-1,2,4-oxadiazol-3-yl)pyrimidin-2-yl)imino)-$\lambda^6$-sulfanone; (2-fluorophenyl)(trifluoromethyl)((4-(5-(trifluoromethyl)-1,2,4-oxadiazol-3-yl)phenyl)imino)-$\lambda^6$-sulfanone; (2-methoxyethyl)(methyl)((4-((5-(trifluoromethyl)-1,2,4-oxadiazol-3-yl)methyl)phenyl)imino)-$\lambda^6$-sulfanone; (2-methoxyethyl)(methyl)((4-(5-(trifluoromethyl)-1,2,4-oxadiazol-3-yl)benzyl)imino)-$\lambda^6$-sulfanone; (2-methoxyphenyl)(methyl)((4-((5-(trifluoromethyl)-1,2,4-oxadiazol-3-yl)methyl)phenyl)imino)-$\lambda^6$-sulfanone; (3-fluorophenyl)(methyl)((4-((5-

(trifluoromethyl)-1,2,4-oxadiazol-3-yl)methyl)phenyl)imino)-λ⁶-sulfanone; (3-fluoropyridin-4-yl)(methyl)((4-((5-(trifluoromethyl)-1,2,4-oxadiazol-3-yl)methyl)phenyl)imino)-λ⁶-sulfanone; (3-methoxyphenyl)(methyl)((4-((5-(trifluoromethyl)-1,2,4-oxadiazol-3-yl)methyl)phenyl)imino)-λ⁶-sulfanone; (3-methoxypyridin-4-yl)(methyl)((4-((5-(trifluoromethyl)-1,2,4-oxadiazol-3-yl)methyl)phenyl)imino)-λ⁶-sulfanone; (3-methoxypyridin-4-yl)(methyl)((4-(5-(trifluoromethyl)-1,2,4-oxadiazol-3-yl)benzyl)imino)-λ⁶-sulfanone; (4-(difluoromethyl)phenyl)(methyl)((4-(5-(trifluoromethyl)-1,2,4-oxadiazol-3-yl)phenyl)imino)-λ⁶-sulfanone; (4-fluoro-2-methoxyphenyl)(methyl)((4-((5-(trifluoromethyl)-1,2,4-oxadiazol-3-yl)methyl)phenyl)imino)-λ⁶-sulfanone; (4-fluoro-2-methoxyphenyl)(methyl)((4-(5-(trifluoromethyl)-1,2,4-oxadiazol-3-yl)benzyl)imino)-λ⁶-sulfanone; (4-fluorophenyl)(methyl)((4-((5-(trifluoromethyl)-1,2,4-oxadiazol-3-yl)methyl)phenyl)imino)-λ⁶-sulfanone; (4-methoxyphenyl)(methyl)((4-((5-(trifluoromethyl)-1,2,4-oxadiazol-3-yl)methyl)phenyl)imino)-λ⁶-sulfanone; (4-methoxyphenyl)(methyl)((5-(5-(trifluoromethyl)-1,2,4-oxadiazol-3-yl)pyridin-2-yl)imino)-λ⁶-sulfanone; (4-methoxyphenyl)(methyl)((5-(5-(trifluoromethyl)-1,2,4-oxadiazol-3-yl)pyrimidin-2-yl)imino)-λ⁶-sulfanone; (4-methoxyphenyl)(trifluoromethyl)((4-(5-(trifluoromethyl)-1,2,4-oxadiazol-3-yl)phenyl)imino)-λ⁶-sulfanone; (cyclobutylimino)(methyl)(4-(5-(trifluoromethyl)-1,2,4-oxadiazol-3-yl)phenyl)-λ⁶-sulfanone; (cyclobutylmethyl)(methyl)((4-((5-(trifluoromethyl)-1,2,4-oxadiazol-3-yl)methyl)phenyl)imino)-λ⁶-sulfanone; (cyclobutylmethyl)(methyl)((4-(5-(trifluoromethyl)-1,2,4-oxadiazol-3-yl)benzyl)imino)-λ⁶-sulfanone; (cyclohexylimino)(methyl)(4-(5-(trifluoromethyl)-1,2,4-oxadiazol-3-yl)phenyl)-λ⁶-sulfanone; (cyclopentylimino)(methyl)(4-(5-(trifluoromethyl)-1,2,4-oxadiazol-3-yl)phenyl)-λ⁶-sulfanone; (cyclopentylmethyl)(methyl)((4-((5-(trifluoromethyl)-1,2,4-oxadiazol-3-yl)methyl)phenyl)imino)-λ⁶-sulfanone; (cyclopentylmethyl)(methyl)((4-(5-(trifluoromethyl)-1,2,4-oxadiazol-3-yl)benzyl)imino)-λ⁶-sulfanone; (cyclopropylimino)(methyl)(4-(5-(trifluoromethyl)-1,2,4-oxadiazol-3-yl)phenyl)-λ⁶-sulfanone; (cyclopropylmethyl)(2-fluorobenzyl)((4-(5-(trifluoromethyl)-1,2,4-oxadiazol-3-yl)phenyl)imino)-λ⁶-sulfanone; (cyclopropylmethyl)(2-fluorophenyl)((4-(5-(trifluoromethyl)-1,2,4-oxadiazol-3-yl)phenyl)imino)-λ⁶-sulfanone; (cyclopropylmethyl)(4-methoxyphenyl)((4-(5-(trifluoromethyl)-1,2,4-oxadiazol-3-yl)phenyl)imino)-λ⁶-sulfanone; (cyclopropylmethyl)(methyl)((4-((5-(trifluoromethyl)-1,2,4-oxadiazol-3-yl)methyl)phenyl)imino)-λ⁶-sulfanone; (cyclopropylmethyl)(methyl)((4-(5-(trifluoromethyl)-1,2,4-oxadiazol-3-yl)benzyl)imino)-λ⁶-sulfanone; (cyclopropylmethyl)(phenyl)((4-(5-(trifluoromethyl)-1,2,4-oxadiazol-3-yl)phenyl)imino)-λ⁶-sulfanone; (cyclopropylmethyl)(pyridin-2-yl)((4-(5-(trifluoromethyl)-1,2,4-oxadiazol-3-yl)phenyl)imino)-λ⁶-sulfanone; (furan-3-ylimino)(methyl)(4-(5-(trifluoromethyl)-1,2,4-oxadiazol-3-yl)phenyl)-λ⁶-sulfanone; 1-methyl-N-(methyl(oxo)(4-(5-(trifluoromethyl)-1,2,4-oxadiazol-3-yl)phenyl)-λ⁶-sulfaneylidene)-1H-imidazole-4-carboxamide; 1-methyl-N-(methyl(oxo)(4-(5-(trifluoromethyl)-1,2,4-oxadiazol-3-yl)phenyl)-λ⁶-sulfaneylidene)-1H-imidazole-5-carboxamide; 2,4-difluoro-N-(methyl(oxo)(4-(5-(trifluoromethyl)-1,2,4-oxadiazol-3-yl)phenyl)-λ⁶-sulfaneylidene)benzamide; 2-fluoro-4-methoxy-N-(methyl(oxo)(4-(5-(trifluoromethyl)-1,2,4-oxadiazol-3-yl)phenyl)-λ⁶-sulfaneylidene)benzamide; 2-fluoro-N-((2-fluorobenzyl)(methyl)(oxo)-λ⁶-sulfaneylidene)-4-(5-(trifluoromethyl)-1,2,4-oxadiazol-3-yl)benzamide; 2-fluoro-N-((2-fluorophenyl)(methyl)(oxo)-λ⁶-sulfaneylidene)-4-(5-(trifluoromethyl)-1,2,4-oxadiazol-3-yl)benzamide; 2-fluoro-N-((4-methoxyphenyl)(methyl)(oxo)-λ⁶-sulfaneylidene)-4-(5-(trifluoromethyl)-1,2,4-oxadiazol-3-yl)benzamide; 2-fluoro-N-(4-oxido-1,4,λ⁶-oxathian-4-ylidene)-4-(5-(trifluoromethyl)-1,2,4-oxadiazol-3-yl)benzamide; 2-fluoro-N-(methyl(oxo)(pyridin-2-yl)-λ⁶-sulfaneylidene)-4-(5-(trifluoromethyl)-1,2,4-oxadiazol-3-yl)benzamide; 2-fluoro-N-(methyl(oxo)(pyridin-4-yl)-λ⁶-sulfaneylidene)-4-(5-(trifluoromethyl)-1,2,4-oxadiazol-3-yl)benzamide; 2-methoxy-N-((4-methoxyphenyl)(methyl)(oxo)-λ⁶-sulfaneylidene)-4-(5-(trifluoromethyl)-1,2,4-oxadiazol-3-yl)benzamide; 2-methoxy-N-(4-oxido-1,4λ⁶-oxathian-4-ylidene)-4-(5-(trifluoromethyl)-1,2,4-oxadiazol-3-yl)benzamide; 2-methoxy-N-(methyl(oxo)(4-(5-(trifluoromethyl)-1,2,4-oxadiazol-3-yl)phenyl)-λ⁶-sulfaneylidene)benzamide; 2-methoxy-N-(methyl(oxo)(pyridin-2-yl)-λ⁶-sulfaneylidene)-4-(5-(trifluoromethyl)-1,2,4-oxadiazol-3-yl)benzamide; 2-methoxy-N-(methyl(oxo)(pyridin-4-yl)-λ⁶-sulfaneylidene)-4-(5-(trifluoromethyl)-1,2,4-oxadiazol-3-yl)benzamide; 3-fluoro-N-((2-fluorobenzyl)(methyl)(oxo)-λ⁶-sulfaneylidene)-4-(5-(trifluoromethyl)-1,2,4-oxadiazol-3-yl)benzamide; 3-fluoro-N-((2-fluorophenyl)(methyl)(oxo)-λ⁶-sulfaneylidene)-4-(5-(trifluoromethyl)-1,2,4-oxadiazol-3-yl)benzamide; 3-fluoro-N-(4-oxido-1,4λ⁶-oxathian-4-ylidene)-4-(5-(trifluoromethyl)-1,2,4-oxadiazol-3-yl)benzamide; 3-fluoro-N-(methyl(oxo)(pyridin-2-yl)-λ⁶-sulfaneylidene)-4-(5-(trifluoromethyl)-1,2,4-oxadiazol-3-yl)benzamide; 3-fluoro-N-(methyl(oxo)(pyridin-4-yl)-λ⁶-sulfaneylidene)-4-(5-(trifluoromethyl)-1,2,4-oxadiazol-3-yl)benzamide; 3-methoxy-N-((4-methoxyphenyl)(methyl)(oxo)-λ⁶-sulfaneylidene)-4-(5-(trifluoromethyl)-1,2,4-oxadiazol-3-yl)benzamide; 3-methoxy-N-(4-oxido-1,4λ⁶-oxathian-4-ylidene)-4-(5-(trifluoromethyl)-1,2,4-oxadiazol-3-yl)benzamide; 3-methoxy-N-(methyl(oxo)(pyridin-2-yl)-λ⁶-sulfaneylidene)-4-(5-(trifluoromethyl)-1,2,4-oxadiazol-3-yl)benzamide; 3-methoxy-N-(methyl(oxo)(pyridin-4-yl)-λ⁶-sulfaneylidene)-4-(5-(trifluoromethyl)-1,2,4-oxadiazol-3-yl)benzamide; 4-(5-(trifluoromethyl)-1,2,4-oxadiazol-3-yl)-N-((trifluoromethyl)sulfonyl)benzamide; 4-fluoro-N-(methyl(oxo)(4-(5-(trifluoromethyl)-1,2,4-oxadiazol-3-yl)phenyl)-λ⁶-sulfaneylidene)benzamide; 4-methoxy-N-(methyl(oxo)(4-(5-(trifluoromethyl)-1,2,4-oxadiazol-3-yl)phenyl)-λ⁶-sulfaneylidene)benzamide; 5-methoxy-N-(methyl(oxo)(4-(5-(trifluoromethyl)-1,2,4-oxadiazol-3-yl)phenyl)-λ⁶-sulfaneylidene)picolinamide; allyl(methyl)((4-((5-(trifluoromethyl)-1,2,4-oxadiazol-3-yl)methyl)phenyl)imino)-λ⁶-sulfanone; allyl(methyl)((4-(5-(trifluoromethyl)-1,2,4-oxadiazol-3-yl)benzyl)imino)-λ⁶-sulfanone; allyl(methyl)((4-(5-(trifluoromethyl)-1,2,4-oxadiazol-3-yl)phenyl)imino)-λ⁶-sulfanone; cyclopentyl(methyl)((4-(5-(trifluoromethyl)-1,2,4-oxadiazol-3-yl)phenyl)imino)-λ⁶-sulfanone; cyclopropyl(methyl)((4-((5-(trifluoromethyl)-1,2,4-oxadiazol-3-yl)methyl)phenyl)imino)-λ⁶-sulfanone; cyclopropyl(methyl)((4-(5-(trifluoromethyl)-1,2,4-oxadiazol-3-yl)benzyl)imino)-λ⁶-sulfanone; cyclopropyl(methyl)((4-(5-(trifluoromethyl)-1,2,4-oxadiazol-3-yl)phenyl)imino)-λ⁶-sulfanone; isobutyl(methyl)((4-((5-(trifluoromethyl)-1,2,4-oxadiazol-3-yl)methyl)phenyl)imino)-λ⁶-sulfanone; isobutyl(methyl)((4-(5-(trifluoromethyl)-1,2,4-oxadiazol-3-yl)benzyl)imino)-λ⁶-sulfanone; isobutyl(methyl)((4-(5-(trifluoromethyl)-1,2,4-oxadiazol-3-yl)phenyl)imino)-λ⁶-sulfanone; isopropyl(4-methoxyphenyl)((4-(5-(trifluoromethyl)-1,2,4-oxadiazol-3-yl)phenyl)imino)-λ⁶-sulfanone; isopropyl(phenyl)((4-(5-

(trifluoromethyl)-1,2,4-oxadiazol-3-yl)phenyl)imino)-λ$^6$-sulfanone; isopropyl(pyridin-2-yl)((4-(5-(trifluoromethyl)-1,2,4-oxadiazol-3-yl)phenyl)imino)-λ$^6$-sulfanone; methyl((1-methyl-1H-imidazol-4-yl)imino)(4-(5-(trifluoromethyl)-1,2,4-oxadiazol-3-yl)phenyl)-λ$^6$-sulfanone; methyl((1-methyl-1H-imidazol-5-yl)imino)(4-(5-(trifluoromethyl)-1,2,4-oxadiazol-3-yl)phenyl)-λ$^6$-sulfanone; methyl(oxazol-4-yl)((4-((5-(trifluoromethyl)-1,2,4-oxadiazol-3-yl)methyl)phenyl)imino)-λ$^6$-sulfanone; methyl(oxazol-4-yl)((4-(5-(trifluoromethyl)-1,2,4-oxadiazol-3-yl)benzyl)imino)-λ$^6$-sulfanone; methyl(oxazol-5-yl)((4-((5-(trifluoromethyl)-1,2,4-oxadiazol-3-yl)methyl)phenyl)imino)-λ$^6$-sulfanone; methyl(oxazol-5-yl)((4-(5-(trifluoromethyl)-1,2,4-oxadiazol-3-yl)benzyl)imino)-λ$^6$-sulfanone; methyl(oxazol-5-ylimino)(4-(5-(trifluoromethyl)-1,2,4-oxadiazol-3-yl)phenyl)-λ$^6$-sulfanone; methyl(perfluoroethyl)((4-((5-(trifluoromethyl)-1,2,4-oxadiazol-3-yl)methyl)phenyl)imino)-λ$^6$-sulfanone; methyl(perfluoroethyl)((4-(5-(trifluoromethyl)-1,2,4-oxadiazol-3-yl)benzyl)imino)-λ$^6$-sulfanone; methyl(phenyl)((4-((5-(trifluoromethyl)-1,2,4-oxadiazol-3-yl)methyl)phenyl)imino)-λ$^6$-sulfanone; methyl(phenyl)((5-(5-(trifluoromethyl)-1,2,4-oxadiazol-3-yl)pyridin-2-yl)imino)-λ$^6$-sulfanone; methyl(phenyl)((5-(5-(trifluoromethyl)-1,2,4-oxadiazol-3-yl)pyrimidin-2-yl)imino)-λ$^6$-sulfanone; methyl(phenylimino)(4-(5-(trifluoromethyl)-1,2,4-oxadiazol-3-yl)phenyl)-λ$^6$-sulfanone; methyl(prop-2-yn-1-yl)((4-((5-(trifluoromethyl)-1,2,4-oxadiazol-3-yl)methyl)phenyl)imino)-λ$^6$-sulfanone; methyl(prop-2-yn-1-yl)((4-(5-(trifluoromethyl)-1,2,4-oxadiazol-3-yl)benzyl)imino)-λ$^6$-sulfanone; methyl(prop-2-yn-1-yl)((4-(5-(trifluoromethyl)-1,2,4-oxadiazol-3-yl)phenyl)imino)-λ$^6$-sulfanone; methyl(pyridin-2-yl)((4-((5-(trifluoromethyl)-1,2,4-oxadiazol-3-yl)methyl)phenyl)imino)-λ$^6$-sulfanone; methyl(pyridin-2-yl)((5-(5-(trifluoromethyl)-1,2,4-oxadiazol-3-yl)pyridin-2-yl)imino)-λ$^6$-sulfanone; methyl(pyridin-2-yl)((5-(5-(trifluoromethyl)-1,2,4-oxadiazol-3-yl)pyrimidin-2-yl)imino)-λ$^6$-sulfanone; methyl(pyridin-2-ylimino)(4-(5-(trifluoromethyl)-1,2,4-oxadiazol-3-yl)phenyl)-λ$^6$-sulfanone; methyl(pyridin-3-yl)((4-((5-(trifluoromethyl)-1,2,4-oxadiazol-3-yl)methyl)phenyl)imino)-λ$^6$-sulfanone; methyl(pyridin-4-yl)((4-((5-(trifluoromethyl)-1,2,4-oxadiazol-3-yl)methyl)phenyl)imino)-λ$^6$-sulfanone; methyl(pyrimidin-2-yl)((4-((5-(trifluoromethyl)-1,2,4-oxadiazol-3-yl)methyl)phenyl)imino)-λ$^6$-sulfanone; methyl(pyrimidin-2-yl)((4-(5-(trifluoromethyl)-1,2,4-oxadiazol-3-yl)benzyl)imino)-λ$^6$-sulfanone; methyl(pyrimidin-2-ylimino)(4-(5-(trifluoromethyl)-1,2,4-oxadiazol-3-yl)phenyl)-λ$^6$-sulfanone; methyl(pyrimidin-4-yl)((4-((5-(trifluoromethyl)-1,2,4-oxadiazol-3-yl)methyl)phenyl)imino)-λ$^6$-sulfanone; methyl(pyrimidin-4-yl)((4-(5-(trifluoromethyl)-1,2,4-oxadiazol-3-yl)benzyl)imino)-λ$^6$-sulfanone; methyl(pyrimidin-4-ylimino)(4-(5-(trifluoromethyl)-1,2,4-oxadiazol-3-yl)phenyl)-λ$^6$-sulfanone; methyl(thiazol-4-yl)((4-((5-(trifluoromethyl)-1,2,4-oxadiazol-3-yl)methyl)phenyl)imino)-λ$^6$-sulfanone; methyl(thiazol-4-yl)((4-(5-(trifluoromethyl)-1,2,4-oxadiazol-3-yl)benzyl)imino)-λ$^6$-sulfanone; methyl(thiazol-5-yl)((4-((5-(trifluoromethyl)-1,2,4-oxadiazol-3-yl)methyl)phenyl)imino)-λ$^6$-sulfanone; methyl(thiazol-5-yl)((4-(5-(trifluoromethyl)-1,2,4-oxadiazol-3-yl)benzyl)imino)-λ$^6$-sulfanone; methyl(thiazol-5-ylimino)(4-(5-(trifluoromethyl)-1,2,4-oxadiazol-3-yl)phenyl)-λ$^6$-sulfanone; methyl(thiophen-2-yl)((4-((5-(trifluoromethyl)-1,2,4-oxadiazol-3-yl)methyl)phenyl)imino)-λ$^6$-sulfanone; methyl(thiophen-2-yl)((4-(5-(trifluoromethyl)-1,2,4-oxadiazol-3-yl)benzyl)imino)-λ$^6$-sulfanone; methyl(thiophen-2-ylimino)(4-(5-(trifluoromethyl)-1,2,4-oxadiazol-3-yl)phenyl)-λ$^6$-sulfanone; methyl(thiophen-3-yl)((4-((5-(trifluoromethyl)-1,2,4-oxadiazol-3-yl)methyl)phenyl)imino)-λ$^6$-sulfanone; methyl(thiophen-3-yl)((4-(5-(trifluoromethyl)-1,2,4-oxadiazol-3-yl)benzyl)imino)-λ$^6$-sulfanone; methyl(thiophen-3-ylimino)(4-(5-(trifluoromethyl)-1,2,4-oxadiazol-3-yl)phenyl)-λ$^6$-sulfanone; methyl(trifluoromethyl)((4-((5-(trifluoromethyl)-1,2,4-oxadiazol-3-yl)methyl)phenyl)imino)-λ$^6$-sulfanone; methyl(trifluoromethyl)((4-(5-(trifluoromethyl)-1,2,4-oxadiazol-3-yl)benzyl)imino)-λ$^6$-sulfanone; N-(((1-methylazetidin-3-yl)methyl)sulfonyl)-4-(5-(trifluoromethyl)-1,2,4-oxadiazol-3-yl)benzamide; N-((2-(dimethylamino)ethyl)(methyl)(oxo)-λ$^6$-sulfaneylidene)-4-((5-(trifluoromethyl)-1,2,4-oxadiazol-3-yl)methyl)benzamide; N-((2-(dimethylamino)ethyl)sulfonyl)-4-(5-(trifluoromethyl)-1,2,4-oxadiazol-3-yl)benzamide; N-((2-(dimethylamino)ethyl)sulfonyl)-N-methyl-4-(5-(trifluoromethyl)-1,2,4-oxadiazol-3-yl)benzamide; N-((2,4-difluorophenyl)(methyl)(oxo)-λ$^6$-sulfaneylidene)-4-((5-(trifluoromethyl)-1,2,4-oxadiazol-3-yl)methyl)benzamide; N-((2-fluoro-4-methoxyphenyl)(methyl)(oxo)-λ$^6$-sulfaneylidene)-4-((5-(trifluoromethyl)-1,2,4-oxadiazol-3-yl)methyl)benzamide; N-((2-fluorobenzyl)(methyl)(oxo)-λ$^6$-sulfaneylidene)-2-methoxy-4-(5-(trifluoromethyl)-1,2,4-oxadiazol-3-yl)benzamide; N-((2-fluorobenzyl)(methyl)(oxo)-λ$^6$-sulfaneylidene)-3-methoxy-4-(5-(trifluoromethyl)-1,2,4-oxadiazol-3-yl)benzamide; N-((2-fluorobenzyl)(methyl)(oxo)-λ$^6$-sulfaneylidene)-5-(5-(trifluoromethyl)-1,2,4-oxadiazol-3-yl)picolinamide; N-((2-fluorobenzyl)(methyl)(oxo)-λ$^6$-sulfaneylidene)-5-(5-(trifluoromethyl)-1,2,4-oxadiazol-3-yl)pyrazine-2-carboxamide; N-((2-fluorobenzyl)(methyl)(oxo)-λ$^6$-sulfaneylidene)-5-(5-(trifluoromethyl)-1,2,4-oxadiazol-3-yl)pyrimidine-2-carboxamide; N-((2-fluorobenzyl)(methyl)(oxo)-λ$^6$-sulfaneylidene)-6-(5-(trifluoromethyl)-1,2,4-oxadiazol-3-yl)nicotinamide; N-((2-fluorobenzyl)(oxo)(trifluoromethyl)-λ$^6$-sulfaneylidene)-4-(5-(trifluoromethyl)-1,2,4-oxadiazol-3-yl)benzamide; N-((2-fluorophenyl)(methyl)(oxo)-λ$^6$-sulfaneylidene)-2-methoxy-4-(5-(trifluoromethyl)-1,2,4-oxadiazol-3-yl)benzamide; N-((2-fluorophenyl)(methyl)(oxo)-λ$^6$-sulfaneylidene)-3-methoxy-4-(5-(trifluoromethyl)-1,2,4-oxadiazol-3-yl)benzamide; N-((2-fluorophenyl)(methyl)(oxo)-λ$^6$-sulfaneylidene)-4-((5-(trifluoromethyl)-1,2,4-oxadiazol-3-yl)methyl)benzamide; N-((2-fluorophenyl)(methyl)(oxo)-λ$^6$-sulfaneylidene)-5-(5-(trifluoromethyl)-1,2,4-oxadiazol-3-yl)pyrazine-2-carboxamide; N-((2-fluorophenyl)(methyl)(oxo)-λ$^6$-sulfaneylidene)-5-(5-(trifluoromethyl)-1,2,4-oxadiazol-3-yl)pyrimidine-2-carboxamide; N-((2-fluorophenyl)(methyl)(oxo)-λ$^6$-sulfaneylidene)-6-(5-(trifluoromethyl)-1,2,4-oxadiazol-3-yl)nicotinamide; N-((2-fluorophenyl)(oxo)(trifluoromethyl)-λ$^6$-sulfaneylidene)-4-(5-(trifluoromethyl)-1,2,4-oxadiazol-3-yl)benzamide; N-((2-methoxyethyl)(methyl)(oxo)-λ$^6$-sulfaneylidene)-4-((5-(trifluoromethyl)-1,2,4-oxadiazol-3-yl)methyl)benzamide; N-((2-methoxyethyl)sulfonyl)-4-(5-(trifluoromethyl)-1,2,4-oxadiazol-3-yl)benzamide; N-((2-methoxyethyl)sulfonyl)-N-methyl-4-(5-(trifluoromethyl)-1,2,4-oxadiazol-3-yl)benzamide; N-((2-methoxyphenyl)(methyl)(oxo)-λ$^6$-sulfaneylidene)-4-((5-(trifluoromethyl)-1,2,4-oxadiazol-3-yl)methyl)benzamide; N-((3-fluorophenyl)(methyl)(oxo)-λ$^6$-sulfaneylidene)-4-((5-(trifluoromethyl)-1,2,4-oxadiazol-3-yl)methyl)benzamide; N-((3-fluoropyridin-4-yl)(methyl)(oxo)-λ$^6$-sulfaneylidene)-4-((5-(trifluoromethyl)-1,2,4-oxadiazol-3-yl)methyl)benzamide; N-((3-methoxyphenyl)(methyl)(oxo)-λ$^6$-sulfaneylidene)-4-((5-(trifluoromethyl)-1,2,4-oxadiazol-3-yl)methyl)benzamide; N-((3-methoxypyridin-4-yl)(methyl)(oxo)-$\lambda^6$-sulfaneylidene)-4-((5-(trifluoromethyl)-1,2,4-oxadiazol-3-yl)methyl)benzamide; N-((4-(difluoromethyl)phenyl)(methyl)(oxo)-$\lambda^6$-sulfaneylidene)-4-(5-(trifluoromethyl)-1,2,4-oxadiazol-3-yl)benzamide; N-((4-chlorophenyl)(cyclopropylmethyl)(oxo)-$\lambda^6$-sulfaneylidene)-4-(5-(trifluoromethyl)-1,2,4-oxadiazol-3-yl)benzamide; N-((4-chlorophenyl)(methyl)(oxo)-$\lambda^6$-sulfaneylidene)-2-fluoro-4-(5-(trifluoromethyl)-1,2,4-oxadiazol-3-yl)benzamide; N-((4-chlorophenyl)(methyl)(oxo)-$\lambda^6$-sulfaneylidene)-2-methoxy-4-(5-(trifluoromethyl)-1,2,4-oxadiazol-3-yl)benzamide; N-((4-chlorophenyl)(methyl)(oxo)-$\lambda^6$-sulfaneylidene)-3-fluoro-4-(5-(trifluoromethyl)-1,2,4-oxadiazol-3-yl)benzamide; N-((4-chlorophenyl)(methyl)(oxo)-$\lambda^6$-sulfaneylidene)-3-methoxy-4-(5-(trifluoromethyl)-1,2,4-oxadiazol-3-yl)benzamide; N-((4-chlorophenyl)(methyl)(oxo)-$\lambda^6$-sulfaneylidene)-5-(5-(trifluoromethyl)-1,2,4-oxadiazol-3-yl)picolinamide; N-((4-chlorophenyl)(methyl)(oxo)-$\lambda^6$-sulfaneylidene)-5-(5-(trifluoromethyl)-1,2,4-oxadiazol-3-yl)pyrazine-2-carboxamide; N-((4-chlorophenyl)(methyl)(oxo)-$\lambda^6$-sulfaneylidene)-5-(5-(trifluoromethyl)-1,2,4-oxadiazol-3-yl)pyrimidine-2-carboxamide; N-((4-chlorophenyl)(methyl)(oxo)-$\lambda^6$-sulfaneylidene)-6-(5-(trifluoromethyl)-1,2,4-oxadiazol-3-yl)nicotinamide; N-((4-chlorophenyl)(oxo)(trifluoromethyl)-$\lambda^6$-sulfaneylidene)-4-(5-(trifluoromethyl)-1,2,4-oxadiazol-3-yl)benzamide; N-((4-fluoro-2-methoxyphenyl)(methyl)(oxo)-$\lambda^6$-sulfaneylidene)-4-((5-(trifluoromethyl)-1,2,4-oxadiazol-3-yl)methyl)benzamide; N-((4-fluorophenyl)(methyl)(oxo)-$\lambda^6$-sulfaneylidene)-4-((5-(trifluoromethyl)-1,2,4-oxadiazol-3-yl)methyl)benzamide; N-((4-fluorophenyl)(methyl)(oxo)-$\lambda^6$-sulfaneylidene)-5-(5-(trifluoromethyl)-1,2,4-oxadiazol-3-yl)pyrimidine-2-carboxamide; N-((4-methoxyphenyl)(methyl)(oxo)-$\lambda^6$-sulfaneylidene)-4-((5-(trifluoromethyl)-1,2,4-oxadiazol-3-yl)methyl)benzamide; N-((4-methoxyphenyl)(methyl)(oxo)-$\lambda^6$-sulfaneylidene)-5-(5-(trifluoromethyl)-1,2,4-oxadiazol-3-yl)pyrazine-2-carboxamide; N-((4-methoxyphenyl)(methyl)(oxo)-$\lambda^6$-sulfaneylidene)-5-(5-(trifluoromethyl)-1,2,4-oxadiazol-3-yl)pyrimidine-2-carboxamide; N-((4-methoxyphenyl)(methyl)(oxo)-$\lambda^6$-sulfaneylidene)-6-(5-(trifluoromethyl)-1,2,4-oxadiazol-3-yl)nicotinamide; N-((4-methoxyphenyl)(oxo)(trifluoromethyl)-$\lambda^6$-sulfaneylidene)-4-(5-(trifluoromethyl)-1,2,4-oxadiazol-3-yl)benzamide; N-((cyclobutylmethyl)(methyl)(oxo)-$\lambda^6$-sulfaneylidene)-4-((5-(trifluoromethyl)-1,2,4-oxadiazol-3-yl)methyl)benzamide; N-((cyclobutylmethyl)sulfonyl)-4-(5-(trifluoromethyl)-1,2,4-oxadiazol-3-yl)benzamide; N-((cyclobutylmethyl)sulfonyl)-N-methyl-4-(5-(trifluoromethyl)-1,2,4-oxadiazol-3-yl)benzamide; N-((cyclopentylmethyl)(methyl)(oxo)-$\lambda^6$-sulfaneylidene)-4-((5-(trifluoromethyl)-1,2,4-oxadiazol-3-yl)methyl)benzamide; N-((cyclopropylmethyl)(2-fluorobenzyl)(oxo)-$\lambda^6$-sulfaneylidene)-4-(5-(trifluoromethyl)-1,2,4-oxadiazol-3-yl)benzamide; N-((cyclopropylmethyl)(2-fluorophenyl)(oxo)-$\lambda^6$-sulfaneylidene)-4-(5-(trifluoromethyl)-1,2,4-oxadiazol-3-yl)benzamide; N-((cyclopropylmethyl)(4-methoxyphenyl)(oxo)-$\lambda^6$-sulfaneylidene)-4-(5-(trifluoromethyl)-1,2,4-oxadiazol-3-yl)benzamide; N-((cyclopropylmethyl)(methyl)(oxo)-$\lambda^6$-sulfaneylidene)-4-((5-(trifluoromethyl)-1,2,4-oxadiazol-3-yl)methyl)benzamide; N-((cyclopropylmethyl)(oxo)(pyridin-2-yl)-$\lambda^6$-sulfaneylidene)-4-(5-(trifluoromethyl)-1,2,4-oxadiazol-3-yl)benzamide; N-((cyclopropylmethyl)(oxo)(pyridin-4-yl)-$\lambda^6$-sulfaneylidene)-4-(5-(trifluoromethyl)-1,2,4-oxadiazol-3-yl)benzamide; N-((oxetan-3-ylmethyl)sulfonyl)-4-(5-(trifluoromethyl)-1,2,4-oxadiazol-3-yl)benzamide; N-((perfluoroethyl)sulfonyl)-4-(5-(trifluoromethyl)-1,2,4-oxadiazol-3-yl)benzamide; N-(1-oxido-1,6-thietan-1-ylidene)-4-((5-(trifluoromethyl)-1,2,4-oxadiazol-3-yl)methyl)benzamide; N-(1-oxidotetrahydro-1$\lambda^6$-thiophen-1-ylidene)-4-((5-(trifluoromethyl)-1,2,4-oxadiazol-3-yl)methyl)benzamide; N-(1-oxidotetrahydro-2H-1$\lambda^6$-thiopyran-1-ylidene)-4-((5-(trifluoromethyl)-1,2,4-oxadiazol-3-yl)methyl)benzamide; N-(4-oxido-1,4$\lambda^6$-oxathian-4-ylidene)-4-((5-(trifluoromethyl)-1,2,4-oxadiazol-3-yl)methyl)benzamide; N-(4-oxido-1,4$\lambda^6$-oxathian-4-ylidene)-5-(5-(trifluoromethyl)-1,2,4-oxadiazol-3-yl)pyrazine-2-carboxamide; N-(4-oxido-1,4$\lambda^6$-oxathian-4-ylidene)-5-(5-(trifluoromethyl)-1,2,4-oxadiazol-3-yl)pyrimidine-2-carboxamide; N-(4-oxido-1,4$\lambda^6$-oxathian-4-ylidene)-6-(5-(trifluoromethyl)-1,2,4-oxadiazol-3-yl)nicotinamide; N-(allyl(methyl)(oxo)-$\lambda^6$-sulfaneylidene)-4-((5-(trifluoromethyl)-1,2,4-oxadiazol-3-yl)methyl)benzamide; N-(allylsulfonyl)-4-(5-(trifluoromethyl)-1,2,4-oxadiazol-3-yl)benzamide; N-(allylsulfonyl)-N-methyl-4-(5-(trifluoromethyl)-1,2,4-oxadiazol-3-yl)benzamide; N-(cyclopentyl(methyl)(oxo)-$\lambda^6$-sulfaneylidene)-4-(5-(trifluoromethyl)-1,2,4-oxadiazol-3-yl)benzamide; N-(cyclopropyl(methyl)(oxo)-$\lambda^6$-sulfaneylidene)-4-((5-(trifluoromethyl)-1,2,4-oxadiazol-3-yl)methyl)benzamide; N-(cyclopropyl(methyl)(oxo)-$\lambda^6$-sulfaneylidene)-4-(5-(trifluoromethyl)-1,2,4-oxadiazol-3-yl)benzamide; N-(cyclopropylsulfonyl)-4-(5-(trifluoromethyl)-1,2,4-oxadiazol-3-yl)benzamide; N-(ethylsulfonyl)-4-(5-(trifluoromethyl)-1,2,4-oxadiazol-3-yl)benzamide; N-(isobutyl(methyl)(oxo)-$\lambda^6$-sulfaneylidene)-4-((5-(trifluoromethyl)-1,2,4-oxadiazol-3-yl)methyl)benzamide; N-(isobutyl(methyl)(oxo)-$\lambda^6$-sulfaneylidene)-4-(5-(trifluoromethyl)-1,2,4-oxadiazol-3-yl)benzamide; N-(isobutylsulfonyl)-4-(5-(trifluoromethyl)-1,2,4-oxadiazol-3-yl)benzamide; N-(isobutylsulfonyl)-N-methyl-4-(5-(trifluoromethyl)-1,2,4-oxadiazol-3-yl)benzamide; N-(isopropyl(methyl)(oxo)-$\lambda^6$-sulfaneylidene)-4-(5-(trifluoromethyl)-1,2,4-oxadiazol-3-yl)benzamide; N-(isopropylsulfonyl)-4-(5-(trifluoromethyl)-1,2,4-oxadiazol-3-yl)benzamide; N-(methyl(oxo)(4-(5-(trifluoromethyl)-1,2,4-oxadiazol-3-yl)phenyl)-$\lambda^6$-sulfaneylidene)cyclobutanecarboxamide; N-(methyl(oxo)(4-(5-(trifluoromethyl)-1,2,4-oxadiazol-3-yl)phenyl)-$\lambda^6$-sulfaneylidene)cyclohexanecarboxamide; N-(methyl(oxo)(4-(5-(trifluoromethyl)-1,2,4-oxadiazol-3-yl)phenyl)-$\lambda^6$-sulfaneylidene)cyclopentanecarboxamide; N-(methyl(oxo)(4-(5-(trifluoromethyl)-1,2,4-oxadiazol-3-yl)phenyl)-$\lambda^6$-sulfaneylidene)furan-3-carboxamide; N-(methyl(oxo)(4-(5-(trifluoromethyl)-1,2,4-oxadiazol-3-yl)phenyl)-$\lambda^6$-sulfaneylidene)oxazole-5-carboxamide; N-(methyl(oxo)(4-(5-(trifluoromethyl)-1,2,4-oxadiazol-3-yl)phenyl)-$\lambda^6$-sulfaneylidene)picolinamide; N-(methyl(oxo)(4-(5-(trifluoromethyl)-1,2,4-oxadiazol-3-yl)phenyl)-$\lambda^6$-sulfaneylidene)pyrimidine-2-carboxamide; N-(methyl(oxo)(4-(5-(trifluoromethyl)-1,2,4-oxadiazol-3-yl)phenyl)-$\lambda^6$-sulfaneylidene)pyrimidine-4-carboxamide; N-(methyl(oxo)(4-(5-(trifluoromethyl)-1,2,4-oxadiazol-3-yl)phenyl)-$\lambda^6$-sulfaneylidene)thiazole-5-carboxamide; N-(methyl(oxo)(4-(5-(trifluoromethyl)-1,2,4-oxadiazol-3-yl)phenyl)-$\lambda^6$-sulfaneylidene)thiophene-2-carboxamide; N-(methyl(oxo)(4-(5-(trifluoromethyl)-1,2,4-oxadiazol-3-yl)phenyl)-$\lambda^6$-sulfaneylidene)thiophene-3-carboxamide; N-(methyl(oxo)(perfluoroethyl)-$\lambda^6$-sulfaneylidene)-4-((5-(trifluoromethyl)-1,2,4-oxadiazol-3-yl)methyl)benzamide; N-(methyl(oxo)(phenyl)-$\lambda^6$-sulfaneylidene)-5-(5-(trifluoromethyl)-1,2,4-oxadiazol-3-yl)pyrimidine-2-carboxamide; N-(methyl(oxo)(prop-2-yn-1-yl)-$\lambda^6$-sulfaneylidene)-4-((5-(trifluoromethyl)-1,2,4-oxadiazol-3-yl)methyl)benzamide;

N-(methyl(oxo)(prop-2-yn-1-yl)-$\lambda^6$-sulfaneylidene)-4-(5-(trifluoromethyl)-1,2,4-oxadiazol-3-yl)benzamide; N-(methyl(oxo)(propyl)-$\lambda^6$-sulfaneylidene)-4-(5-(trifluoromethyl)-1,2,4-oxadiazol-3-yl)benzamide; N-(methyl(oxo)(pyridin-2-yl)-$\lambda^6$-sulfaneylidene)-4-((5-(trifluoromethyl)-1,2,4-oxadiazol-3-yl)methyl)benzamide; N-(methyl(oxo)(pyridin-2-yl)-$\lambda^6$-sulfaneylidene)-5-(5-(trifluoromethyl)-1,2,4-oxadiazol-3-yl)pyrazine-2-carboxamide; N-(methyl(oxo)(pyridin-2-yl)-$\lambda^6$-sulfaneylidene)-5-(5-(trifluoromethyl)-1,2,4-oxadiazol-3-yl)pyrimidine-2-carboxamide; N-(methyl(oxo)(pyridin-2-yl)-$\lambda^6$-sulfaneylidene)-6-(5-(trifluoromethyl)-1,2,4-oxadiazol-3-yl)nicotinamide; N-(methyl(oxo)(pyridin-3-yl)-$\lambda^6$-sulfaneylidene)-4-((5-(trifluoromethyl)-1,2,4-oxadiazol-3-yl)methyl)benzamide; N-(methyl(oxo)(pyridin-4-yl)-$\lambda^6$-sulfaneylidene)-4-((5-(trifluoromethyl)-1,2,4-oxadiazol-3-yl)methyl)benzamide; N-(methyl(oxo)(pyridin-4-yl)-$\lambda^6$-sulfaneylidene)-5-(5-(trifluoromethyl)-1,2,4-oxadiazol-3-yl)picolinamide; N-(methyl(oxo)(pyridin-4-yl)-$\lambda^6$-sulfaneylidene)-5-(5-(trifluoromethyl)-1,2,4-oxadiazol-3-yl)pyrazine-2-carboxamide; N-(methyl(oxo)(pyridin-4-yl)-$\lambda^6$-sulfaneylidene)-5-(5-(trifluoromethyl)-1,2,4-oxadiazol-3-yl)pyrimidine-2-carboxamide; N-(methyl(oxo)(pyridin-4-yl)-$\lambda^6$-sulfaneylidene)-6-(5-(trifluoromethyl)-1,2,4-oxadiazol-3-yl)nicotinamide; N-(methyl(oxo)(pyrimidin-2-yl)-$\lambda^6$-sulfaneylidene)-4-((5-(trifluoromethyl)-1,2,4-oxadiazol-3-yl)methyl)benzamide; N-(methyl(oxo)(pyrimidin-4-yl)-$\lambda^6$-sulfaneylidene)-4-((5-(trifluoromethyl)-1,2,4-oxadiazol-3-yl)methyl)benzamide; N-(methyl(oxo)(trifluoromethyl)-$\lambda^6$-sulfaneylidene)-4-((5-(trifluoromethyl)-1,2,4-oxadiazol-3-yl)methyl)benzamide; N-(oxo(pyridin-2-yl)(trifluoromethyl)-$\lambda^6$-sulfaneylidene)-4-(5-(trifluoromethyl)-1,2,4-oxadiazol-3-yl)benzamide; N-(oxo(pyridin-4-yl)(trifluoromethyl)-$\lambda^6$-sulfaneylidene)-4-(5-(trifluoromethyl)-1,2,4-oxadiazol-3-yl)benzamide; N-(prop-2-yn-1-ylsulfonyl)-4-(5-(trifluoromethyl)-1,2,4-oxadiazol-3-yl)benzamide; N-(propylsulfonyl)-4-(5-(trifluoromethyl)-1,2,4-oxadiazol-3-yl)benzamide; N-methyl-4-(5-(trifluoromethyl)-1,2,4-oxadiazol-3-yl)-N-((trifluoromethyl)sulfonyl)benzamide; N-methyl-N-(((1-methylazetidin-3-yl)methyl)sulfonyl)-4-(5-(trifluoromethyl)-1,2,4-oxadiazol-3-yl)benzamide; N-methyl-N-((oxetan-3-ylmethyl)sulfonyl)-4-(5-(trifluoromethyl)-1,2,4-oxadiazol-3-yl)benzamide; N-methyl-N-((perfluoroethyl)sulfonyl)-4-(5-(trifluoromethyl)-1,2,4-oxadiazol-3-yl)benzamide; N-methyl-N-(prop-2-yn-1-ylsulfonyl)-4-(5-(trifluoromethyl)-1,2,4-oxadiazol-3-yl)benzamide; phenyl(trifluoromethyl)((4-(5-(trifluoromethyl)-1,2,4-oxadiazol-3-yl)phenyl)imino)-$\lambda^6$-sulfanone; and pyridin-2-yl(trifluoromethyl)((4-(5-(trifluoromethyl)-1,2,4-oxadiazol-3-yl)phenyl)imino)-$\lambda^6$-sulfanone.

The present invention also relates to intermediates useful in the preparation of the compounds of Formula I. Such intermediates include but are not limited to Ia and Ib;

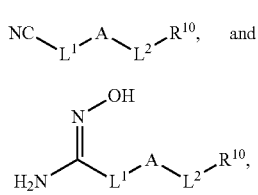

wherein $L^1$, A, $L^2$, $R^{10}$ are as defined herein before.

The present invention relates to a process for preparing the compound claimed in claim 1.

The process of the present invention comprises one or more steps selected from a to p depending upon the definition of $L^2$.

In step (a), a compound of formula 1 is esterified into a compound of formula 2 using suitable esterifying reactant and reagent:

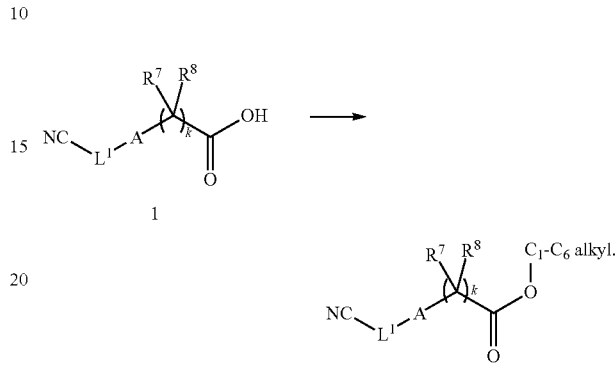

In step (b), the compound of formula 2 by reacting with hydroxyl amine hydrochloride in the presence of suitable base is converted into a compound of formula 3 or the compound of formula 1 by reacting with hydroxyl amine is converted into a compound of formula 3':

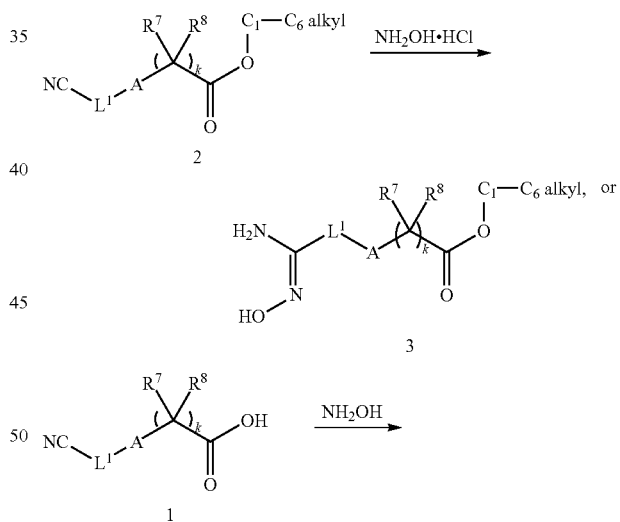

In step (c), the compound of formula 3 and a compound of formula 8 are cyclized to obtain a compound of formula 4 or the compound of formula 3' and a compound of formula 8 are cyclized to obtain a compound of formula 5:

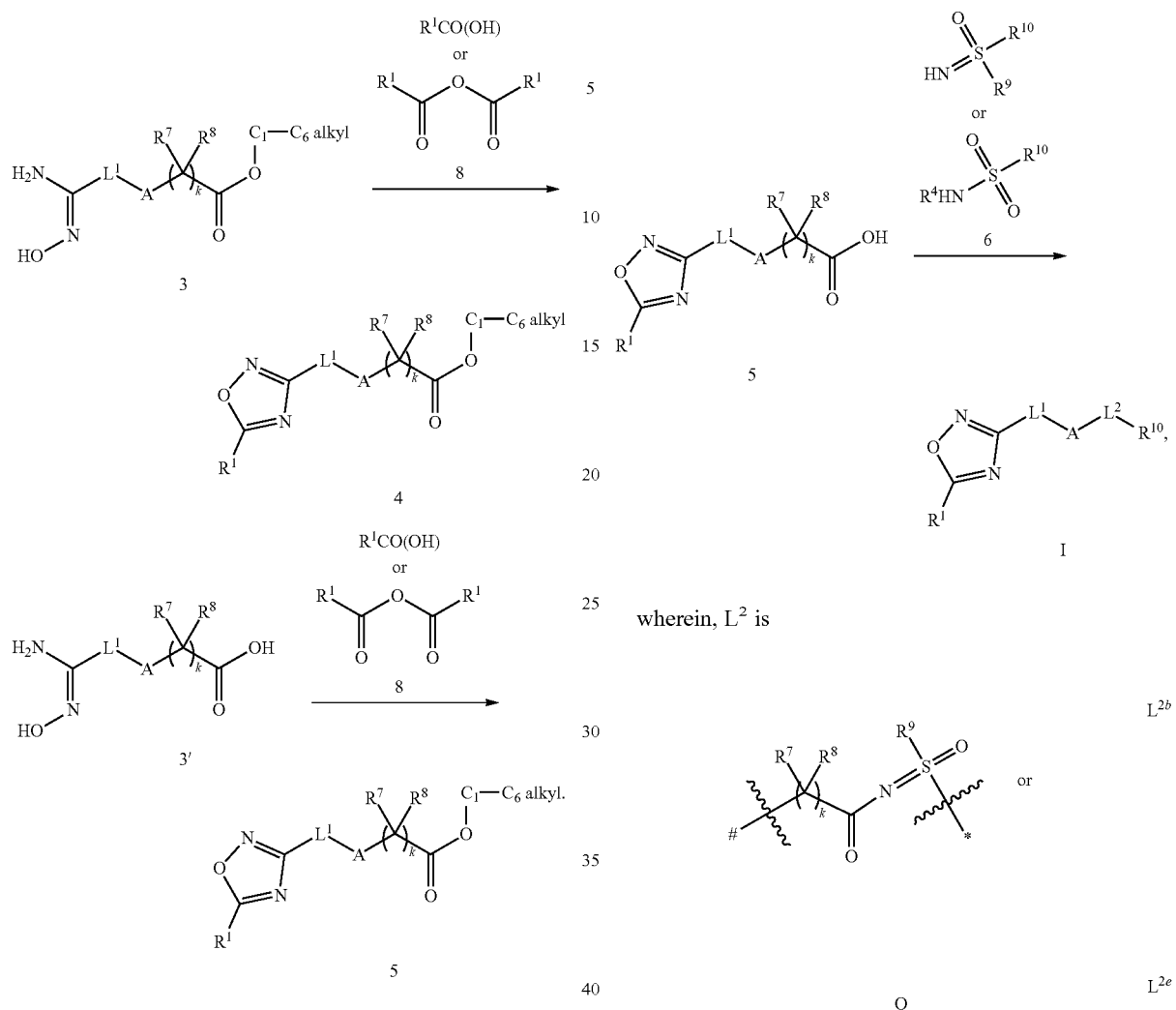

In step (d), the compound of formula 4 is hydrolyzed into a compound of formula 5:

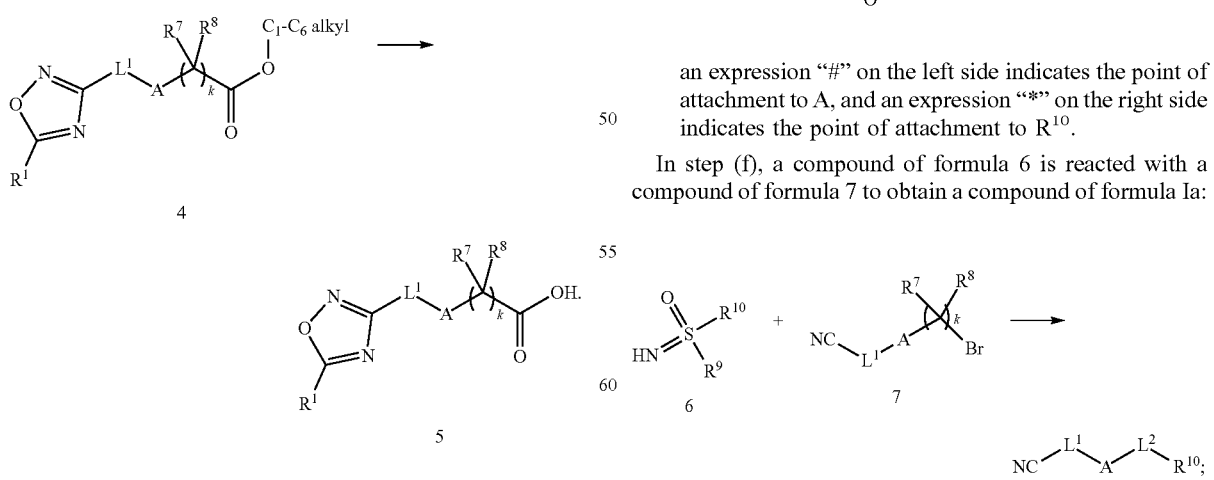

In step (e), the compound of formula 5 and a compound of formula 6 are reacted to obtain the compound of formula I:

wherein, $L^2$ is $L^{2b}$ or $L^{2e}$;

an expression "#" on the left side indicates the point of attachment to A, and an expression "*" on the right side indicates the point of attachment to $R^{10}$.

In step (f), a compound of formula 6 is reacted with a compound of formula 7 to obtain a compound of formula Ia:

wherein, L² is

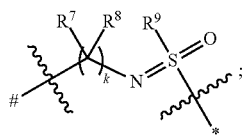

an expression "#" on the left side indicates the point of attachment to A, and an expression "*" on the right side indicates the point of attachment to R¹⁰.

In step (g), the compound of formula Ia by reacting with hydroxyl amine hydrochloride is converted into a compound of formula Ib:

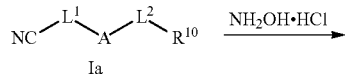

wherein, L² steps f to is

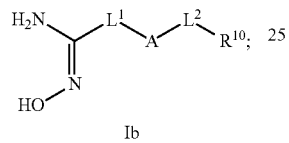

an expression "#" on the left side indicates the point of attachment to A, and an expression "*" on the right side indicates the point of attachment to R¹⁰.

In step (h), the compound of formula b and a compound of formula 8 are cyclized to obtain a compound of formula I:

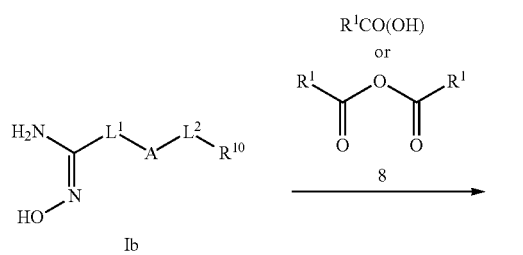

wherein, L² is

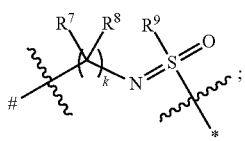

an expression "#" on the left side indicates the point of attachment to A, and an expression "*" on the right side indicates the point of attachment to R¹⁰.

In step (i), a compound of formula 9 is reacted with ammonium carbamate to obtain a compound of formula 10:

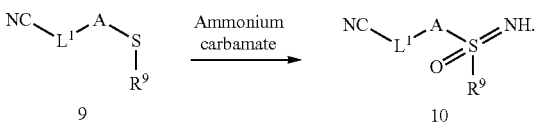

In step (j), the compound of formula 10 is reacted with a compound of formula 11 to obtain a compound of formula Ia:

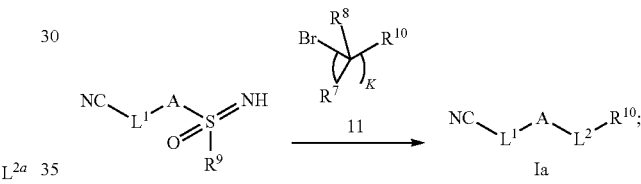

wherein, L² is

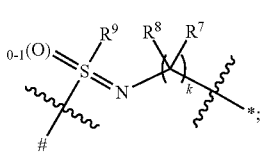

an expression "#" on the left side indicates the point of attachment to A, and an expression "*" on the right side indicates the point of attachment to R¹⁰.

In step (k), the compound of formula Ia is reacted with hydroxyl amine hydrochloride to obtain a compound of formula Ib:

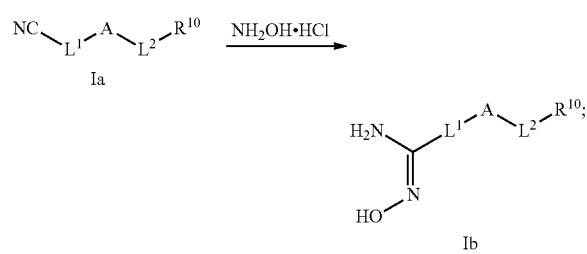

wherein, L² is

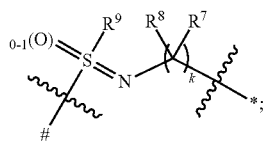

an expression "#" on the left side indicates the point of attachment to A, and an expression "*" on the right side indicates the point of attachment to R¹⁰.

In step (l), the compound of formula Ib and the compound of formula 8 are cyclized to obtain the compound of formula I:

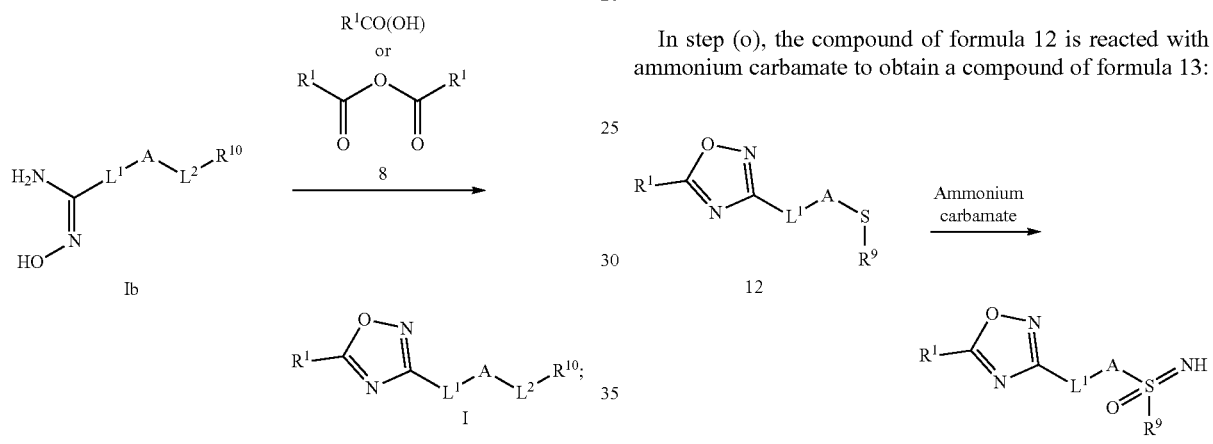

wherein, L² is

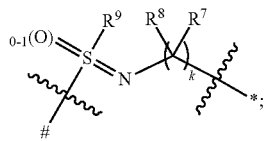

an expression "#" on the left side indicates the point of attachment to A, and an expression "*" on the right side indicates the point of attachment to R¹⁰.

In step (m), the compound of formula 9 is imidized to obtain a compound of formula 11:

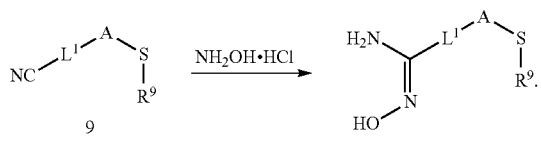

In step (n), the compound of formula 11 is cyclized with the compound of formula 8 to obtain a compound of formula 12:

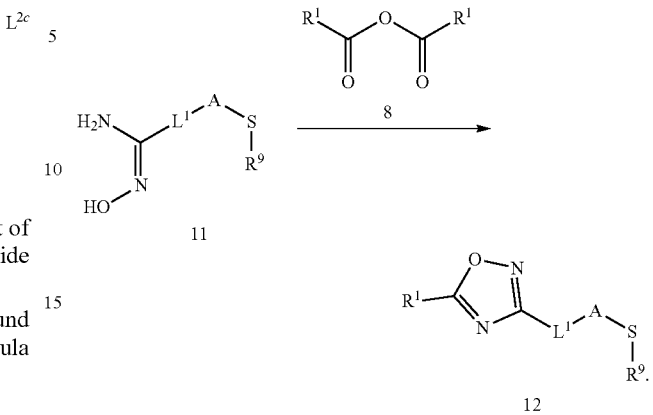

In step (o), the compound of formula 12 is reacted with ammonium carbamate to obtain a compound of formula 13:

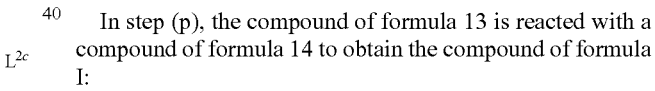

In step (p), the compound of formula 13 is reacted with a compound of formula 14 to obtain the compound of formula I:

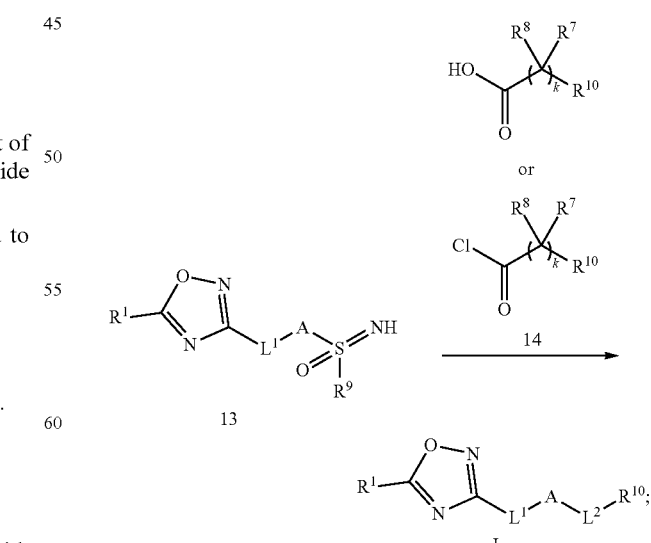

wherein, $L^2$ is

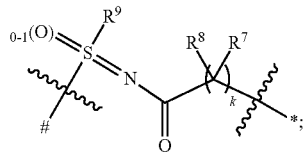

an expression "#" on the left side indicates the point of attachment to A, and an expression "*" on the right side indicates the point of attachment to $R^{10}$.

Compound/s of the present invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compound/s of the present invention may be present as a mixture of stereoisomers, individual stereoisomers or as an optically active form.

An anion part of the salt in case the compound/s of Formula I is a cationic or capable of forming a cation can be inorganic or organic. Alternatively, a cation part of the salt in case the compound/s of Formula I is an anionic or capable of forming anion can be inorganic or organic. Examples of inorganic anion part of the salt include but are not limited to chloride, bromide, iodide, fluoride, sulfate, phosphate, nitrate, nitrite, hydrogen carbonates, hydrogen sulfate. Examples of organic anion part of the salt include but are not limited to formate, alkanoates, carbonates, acetates, trifluoroacetate, trichloroacetate, propionate, glycolate, thiocyanate, lactate, succinate, malate, citrates, benzoates, cinnamates, oxalates, alkylsulphates, alkylsulphonates, arylsulphonates aryldisulphonates, alkylphosphonates, arylphosphonates, aryldiphosphonates, p-toluenesulphonate, and salicylate. Examples of inorganic cation part of the salt include but are not limited to alkali and alkaline earth metals. Examples of organic cation part of the salt include but are not limited to pyridine, methyl amine, imidazole, benzimidazole, hitidine, phosphazene, tetramethyl ammonium, tetrabutylammonium, choline and trimethylamine.

Metal ions in metal complexes of the compound/s of Formula I are especially the ions of the elements of the second main group, especially calcium and magnesium, of the third and fourth main group, especially aluminium, tin and lead, and also of the first to eighth transition groups, especially chromium, manganese, iron, cobalt, nickel, copper, zinc and others. Particular preference is given to the metal ions of the elements of the fourth period and the first to eighth transition groups. Here, the metals can be present in the various valencies that they can assume.

Compound/s selected from Formula I, (including all stereoisomers, N-oxides, and salts thereof), typically may exist in more than one form. Formula I thus includes all crystalline and non-crystalline forms of the compound/s that Formula I represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula I can exhibit beneficial effects (e.g., suitability for preparation of useful formulations, improved biological performance) relative to another polymorph or a mixture of polymorphs of the same compound represented by Formula I. Preparation and isolation of a particular polymorph of a compound represented by Formula I can be achieved by methods known to those skilled in the art including, for example, crystallization using selected solvents and temperatures.

In another embodiment the present invention relates to a composition comprising the compound/s of Formula I agriculturally acceptable salts, metal complexes, constitutional isomers, stereo-isomers, diastereoisomers, enantiomers, chiral isomers, atropisomers, conformers, rotamers, tautomers, optical isomers, polymorphs, geometric isomers, or N-oxides thereof optionally with one or more additional active ingredient with the auxiliary such as inert carrier or any other essential ingredient such as surfactants, additives, solid diluents and liquid diluents.

The compound/s of Formula I and the compositions according to the invention, respectively, are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compound/s of Formula I and the compositions according to the invention are particularly important in the control of a multitude of phytopathogenic fungi on various cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e. g. conifers; and on the plant propagation material, such as seeds, and the crop material of these plants. Particularly, the compound/s of Formula I and the compositions according to the invention are important in the control of phytopathogenic fungi on soybeans and on the plant propagation material, such as seeds, and the crop material of soybeans. Accordingly, the present invention also includes a composition comprising at least one compound of Formula I and seed. The amount of the compound/s of Formula I in the composition ranges from 0.1 gai (gram per active ingredient) to 10 kgai (kilogram per active ingredient) per 100 kg of seeds.

Preferably, compound/s of Formula I and compositions thereof, respectively are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative or reproductive parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts, twigs, flowers, and other parts of plants, including seedlings and young plants, which are to be transplanted after germination or after emergence from soil.

These young plants may also be protected before transplantation by a total or partial treatment by immersion or pouring.

Preferably, treatment of plant propagation materials with compound/s of Formula I and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties. Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1 185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. Cry1A(b), Cry1A(c), Cry1F, Cry1F(a2), Cry11A(b), Cry111A, Cry111B(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO02/015701). Further examples of such toxins or genetically modified plants capable of synthesizing such toxins are disclosed, e. g., in EP374753, WO93/007278, WO95/34656, EP427 529, EP451 878, WO03/18810 und WO03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink (corn cultivars producing the Cry9c toxin), Herculex® RW (corn cultivars producing Cry34Ab1, Cry35Ab1 and the enzyme phosphinothricin-N-acetyltransferase [PAT]); NuCOTN® 33B (cotton cultivars producing the Cry1Ac toxin), Bollgard® I (cotton cultivars producing the Cry1 Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt1 1 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1 F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP392225), plant disease resistance genes (e. g. potato cultivars, which express resistance genes acting against *Phytophthora infestans* derived from the Mexican wild potato *Solanum bulbocastanum*) or T4-lysozym (e. g. potato cultivars capable of synthesizing these proteins with increased resistance against bacteria such as *Erwinia* amylvora). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The present invention also relates to a method for controlling or preventing infestation of plants by phytopathogenic micro-organisms in agricultural crops and or horticultural crops wherein an effective amount of at least one compound of formula I or the combination of the present invention or the composition of the present invention, is applied to the seeds of plants. The compound/s, combination/s and composition/s of the present invention can be used for controlling or preventing plant diseases. The compound/s of Formula I and compositions thereof, respectively, are particularly suitable for controlling the following plant diseases:

*Albugo* spp. (white rust) on ornamentals, vegetables (e. g. *A. Candida*) and sunflowers (e. g. *A. tragopogonis*); *Altemaria* spp. (*Alternaria* leaf spot) on vegetables, rape (*A. brassicola* or *brassicae*), sugar beets (*A. tenuis*), fruits, rice, soybeans, potatoes (e. g. *A. solani* or *A. alternata*), tomatoes (e. g. *A. solani* or *A. alternata*) and wheat; *Aphanomyces* spp. on sugar beets and vegetables; *Ascochyta* spp. on cereals and vegetables, e. g. *A. tritici* (anthracnose) on wheat and *A. hordei* on barley; *Bipolaris* and *Drechslera* spp. (teleomorph: *Cochliobolus* spp.), e. g. Southern leaf blight (*D. maydis*) or Northern leaf blight (*B. zeicola*) on corn, e. g. spot blotch (6. *sorokiniana*) on cereals and e. g. *B. oryzae* on rice and turfs; Blumeria (formerly *Erysiphe*) *graminis* (powdery mildew) on cereals (e. g. on wheat or barley); *Botrytis cinerea* (teleomorph: *Botryotinia fuckeliana*: grey mold) on fruits and berries (e. g. strawberries), vegetables (e. g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e. g. *C. ulmi* (Dutch elm disease) on elms; *Cercospora* spp. (*Cercospora* leaf spots) on corn (e. g. Gray leaf spot: *C. zeae-maydis*), rice, sugar beets (e. g. *C. beticola*), sugar cane, vegetables, coffee, soybeans (e. g. *C. sojina* or *C. kikuchii*) and rice; *Cladosporium* spp. on tomatoes (e. g. *C. fulvum*: leaf mold) and cereals, e. g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e. g. *C. sativus*, anamorph: *B. sorokiniana*) and rice (e. g. *C. miyabeanus*, anamorph: *H. oryzae*); *Colletotrichum* (teleomorph: *Glomerella*) spp. (anthracnose) on cotton (e. g. *C. gossypii*), corn (e. g. *C. graminicola*: Anthracnose stalk rot), soft fruits, potatoes (e. g. C. coccodes: black dot), beans (e. g. *C. lindemuthianum*) and soybeans (e. g. *C. truncatum* or *C. gloeosporioides*); *Corticium* spp., e. g. *C. sasakii* (sheath blight) on rice; *Corynespora cassiicola* (leaf spots) on soybeans and ornamentals; *Cycloconium* spp., e. g. *C. oleaginum* on olive trees; *Cylindrocarpon* spp. (e. g. fruit tree canker or young vine decline, teleomorph: *Nectria* or *Neonectria* spp.) on fruit trees, vines (e. g. *C. liriodendri*, teleomorph: *Neonectria liriodendri*: Black Foot Disease) and ornamentals; Dematophora (teleomorph: *Rosellinia*) necatrix (root and stem rot) on soybeans; *Diaporthe* spp., e. g. *D. phaseolorum* (damping off) on soybeans; *Drechslera* (syn. *Helminthosporium*, teleomorph: *Pyrenophora*) spp. on corn, cereals, such as barley (e. g. *D. teres*, net blotch) and wheat (e. g. *D. tritici*-repentis: tan spot), rice and turf; Esca (dieback, apoplexy) on vines, caused by Formitiporia (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; Elsinoe spp. on pome fruits (£. *pyri*), soft fruits (£. *veneta*: anthracnose) and vines (£. *ampelina*: anthracnose); *Entyloma oryzae* (leaf smut) on rice; *Epicoccum* spp. (black mold) on wheat; *Erysiphe* spp. (powdery mildew) on sugar beets (£. *betae*), vegetables (e. g. *E. pisi*), such as cucurbits (e. g. *E. cichoracearum*), cabbages, rape (e. g. *E. cruciferarum*); Eutypa lata (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e. g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e. g. wheat or barley), *F. oxysporum* on tomatoes, *F. solani* (f. sp. glycines now syn. *F. virguliforme*) and *F. tucumaniae* and *F. brasiliense* each causing sudden death syndrome on soybeans, and *F. verticillioides* on corn; *Gaeumannomyces graminis* (take-all) on cereals (e. g. wheat or barley) and corn; *Gibberella* spp. on cereals (e. g. *G. zeae*) and rice (e. g. *G. fujikuroi*: Bakanae disease); *Glomerella cingulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e. g. *G. sabinae* (rust) on pears; *Helminthosporium* spp. (syn. *Drechslera*, teleomorph: *Cochliobolus*) on corn, cereals and rice; *Hemileia* spp., e. g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e. g. wheat or barley); *Microsphaera diffusa* (powdery mildew) on soybeans; *Monilinia* spp., e. g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e. g. *M. graminicola* (anamorph: *Septoria tritici*, *Septoria* blotch) on wheat or *M. fjiensis* (black Sigatoka disease) on bananas; *Peronospora* spp. (downy mildew) on cabbage (e. g. *P. brassicae*), rape (e. g. *P. parasitica*), onions (e. g. *P. destructor*), tobacco (*P. tabacina*) and soybeans (e. g. *P. manshurica*); *Phakopsora pachyrhizi* and *P. meibomiae* (soybean rust) on soybeans; *Phialophora* spp. e. g. on vines (e. g. *P. tracheiphila* and *P. tetraspora*) and soybeans (e. g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e. g. *P. viticola*: can and leaf spot) and soybeans (e. g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e. g. *P. capsici*), soybeans (e. g. *P. megasperma*, syn. *P. sojae*), soybeans, potatoes and tomatoes (e. g. *P. infestans*: late blight) and broad-leaved trees (e. g. *P. ramorum*: sudden oak death); *Plasmodiophora brassicae* (club root) on cabbage, rape, radish and other plants; *Plasmopara* spp., e. g. *P. viticola* (grapevine downy mildew) on vines and *P. halstedii* on sunflowers; *Podosphaera* spp. (powdery mildew) on rosaceous plants, hop, pome and soft fruits, e. g. *P. leucotricha* on apples; *Polymyxa* spp., e. g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e. g. wheat or barley; *Pseudoperonospora* (downy mildew) on various plants, e. g. *P. cubensis* on cucurbits or *P. humili* on hop; Pseudopezicula *tracheiphila* (red fire disease or .rotbrenner', anamorph: *Phialophora*) on vines; *Puccinia* spp. (rusts) on various plants, e. g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye, *P. kuehnii* (orange rust) on sugar cane and *P. asparagi* on asparagus; *Pyrenophora* (anamorph: *Drechslera*) *tritici*-repentis (tan spot) on wheat or *P. teres* (net blotch) on barley; *Pyricularia* spp., e. g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e. g. *P. ultimum* or *P. aphanidermatum*); *Ramularia* spp., e. g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e. g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; Rhynchosporium secalis (scald) on barley, rye and triticale; Sarocladium *oryzae* and S. attenuatum (sheath rot) on rice; *Sclerotinia* spp. (stem rot or white mold) on vegetables and field crops, such as rape, sunflowers (e. g. *S. sclerotiorum*) and soybeans (e. g. *S. rolfsii* or *S. sclerotiorum*); *Septoria* spp. on various plants, e. g. *S. glycines* (brown spot) on soybeans, *S. tritici* (*Septoria* blotch) on wheat and S. (syn. *Stagonospora*) *nodorum* (*Stagonospora* blotch) on cereals; Uncinula (syn. *Erysiphe*) necator (powdery mildew, anamorph: *Oidium tuckeri*) on vines; *Setospaeria* spp. (leaf blight) on corn (e. g. *S. turcicum*, syn. *Helminthosporium turcicum*) and turf; *Sphacelotheca* spp. (smut) on corn, (e. g. *S. reiliana*: head smut), sorghum und sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e. g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e. g. *T. deformans* (leaf curl disease) on peaches and *T. pruni* (plum pocket) on plums; *Thielaviopsis* spp. (black root rot) on tobacco, pome fruits, vegetables, soybeans and cotton, e. g. *T. basicola* (syn. *Chalara elegans*); *Tilletia* spp. (common bunt or stinking smut) on cereals, such as e. g. *T. tritici* (syn. *T. caries*, wheat bunt) and *T. controversa* (dwarf bunt) on wheat; *Typhula incarnata* (grey snow mold) on barley or wheat; *Urocystis* spp., e. g. *U. occulta* (stem smut) on rye; *Uromyces* spp. (rust) on vegetables, such as beans (e. g. *U. appendiculatus*, syn. *U. phaseoli*) and sugar beets (e. g. *U. betae*); *Ustilago* spp. (loose smut) on cereals (e. g. *U. nuda* and *U. avaenae*), corn (e. g. *U. maydis*: corn smut) and sugar cane; *Venturia* spp. (scab) on apples (e. g. *V. inaequalis*) and pears; and *Verticillium* spp. (wilt) on various plants, such as fruits and ornamentals, vines, soft fruits, vegetables and field crops, e. g. *V. dahliae* on strawberries, rape, potatoes and tomatoes.

The compounds of formula I, the combinations or the compositions thereof may be used to treat several fungal pathogens. Non-limiting examples of pathogens of fungal diseases which can be treated in accordance with the invention include:

Ustilaginales such as *Ustilaginoidea virens*, *Ustilago nuda*, *Ustilago tritici*, *Ustilago zeae*, rusts for example those caused by Pucciniales such as *Cerotelium fici*, *Chrysomyxa arctostaphyli*, *Coleosporium ipomoeae*, *Hemileia vastatrix*, *Puccinia arachidis*, *Puccinia cacabata*, *Puccinia graminis*, *Puccinia recondita*, *Puccinia sorghi*, *Puccinia hordei*, *Puccinia striiformis* fsp. Hordei, *Puccinia striiformis* fsp. Secalis, *Pucciniastrum coryli*, or Uredinales such as *Cronartium ribicola*, *Gymnosporangium juniperi-viginianae*, *Melampsora medusae*, *Phakopsora pachyrhizi*, *Phragmidium mucronatum*, *Physopella ampelosidis*, *Tranzschelia discolor* and *Uromyces viciae-fabae*; and other rots and diseases such as those caused by *Cryptococcus* spp., *Exobasidium vexans*, *Marasmiellus inoderma*, *Mycena* spp., *Sphacelotheca reiliana*, *Typhula ishikariensis*, *Urocystis agropyri*, *ltersonilia perplexans*, *Corticium invisum*, *Laetisaria fuciformis*, *Waitea circinata*, *Rhizoctonia solani*,

*Thanetephorus cucurmeris, Entyloma dahliae, Entylomella microspora, Neovossia moliniae* and *Tilletia caries*. Blastocladiomycetes, such as *Physoderma maydis*. Mucoromycetes, such as *Choanephora cucurbitarum.; Mucor* spp.; and *Rhizopus arrhizus*, In another embodiment diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* or *Phakopsora meibomiae; Puccinia* species, for example *Puccinia recondita, Puccinia graminis* oder *Puccinia striiformis; Uromyces* species, for example *Uromyces appendiculatus;*

In particular, *Cronartium ribicola* (White pine blister rust); *Gymnosporangium juniperi-virginianae* (Cedar-apple rust); *Hemileia vastatrix* (Coffee rust); *Phakopsora meibomiae* and *P. pachyrhizi* (Soybean rust); *Puccinia coronata* (Crown Rust of Oats and Ryegrass); *Puccinia graminis* (Stem rust of wheat and Kentucky bluegrass, or black rust of cereals); *Puccinia hemerocallidis* (Daylily rust); *Puccinia persistens* subsp. *triticina* (wheat rust or 'brown or red rust'); *Puccinia sorghi* (rust in corn); *Puccinia striiformis* ('Yellow rust' in cereals); *Uromyces appendiculatus* (rust of beans); *Uromyces phaseoli* (Bean rust); *Puccinia melanocephala* ('Brown rust' in sugarcane); *Puccinia kuehnii* ('Orange rust' in sugarcane).

Plants which can be treated in accordance with the invention include the following: cotton, flax, grapevine, fruits, vegetables, such as *Rosaceae* sp (for example pome fruits such as apples, pears, apricots, cherries, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Vitaceae* sp. (for example grapes); *Solanaceae* sp. (for example tomatoes, peppers), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Poaceae/Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); Malvaceae (for example cotton); useful plants and ornamental plants for gardens and wooded areas; and genetically modified varieties of each of these plants.

More preference is given to controlling the following diseases of soya beans: Fungal diseases on leaves, stems, pods and seeds caused, for example, by *Altemaria* leaf spot (*Altemaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frog-eye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectiia crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidennatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The present invention also relates to the use of compounds of formula I, the combinations or the compositions thereof for controlling or preventing the following plant diseases: *Puccinia* spp. (rusts) on various plants, for example, but not limited to *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e. g. wheat, barley or rye and *Phakopsoraceae* spp. on various plants, in particular *Phakopsora pachyrhizi* and *P. meibomiae* (soybean rust) on soybeans, *Hemileia vastatrix* (Coffee rust), *Uromyces appendiculatus, Uromyces fabae* and *Uromyces phaseoli* (rust of beans).

The present invention further relates to the use of compounds of formula I, the combinations or the compositions thereof for controlling or preventing against phytopathogenic fungi such as *Phakopsora pachyrhizi, Phakopsora meibomiae*, of agricultural crops and or horticultural crops.

The compound/s of Formula I, the combinations and the compositions thereof, respectively, are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, cooling lubricants, fiber or fabrics, against the infestation and destruction by harmful microorganisms, such as fungi and bacteria.

As to the protection of wood and other materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Por/a* spp., *Serpula* spp. and *Tyromyces* spp., Deuteromycetes such as *Aspergillus* spp., *Cladosporium* spp., *Penicillium* spp., *Trichoderma* spp., *Altemaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

In one embodiment the compound/s of Formula I, the combinations and the compositions thereof, respectively, are particularly suitable for controlling the following plant diseases: *Phakopsora pachyrhizi* and *P. meibomiae* (soybean rust) on soybeans.

The present invention further relates to a method for controlling or preventing phytopathogenic fungi. The method comprises treating the fungi or the materials, plants, plant parts, locus thereof, soil or seeds to be protected against fungal attack, with an effective amount of at least one compound of Formula I or the combinations or the compositions comprising at least one compound of Formula I.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compound/s of Formula I, the combinations and the compositions thereof, respectively, may be used for improving the health of a plant. The invention also relates to a method for improving plant health by treating a plant, its propagation material and/or the locus where the plant is growing or is to grow with an effective amount of compound/s I and compositions thereof, respectively.

The term "plant health" is to be understood to denote a condition of the plant and/or its products which is determined by several indicators alone or in combination with each other such as yield (e. g. increased biomass and/or increased content of valuable ingredients), plant vigor (e. g. improved plant growth and/or greener leaves ("greening effect")), quality (e. g. improved content or composition of certain ingredients) and tolerance to abiotic and/or biotic stress. The above identified indicators for the health condition of a plant may be interdependent or may result from each other.

The compound/s of Formula I can be present in different crystal modifications or polymorphs whose biological activity may differ. They are likewise subject matter of the present invention.

The compound/s of Formula I are employed as such or in the form of compositions for treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with compound/s of Formula I, the combinations and the compositions thereof protectively either at or before planting or transplanting.

The invention also relates to agrochemical compositions comprising an auxiliary and at least one compound of Formula I.

An agrochemical composition comprises a fungicidally effective amount of a compound of Formula I. The term "effective amount" denotes an amount of the composition or of the compound/s of Formula I, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound of Formula I used.

The compound/s of Formula I, their -oxides, metal complexes, isomers, polymorphs or the agriculturally acceptable salts thereof can be converted into customary types of agrochemical compositions, e. g. solutions, emulsions, suspensions, dusts, powders, pastes, granules, pressings, capsules, and mixtures thereof. Examples for composition types are suspensions (e. g. SC, OD, FS), emulsifiable concentrates (e. g. EC), emulsions (e. g. EW, EO, ES, ME), capsules (e. g. CS, ZC), pastes, pastilles, wettable powders or dusts (e. g. WP, SP, WS, DP, DS), pressings (e. g. BR, TB, DT), granules (e. g. WG, SG, GR, FG, GG, MG), insecticidal articles (e. g. LN), as well as gel formulations for the treatment of plant propagation materials such as seeds (e. g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e. g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e. g. ethanol, propanol, butanol, benzyl alcohol, cyclohexanol; glycols; DMSO; ketones, e. g. cyclohexanone; esters, e. g. lactates, carbonates, fatty acid esters, gamma-butyrolactone; fatty acids; phosphonates; amines; amides, e. g. N-methyl pyrrolidone, fatty acid dimethyl amides; and mixtures thereof. Suitable solid carriers or fillers are mineral earths, e. g. silicates, silica gels, talc, kaolins, limestone, lime, chalk, clays, dolomite, diatomaceous earth, bentonite, calcium sulfate, magnesium sulfate, magnesium oxide; polysaccharides, e. g. cellulose, starch; fertilizers, e. g. ammonium sulfate, ammonium phosphate, ammonium nitrate, ureas; products of vegetable origin, e. g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl sulfonates, diphenyl sulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide.

Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinyl pyrrolidone, vinyl alcohols, or vinyl acetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinyl amines or polyethylene amines.

Suitable adjuvants are compounds, which have a negligible or even no pesticidal activity themselves, and which improve the biological performance of the compounds of Formula I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e. g. xanthan gum, carboxymethyl cellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e. g. in red, blue, or green) are pigments of low water solubility and water-soluble dyes. Examples are inorganic colorants (e. g. iron oxide, titanoxide, iron hexacyanoferrate) and organic colorants (e. g. alizarin-, azo- and phthalocyanine colorants).

Suitable tackifiers or binders are polyvinyl pyrrolidones, polyvinyl acetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound of Formula I and 5-15 wt % wetting agent (e. g. alcohol alkoxylates) are dissolved in water and/or in a water-soluble solvent (e. g. alcohols) ad 100 wt %. The active substance dissolves upon dilution with water.

ii) Dispersible Concentrates (DC)

5-25 wt % of a compound of Formula I and 1-10 wt % dispersant (e. g. polyvinyl pyrrolidone) are dissolved in organic solvent (e. g. cyclohexanone) ad 100 wt %. Dilution with water gives a dispersion.

iii) Emulsifiable Concentrates (EC)

15-70 wt % of a compound of Formula I and 5-10 wt % emulsifiers (e. g. calcium dodecylbenzenesulfonate and castor oil ethoxylate) are dissolved in water-insoluble organic solvent (e. g. aromatic hydrocarbon) ad 100 wt %. Dilution with water gives an emulsion.

iv) Emulsions (EW, EO, ES)

5-40 wt % of a compound of Formula I and 1-10 wt % emulsifiers (e. g. calcium dodecylbenzenesulfonate and castor oil ethoxylate) are dissolved in 20-40 wt % water-insoluble organic solvent (e. g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a compound of Formula I are comminuted with addition of 2-10 wt % dispersants and wetting agents (e. g. sodium lignosulfonate and alcohol ethoxylate), 0.1-2 wt % thickener (e. g. xanthan gum) and water ad 100 wt % to give a fine active substance suspension. Dilution with water gives a stable suspension of the active substance. For FS type composition up to 40 wt % binder (e. g. polyvinyl alcohol) is added.

vi) Water-Dispersible Granules and Water-Soluble Granules (WG, SG)

50-80 wt % of a compound of Formula I are ground finely with addition of dispersants and wetting agents (e. g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance. vii) Water-dispersible powders and water-soluble powders (WP, SP, WS) 50-80 wt % of a compound of Formula I are ground in a rotor-stator mill with addition of 1-5 wt % dispersants (e. g. sodium lignosulfonate), 1-3 wt % wetting agents (e. g. alcohol ethoxylate) and solid carrier (e. g. silica gel) ad 100 wt %. Dilution with water gives a stable dispersion or solution of the active substance.

viii) Gel (GW, GF)

In an agitated ball mill, 5-25 wt % of a compound of Formula I are comminuted with addition of 3-10 wt % dispersants (e. g. sodium lignosulfonate), 1-5 wt % thickener (e. g. carboxymethyl cellulose) and water ad 100 wt % to give a fine suspension of the active substance. Dilution with water gives a stable suspension of the active substance.

ix) Microemulsion (ME)

5-20 wt % of a compound of Formula I are added to 5-30 wt % organic solvent blend (e. g. fatty acid dimethyl amide and cyclohexanone), 10-25 wt % surfactant blend (e. g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a compound of Formula I, 0-40 wt % water insoluble organic solvent (e. g. aromatic hydrocarbon), 2-15 wt % acrylic monomers (e. g. methylmethacrylate, methacrylic acid and a di- or triacrylate) are dispersed into an aqueous solution of a protective colloid (e. g. polyvinyl alcohol). Radical polymerization results in the formation of poly(meth)acrylate microcapsules. Alternatively, an oil phase comprising 5-50 wt % of a compound of Formula I according to the invention, 0-40 wt % water insoluble organic solvent (e. g. aromatic hydrocarbon), and an isocyanate monomer (e. g. diphenylmethene-4,4'-diisocyanatae) are dispersed into an aqueous solution of a protective colloid (e. g. polyvinyl alcohol). The addition of a polyamine (e. g. hexamethylenediamine) results in the formation of polyurea microcapsules. The monomers amount to 1-10 wt %. The wt % relate to the total CS composition.

xi) Dustable Powders (DP, DS)

1-10 wt % of a compound of Formula I are ground finely and mixed intimately with solid carrier (e. g. finely divided kaolin) ad 100 wt %.

xii) Granules (GR, FG)

0.5-30 wt % of a compound of Formula I are ground finely and associated with solid carrier (e. g. silicate) ad 100 wt %. Granulation is achieved by extrusion, spray-drying or fluidized bed.

xiii) Ultra-Low Volume Liquids (UL)

1-50 wt % of a compound of Formula I are dissolved in organic solvent (e. g. aromatic hydrocarbon) ad 100 wt %.

The compositions types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active ingredient (ai). The active ingredients (ai) are employed in a purity of from 90% to 100%, preferably from 95% to 100% (according to NMR spectrum).

For the purposes of treatment of plant propagation materials, particularly seeds, solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC), and gels (GF) are usually employed. The compositions in question give, after two-to-tenfold dilution, active substance concentrations of from 0.01 to 60% by weight, preferably from 0.1 to 40%, in the ready-to-use preparations.

Application can be carried out before or during sowing. Methods for applying compound/s of Formula I, the combinations and the compositions thereof, respectively, onto plant propagation material, especially seeds, include dressing, coating, pelleting, dusting, and soaking as well as in-furrow application methods. Preferably, compound/s of Formula I, the combinations and the compositions thereof, respectively, are applied on to the plant propagation material by a method such that germination is not induced, e. g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 1.0 kg per ha, and in particular from 0.1 to 1.0 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e. g. herbicides, insecticides, fungicides, growth regulators, safeners, biopesticides) may be added to the active substances or the compositions comprising them as premix or, if appropriate not until immediately prior to use (tank mix). These agents can be admixed with the compositions according to the invention in a weight ratio of 1:100 to 100:1, preferably 1:20 to 20:1.

A pesticide is generally a chemical or biological agent (such as pesticidally active ingredient, compound, composition, virus, bacterium, antimicrobial or disinfectant) that through its effect deters, incapacitates, kills or otherwise discourages pests. Target pests can include insects, plant pathogens, weeds, mollusks, birds, mammals, fish, nematodes (roundworms), and microbes that destroy property, cause nuisance, spread disease or are vectors for disease. The term "pesticide" includes also plant growth regulators that alter the expected growth, flowering, or reproduction rate of plants; defoliants that cause leaves or other foliage to drop from a plant, usually to facilitate harvest; desiccants that promote drying of living tissues, such as unwanted plant tops; plant activators that activate plant physiology for defense of against certain pests; safeners that reduce unwanted herbicidal action of pesticides on crop plants; and plant growth promoters that affect plant physiology e.g. to increase plant growth, biomass, yield or any other quality parameter of the harvestable goods of a crop plant.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank or any other kind of vessel used for applications (e. g. seed treater drums, seed pelleting machinery, knapsack sprayer) and further auxiliaries may be added, if appropriate.

Consequently, one embodiment of the invention is a kit for preparing a usable pesticidal composition, the kit comprising a) a composition comprising component 1) as defined herein and at least one auxiliary; and b) a composition comprising component 2) as defined herein and at least one auxiliary; and optionally c) a composition comprising at least one auxiliary and optionally a further active component 3) as defined herein.

The compound/s of Formula I, the combinations and the compositions thereof comprising them in the use as fungicides with other fungicides may result in an expansion of the fungicidal spectrum of activity being obtained or in a prevention of fungicide resistance development. Furthermore, in many cases, extraordinary effects are obtained.

The present invention also relates to the combination comprising at least one compound of Formula I and at least one further pesticidally active substance selected from the group of fungicides, insecticides, nematicides, acaricides, biopesticides, herbicides, safeners, plant growth regulators, antibiotics, fertilizers and nutrients. The pesticidally active substances reported in W2015185485 pages 36-43 and WO2017093019 pages 42-56 can be used in conjunction with which the compound/s of Formula I.

The active substances referred to as component 2, their preparation and their activity e. g. against harmful fungi is known (cf.: http://www.alanwood.net/pesticides/); these substances are commercially available. The compounds described by IUPAC nomenclature, their preparation and their pesticidal activity are also known (cf. Can. J. Plant Sci. 48(6), 587-94, 1968; EP141317; EP152031; EP226917; EP243970; EP256503; EP428941; EP532022; EP1028125; EP1035122; EP1201648; EP1122244, JP2002316902; DE19650197; DE10021412; DE102005009458; U.S. Pat. Nos. 3,296,272; 3,325,503; WO9846608; WO9914187; WO9924413; WO9927783; WO0029404; WO0046148; WO0065913; WO0154501; WO 0156358; WO0222583; WO0240431; WO0310149; WO0311853; WO0314103; WO0316286; WO0353145; WO0361388; WO0366609; WO0374491; WO0449804; WO0483193; WO05120234; WO05123689; WO05123690; WO0563721; WO0587772; WO0587773; WO0615866; WO0687325; WO0687343; WO0782098; WO0790624; WO11028657; WO2012168188; WO2007006670; WO201177514; WO13047749; WO10069882; WO13047441; WO0316303; WO0990181; WO13007767; WO1310862; WO13127704; WO13024009; WO13024010; WO13047441; WO13162072; WO13092224 and WO11135833.

The present invention furthermore relates to agrochemical mixtures comprising at least one compound of Formula I (component 1) and at least one further active substance useful for plant protection, e. g. selected from the groups A) to O) (component 2), in particular one further fungicide, e. g. one or more fungicide from the groups A) to K), as described above, and if desired one suitable solvent or solid carrier. Furthermore, combating harmful fungi with a mixture of compound/s of Formula I and at least one fungicide from groups A) to K), as described above, is advantageous than combating those fungi with individual compound/s of Formula I or individual fungicides from groups A) to K).

By applying compound/s of Formula I together with at least one pesticidally active substance from groups A) to O) an enhanced effect can be obtained.

This can be obtained by applying the compound/s of Formula I and at least one further pesticidally active substance simultaneously, either jointly (e. g. as tank-mix) or separately, or in succession, wherein the time interval between the individual applications is selected to ensure that the active substance applied first still occurs at the site of action in a sufficient amount at the time of application of the further pesticidally active substance(s). The order of application is not essential for working of the present invention.

When applying compound/s of Formula I and a pesticidally active substance sequentially the time between both applications may vary e. g. between 2 hours to 7 days. Also a broader range is possible ranging from 0.25 hour to 30 days, preferably from 0.5 hour to 14 days, particularly from 1 hour to 7 days or from 1.5 hours to 5 days, even more preferred from 2 hours to 1 day. In the binary mixtures and compositions according to the invention the weight ratio of the component 1) and the component 2) generally depends from the properties of the active components used, usually it is in the range of 1:100 to 100:1, regularly in the range of 1:50 to 50:1, preferably in the range of 1:20 to 20:1, more preferably in the range of 1:10 to 10:1, even more preferably in the range of 1:4 to 4:1 and in particular in the range of 1:2 to 2:1.

According to a further embodiment of the binary mixtures and compositions thereof, the weight ratio of the component 1) and the component 2) usually is in the range of 1000:1 to 1:1000, often in the range of 100:1 to 1:100, regularly in the range of 50:1 to 1:50, preferably in the range of 20:1 to 1:20, more preferably in the range of 10:1 to 1:10, even more preferably in the range of 4:1 to 1:4 and in particular in the range of 2:1 to 1:2.

In the ternary mixtures, i.e. compositions according to the invention comprising the component 1) and component 2) and a compound III (component 3), the weight ratio of component 1) and component 2) depends from the properties of the active substances used, usually it is in the range of 1:100 to 100:1, regularly in the range of 1:50 to 50:1, preferably in the range of 1:20 to 20:1, more preferably in the range of 1:10 to 10:1 and in particular in the range of 1:4 to 4:1, and the weight ratio of component 1) and component 3) usually it is in the range of 1:100 to 100:1, regularly in the range of 1:50 to 50:1, preferably in the range of 1:20 to 20:1, more preferably in the range of 1:10 to 10:1 and in particular in the range of 1:4 to 4:1.

Any further active components are, if desired, added in a ratio of 20:1 to 1:20 to the component 1).

These ratios are also suitable for inventive mixtures applied by seed treatment.

The present invention also relates to a process for preparing the compound/s of the present invention. The process for preparing the compound/s of the present invention is described in the experimental section in more detail.

The invention disclosed in the present disclosure shall now be elaborated with the help of non-limiting schemes and examples.

CHEMISTRY EXAMPLES

General Synthetic Scheme:

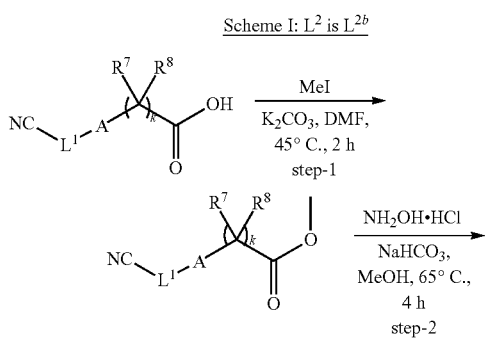

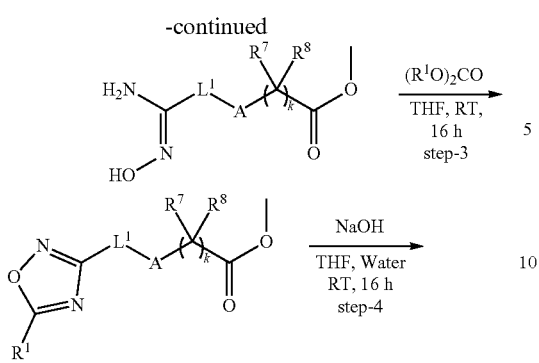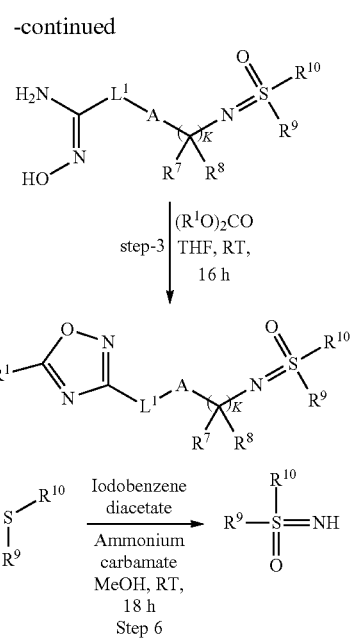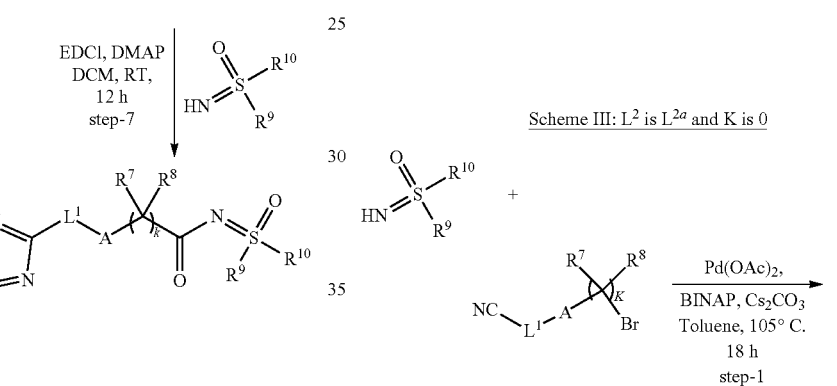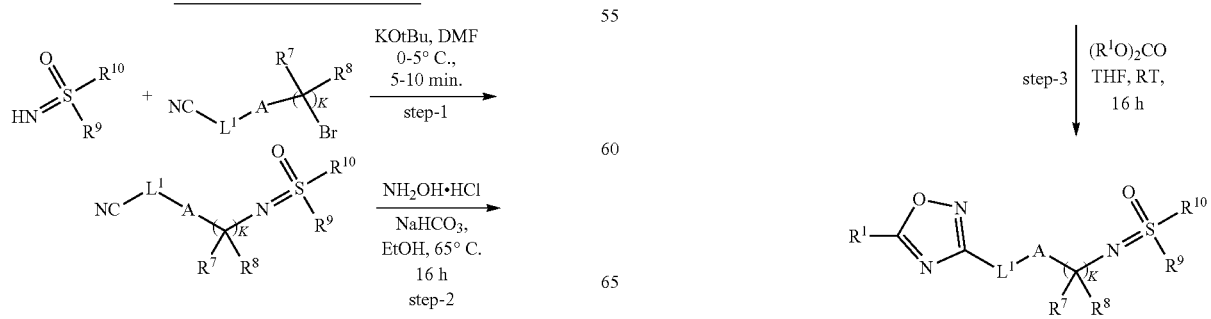

-continued

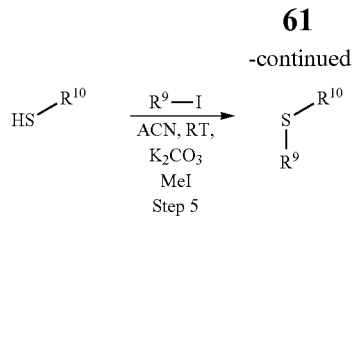

Example 1

Preparation of N-((2-fluorophenyl)(methyl)(oxo)-λ⁶-sulfanylidene)-4-(5-(trifluoromethyl)-1,2,4-oxadiazol-3-yl)benzamide (Compound 3)

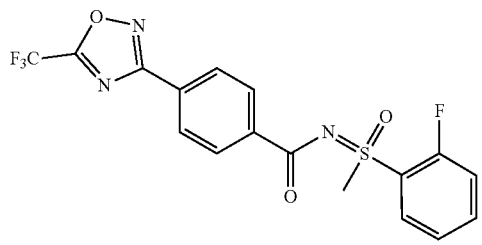 [SMILES: CS(=O)(=NC(=O)c1ccc(-c2noc(C(F)(F)F)n2)cc1)c1ccccc1F]

Step-1: Methyl 4-cyanobenzoate

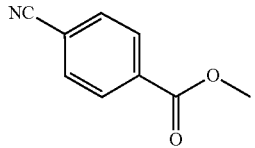

To a stirred solution of 4-cyanobenzoic acid (25 g, 170 mmol) in N, N-dimethyl formamide (120 mL), potassium carbonate (35.2 g, 255 mmol) was added at 25° C. and cooled to 0° C. To the resulting reaction mixture, methyl iodide (15.9 mL, 255 mmol) was slowly added. The resulting reaction mixture was stirred at 45° C. for 2 h. After completion of the reaction, the reaction mixture was cooled to 25° C. and crushed ice was poured into it with stirring. Stirring was continued for 10 minutes to obtain a precipitate. The precipitate was filtered, washed with water and dried under reduced pressure to obtain methyl 4-cyanobenzoate (24.6 g, 153 mmol, 90% yield).

Step-2: Methyl-4-(N'-hydroxycarbamimidoyl)benzoate

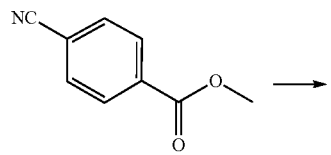

-continued

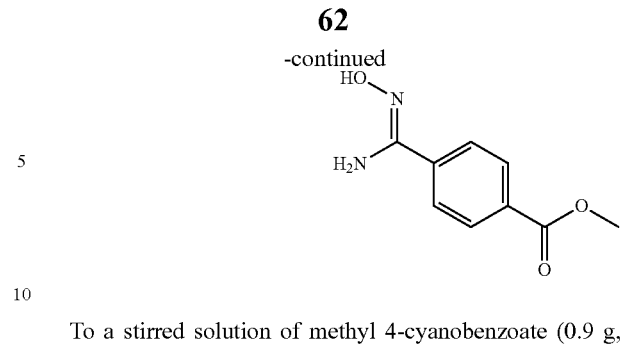

To a stirred solution of methyl 4-cyanobenzoate (0.9 g, 5.6 mmol) in methanol (12 mL), sodium bicarbonate (0.5 g, 6.1 mmol) and hydroxylamine hydrochloride (0.4 g, 5.6 mmol) were added. The resulting reaction mixture was heated to reflux for 4 h. After completion of the reaction, the reaction mixture was cooled to 25° C. and filtered. The filtrate was concentrated under reduced pressure to obtain methyl-4-(N'-hydroxycarbamimidoyl)benzoate (0.9 g, 4.6 mmol, 83% yield).

Step-3: Methyl 4-(5-(trifluoromethyl)-1,2,4-oxadiazol-3-yl)benzoate

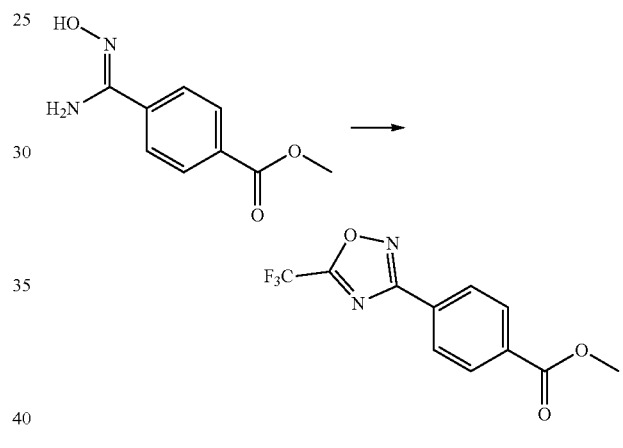

To a stirred solution of methyl-4-(N'-hydroxycarbamimidoyl)benzoate (0.9 g, 4.6 mmol) in tetrahydrofuran (10 mL), trifluoroacetic anhydride (1.0 mL, 7.0 mmol) was added at 0° C. under nitrogen atmosphere. The resulting reaction mixture was stirred at 25° C. for 16 h and diluted with ethyl acetate (30 mL). Ethyl acetate layer was washed three times with aq. sat. Sodium bicarbonate (30 mL), dried over anhydrous sodium sulphate and concentrated under reduced pressure. The crude residue was purified by column chromatography (eluent 0-30% ethyl acetate in hexane) on silica gel to obtain methyl 4-(5-(trifluoromethyl)-1,2,4-oxadiazol-3-yl)benzoate (0.6 g, 2.0 mmol, 44% yield).

Step 4: 4-(5-(Trifluoromethyl)-1,2,4-oxadiazol-3-yl)benzoic acid

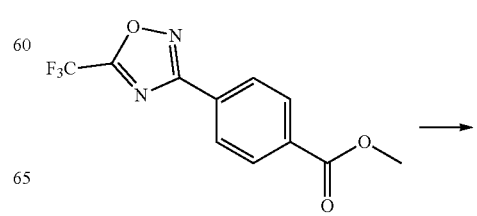

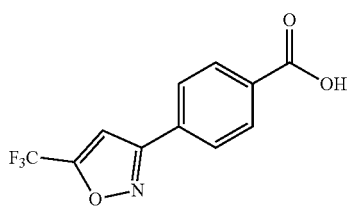

To a stirred solution of methyl 4-(5-(trifluoromethyl)-1,2,4-oxadiazol-3-yl)benzoate (15 g, 55.1 mmol) in tetrahydrofuran (120 mL), a solution of sodium hydroxide (4.0 g, 99 mmol) in water (30 mL) was added dropwise by a dropping funnel at 0° C. The resulting reaction mixture was stirred for 16 h at 25° C. After completion of the reaction, the solvent was removed by evaporation under reduced pressure. Water (50 mL) was added to the residue and cooled to 0° C. and acidified to pH 3 with 3N aqueous hydrochloric acid. The precipitate was collected by filtration, washed with water, and dried to obtain 4-(5-(trifluoromethyl)-1,2,4-oxadiazol-3-yl)benzoic acid (11.2 g, 43.4 mmol, 79% yield).

Step-5 (2-fluorophenyl)(methyl)sulfane

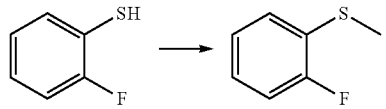

To a stirred solution of 2-fluorobenzenethiol (2.7 g, 21.07 mmol) in acetonitrile (20 mL), potassium carbonate (7.3 g, 52.7 mmol) was added at 0° C. Ice bath was removed and the reaction mixture was stirred for 30 min at 25° C. The reaction mixture was cooled again to 0° C. and methyl iodide (1.6 mL, 25.3 mmol) was added slowly. The reaction mixture was stirred at 25° C. for 4 h. After completion of the reaction, the reaction mixture was diluted with ethyl acetate (40 mL) and washed three times with water (15 mL). The ethyl acetate layer was separated, dried over anhydrous sodium sulphate and concentrated under reduced pressure to obtain (2-fluorophenyl)(methyl)sulfane (2.2 g, 15.5 mmol, 73% yield). The crude product was used as such in the next step without purification.

Step-6: (2-Fluorophenyl)(imino)(methyl)-λ$^6$-sulfanone

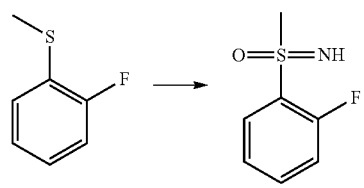

To a stirred solution of (2-fluorophenyl)(methyl)sulfane (2.7 g, 19.0 mmol) in methanol (38.0 mL), was added ammonium carbamate (3.26 g, 41.8 mmol). Then diacetoxy iodobenzene (13.5 g, 41.8 mmol) was slowly added portion wise at 0° C. The resulting reaction was stirred at 25° C. for 12 h. After completion of the reaction, methanol was evaporated under reduced pressure, diluted with ethyl acetate (60 mL) and washed with water (20 mL). The ethyl acetate layer was washed two times with aq. saturated sodium bicarbonate solution (20 mL), dried over anhydrous sodium sulphate and concentrated under reduced pressure. The crude residue was purified using column chromatography on silica gel to obtain (2-fluorophenyl)(imino)(methyl)-λ$^6$-sulfanone (2.0 g, 11.6 mmol, 61% yield).

Step 7: Preparation of N-((2-fluorophenyl)(methyl)(oxo)-λ$^6$-sulfanylidene)-4-(5-(trifluoromethyl)-1,2,4-oxadiazol-3-yl)benzamide (Compound 3)

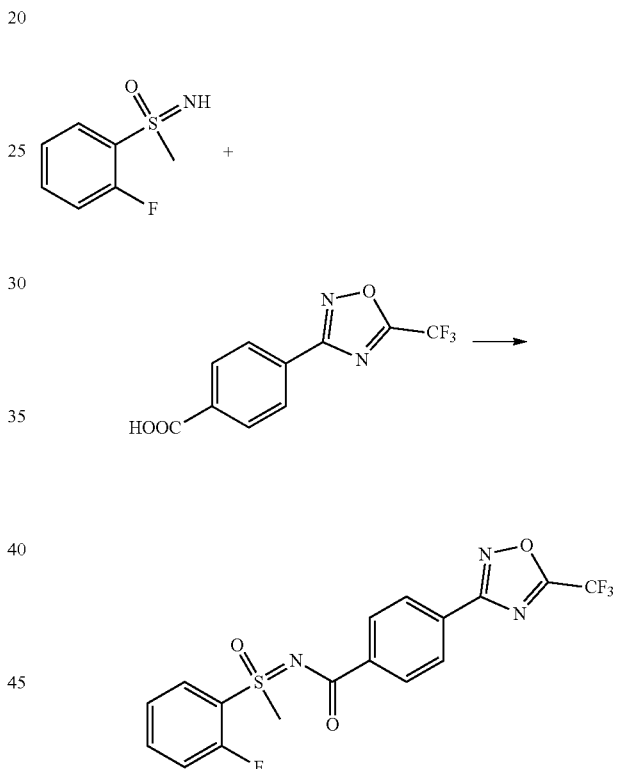

To a stirred solution of 4-(5-(trifluoromethyl)-1,2,4-oxadiazol-3-yl)benzoic acid (0.5 g, 1.9 mmol) in dry dichloromethane (10 mL), 1-(3-Dimethylaminopropyl)-3-ethylcarbodiimide hydrochloride (0.7 g, 3.9 mmol) and 4-dimethylaminopyridine (0.7 g, 5.8 mmol) were added at 5° C. under nitrogen atmosphere. Then (2-fluorophenyl)(imino)(methyl)-λ$^6$-sulfanone (0.5 g, 3.0 mmol) was added, and the reaction mixture was stirred at 25° C. for 16 h. After completion of the reaction, product was extracted by dichloromethane (30 mL). The dichloromethane layer was washed two times with brine solution (10 mL), dried over anhydrous sodium sulphate and concentrated. The residue was purified by column chromatography on silica gel using hexane to 60% ethyl acetate in hexane as an eluent to obtain N-((2-fluorophenyl)(methyl)(oxo)-λ$^6$-sulfanylidene)-4-(5-(trifluoromethyl)-1,2,4-oxadiazol-3-yl)benzamide (0.1 g, 0.3 mmol, 16% yield).

TABLE NO. 1

The following compounds were prepared by the procedure analogous to that of the
Compound 3 using appropriate starting materials.

| Compound No. | IUPAC Name | Structure | Yield |
|---|---|---|---|
| 1 | N-((4-chlorophenyl)(methyl)(oxo)-$\lambda^6$-sulfanylidene)-4-(5-(trifluoromethyl)-1,2,4-oxadiazol-3-yl)benzamide | 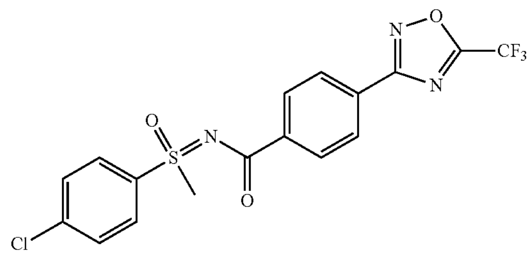 [SMILES: CS(=O)(=NC(=O)c1ccc(-c2noc(C(F)(F)F)n2)cc1)c1ccc(Cl)cc1] | 0.5 g, 53.0% yield |
| 2 | N-(methyl(oxo)(pyridin-2-yl)-$\lambda^6$-sulfanylidene)-4-(5-(trifluoromethyl)-1,2,4-oxadiazol-3-yl)benzamide | 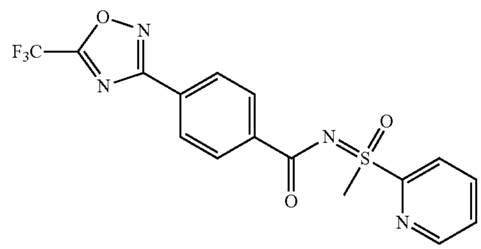 [SMILES: CS(=O)(=NC(=O)c1ccc(-c2noc(C(F)(F)F)n2)cc1)c1ccccn1] | 0.4 g, 46.0% yield |
| 4 | N-(methyl(oxo)(pyridin-4-yl)-$\lambda^6$-sulfanylidene)-4-(5-(trifluoromethyl)-1,2,4-oxadiazol-3-yl)benzamide | 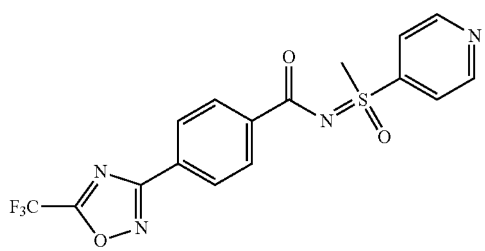 [SMILES: CS(=O)(=NC(=O)c1ccc(-c2noc(C(F)(F)F)n2)cc1)c1ccncc1] | 0.1 g, 15.0% yield |
| 5 | N-((3-fluorophenyl)(methyl)(oxo)-$\lambda^6$-sulfanylidene)-4-(5-(trifluoromethyl)-1,2,4-oxadiazol-3-yl)benzamide | 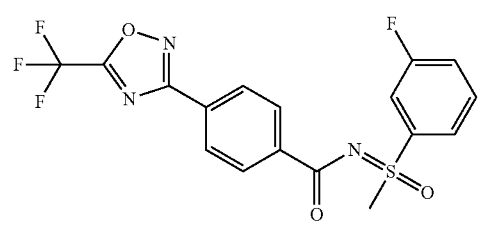 [SMILES: CS(=O)(=NC(=O)c1ccc(-c2noc(C(F)(F)F)n2)cc1)c1cccc(F)c1] | 0.1 g, 18.0% yield |
| 6 | N-((4-fluorophenyl)(methyl)(oxo)-$\lambda^6$-sulfanylidene)-4-(5-(trifluoromethyl)-1,2,4-oxadiazol-3-yl)benzamide | 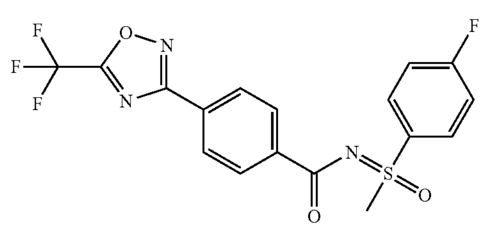 [SMILES: CS(=O)(=NC(=O)c1ccc(-c2noc(C(F)(F)F)n2)cc1)c1ccc(F)cc1] | 0.4 g, 50.0% yield |
| 7 | N-(methyl(oxo)(4-(trifluoromethyl)phenyl)-$\lambda^6$-sulfanylidene)-4-(5-(trifluoromethyl)-1,2,4-oxadiazol-3-yl)benzamide | 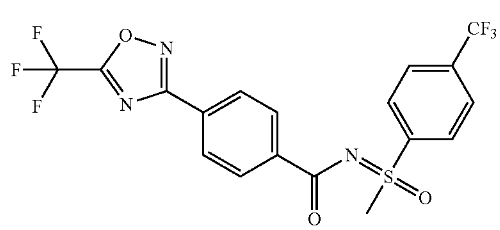 [SMILES: CS(=O)(=NC(=O)c1ccc(-c2noc(C(F)(F)F)n2)cc1)c1ccc(C(F)(F)F)cc1] | 0.3 g, 31.0% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 8 | N-((4-bromophenyl)(methyl)(oxo)-λ$^6$-sulfanylidene)-4-(5-(trifluoromethyl)-1,2,4-oxadiazol-3-yl)benzamide | 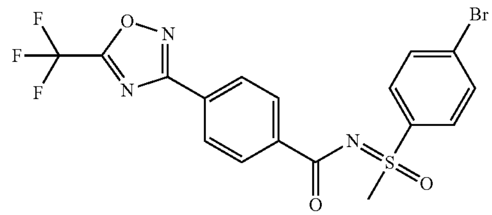 [SMILES: CS(=O)(=NC(=O)c1ccc(-c2noc(C(F)(F)F)n2)cc1)c1ccc(Br)cc1] | 0.4 g, 45.0% yield |
| 9 | N-(methyl(oxo)(phenyl)-λ$^6$-sulfanylidene)-4-(5-(trifluoromethyl)-1,2,4-oxadiazol-3-yl)benzamide | 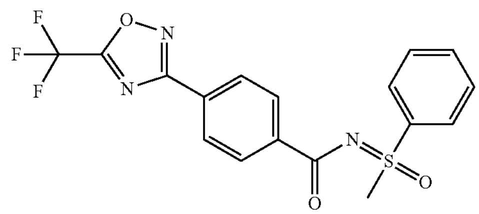 [SMILES: CS(=O)(=NC(=O)c1ccc(-c2noc(C(F)(F)F)n2)cc1)c1ccccc1] | 0.1 g, 27.0% yield |
| 10 | N-((4-methoxyphenyl)(methyl)(oxo)-λ$^6$-sulfanylidene)-4-(5-(trifluoromethyl)-1,2,4-oxadiazol-3-yl)benzamide | 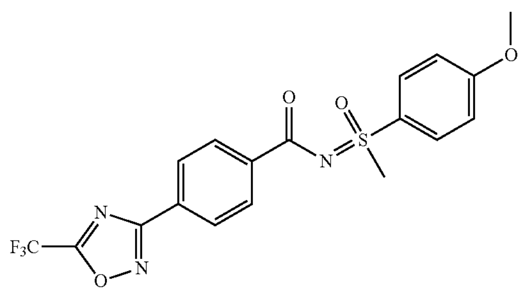 [SMILES: COc1ccc(S(C)(=O)=NC(=O)c2ccc(-c3noc(C(F)(F)F)n3)cc2)cc1] | 0.1 g, 17.0% yield |
| 12 | N-(methyl(oxo)(4-(trifluoromethoxy)phenyl)-λ$^6$-sulfanylidene)-4-(5-(trifluoromethyl)-1,2,4-oxadiazol-3-yl)benzamide | 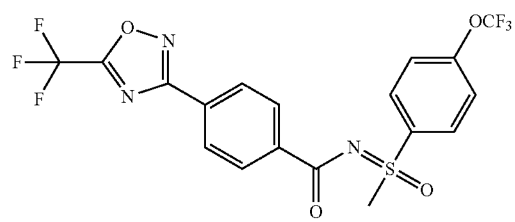 [SMILES: CS(=O)(=NC(=O)c1ccc(-c2noc(C(F)(F)F)n2)cc1)c1ccc(OC(F)(F)F)cc1] | 0.2 g, 17.0% yield |
| 30 | N-(methyl(oxo)(p-tolyl)-λ$^6$-sulfaneylidene)-4-(5-(trifluoromethyl)-1,2,4-oxadiazol-3-yl)benzamide | 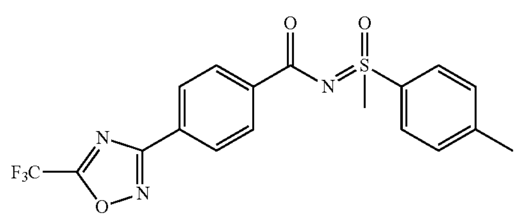 [SMILES: Cc1ccc(S(C)(=O)=NC(=O)c2ccc(-c3noc(C(F)(F)F)n3)cc2)cc1] | 0.2 g, 20% yield |
| 31 | N-((4-cyanobenzyl)(methyl)(oxo)-λ$^6$-sulfaneylidene)-4-(5-(trifluoromethyl)-1,2,4-oxadiazol-3-yl)benzamide | 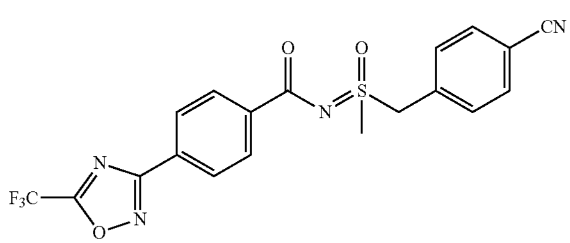 [SMILES: CS(=O)(Cc1ccc(C#N)cc1)=NC(=O)c1ccc(-c2noc(C(F)(F)F)n2)cc1] | 0.2 g, 45% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 32 | N-((2,6-difluorobenzyl)(methyl)(oxo)-$\lambda^6$-sulfaneylidene)-4-(5-(trifluoromethyl)-1,2,4-oxadiazol-3-yl)benzamide | 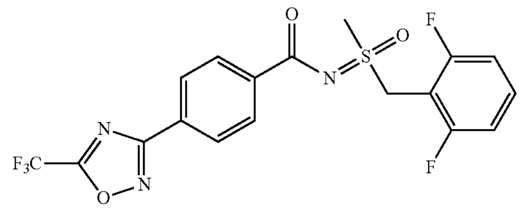 [SMILES: CS(=O)(Cc1c(F)cccc1F)=NC(=O)c1ccc(-c2noc(C(F)(F)F)n2)cc1] | 0.3 g, 50% yield |
| 33 | N-((2,3-difluorobenzyl)(methyl)(oxo)-$\lambda^6$-sulfaneylidene)-4-(5-(trifluoromethyl)-1,2,4-oxadiazol-3-yl)benzamide | 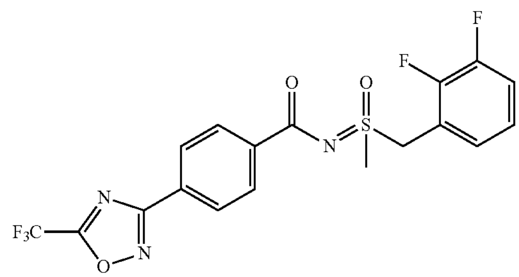 [SMILES: CS(=O)(Cc1cccc(F)c1F)=NC(=O)c1ccc(-c2noc(C(F)(F)F)n2)cc1] | 0.3 g, 65% yield |
| 34 | N-((4-methoxybenzyl)(methyl)(oxo)-$\lambda^6$-sulfaneylidene)-4-(5-(trifluoromethyl)-1,2,4-oxadiazol-3-yl)benzamide | 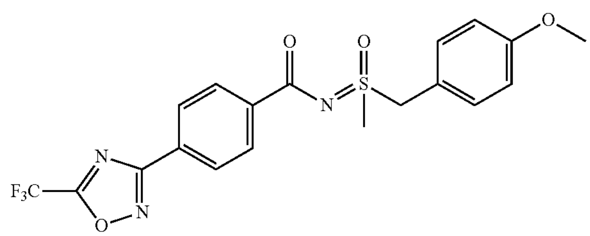 [SMILES: COc1ccc(CS(C)(=O)=NC(=O)c2ccc(-c3noc(C(F)(F)F)n3)cc2)cc1] | 0.3 g, 55% yield |
| 35 | N-((4-bromobenzyl)(methyl)(oxo)-$\lambda^6$-sulfaneylidene)-4-(5-(trifluoromethyl)-1,2,4-oxadiazol-3-yl)benzamide | 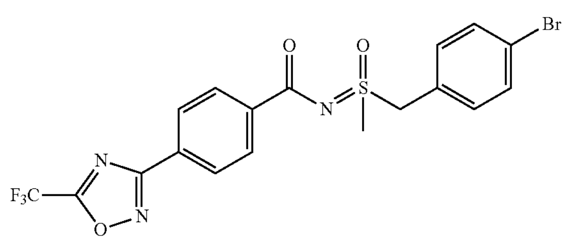 [SMILES: CS(=O)(Cc1ccc(Br)cc1)=NC(=O)c1ccc(-c2noc(C(F)(F)F)n2)cc1] | 0.4 g, 62% yield |
| 36 | N-((2,6-difluorophenyl)(methyl)(oxo)-$\lambda^6$-sulfaneylidene)-4-(5-(trifluoromethyl)-1,2,4-oxadiazol-3-yl)benzamide | 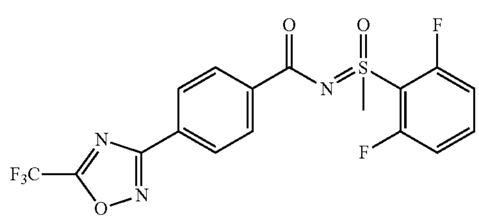 [SMILES: CS(=O)(=NC(=O)c1ccc(-c2noc(C(F)(F)F)n2)cc1)c1c(F)cccc1F] | 0.2 g, 31% yield |
| 37 | N-((2,4-difluorobenzyl)(methyl)(oxo)-$\lambda^6$-sulfaneylidene)-4-(5-(trifluoromethyl)-1,2,4-oxadiazol-3-yl)benzamide | 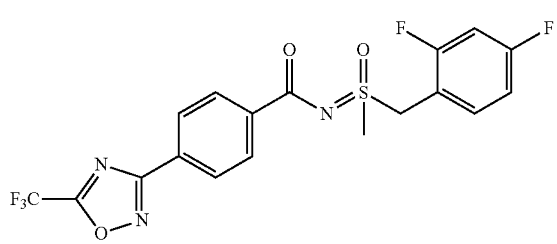 [SMILES: CS(=O)(Cc1ccc(F)cc1F)=NC(=O)c1ccc(-c2noc(C(F)(F)F)n2)cc1] | 0.4 g, 69% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 38 | N-((2-fluorobenzyl)(methyl)(oxo)-$\lambda^6$-sulfaneylidene)-4-(5-(trifluoromethyl)-1,2,4-oxadiazol-3-yl)benzamide | 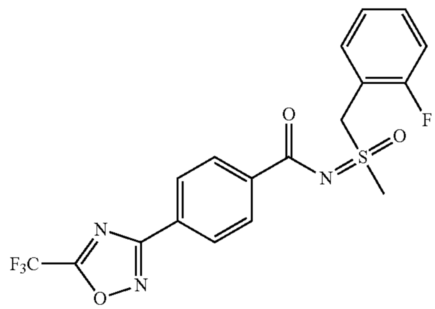 [SMILES: CS(=O)(Cc1ccccc1F)=NC(=O)c1ccc(-c2noc(C(F)(F)F)n2)cc1] | 0.1 g, 40.1% |
| 39 | N-((3-fluorobenzyl)(methyl)(oxo)-$\lambda^6$-sulfaneylidene)-4-(5-(trifluoromethyl)-1,2,4-oxadiazol-3-yl)benzamide | 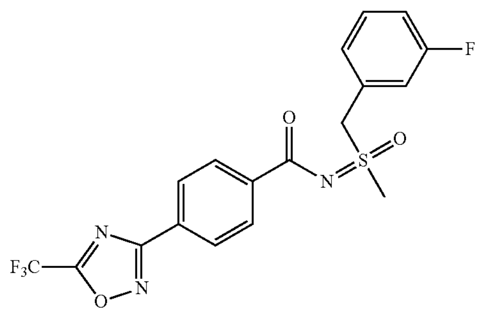 [SMILES: CS(=O)(Cc1cccc(F)c1)=NC(=O)c1ccc(-c2noc(C(F)(F)F)n2)cc1] | 0.1 g, 26% |
| 40 | N-(methyl(2-methylbenzyl)(oxo)-$\lambda^6$-sulfaneylidene)-4-(5-(trifluoromethyl)-1,2,4-oxadiazol-3-yl)benzamide | 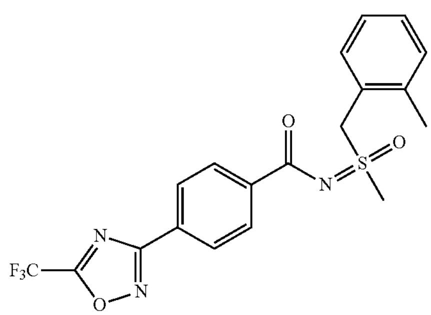 [SMILES: Cc1ccccc1CS(C)(=O)=NC(=O)c1ccc(-c2noc(C(F)(F)F)n2)cc1] | 0.2 g, 30% |
| 41 | N-((3,5-dimethylphenyl)(methyl)(oxo)-$\lambda^6$-sulfaneylidene)-4-(5-(trifluoromethyl)-1,2,4-oxadiazol-3-yl)benzamide | 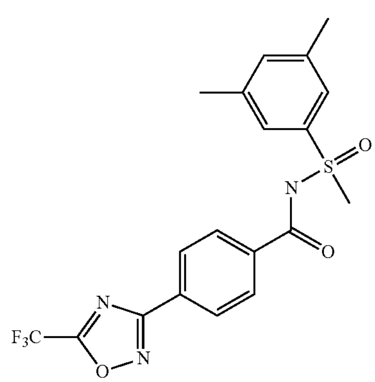 | 0.4 g, 72% |
| 42 | N-((4-cyanophenyl)(methyl)(oxo)-$\lambda^6$-sulfaneylidene)-4-(5-(trifluoromethyl)-1,2,4-oxadiazol-3-yl)benzamide | 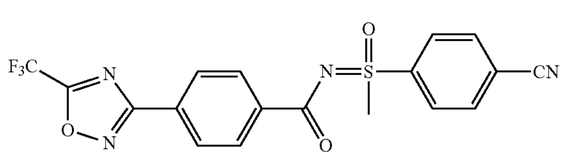 [SMILES: CS(=O)(=NC(=O)c1ccc(-c2noc(C(F)(F)F)n2)cc1)c1ccc(C#N)cc1] | 0.4 g, 71% yield |

TABLE NO. 1-continued

The following compounds were prepared by the procedure analogous to that of the
Compound 3 using appropriate starting materials.

| Compound No. | IUPAC Name | Structure | Yield |
|---|---|---|---|
| 43 | N-(1-oxidotetrahydro-2H-1$\lambda^6$-thiopyran-1-ylidene)-4-(5-(trifluoromethyl)-1,2,4-oxadiazol-3-yl)benzamide | 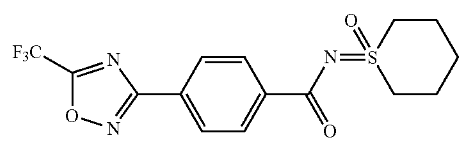 [SMILES: O=C(N=S1(=O)CCCCC1)c1ccc(-c2noc(C(F)(F)F)n2)cc1] | 0.3 g, 62% yield |
| 44 | N-(methyl(oxo)(m-tolyl)-$\lambda^6$-sulfaneylidene)-4-(5-(trifluoromethyl)-1,2,4-oxadiazol-3-yl)benzamide | 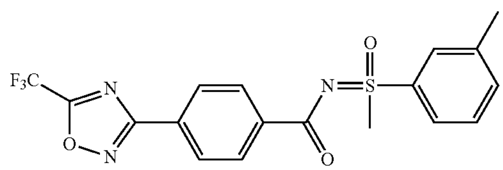 [SMILES: Cc1cccc(S(C)(=O)=NC(=O)c2ccc(-c3noc(C(F)(F)F)n3)cc2)c1] | 0.4 g, 83% yield |
| 45 | N-(methyl(3-methylbenzyl)(oxo)-$\lambda^6$-sulfaneylidene)-4-(5-(trifluoromethyl)-1,2,4-oxadiazol-3-yl)benzamide | 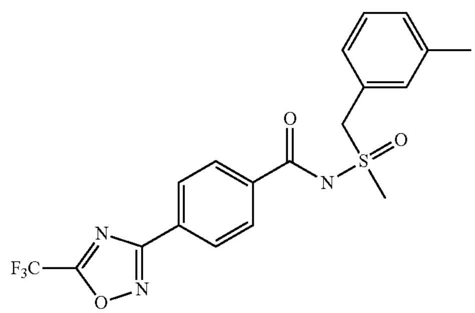 | 0.2 g, 48% |
| 46 | N-((3-methoxyphenyl)(methyl)(oxo)-$\lambda^6$-sulfaneylidene)-4-(5-(trifluoromethyl)-1,2,4-oxadiazol-3-yl)benzamide | 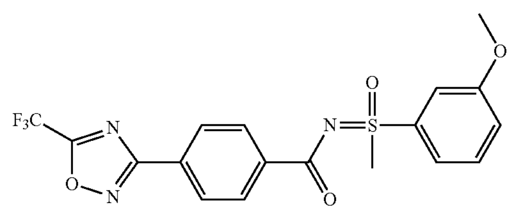 [SMILES: COc1cccc(S(C)(=O)=NC(=O)c2ccc(-c3noc(C(F)(F)F)n3)cc2)c1] | 0.4 g, 76% yield |
| 47 | N-((2,4-difluorophenyl)(methyl)(oxo)-$\lambda^6$-sulfaneylidene)-4-(5-(trifluoromethyl)-1,2,4-oxadiazol-3-yl)benzamide | 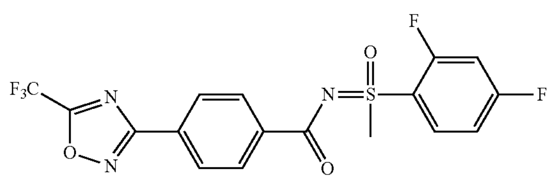 [SMILES: CS(=O)(=NC(=O)c1ccc(-c2noc(C(F)(F)F)n2)cc1)c1ccc(F)cc1F] | 0.3 g, 59% yield |
| 48 | N-(methyl(oxo)(thiazol-2-yl)-$\lambda^6$-sulfaneylidene)-4-(5-(trifluoromethyl)-1,2,4-oxadiazol-3-yl)benzamide | 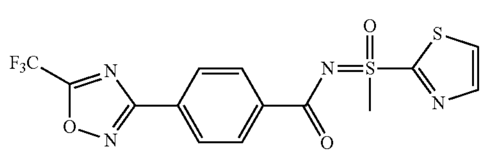 [SMILES: CS(=O)(=NC(=O)c1ccc(-c2noc(C(F)(F)F)n2)cc1)c1nccs1] | 0.3 g, 74% yield |
| 49 | N-((4-fluorobenzyl)(methyl)(oxo)-$\lambda^6$-sulfaneylidene)-4-(5-(trifluoromethyl)-1,2,4-oxadiazol-3-yl)benzamide | 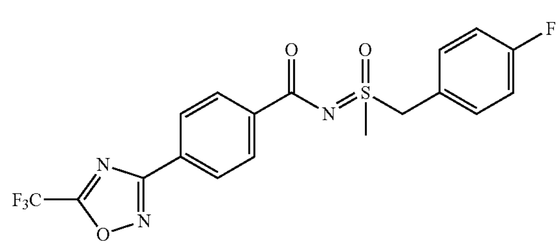 [SMILES: CS(=O)(Cc1ccc(F)cc1)=NC(=O)c1ccc(-c2noc(C(F)(F)F)n2)cc1] | 0.3 g, 69% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 50 | N-(methyl(oxo)(4-(trifluoromethyl)benzyl)-λ⁶-sulfaneylidene)-4-(5-(trifluoromethyl)-1,2,4-oxadiazol-3-yl)benzamide | 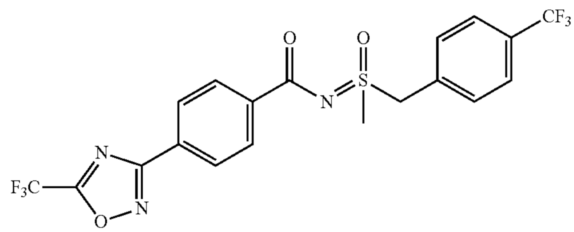 [SMILES: CS(=O)(Cc1ccc(C(F)(F)F)cc1)=NC(=O)c1ccc(-c2noc(C(F)(F)F)n2)cc1] | 0.3 g, 68% yield |
| 51 | N-((2,6-dichlorobenzyl)(methyl)(oxo)-λ⁶-sulfaneylidene)-4-(5-(trifluoromethyl)-1,2,4-oxadiazol-3-yl)benzamide | 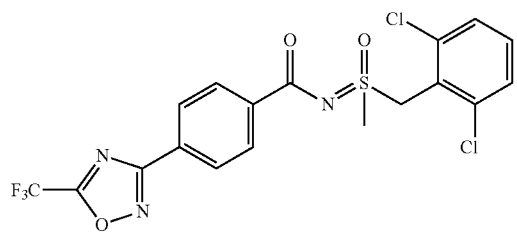 [SMILES: CS(=O)(Cc1c(Cl)cccc1Cl)=NC(=O)c1ccc(-c2noc(C(F)(F)F)n2)cc1] | 0.3 g, 54% yield |
| 52 | N-(methyl(oxo)(pyridin-2-ylmethyl)-λ⁶-sulfaneylidene)-4-(5-(trifluoromethyl)-1,2,4-oxadiazol-3-yl)benzamide | 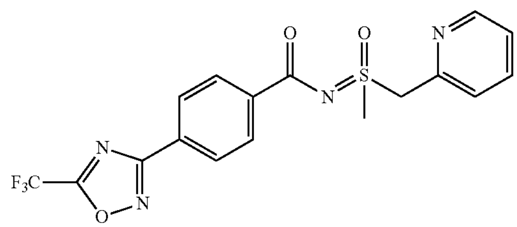 [SMILES: CS(=O)(Cc1ccccn1)=NC(=O)c1ccc(-c2noc(C(F)(F)F)n2)cc1] | 0.1 g, 27% yield |
| 53 | N-(methyl(4-methylthiazol-2-yl)(oxo)-λ⁶-sulfaneylidene)-4-(5-(trifluoromethyl)-1,2,4-oxadiazol-3-yl)benzamide | 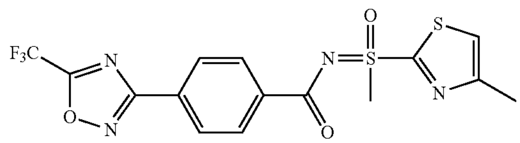 [SMILES: Cc1csc(S(C)(=O)=NC(=O)c2ccc(-c3noc(C(F)(F)F)n3)cc2)n1] | 0.3 g, 63% yield |
| 54 | N-(methyl(5-methyl-1,3,4-thiadiazol-2-yl)(oxo)-λ⁶-sulfaneylidene)-4-(5-(trifluoromethyl)-1,2,4-oxadiazol-3-yl)benzamide | 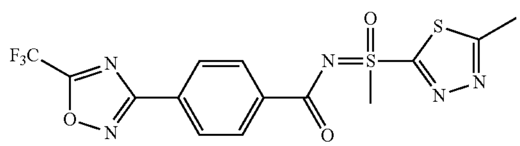 [SMILES: Cc1nnc(S(C)(=O)=NC(=O)c2ccc(-c3noc(C(F)(F)F)n3)cc2)s1] | 0.3 g, 50% yield |
| 55 | N-((2,5-dichlorophenyl)(methyl)(oxo)-λ⁶-sulfaneylidene)-4-(5-(trifluoromethyl)-1,2,4-oxadiazol-3-yl)benzamide | 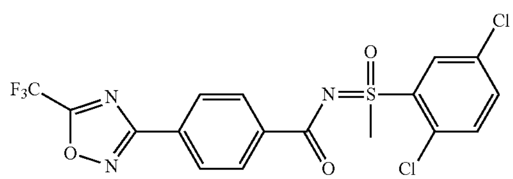 [SMILES: CS(=O)(=NC(=O)c1ccc(-c2noc(C(F)(F)F)n2)cc1)c1cc(Cl)ccc1Cl] | 0.3 g, 62% yield |
| 56 | N-((2,4-dimethoxyphenyl)(methyl)(oxo)-λ⁶-sulfaneylidene)-4-(5-(trifluoromethyl)-1,2,4-oxadiazol-3-yl)benzamide | 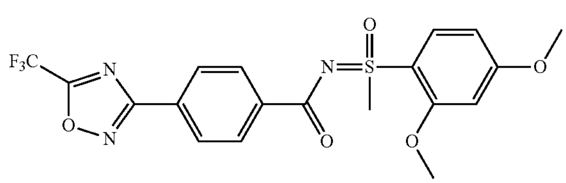 [SMILES: COc1ccc(S(C)(=O)=NC(=O)c2ccc(-c3noc(C(F)(F)F)n3)cc2)c(OC)c1] | 0.4 g, 71% yield |
| 57 | N-((3,4-difluorophenyl)(methyl)(oxo)-λ⁶-sulfaneylidene)-4-(5-(trifluoromethyl)-1,2,4-oxadiazol-3-yl)benzamide | 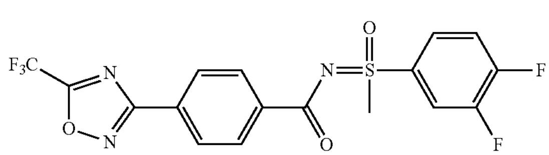 [SMILES: CS(=O)(=NC(=O)c1ccc(-c2noc(C(F)(F)F)n2)cc1)c1ccc(F)c(F)c1] | 0.3 g, 59% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 58 | N-(4-oxido-1,4λ⁶-oxathian-4-ylidene)-4-(5-(trifluoromethyl)-1,2,4-oxadiazol-3-yl)benzamide | 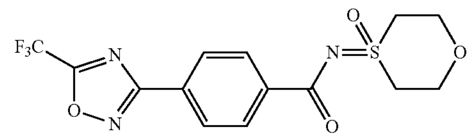 [SMILES: O=C(N=S1(=O)CCOCC1)c1ccc(-c2noc(C(F)(F)F)n2)cc1] | 0.3 g, 57% yield |
| 59 | N-(mehtyl(oxo)(pyridin-4-ylmethyl)-λ⁶-sulfaneylidene)-4-(5-(trifluoromethyl)-1,2,4-oxadiazol-3-yl)benzamide | 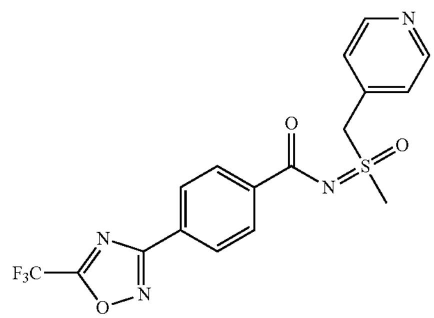 [SMILES: CS(=O)(Cc1ccncc1)=NC(=O)c1ccc(-c2noc(C(F)(F)F)n2)cc1] | 0.1 g, 29% yield |
| 60 | N-((4-chlorobenzyl)(methyl)(oxo)-λ⁶-sulfaneylidene)-4-(5-(trifluoromethyl)-1,2,4-oxadiazol-3-yl)benzamide | 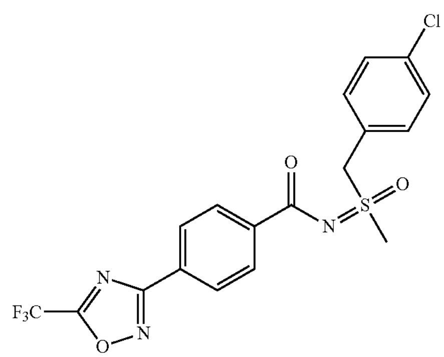 [SMILES: CS(=O)(Cc1ccc(Cl)cc1)=NC(=O)c1ccc(-c2noc(C(F)(F)F)n2)cc1] | 0.1 g, 31% yield |
| 61 | N-((4-chloro-3-fluorobenzyl)(methyl)(oxo)-λ⁶-sulfaneylidene)-4-(5-(trifluoromethyl)-1,2,4-oxadiazol-3-yl)benzamide | 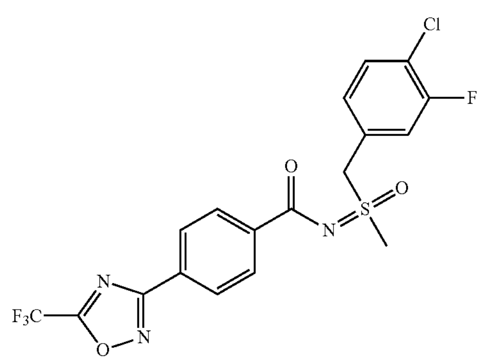 [SMILES: CS(=O)(Cc1ccc(Cl)c(F)c1)=NC(=O)c1ccc(-c2noc(C(F)(F)F)n2)cc1] | 0.1 g, 30% yield |
| 62 | N-((2,5-difluorobenzyl)(methyl)(oxo)-λ⁶-sulfaneylidene)-4-(5-(trifluoromethyl)-1,2,4-oxadiazol-3-yl)benzamide | 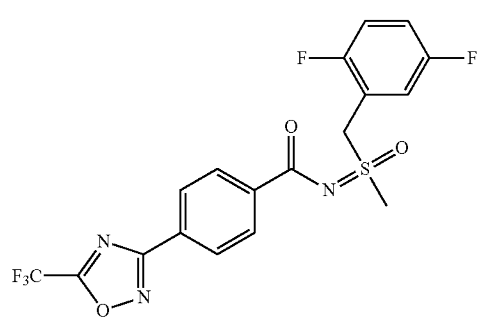 [SMILES: CS(=O)(Cc1cc(F)ccc1F)=NC(=O)c1ccc(-c2noc(C(F)(F)F)n2)cc1] | 0.1 g, 16% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 63 | N-((2-fluorophenyl)(methyl)(oxo)-$\lambda^6$-sulfaneylidene)-3-(5-(trifluoromethyl)-1,2,4-oxadiazol-3-yl)benzamide | 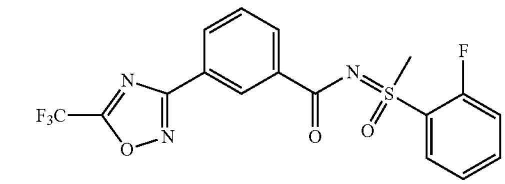 [SMILES: CS(=O)(=NC(=O)c1cccc(-c2noc(C(F)(F)F)n2)c1)c1ccccc1F] | 0.1 g, 17% yield |
| 64 | N-(methyl(oxo)(4-(trifluoromethyl)phenyl)-$\lambda^6$-sulfaneylidene)-3-(5-(trifluoromethyl)-1,2,4-oxadiazol-3-yl)benzamide | 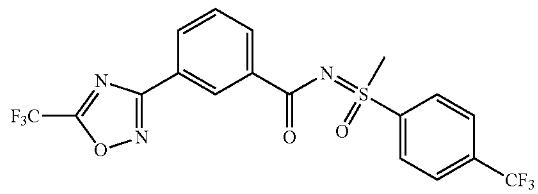 [SMILES: CS(=O)(=NC(=O)c1cccc(-c2noc(C(F)(F)F)n2)c1)c1ccc(C(F)(F)F)cc1] | 0.1 g, 18% yield |
| 65 | N-((4-fluorophenyl)(methyl)(oxo)-$\lambda^6$-sulfaneylidene)-3-(5-(trifluoromethyl)-1,2,4-oxadiazol-3-yl)benzamide | 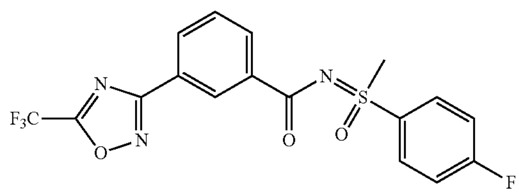 [SMILES: CS(=O)(=NC(=O)c1cccc(-c2noc(C(F)(F)F)n2)c1)c1ccc(F)cc1] | 0.5 g, 78% yield |
| 66 | N-(methyl(oxo)(pyridin-2-yl)-$\lambda^6$-sulfaneylidene)-3-(5-(trifluoromethyl)-1,2,4-oxadiazol-3-yl)benzamide | 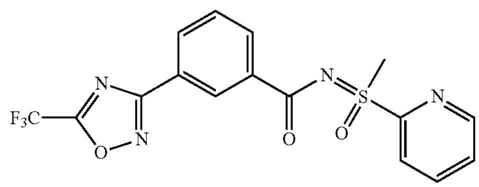 [SMILES: CS(=O)(=NC(=O)c1cccc(-c2noc(C(F)(F)F)n2)c1)c1ccccn1] | 0.2 g, 32% yield |
| 67 | N-(methyl(oxo)(phenyl)-$\lambda^6$-sulfaneylidene)-3-(5-(trifluoromethyl)-1,2,4-oxadiazol-3-yl)benzamide | 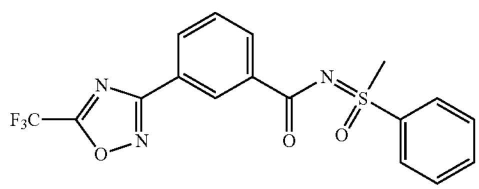 [SMILES: CS(=O)(=NC(=O)c1cccc(-c2noc(C(F)(F)F)n2)c1)c1ccccc1] | 0.4 g, 78% yield |
| 68 | N-((2,6-difluorobenzyl)(methyl)(oxo)-$\lambda^6$-sulfaneylidene)-3-(5-(trifluoromethyl)-1,2,4-oxadiazol-3-yl)benzamide | 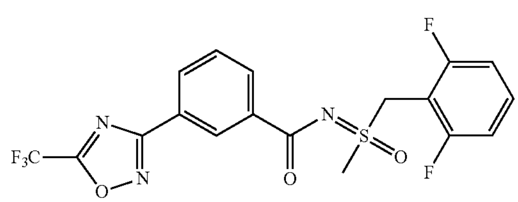 [SMILES: CS(=O)(Cc1c(F)cccc1F)=NC(=O)c1cccc(-c2noc(C(F)(F)F)n2)c1] | 0.3 g, 55% yield |
| 69 | N-((2,4-difluorobenzyl)(methyl)(oxo)-$\lambda^6$-sulfaneylidene)-3-(5-(trifluoromethyl)-1,2,4-oxadiazol-3-yl)benzamide | 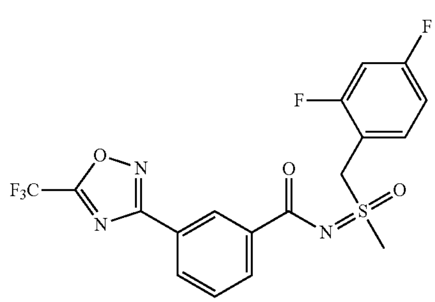 [SMILES: CS(=O)(Cc1ccc(F)cc1F)=NC(=O)c1cccc(-c2noc(C(F)(F)F)n2)c1] | 0.3 g, 64% yield |

TABLE NO. 1-continued

The following compounds were prepared by the procedure analogous to that of the
Compound 3 using appropriate starting materials.

| Compound No. | IUPAC Name | Structure | Yield |
|---|---|---|---|
| 70 | N-((4-methoxybenzyl)(methyl)(oxo)-λ⁶-sulfaneylidene)-3-(5-(trifluoromethyl)-1,2,4-oxadiazol-3-yl)benzamide | 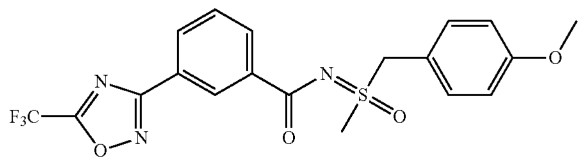 [SMILES: COc1ccc(CS(C)(=O)=NC(=O)c2cccc(-c3noc(C(F)(F)F)n3)c2)cc1] | 0.2 g, 40% yield |
| 71 | N-((4-methoxyphenyl)(methyl)(oxo)-λ⁶-sulfaneylidene)-3-(5-(trifluoromethyl)-1,2,4-oxadiazol-3-yl)benzamide | 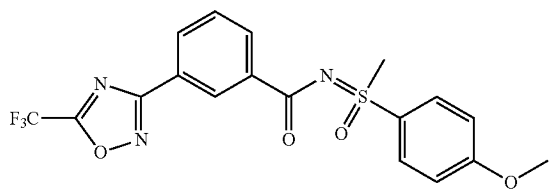 [SMILES: COc1ccc(S(C)(=O)=NC(=O)c2cccc(-c3noc(C(F)(F)F)n3)c2)cc1] | 0.4 g, 60% yield |
| 72 | N-((2,6-difluorophenyl)(methyl)(oxo)-λ⁶-sulfaneylidene)-3-(5-(trifluoromethyl)-1,2,4-oxadiazol-3-yl)benzamide | 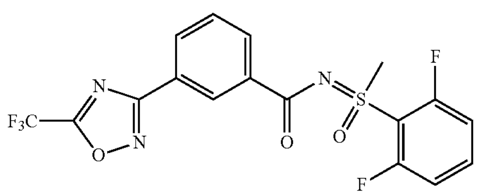 [SMILES: CS(=O)(=NC(=O)c1cccc(-c2noc(C(F)(F)F)n2)c1)c1c(F)cccc1F] | 0.4 g, 73% yield |
| 73 | N-(methyl(oxo)(thiazol-2-yl)-λ⁶-sulfaneylidene)-3-(5-(trifluoromethyl)-1,2,4-oxadiazol-3-yl)benzamide | 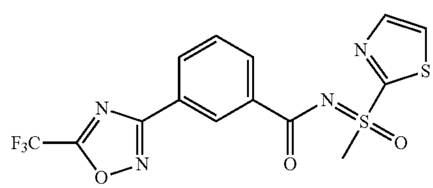 [SMILES: CS(=O)(=NC(=O)c1cccc(-c2noc(C(F)(F)F)n2)c1)c1nccs1] | 0.2 g, 51% yield |
| 74 | N-(1-oxidotetrahydro-2H-1λ⁶-thiopyran-1-ylidene)-3-(5-(trifluoromethyl)-1,2,4-oxadiazol-3-yl)benzamide | 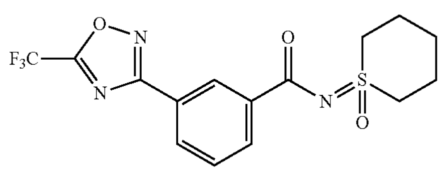 [SMILES: O=C(N=S1(=O)CCCCC1)c1cccc(-c2noc(C(F)(F)F)n2)c1] | 0.1 g, 31% yield |
| 75 | N-((4-cyanobenzyl)(methyl)(oxo)-λ⁶-sulfaneylidene)-3-(5-(trifluoromethyl)-1,2,4-oxadiazol-3-yl)benzamide | 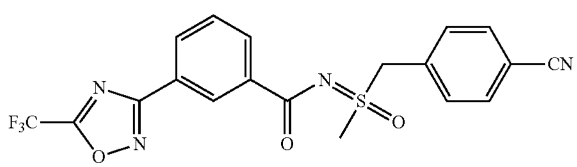 [SMILES: CS(=O)(Cc1ccc(C#N)cc1)=NC(=O)c1cccc(-c2noc(C(F)(F)F)n2)c1] | 0.3 g, 54% yield |
| 76 | N-((4-fluorophenyl)(isopropyl)(oxo)-λ⁶-sulfaneyldene)-4-(5-(trifluoromethyl)-1,2,4-oxadiazol-3-yl)benzamide | 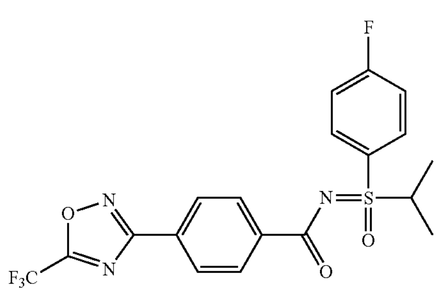 | 0.1 g, 37% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 77 | N-(isopropyl(4-methoxyphenyl)(oxo)-$\lambda^6$-sulfaneylidene)-4-(5-(trifluoromethyl)-1,2,4-oxadiazol-3-yl)benzamide | 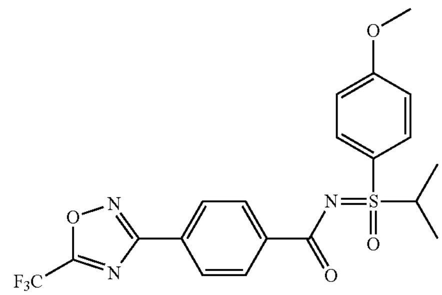 [SMILES: COc1ccc(S(=O)(=NC(=O)c2ccc(-c3noc(C(F)(F)F)n3)cc2)C(C)C)cc1] | 0.2 g, 39% yield |
| 78 | N-((4-chlorophenyl)(isopropyl)(oxo)-$\lambda^6$-sulfaneylidene)-4-(5-(trifluoromethyl)-1,2,4-oxadiazol-3-yl)benzamide | 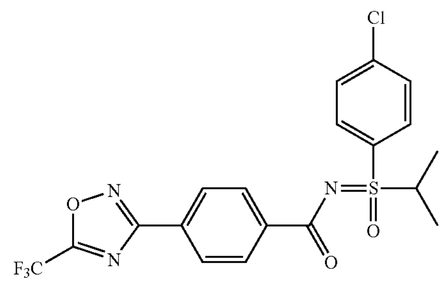 [SMILES: CC(C)S(=O)(=NC(=O)c1ccc(-c2noc(C(F)(F)F)n2)cc1)c1ccc(Cl)cc1] | 0.2 g 43% yield |
| 79 | N-(isopropyl(oxo)(pyridin-2-yl)-$\lambda^6$-sulfaneylidene)-4-(5-(trifluoromethyl)-1,2,4-oxadiazol-3-yl)benzamide | 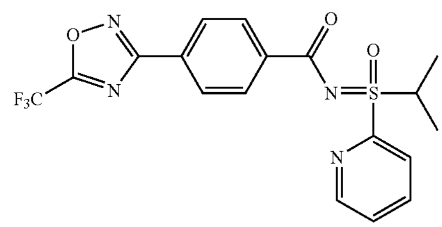 [SMILES: CC(C)S(=O)(=NC(=O)c1ccc(-c2noc(C(F)(F)F)n2)cc1)c1ccccn1] | 0.3 g, 54% yield |
| 80 | N-(isopropyl(oxo)(phenyl)-$\lambda^6$-sulfaneylidene)-4-(5-(trifluoromethyl)-1,2,4-oxadiazol-3-yl)benzamide | 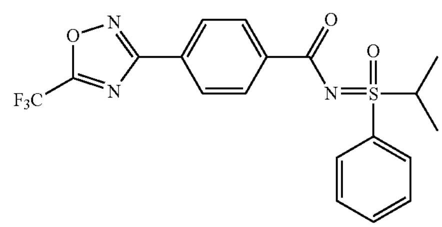 [SMILES: CC(C)S(=O)(=NC(=O)c1ccc(-c2noc(C(F)(F)F)n2)cc1)c1ccccc1] | 0.3 g, 43% yield |
| 81 | 3-fluoro-N-((4-methoxyphenyl)(methyl)(oxo)-$\lambda^6$-sulfaneylidene)-4-(5-(trifluoromethyl)-1,2,4-oxadiazol-3-yl)benzamide | 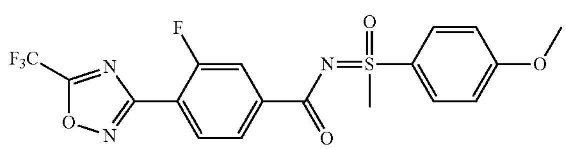 [SMILES: COc1ccc(S(C)(=O)=NC(=O)c2ccc(-c3noc(C(F)(F)F)n3)c(F)c2)cc1] | 0.4 g, 80% yield |
| 82 | N-((3-bromophenyl)(ethyl)(oxo)-$\lambda^6$-sulfaneylidene)-4-(5-(trifluoromethyl)-1,2,4-oxadiazol-3-yl)benzamide | 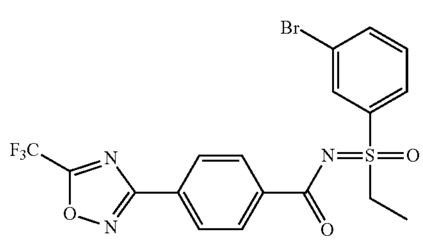 [SMILES: CCS(=O)(=NC(=O)c1ccc(-c2noc(C(F)(F)F)n2)cc1)c1cccc(Br)c1] | 0.3 g, 52% yield |

TABLE NO. 1-continued

The following compounds were prepared by the procedure analogous to that of the Compound 3 using appropriate starting materials.

| Compound No. | IUPAC Name | Structure | Yield |
|---|---|---|---|
| 83 | N-(methyl(oxo)(2-phenoxyethyl)-$\lambda^6$-sulfaneylidene)-4-(5-(trifluoromethyl)-1,2,4-oxadiazol-3-yl)benzamide | 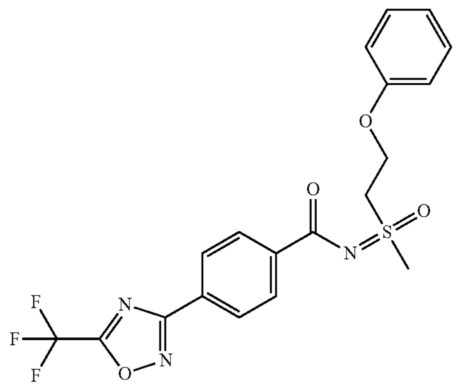 [SMILES: CS(=O)(CCOc1ccccc1)=NC(=O)c1ccc(-c2noc(C(F)(F)F)n2)cc1] | 0.2 g, 49% yield |
| 206 | N-(allyl(methyl)(oxo)-$\lambda^6$-sulfaneylidene)-4-(5-(trifluoromethyl)-1,2,4-oxadiazol-3-yl)benzamide | 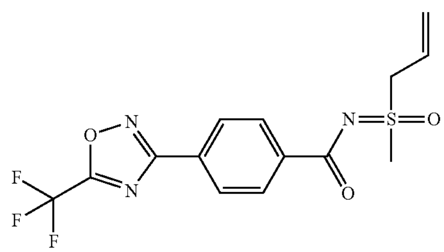 [SMILES: C=CCS(C)(=O)=NC(=O)c1ccc(-c2noc(C(F)(F)F)n2)cc1] | 0.1 g, 22% |
| 207 | N-(ethyl(methyl)(oxo)-$\lambda^6$-sulfaneylidene)-4-(5-(trifluoromethyl)-1,2,4-oxadiazol-3-yl)benzamide | 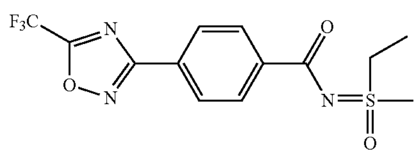 [SMILES: CCS(C)(=O)=NC(=O)c1ccc(-c2noc(C(F)(F)F)n2)cc1] | 0.1 g, 15% yield |
| 208 | N-((2-methoxyethyl)(methyl)(oxo)-$\lambda^6$-sulfaneylidene)-4-(5-(trifluoromethyl)-1,2,4-oxadiazol-3-yl)benzamide | 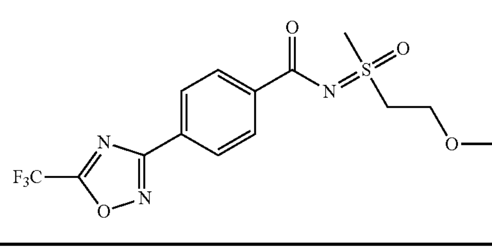 | 0.3 g, 65% yield |

Example-2: 2-fluorophenyl)(methyl)((4-(5-(trifluoromethyl)-1,2,4-oxadiazol-3-yl)phenyl)imino)-λ⁶-sulfanone (Compound 12)

Compound 12

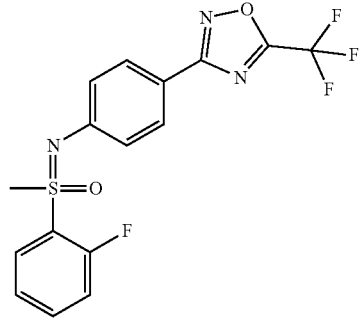

Step 1: 4-(((2-Fluorophenyl)(methyl)(oxo)-λ⁶-sulfanylidene)amino)benzonitrile

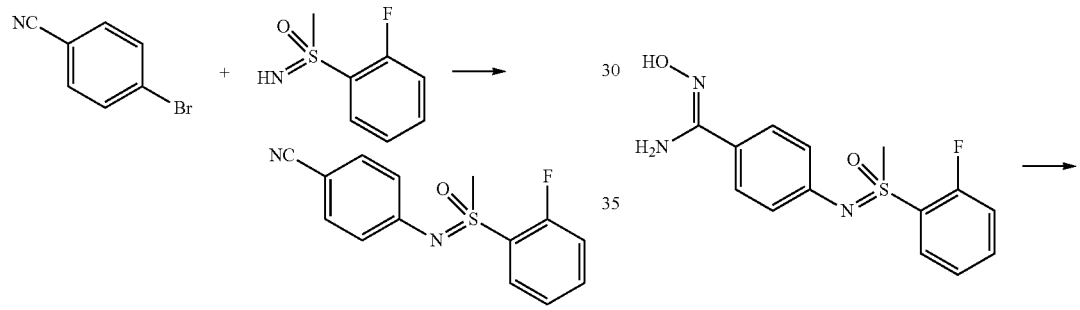

The reaction mixture containing 4-bromobenzonitrile (0.3 g, 1.6 mmol), (2-fluorophenyl)(imino)(methyl)-λ⁶-sulfanone (0.3 g, 2.0 mmol) and cesium carbonate (0.8 g, 2.3 mmol) in toluene (10 mL) was purged with nitrogen for 10 minutes. The racemic BINAP (0.08 g, 0.12 mmol) and palladium(II)acetate (0.02 g, 0.08 mmol) were added and the reaction mixture was stirred at 105° C. for 18 h. After completion of the reaction, the reaction mixture was cooled to 25° C. and was extracted with ethyl acetate (30 mL), the ethyl acetate layer was washed by water (10 mL), dried over anhydrous sodium sulphate and concentrated. The crude product 4-(((2-fluorophenyl)(methyl)(oxo)-λ⁶-sulfanylidene)amino)benzonitrile (0.5 g).

Step 2: 4-(((2-Fluorophenyl)(methyl)(oxo)-λ⁶-sulfanylidene)amino)-N'-hydroxybenzimidamide

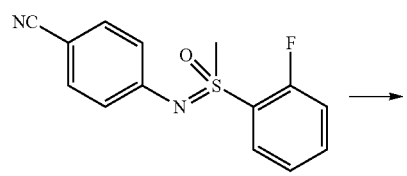

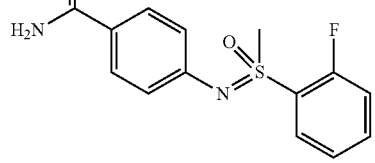

To a stirred solution of 4-(((2-fluorophenyl)(methyl)(oxo)-λ⁶-sulfanylidene)amino)benzonitrile (0.5 g, 1.6 mmol) in ethanol (12 mL), sodium bicarbonate (0.2 g, 3.0 mmol) and hydroxylamine hydrochloride (0.2 g, 3.0 mmol) were added and stirred at 65° C. for 16 h. After completion of the reaction, the reaction mixture was cooled to 25° C. and filtered. The filtrate was concentrated to obtain a crude product (Z)-4-(((2-fluorophenyl)(methyl)(oxo)-λ⁶-sulfanylidene)amino)-N'-hydroxybenzimidamide (0.5 g, 99%).

Step 3: (2-Fluorophenyl)(methyl)((4-(5-(trifluoromethyl)-1,2,4-oxadiazol-3-yl)phenyl)imino)-λ⁶-sulfanone To a stirred solution of (Z)-4-(((2-fluorophenyl)(methyl)(oxo)-λ⁶-sulfanylidene)amino)-N'-hydroxybenzimidamide (0.5 g, 1.6 mmol) in tetrahydrofuran (10 mL), trifluoroacetic anhydride (0.3 mL, 2.4 mmol) was added at 0° C. and stirred at 25° C. for 16 h. After completion of the reaction, the reaction mixture was filtered. The filtrate was concentrated to obtain the crude compound. The crude product was purified by column chromatography on silica gel using eluent hexane to 40% Ethyl acetate in hexane to obtain pure (2-fluorophenyl)(methyl)((4-(5-(trifluoromethyl)-1,2,4-oxadiazol-3-yl)phenyl)imino)-λ⁶-sulfanone (0.4 g, 60% yield).

TABLE NO. 2

The following compounds were prepared by the procedure analogous to that of the compound 12 using appropriate starting materials.

| Compound No. | IUPAC Name | Structure | Yield |
|---|---|---|---|
| 13 | (4-chlorophenyl)(methyl)((4-(5-(trifluoromethyl)-1,2,4-oxadiazol-3-yl)phenyl)imino)-$\lambda^6$-sulfanone | 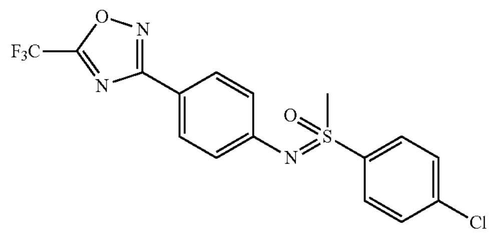 [SMILES: CS(=O)(=Nc1ccc(-c2noc(C(F)(F)F)n2)cc1)c1ccc(Cl)cc1] | 0.39 g, 62.0% yield |
| 14 | (3-fluorophenyl)(methyl)((4-(5-(trifluoromethyl)-1,2,4-oxadiazol-3-yl)phenyl)imino)-$\lambda^6$-sulfanone | 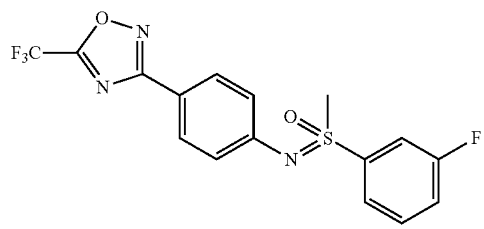 [SMILES: CS(=O)(=Nc1ccc(-c2noc(C(F)(F)F)n2)cc1)c1cccc(F)c1] | 0.29 g, 48.0% yield |
| 15 | methyl(pyridin-4-yl)((4-(5-(trifluoromethyl)-1,2,4-oxadiazol-3-yl)phenyl)imino)-$\lambda^6$-sulfanone | 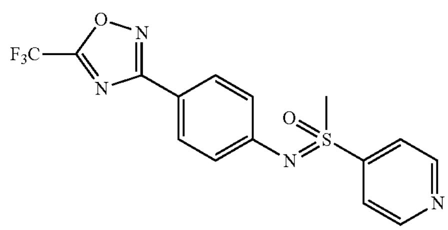 [SMILES: CS(=O)(=Nc1ccc(-c2noc(C(F)(F)F)n2)cc1)c1ccncc1] | 0.13 g, 22.0% yield |
| 16 | methyl(pyridin-2-yl)((4-(5-(trifluoromethyl)isoxazol-3-yl)phenyl)imino)-$\lambda^6$-sulfanone | 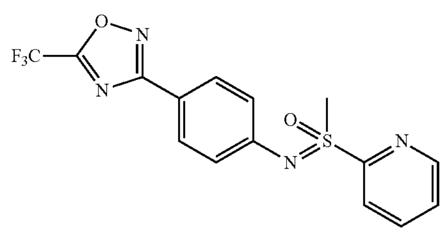 [SMILES: CS(=O)(=Nc1ccc(-c2noc(C(F)(F)F)n2)cc1)c1ccccn1] | 0.335 g, 56.0% yield |
| 17 | (4-fluorophenyl)(methyl)((4-(5-(trifluoromethyl)-1,2,4-oxadiazol-3-yl)phenyl)imino)-$\lambda^6$-sulfanone | 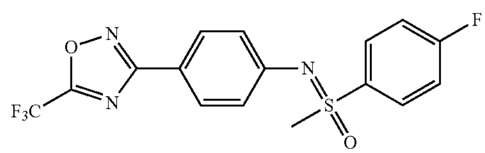 [SMILES: CS(=O)(=Nc1ccc(-c2noc(C(F)(F)F)n2)cc1)c1ccc(F)cc1] | 198 mg, 45.0% yield |
| 18 | methyl(phenyl)((4-(5-(trifluoromethyl)-1,2,4-oxadiazol-3-yl)phenyl)imino)-$\lambda^6$-sulfanone | 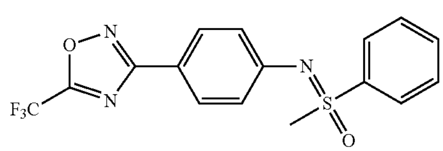 [SMILES: CS(=O)(=Nc1ccc(-c2noc(C(F)(F)F)n2)cc1)c1ccccc1] | 285 mg, 48.0% yield |
| 19 | methyl((4-(5-(trifluoromethyl)-1,2,4-oxadiazol-3-yl)phenyl)imino)(4-(trifluoromethyl)phenyl)-$\lambda^6$-sulfanone | 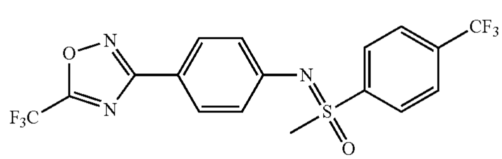 [SMILES: CS(=O)(=Nc1ccc(-c2noc(C(F)(F)F)n2)cc1)c1ccc(C(F)(F)F)cc1] | 382 mg, 54.0% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 20 | (4-methoxyphenyl)(methyl)((4-(5-(trifluoromethyl)-1,2,4-oxadiazol-3-yl)phenyl)imino)-$\lambda^6$-sulfanone | 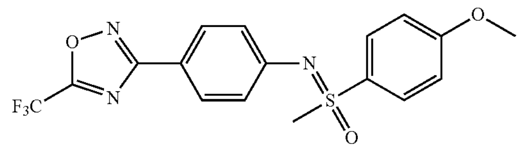 [SMILES: COc1ccc(S(C)(=O)=Nc2ccc(-c3noc(C(F)(F)F)n3)cc2)cc1] | 414 mg, 64.0% yield |
| 21 | methyl(4-(trifluoromethoxy)phenyl)((4-(5-(trifluoromethyl)-1,2,4-oxadiazol-3-yl)phenyl)imino)-$\lambda^6$-sulfanone | 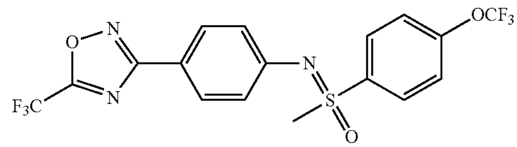 [SMILES: CS(=O)(=Nc1ccc(-c2noc(C(F)(F)F)n2)cc1)c1ccc(OC(F)(F)F)cc1] | 373 mg, 55.0% yield |
| 84 | (2,6-difluorophenyl)(methyl)((4-(5-(trifluoromethyl)-1,2,4-oxadiazol-3-yl)phenyl)imino)-$\lambda^6$-sulfanone | 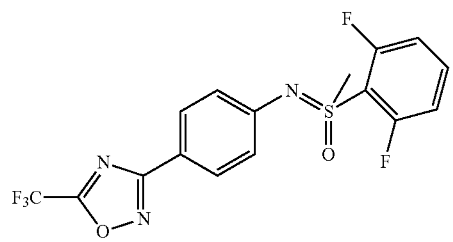 [SMILES: CS(=O)(=Nc1ccc(-c2noc(C(F)(F)F)n2)cc1)c1c(F)cccc1F] | 0.2 g, 28% yield |
| 85 | (2,6-difluorobenzyl)(methyl)((4-(5-(trifluoromethyl)-1,2,4-oxadiazol-3-yl)phenyl)imino)-$\lambda^6$-sulfanone | 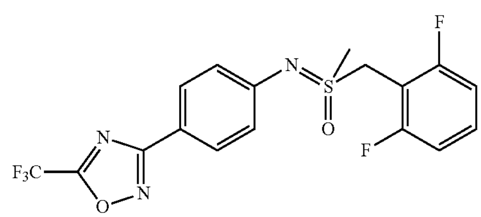 [SMILES: CS(=O)(Cc1c(F)cccc1F)=Nc1ccc(-c2noc(C(F)(F)F)n2)cc1] | 0.3 g, 47% yield |
| 86 | (2,4-difluorobenzyl)(methyl)((4-(5-(trifluoromethyl)-1,2,4-oxadiazol-3-yl)phenyl)imino)-$\lambda^6$-sulfanone | 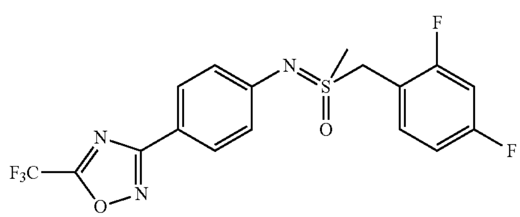 [SMILES: CS(=O)(Cc1ccc(F)cc1F)=Nc1ccc(-c2noc(C(F)(F)F)n2)cc1] | 0.2 g, 33% yield |
| 87 | (2,3-difluorobenzyl)(methyl)((4-(5-(trifluoromethyl)-1,2,4-oxadiazol-3-yl)phenyl)imino)-$\lambda^6$-sulfanone | 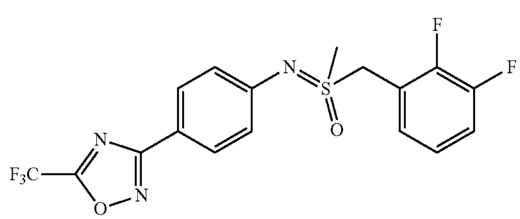 [SMILES: CS(=O)(Cc1cccc(F)c1F)=Nc1ccc(-c2noc(C(F)(F)F)n2)cc1] | 0.2 g, 37% yield |
| 88 | methyl(2-methylbenzyl)((4-(5-(trifluoromethyl)-1,2,4-oxadiazol-3-yl)phenyl)imino)-$\lambda^6$-sulfanone | 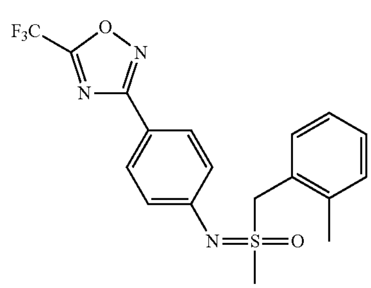 [SMILES: Cc1ccccc1CS(C)(=O)=Nc1ccc(-c2noc(C(F)(F)F)n2)cc1] | 0.2 g, 36% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 89 | (4-fluorobenzyl)(methyl)((4-(5-(trifluoromethyl)-1,2,4-oxadiazol-3-yl)phenyl)imino)-λ⁶-sulfanone | 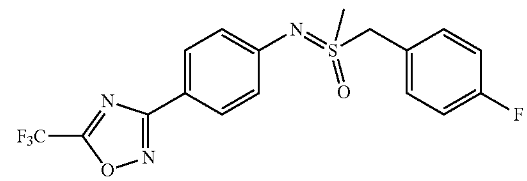 [SMILES: CS(=O)(Cc1ccc(F)cc1)=Nc1ccc(-c2noc(C(F)(F)F)n2)cc1] | 0.2 g, 34% yield |
| 90 | methyl((4-(5-(trifluoromethyl)-1,2,4-oxadiazol-3-yl)phenyl)imino)(4-(trifluoromethyl)benzyl)-λ⁶-sulfanone | 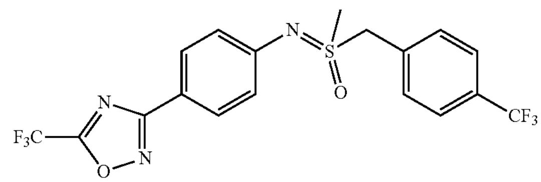 [SMILES: CS(=O)(Cc1ccc(C(F)(F)F)cc1)=Nc1ccc(-c2noc(C(F)(F)F)n2)cc1] | 0.3 g, 45% yield |
| 91 | (2,6-dichlorobenzyl)(methyl)((4-(5-(trifluoromethyl)-1,2,4-oxadiazol-3-yl)phenyl)imino)-λ⁶-sulfanone | 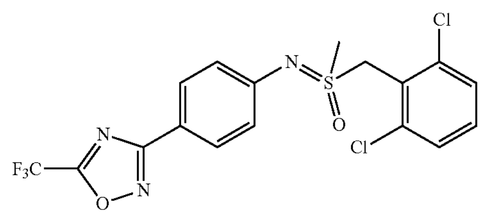 [SMILES: CS(=O)(Cc1c(Cl)cccc1Cl)=Nc1ccc(-c2noc(C(F)(F)F)n2)cc1] | 0.3 g, 47% yield |
| 92 | (4-bromobenzyl)(methyl)((4-(5-(trifluoromethyl)-1,2,4-oxadiazol-3-yl)phenyl)imino)-λ⁶-sulfanone | 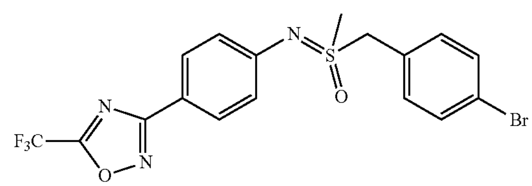 [SMILES: CS(=O)(Cc1ccc(Br)cc1)=Nc1ccc(-c2noc(C(F)(F)F)n2)cc1] | 0.2 g, 32% yield |
| 93 | methyl(pyridin-2-ylmethyl)((4-(5-(trifluoromethyl)-1,2,4-oxadiazol-3-yl)phenyl)imino)-λ⁶-sulfanone | 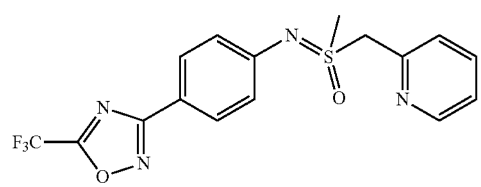 [SMILES: CS(=O)(Cc1ccccn1)=Nc1ccc(-c2noc(C(F)(F)F)n2)cc1] | 0.2 g, 42% yield |
| 94 | (2-fluorobenzyl)(methyl)((4-(5-(trifluoromethyl)-1,2,4-oxadiazol-3-yl)phenyl)imino)-λ⁶-sulfanone | 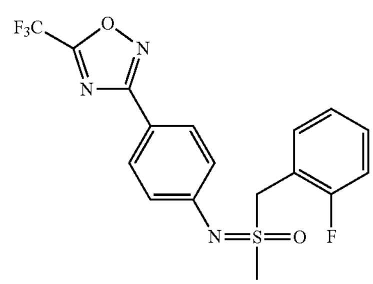 | 0.3 g, 27% yield |
| 95 | (3-fluorobenzyl)(methyl)((4-(5-(trifluoromethyl)-1,2,4-oxadiazol-3-yl)phenyl)imino)-λ⁶-sulfanone | 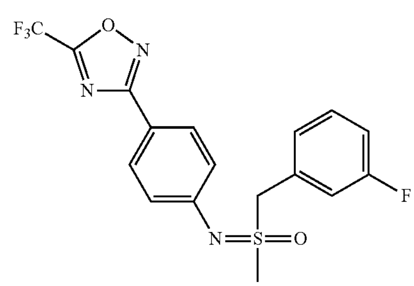 [SMILES: CS(=O)(Cc1cccc(F)c1)=Nc1ccc(-c2noc(C(F)(F)F)n2)cc1] | 0.4 g, 41% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 96 | (2,4-dimethoxyphenyl)(methyl)((4-(5-(trifluoromethyl)-1,2,4-oxadiazol-3-yl)phenyl)imino)-$\lambda^6$-sulfanone | 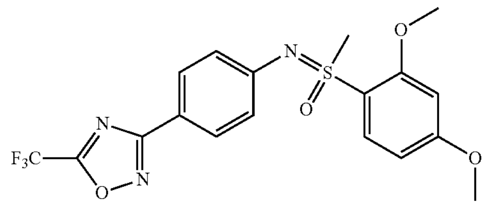 [SMILES: COc1ccc(S(C)(=O)=Nc2ccc(-c3noc(C(F)(F)F)n3)cc2)c(OC)c1] | 0.3 g, 50% yield |
| 97 | (3,4-difluorophenyl)(methyl)((4-(5-(trifluoromethyl)-1,2,4-oxadiazol-3-yl)phenyl)imino)-$\lambda^6$-sulfanone | 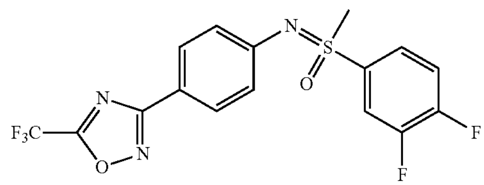 [SMILES: CS(=O)(=Nc1ccc(-c2noc(C(F)(F)F)n2)cc1)c1ccc(F)c(F)c1] | 0.4 g 60% yield |
| 98 | (4-chlorobenzyl)(methyl)((4-(5-(trifluoromethyl)-1,2,4-oxadiazol-3-yl)phenyl)imino)-$\lambda^6$-sulfanone | 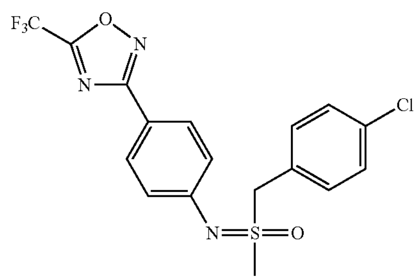 [SMILES: CS(=O)(Cc1ccc(Cl)cc1)=Nc1ccc(-c2noc(C(F)(F)F)n2)cc1] | 0.1 g, 40% yield |
| 99 | (4-chloro-3-florobenzyl)(methyl)((4-(5-(trifluoromethyl)-1,2,4-oxadiazol-3-yl)phenyl)imino)-$\lambda^6$-sulfanone | 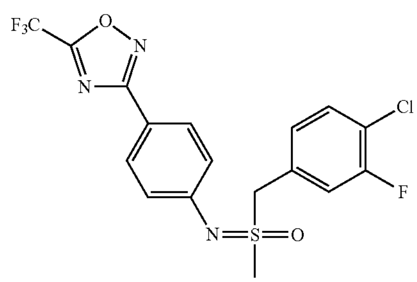 [SMILES: CS(=O)(Cc1ccc(Cl)c(F)c1)=Nc1ccc(-c2noc(C(F)(F)F)n2)cc1] | 0.1 g, 36% yield |
| 100 | (4-methoxyphenyl)(methyl)((3-(5-(trifluoromethyl)-1,2,4-oxadiazol-3-yl)phenyl)imino)-$\lambda^6$-sulfanone | 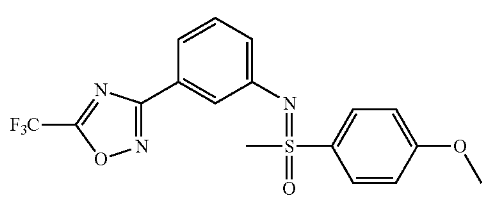 [SMILES: COc1ccc(S(C)(=O)=Nc2cccc(-c3noc(C(F)(F)F)n3)c2)cc1] | 0.6 g, 81% yield |
| 101 | (3-methoxyphenyl)(methyl)((3-(5-(trifluoromethyl)-1,2,4-oxadiazol-3-yl)phenyl)imino)-$\lambda^6$-sulfanone | 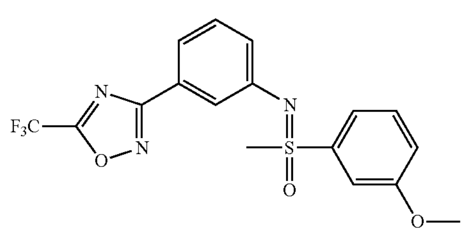 [SMILES: COc1cccc(S(C)(=O)=Nc2cccc(-c3noc(C(F)(F)F)n3)c2)c1] | 0.5 g, 75% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 102 | 1-((3-(5-(trifluoromethyl)-1,2,4-oxadiazol-3-yl)phenyl)imino)hexahydro-1$\lambda^6$-thiopyran 1-oxide | 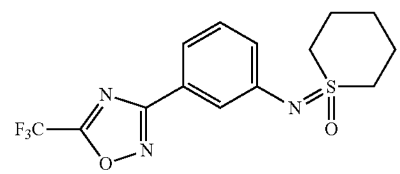 [SMILES: O=S1(=Nc2cccc(-c3noc(C(F)(F)F)n3)c2)CCCCC1] | 0.4 g, 70% yield |
| 103 | (2,4-dimethoxyphenyl)(methyl)((3-(5-(trifluoromethyl)-1,2,4-oxadiazol-3-yl)phenyl)imino)-$\lambda^6$-sulfanone | 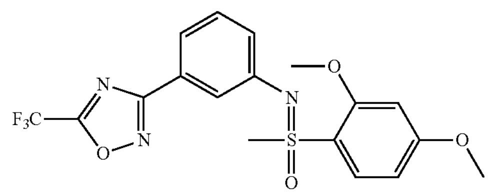 [SMILES: COc1ccc(S(C)(=O)=Nc2cccc(-c3noc(C(F)(F)F)n3)c2)c(OC)c1] | 0.5 g, 73% yield |
| 104 | (4-fluorophenyl)(methyl)((3-(5-(trifluoromethyl)-1,2,4-oxadiazol-3-yl)phenyl)imino)-$\lambda^6$-sulfanone | 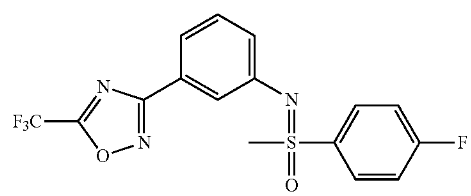 [SMILES: CS(=O)(=Nc1cccc(-c2noc(C(F)(F)F)n2)c1)c1ccc(F)cc1] | 0.4 g, 69% yield |
| 105 | (2-fluorophenyl)(methyl)((3-(5-(trifluoromethyl)-1,2,4-oxadiazol-3-yl)phenyl)imino)-$\lambda^6$-sulfanone | 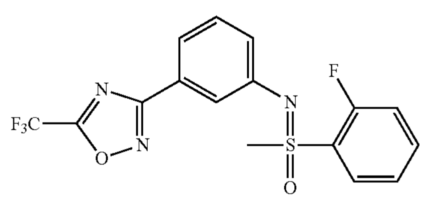 [SMILES: CS(=O)(=Nc1cccc(-c2noc(C(F)(F)F)n2)c1)c1ccccc1F] | 0.4 g, 66% yield |
| 106 | (3-methoxyphenyl)(methyl)((4-(5-(trifluoromethyl)-1,2,4-oxadiazol-3-yl)phenyl)imino)-$\lambda^6$-sulfanone | 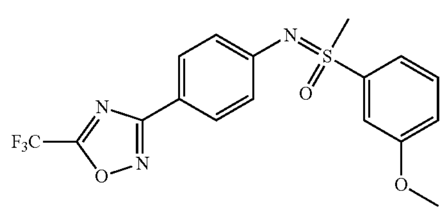 [SMILES: COc1cccc(S(C)(=O)=Nc2ccc(-c3noc(C(F)(F)F)n3)cc2)c1] | 0.5 g, 73% yield |
| 107 | (2,5-dichlorophenyl)(methyl)((4-(5-(trifluoromethyl)-1,2,4-oxadiazol-3-yl)phenyl)imino)-$\lambda^6$-sulfanone | 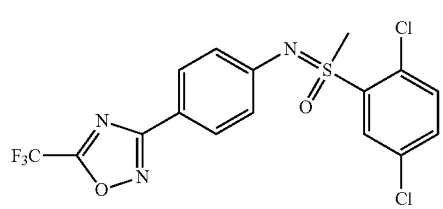 [SMILES: CS(=O)(=Nc1ccc(-c2noc(C(F)(F)F)n2)cc1)c1cc(Cl)ccc1Cl] | 0.3 g, 69% yield |
| 108 | (4-methoxyphenyl)(methyl)((6-(5-(trifluoromethyl)-1,2,4-oxadiazol-3-yl)pyridin-3-yl)imino)-$\lambda^6$-sulfanone | 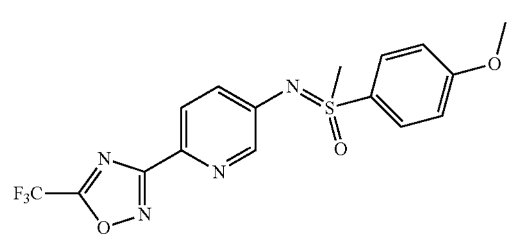 [SMILES: COc1ccc(S(C)(=O)=Nc2ccc(-c3noc(C(F)(F)F)n3)nc2)cc1] | 0.4 g, 68% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 109 | methyl(phenyl)((6-(5-(trifluoromethyl)-1,2,4-oxadiazol-3-yl)pyridin-3-yl)imino)-$\lambda^6$-sulfanone | 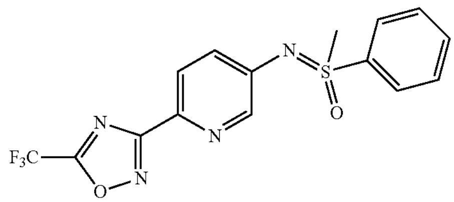 [SMILES: CS(=O)(=Nc1ccc(-c2noc(C(F)(F)F)n2)nc1)c1ccccc1] | 0.4 g, 68% yield |
| 110 | methyl(pyridin-2-yl)((6-(5-(trifluoromethyl)-1,2,4-oxadiazol-3-yl)pyridin-3-yl)imino)-$\lambda^6$-sulfanone | 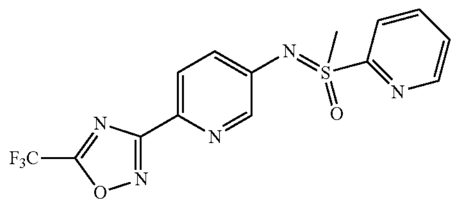 [SMILES: CS(=O)(=Nc1ccc(-c2noc(C(F)(F)F)n2)nc1)c1ccccn1] | 0.2 g, 36% yield |
| 111 | (2,6-difluorobenzyl)(methyl)((6-(5-(trifluoromethyl)-1,2,4-oxadiazol-3-yl)pyridin-3-yl)imino)-$\lambda^6$-sulfanone | 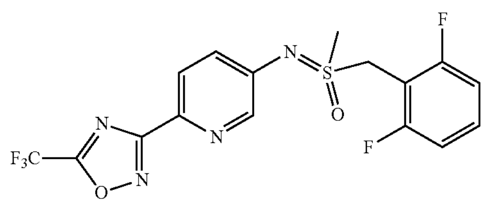 [SMILES: CS(=O)(Cc1c(F)cccc1F)=Nc1ccc(-c2noc(C(F)(F)F)n2)nc1] | 0.2 g, 42% yield |
| 112 | (4-chlorophenyl)(methyl)((3-(5-(trifluoromethyl)-1,2,4-oxadiazol-3-yl)phenyl)imino)-$\lambda^6$-sulfanone | 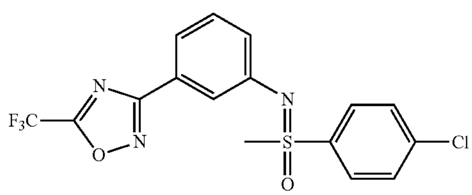 [SMILES: CS(=O)(=Nc1cccc(-c2noc(C(F)(F)F)n2)c1)c1ccc(Cl)cc1] | 0.4 g, 64% yield |
| 113 | methyl(pyridin-2-yl)((3-(5-(trifluoromethyl)-1,2,4-oxadiazol-3-yl)phenyl)imino)-$\lambda^6$-sulfanone | 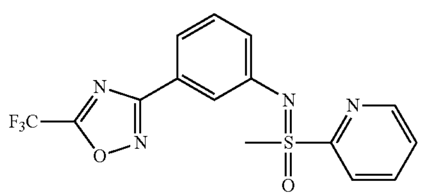 [SMILES: CS(=O)(=Nc1cccc(-c2noc(C(F)(F)F)n2)c1)c1ccccn1] | 0.3 g, 48% yield |
| 114 | methyl(m-tolyl)((3-(5-(trifluoromethyl)-1,2,4-oxadiazol-3-yl)phenyl)imino)-$\lambda^6$-sulfanone | 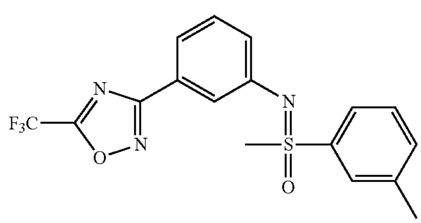 [SMILES: Cc1cccc(S(C)(=O)=Nc2cccc(-c3noc(C(F)(F)F)n3)c2)c1] | 0.4 g, 57% yield |
| 115 | methyl(thiazol-2-yl)((3-(5-(trifluoromethyl)-1,2,4-oxadiazol-3-yl)phenyl)imino)-$\lambda^6$-sulfanone | 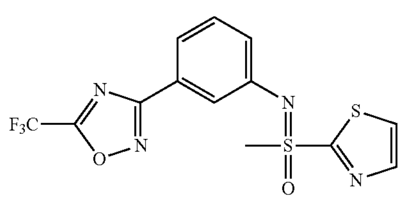 [SMILES: CS(=O)(=Nc1cccc(-c2noc(C(F)(F)F)n2)c1)c1nccs1] | 0.5 g, 71% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 116 | methyl((4-(5-(trifluoromethyl)-1,2,4-oxadiazol-3-yl)phenyl)imino)(4-(trifluoromethyl)pyridin-2-yl)-λ⁶-sulfanone | 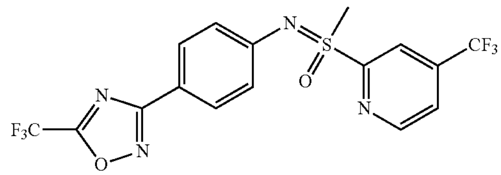 [SMILES: CS(=O)(=Nc1ccc(-c2noc(C(F)(F)F)n2)cc1)c1cc(C(F)(F)F)ccn1] | 0.2 g, 64% yield |
| 117 | methyl(4-methylthiazol-2-yl)((4-(5-(trifluoromethyl)-1,2,4-oxadiazol-3-yl)phenyl)imino)-λ⁶-sulfanone | 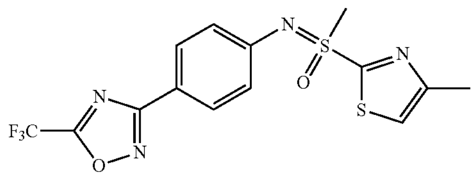 [SMILES: Cc1csc(S(C)(=O)=Nc2ccc(-c3noc(C(F)(F)F)n3)cc2)n1] | 0.3 g, 66% yield |
| 118 | methyl(thiazol-2-yl)((4-(5-(trifluoromethyl)-1,2,4-oxadiazol-3-yl)phenyl)imino)-λ⁶-sulfanone | 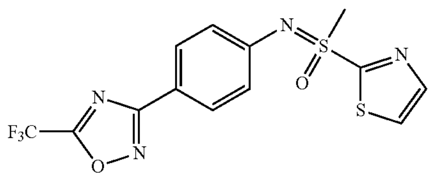 [SMILES: CS(=O)(=Nc1ccc(-c2noc(C(F)(F)F)n2)cc1)c1nccs1] | 0.3 g, 63% yield |
| 119 | (4-chlorophenyl)(methyl)((6-(5-(trifluoromethyl)-1,2,4-oxadiazol-3-yl)pyridin-3-yl)imino)-λ⁶-sulfanone | 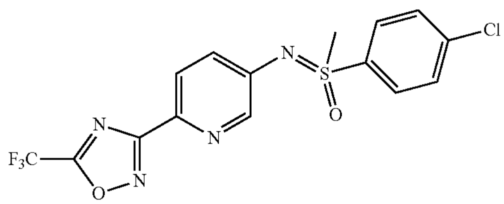 [SMILES: CS(=O)(=Nc1ccc(-c2noc(C(F)(F)F)n2)nc1)c1ccc(Cl)cc1] | 0.4 g, 56% yield |
| 120 | (2,6-difluorophenyl)(methyl)((6-(5-(trifluoromethyl)-1,2,4-oxadiazol-3-yl)pyridin-3-yl)imino)-λ⁶-sulfanone | 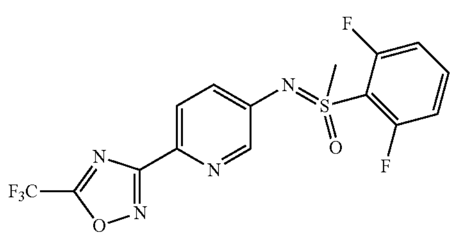 [SMILES: CS(=O)(=Nc1ccc(-c2noc(C(F)(F)F)n2)nc1)c1c(F)cccc1F] | 0.4 g, 75% yield |
| 121 | (3,4-difluorophenyl)(methyl)((3-(5-(trifluoromethyl)-1,2,4-oxadiazol-3-yl)phenyl)imino)-λ⁶-sulfanone | 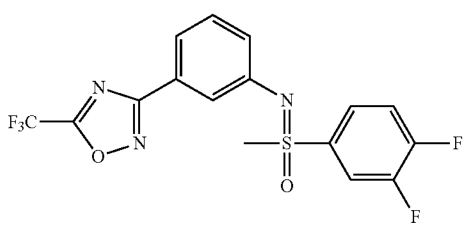 [SMILES: CS(=O)(=Nc1cccc(-c2noc(C(F)(F)F)n2)c1)c1ccc(F)c(F)c1] | 0.6 g, 67% yield |
| 122 | methyl(phenyl)((3-(5-(trifluoromethyl)-1,2,4-oxadiazol-3-yl)phenyl)imino)-λ⁶-sulfanone | 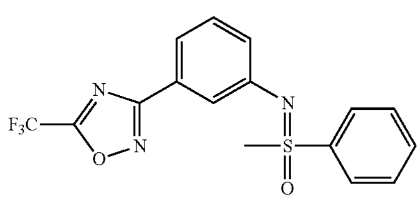 [SMILES: CS(=O)(=Nc1cccc(-c2noc(C(F)(F)F)n2)c1)c1ccccc1] | 0.5 g, 64% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 123 | (4-fluorophenyl)(methyl)((6-(5-(trifluoromethyl)-1,2,4-oxadiazol-3-yl)pyridin-3-yl)imino)-λ⁶-sulfanone | 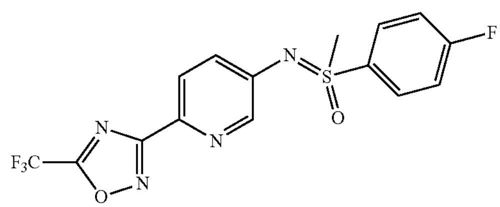 [SMILES: CS(=O)(=Nc1ccc(-c2noc(C(F)(F)F)n2)nc1)c1ccc(F)cc1] | 0.5 g, 72% yield |
| 124 | methyl((6-(5-(trifluoromethyl)-1,2,4-oxadiazol-3-yl)pyridin-3-yl)imino)(4-(trifluoromethyl)phenyl)-λ⁶-sulfanone | 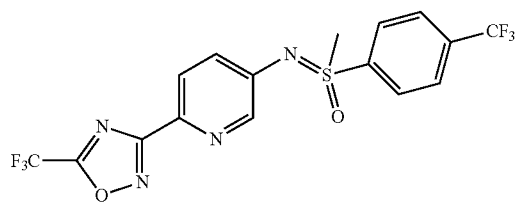 [SMILES: CS(=O)(=Nc1ccc(-c2noc(C(F)(F)F)n2)nc1)c1ccc(C(F)(F)F)cc1] | 0.3 g, 66% yield |
| 125 | (2-fluorophenyl)(methyl)((6-(5-(trifluoromethyl)-1,2,4-oxadiazol-3-yl)pyridin-3-yl)imino)-λ⁶-sulfanone | 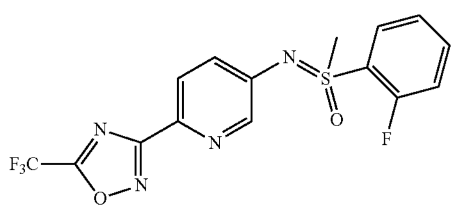 [SMILES: CS(=O)(=Nc1ccc(-c2noc(C(F)(F)F)n2)nc1)c1ccccc1F] | 0.5 g, 73% yield |
| 126 | (4-fluorobenzyl)(methyl)((6-(5-(trifluoromethyl)-1,2,4-oxadiazol-3-yl)pyridin-3-yl)imino)-λ⁶-sulfanone | 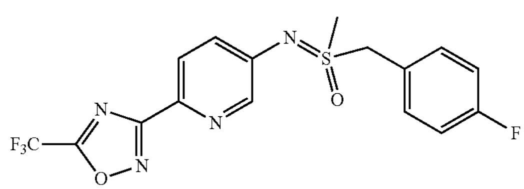 [SMILES: CS(=O)(Cc1ccc(F)cc1)=Nc1ccc(-c2noc(C(F)(F)F)n2)nc1] | 0.4 g, 63% yield |
| 127 | (3-methoxyphenyl)(methyl)((6-(5-(trifluoromethyl)-1,2,4-oxadiazol-3-yl)pyridin-3-yl)imino)-λ⁶-sulfanone | 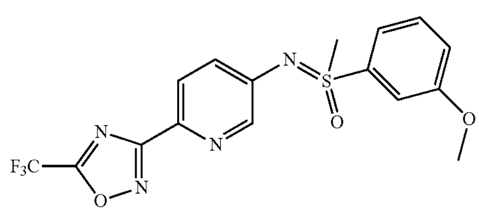 [SMILES: COc1cccc(S(C)(=O)=Nc2ccc(-c3noc(C(F)(F)F)n3)nc2)c1] | 0.3 g, 52% |
| 128 | 1-((6-(5-(trifluoromethyl)-1,2,4-oxadiazol-3-yl)pyridin-3-yl)imino)hexahydro-1λ⁶-thiopyran 1-oxide | 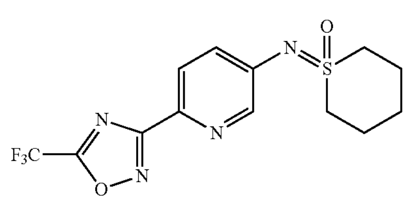 [SMILES: O=S1(=Nc2ccc(-c3noc(C(F)(F)F)n3)nc2)CCCCC1] | 0.4 g, 56% |
| 129 | 4-((6-(5-(trifluoromethyl)-1,2,4-oxadiazol-3-yl)pyridin-3-yl)imino)-1,4λ⁶-oxathiane 4-oxide | 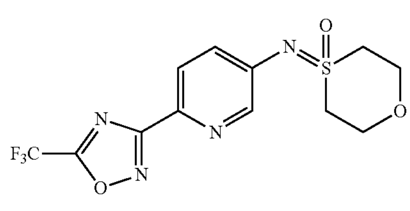 [SMILES: O=S1(=Nc2ccc(-c3noc(C(F)(F)F)n3)nc2)CCOCC1] | 0.4 g, 61% |

TABLE NO. 2-continued

The following compounds were prepared by the procedure analogous to that of the compound 12 using appropriate starting materials.

| Compound No. | IUPAC Name | Structure | Yield |
|---|---|---|---|
| 130 | methyl(p-tolyl)((4-(5-(trifluoromethyl)-1,2,4-oxadiazol-3-yl)phenyl)imino)-$\lambda^6$-sulfanone | 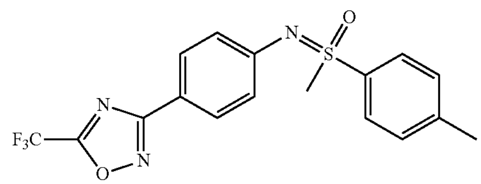 [SMILES: Cc1ccc(S(C)(=O)=Nc2ccc(-c3noc(C(F)(F)F)n3)cc2)cc1] | 0.6 g, 50% |
| 131 | (2,4-difluorophenyl)(methyl)((4-(5-(trifluoromethyl)-1,2,4-oxadiazol-3-yl)phenyl)imino)-$\lambda^6$-sulfanone | 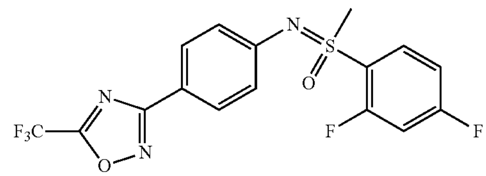 [SMILES: CS(=O)(=Nc1ccc(-c2noc(C(F)(F)F)n2)cc1)c1ccc(F)cc1F] | 0.2 g, 41% yield |
| 132 | methyl((4-(5-(trifluoromethyl)-1,2,4-oxadiazol-3-yl)phenyl)imino)(5-(trifluoromethyl)pyridin-2-yl)-$\lambda^6$-sulfanone | 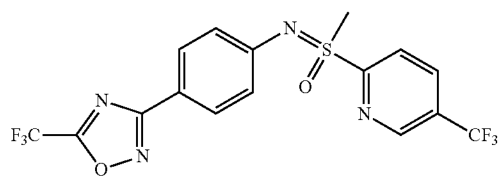 [SMILES: CS(=O)(=Nc1ccc(-c2noc(C(F)(F)F)n2)cc1)c1ccc(C(F)(F)F)cn1] | 0.3 g, 68% yield |
| 133 | 4-((4-(5-(trifluoromethyl)-1,2,4-oxadiazol-3-yl)phenyl)imino)-1,4$\lambda^6$-oxathiane 4-oxide | 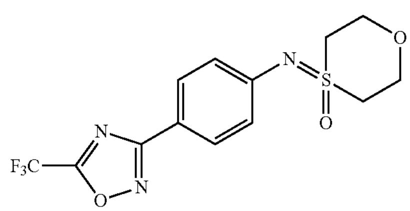 [SMILES: O=S1(=Nc2ccc(-c3noc(C(F)(F)F)n3)cc2)CCOCC1] | 0.1 g, 35% yield |
| 134 | 1-((4-(5-(trifluoromethyl)-1,2,4-oxadiazol-3-yl)phenyl)imino)hexahydro-1$\lambda^6$-thiopyran 1-oxide | 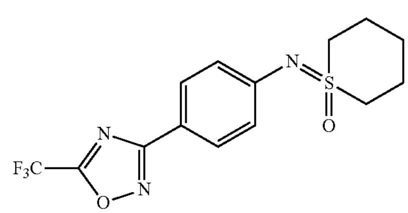 [SMILES: O=S1(=Nc2ccc(-c3noc(C(F)(F)F)n3)cc2)CCCCC1] | 0.5 g, 78% yield |
| 135 | methyl(4-(5-(trifluoromethyl)-1,2,4-oxadiazol-3-yl)phenyl)((4-(5-(trifluoromethyl)-1,2,4-oxadiazol-3-yl)phenyl)imino)-$\lambda^6$-sulfanone | 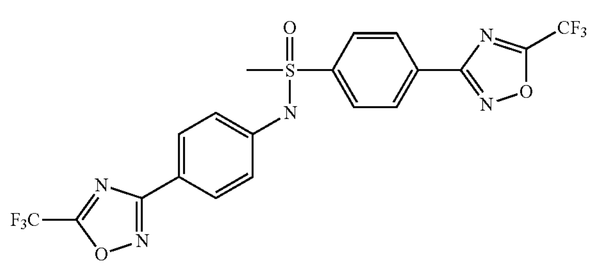 | 0.5 g, 61% yield |
| 136 | methyl(4-(5-(trifluoromethyl)-1,2,4-oxadiazol-3-yl)phenyl)((3-(5-(trifluoromethyl)-1,2,4-oxadiazol-3-yl)phenyl)imino)-$\lambda^6$-sulfanone | 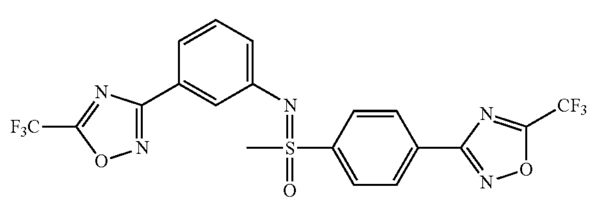 [SMILES: CS(=O)(=Nc1cccc(-c2noc(C(F)(F)F)n2)c1)c1ccc(-c2noc(C(F)(F)F)n2)cc1] | 0.1 g, 31% yield |

TABLE NO. 2-continued

The following compounds were prepared by the procedure analogous to that of the compound 12 using appropriate starting materials.

| Compound No. | IUPAC Name | Structure | Yield |
|---|---|---|---|
| 209 | (2-methoxyethyl)(methyl)((4-(5-(trifluoromethyl)-1,2,4-oxadiazol-3-yl)phenyl)imino)-$\lambda^6$-sulfanone | 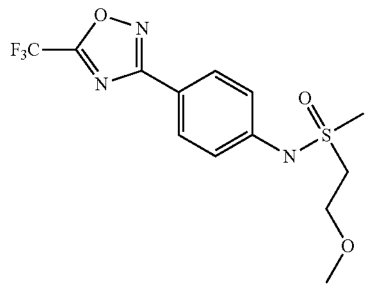 | 0.2 g, 51% |
| 210 | isopropyl(methyl)((4-(5-(trifluoromethyl)-1,2,4-oxadiazol-3-yl)phenyl)imino)-$\lambda^6$-sulfanone | 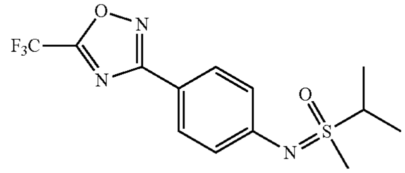 [SMILES: CC(C)S(C)(=O)=Nc1ccc(-c2noc(C(F)(F)F)n2)cc1] | 0.3 g, 53% |
| 211 | methyl(propyl)((4-(5-(trifluoromethyl)-1,2,4-oxadiazol-3-yl)phenyl)imino)-$\lambda^6$-sulfanone | 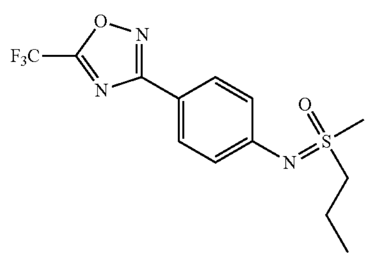 [SMILES: CCCS(C)(=O)=Nc1ccc(-c2noc(C(F)(F)F)n2)cc1] | 0.2 g, 61% |
| 212 | ethyl(methyl)((4-(5-(trifluoromethyl)-1,2,4-oxadiazol-3-yl)phenyl)imino)-$\lambda^6$-sulfanone | 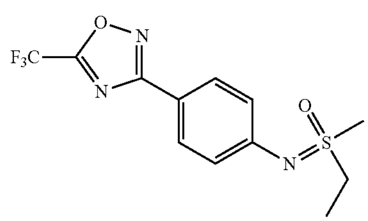 [SMILES: CCS(C)(=O)=Nc1ccc(-c2noc(C(F)(F)F)n2)cc1] | 0.2 g, 52% |
| 213 | ((3-fluoro-4-(5-(trifluoromethyl)-1,2,4-oxadiazol-3-yl)phenyl)imino)(2-fluorophenyl)(methyl)-$\lambda^6$-sulfanone | 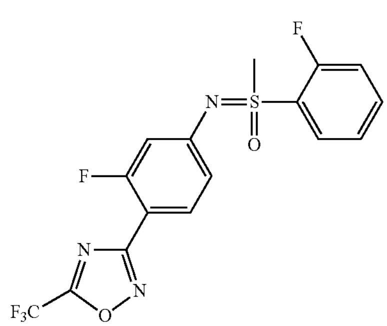 [SMILES: CS(=O)(=Nc1ccc(-c2noc(C(F)(F)F)n2)c(F)c1)c1ccccc1F] | 0.3 g, 48% |

TABLE NO. 2-continued

The following compounds were prepared by the procedure analogous to that of the compound 12 using appropriate starting materials.

| Compound No. | IUPAC Name | Structure | Yield |
|---|---|---|---|
| 214 | ((3-fluroo-4-(5-(trifluoromethyl)-1,2,4-oxadiazol-3-yl)phenyl)imino)(methyl)(phenyl)-$\lambda^6$-sulfanone | 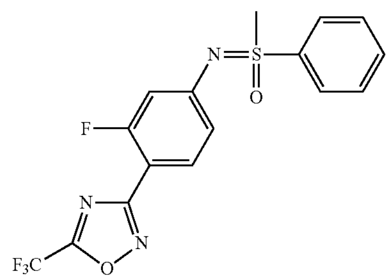 [SMILES: CS(=O)(=Nc1ccc(-c2noc(C(F)(F)F)n2)c(F)c1)c1ccccc1] | 0.4 g, 62% |
| 215 | ((3-fluoro-4-(5-(trifluoromethyl)-1,2,4-oxadiazol-3-yl)phenyl)imino)(methyl)(pyridin-2-yl)-$\lambda^6$-sulfanone | 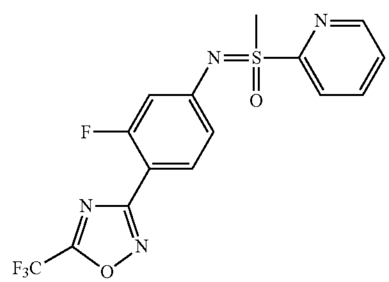 [SMILES: CS(=O)(=Nc1ccc(-c2noc(C(F)(F)F)n2)c(F)c1)c1ccccn1] | 0.1 g, 21% |
| 216 | ((3-methoxy-4-(5-(trifluoromethyl)-1,2,4-oxadiazol-3-yl)phenyl)imino)(methyl)(phenyl)-$\lambda^6$-sulfanone | 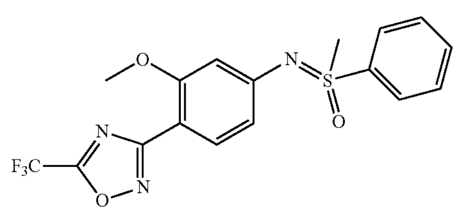 [SMILES: COc1cc(N=S(C)(=O)c2ccccc2)ccc1-c1noc(C(F)(F)F)n1] | 0.2 g 27% |
| 217 | (2-fluorophenyl)((3-methoxy-4-(5-(trifluoromethyl)-1,2,4-oxadiazol-3-yl)phenyl)imino)(methyl)-$\lambda^6$-sulfanone | 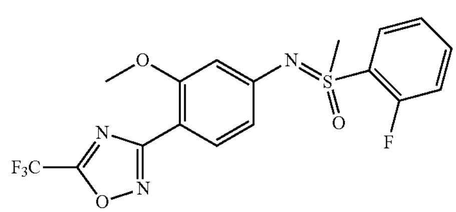 [SMILES: COc1cc(N=S(C)(=O)c2ccccc2F)ccc1-c1noc(C(F)(F)F)n1] | 0.3 g, 56% |
| 218 | ((3-methoxy-4-(5-(trifluoromethyl)-1,2,4-oxadiazol-3-yl)phenyl)imino)(4-methoxyphenyl)(methyl)-$\lambda^6$-sulfanone | 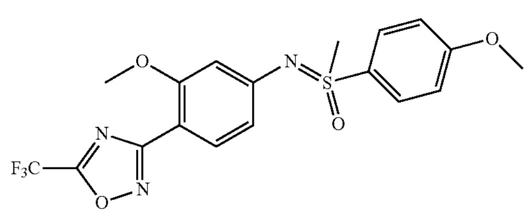 [SMILES: COc1ccc(S(C)(=O)=Nc2ccc(-c3noc(C(F)(F)F)n3)c(OC)c2)cc1] | 0.3 g, 60% |
| 219 | ((3-methoxy-4-(5-(trifluoromethyl)-1,2,4-oxadiazol-3-yl)phenyl)imino)(methyl)(propyl)-$\lambda^6$-sulfanone | 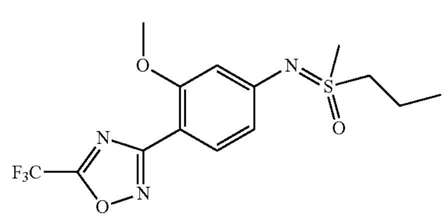 [SMILES: CCCS(C)(=O)=Nc1ccc(-c2noc(C(F)(F)F)n2)c(OC)c1] | 0.4 g, 65% |

TABLE NO. 2-continued

The following compounds were prepared by the procedure analogous to that of the compound 12 using appropriate starting materials.

| Compound No. | IUPAC Name | Structure | Yield |
|---|---|---|---|
| 220 | ((3-methoxy-4-(5-(trifluoromethyl)-1,2,4-oxadiazol-3-yl)phenyl)imino)(methyl)(pyridin-2-yl)-$\lambda^6$-sulfanone | 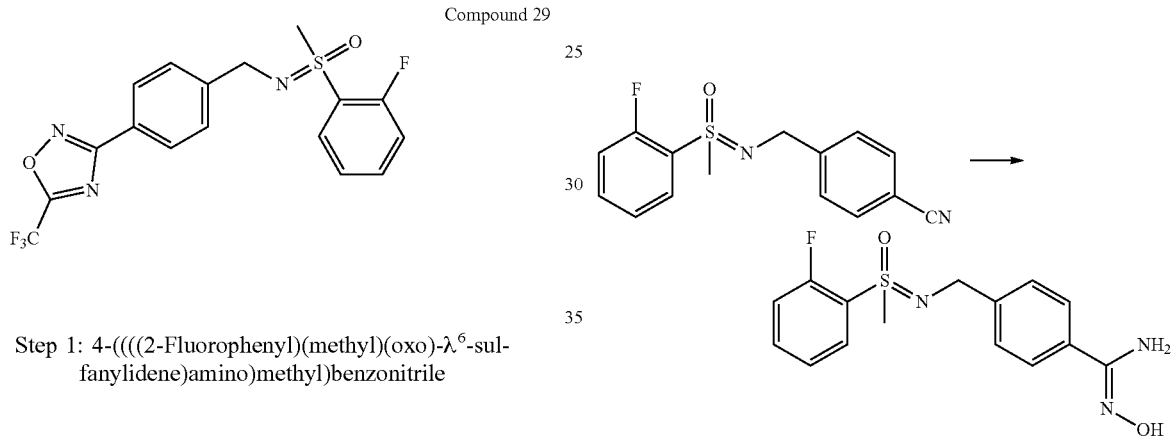 | 0.3 g, 47% |

Example-3: Preparation of (2-fluorophenyl)(methyl)((4-(5-(trifluoromethyl)-1,2,4-oxadiazol-3-yl)benzyl)imino)-$\lambda^6$-sulfanone (Compound 29)

Compound 29

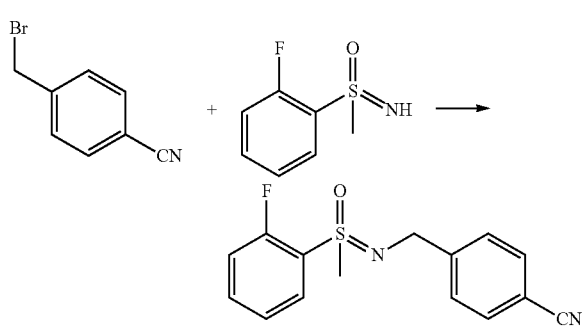

Step 1: 4-((((2-Fluorophenyl)(methyl)(oxo)-$\lambda^6$-sulfanylidene)amino)methyl)benzonitrile To a stirred solution of (2-fluorophenyl)(imino)(methyl)-6-sulfanone (0.3 g, 1.7 mmol)) in N, N-dimethyl formamide (8 mL), potassium tert-butoxide (0.4 g, 3.5 mmol) was added at 0° C. under nitrogen atmosphere. The resulting reaction mixture was stirred at 25° C. for 15 minutes and again cooled to 0° C. Then added 4-(bromomethyl)benzonitrile (0.4 g, 2.1 mmol) and reaction mixture was stirred at 25° C. for 30 minutes. Saturated aqueous ammonium chloride solution (10 mL) and ethyl acetate (40 mL) were added to the reaction mixture and stirred at 0° C. for 10 minutes. The ethyl acetate layer was isolated, washed with water (20 mL), dried over anhydrous sodium sulphate and concentrated under reduced pressure to obtain 4-((((2-fluorophenyl)(methyl)(oxo)-$\lambda^6$-sulfanylidene)amino)methyl)benzonitrile (0.5 g, 1.7 mmol, 96% yield).

Step 2: (Z)-4-((((2-Fluorophenyl)(methyl)(oxo)-$\lambda^6$-sulfanylidene)amino)methyl)-N'-hydroxybenzimidamiden To a stirred solution of 4-((((2-fluorophenyl)(methyl)(oxo)-$\lambda^6$-sulfanylidene)amino)methyl)benzonitrile (0.5 g, 1.7 mmol) in ethanol (12 mL), hydroxylamine hydrochloride (0.2 g, 3.0 mmol) and sodium bicarbonate (0.3 g, 3.3 mmol) were added at 25° C. The resulting reaction mixture was heated to 65° C. for 12 h. After completion of the reaction, the reaction mixture was filtered through sintered funnel. The filtrate was evaporated under reduced pressure to obtain 4-((((2-fluorophenyl)(methyl)(oxo)-$\lambda^6$-sulfanylidene)amino)methyl)-N'-hydroxybenzimidamide (0.5 g).

Step 3: (2-fluorophenyl)(methyl)((4-(5-(trifluoromethyl)-1,2,4-oxadiazol-3-yl)benzyl)imino)-$\lambda^6$-sulfanone

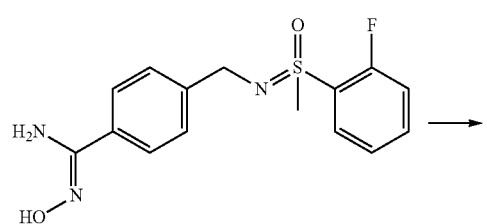

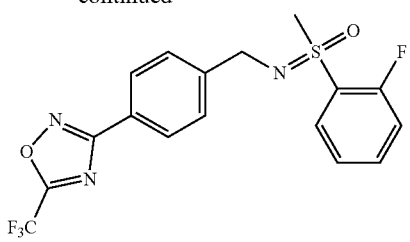

To a stirred solution of 4-(((((2-fluorophenyl)(methyl)(oxo)-λ⁶-sulfanylidene)amino)methyl)-N'-hydroxybenzimidamide (0.5 g, 1.6 mmol)) in tetrahydrofuran (10 mL), trifluoroacetic acid (0.2 mL, 1.6 mmol)) was added at 0° C. under nitrogen atmosphere. The resulting reaction mixture was stirred at 25° C. for 16 h. After completion of the reaction, the reaction mixture was diluted with ethyl acetate (30 mL) and washed three times with water (15 mL). The ethyl acetate layer was washed with aqueous saturated sodium bicarbonate (30 mL) solution, dried over anhydrous sodium sulphate and concentrated under reduced pressure. The crude residue was purified by column chromatography (eluent-hexane to 25% ethyl acetate in hexane) on silica gel to obtain (2-fluorophenyl)(methyl)((4-(5-(trifluoromethyl)-1,2,4-oxadiazol-3-yl)benzyl)imino)-λ⁶-sulfanone as a gum (0.2 g, 0.5 mmol, 28% yield).

TABLE NO. 3

The following compounds were prepared by the procedure analogous to that of the compound no. 29 using appropriate starting materials.

| Compound No. | IUPAC Name | Structure | Yield |
|---|---|---|---|
| 22 | (4-bromophenyl)(methyl)((4-(5-(trifluoromethyl)-1,2,4-oxadiazol-3-yl)benzyl)imino)-λ⁶-sulfanone | 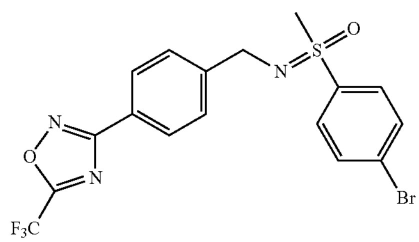 [SMILES: CS(=O)(=NCc1ccc(-c2noc(C(F)(F)F)n2)cc1)c1ccc(Br)cc1] | 135 mg, 24% yield |
| 23 | (4-methoxyphenyl)(methyl)((4-(5-(trifluoromethyl)-1,2,4-oxadiazol-3-yl)benzyl)imino)-λ⁶-sulfanone | 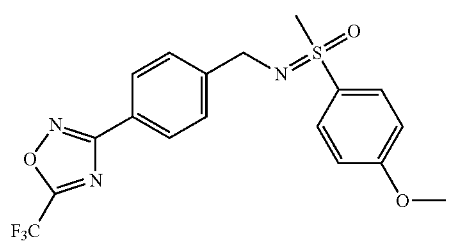 [SMILES: COc1ccc(S(C)(=O)=NCc2ccc(-c3noc(C(F)(F)F)n3)cc2)cc1] | 365 mg, 58% yield |
| 24 | methyl(4-(trifluoromethoxy)phenyl)((4-(5-(trifluoromethyl)-1,2,4-oxadiazol-3-yl)benzyl)imino)-λ⁶-sulfanone | 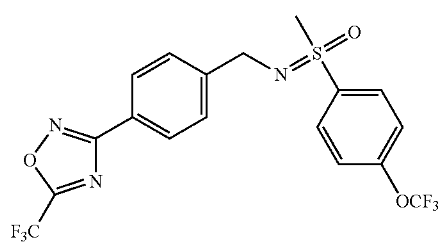 [SMILES: CS(=O)(=NCc1ccc(-c2noc(C(F)(F)F)n2)cc1)c1ccc(OC(F)(F)F)cc1] | 61 mg, 11% yield |
| 25 | methyl((4-(5-(trifluoromethyl)-1,2,4-oxadiazol-3-yl)benzyl)imino)(4-(trifluoromethyl)phenyl)-λ⁶-sulfanone | 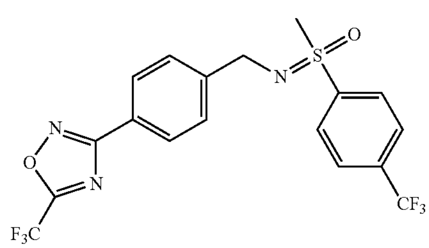 [SMILES: CS(=O)(=NCc1ccc(-c2noc(C(F)(F)F)n2)cc1)c1ccc(C(F)(F)F)cc1] | 125 mg, 22% yield |

TABLE NO. 3-continued

The following compounds were prepared by the procedure analogous to that of the compound no. 29 using appropriate starting materials.

| Compound No. | IUPAC Name | Structure | Yield |
|---|---|---|---|
| 26 | methyl(phenyl)((4-(5-(trifluoromethyl)-1,2,4-oxadiazol-3-yl)benzyl)imino)-λ⁶-sulfanone | 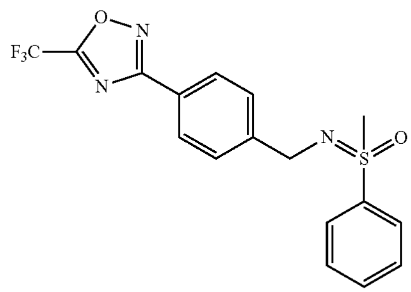 [SMILES: CS(=O)(=NCc1ccc(-c2noc(C(F)(F)F)n2)cc1)c1ccccc1] | 0.3 g, 36% yield |
| 27 | methyl(pyridin-2-yl)((4-(5-(trifluoromethyl)-1,2,4-oxadiazol-3-yl)benzyl)imino)-λ⁶-sulfanone | 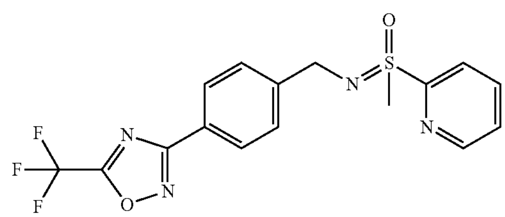 [SMILES: CS(=O)(=NCc1ccc(-c2noc(C(F)(F)F)n2)cc1)c1ccccn1] | 0.2 g, 35% yield |
| 28 | (4-chlorophenyl)(methyl)((4-(5-(trifluoromethyl)-1,2,4-oxadiazol-3-yl)benzyl)imino)-λ⁶-sulfanone | 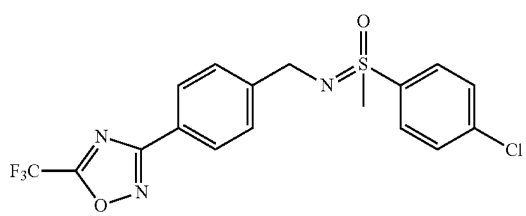 [SMILES: CS(=O)(=NCc1ccc(-c2noc(C(F)(F)F)n2)cc1)c1ccc(Cl)cc1] | 0.2 g 47% yield |
| 137 | methyl(p-tolyl)((4-(5-(trifluoromethyl)-1,2,4-oxadiazol-3-yl)benzyl)imino)-λ⁶-sulfanone | 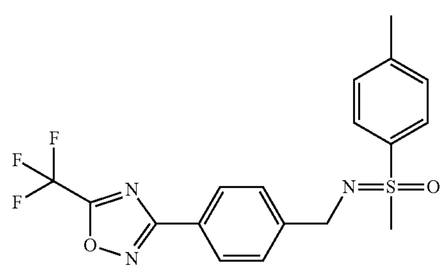 [SMILES: Cc1ccc(S(C)(=O)=NCc2ccc(-c3noc(C(F)(F)F)n3)cc2)cc1] | 0.1 g, 9% yield |
| 138 | methyl(phenyl)((3-(5-(trifluoromethyl)-1,2,4-oxadiazol-3-yl)benzyl)imino)-λ⁶-sulfanone | 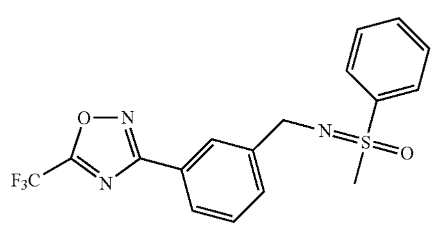 [SMILES: CS(=O)(=NCc1cccc(-c2noc(C(F)(F)F)n2)c1)c1ccccc1] | 0.2 g, 31% yield |
| 139 | (4-methoxyphenyl)(methyl)((3-(5-(trifluoromethyl)-1,2,4-oxadiazol-3-yl)benzyl)imino)-λ⁶-sulfanone | 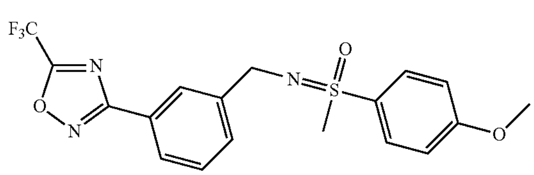 [SMILES: COc1ccc(S(C)(=O)=NCc2cccc(-c3noc(C(F)(F)F)n3)c2)cc1] | 0.4 g, 51% yield |

TABLE NO. 3-continued

The following compounds were prepared by the procedure analogous to that of the compound no. 29 using appropriate starting materials.

| Compound No. | IUPAC Name | Structure | Yield |
|---|---|---|---|
| 140 | (2,4-dimethoxyphenyl)(methyl)((3-(5-(trifluoromethyl)-1,2,4-oxadiazol-3-yl)benzyl)imino)-sulfanone | 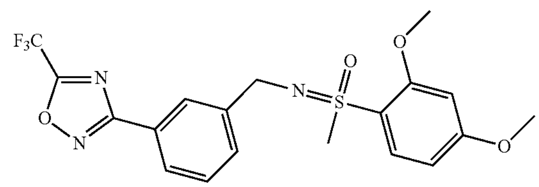 [SMILES: COc1ccc(S(C)(=O)=NCc2cccc(-c3noc(C(F)(F)F)n3)c2)c(OC)c1] | 0.3 g, 44% yield |
| 141 | (3,4-difluorophenyl)(methyl)((3-(5-(trifluoromethyl)-1,2,4-oxadiazol-3-yl)benzyl)imino)-sulfanone | 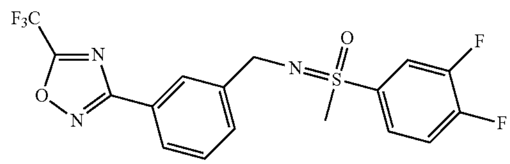 [SMILES: CS(=O)(=NCc1cccc(-c2noc(C(F)(F)F)n2)c1)c1ccc(F)c(F)c1] | 0.3, 43% yield |
| 142 | methyl((3-(5-(trifluoromethyl)-1,2,4-oxadiazol-3-yl)benzyl)imino)(4-((4-(trifluoromethyl)pyridin-2-yl)oxy)phenyl)-$\lambda^6$-sulfanone | 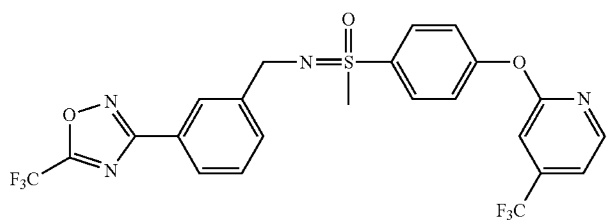 [SMILES: CS(=O)(=NCc1cccc(-c2noc(C(F)(F)F)n2)c1)c1ccc(Oc2cc(C(F)(F)F)ccn2)cc1] | 0.4 g, 79% yield |
| 143 | (4-chlorophenyl)(methyl)((3-(5-(trifluoromethyl)-1,2,4-oxadiazol-3-yl)benzyl)imino)-$\lambda^6$-sulfanone | 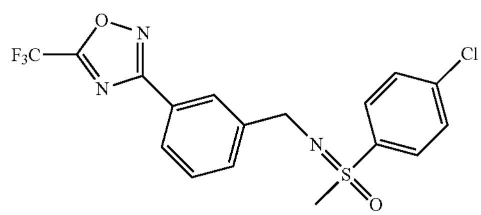 [SMILES: CS(=O)(=NCc1cccc(-c2noc(C(F)(F)F)n2)c1)c1ccc(Cl)cc1] | 0.2 g, 56% yield |
| 144 | methyl(thiazol-2-yl)((3-(5-(trifluoromethyl)-1,2,4-oxadiazol-3-yl)benzyl)imino)-$\lambda^6$-sulfanone | 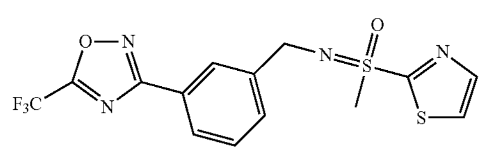 [SMILES: CS(=O)(=NCc1cccc(-c2noc(C(F)(F)F)n2)c1)c1nccs1] | 0.3 g, 57% yield |
| 145 | (4-fluorophenyl)(methyl)((3-(5-(trifluoromethyl)-1,2,4-oxadiazol-3-yl)benzyl)imino)-$\lambda^6$-sulfanone | 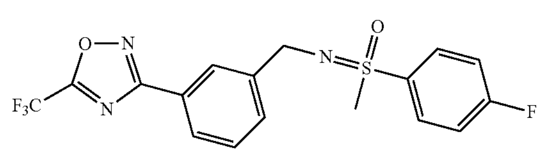 [SMILES: CS(=O)(=NCc1cccc(-c2noc(C(F)(F)F)n2)c1)c1ccc(F)cc1] | 0.3 g, 53% yield |
| 146 | (2-bromo-5-fluorophenyl)(methyl)((3-(5-(trifluoromethyl)-1,2,4-oxadiazol-3-yl)benzyl)imino)-$\lambda^6$-sulfanone | 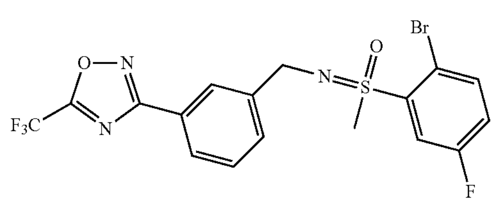 [SMILES: CS(=O)(=NCc1cccc(-c2noc(C(F)(F)F)n2)c1)c1cc(F)ccc1Br] | 0.5 g, 65% yield |
| 147 | (4-bromo-2-fluorophenyl)(methyl)((3-(5-(trifluoromethyl)-1,2,4-oxadiazol-3-yl)benzyl)imino)-$\lambda^6$-sulfanone | 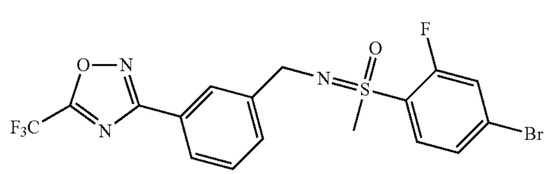 [SMILES: CS(=O)(=NCc1cccc(-c2noc(C(F)(F)F)n2)c1)c1ccc(Br)cc1F] | 0.2 g, 42% yield |

TABLE NO. 3-continued

The following compounds were prepared by the procedure analogous to that of the compound no. 29 using appropriate starting materials.

| Compound No. | IUPAC Name | Structure | Yield |
|---|---|---|---|
| 148 | (2-fluorophenyl)(methyl)((3-(5-(trifluoromethyl)-1,2,4-oxadiazol-3-yl)benzyl)imino)-$\lambda^6$-sulfanone | 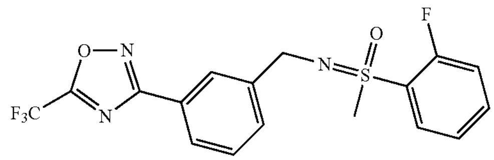 [SMILES: CS(=O)(=NCc1cccc(-c2noc(C(F)(F)F)n2)c1)c1ccccc1F] | 0.2 g, 38% yield |
| 149 | 4-((3-(5-(trifluoromethyl)-1,2,4-oxadiazol-3-yl)benzyl)imino)-1,4$\lambda^6$-oxathiane 4-oxide | 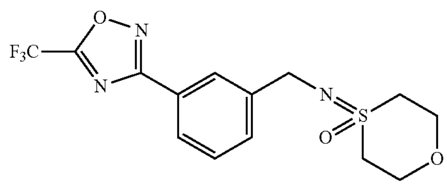 [SMILES: O=S1(=NCc2cccc(-c3noc(C(F)(F)F)n3)c2)CCOCC1] | 0.3 g, 67% yield |
| 150 | isopropyl(4-methoxyphenyl)((4-(5-(trifluoromethyl)-1,2,4-oxadiazol-3-yl)benzyl)imino)-$\lambda^6$-sulfanone | 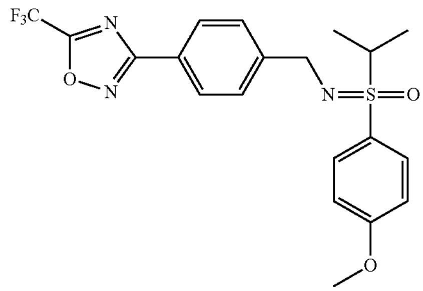 [SMILES: COc1ccc(S(=O)(=NCc2ccc(-c3noc(C(F)(F)F)n3)cc2)C(C)C)cc1] | 0.2 g, 42% yield |
| 151 | isopropyl(phenyl)((4-(5-(trifluoromethyl)-1,2,4-oxadiazol-3-yl)benzyl)imino)-$\lambda^6$-sulfanone | 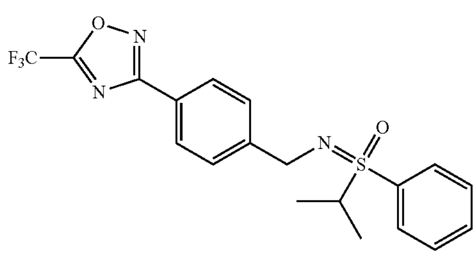 [SMILES: CC(C)S(=O)(=NCc1ccc(-c2noc(C(F)(F)F)n2)cc1)c1ccccc1] | 0.2 g, 40% yield |
| 152 | (4-chlorophenyl)(isopropyl)((4-(5-(trifluoromethyl)-1,2,4-oxadiazol-3-yl)benzyl)imino)-$\lambda^6$-sulfanone | 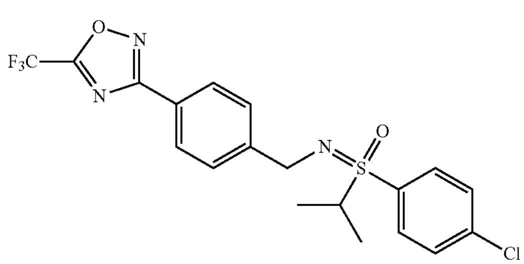 [SMILES: CC(C)S(=O)(=NCc1ccc(-c2noc(C(F)(F)F)n2)cc1)c1ccc(Cl)cc1] | 0.2 g, 38% yield |

Example 4:—Preparation of N-((2-fluorophenyl)sulfonyl)-4-(5-(trifluoromethyl)-1,2,4-oxadiazol-3-yl)benzamide (compound no. 155)

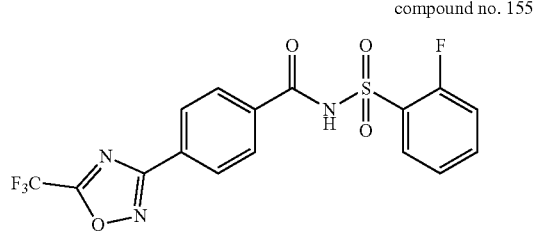 [SMILES: O=C(NS(=O)(=O)c1ccccc1F)c1ccc(-c2noc(C(F)(F)F)n2)cc1]
compound no. 155

Step-1:—2-fluorobenzenesulfonamide

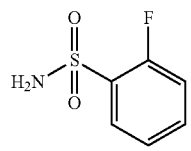 [SMILES: NS(=O)(=O)c1ccccc1F]

To a stirred solution of 25% aqueous ammonia (1.1 mL, 12.8 mmol) in tetrahydrofuran (5 mL), 2-fluorobenzenesulfonyl chloride (0.3 g, 1.3 mmol) was added at 0-5° C. The resulting reaction mixture was stirred at 25° C. for 16 h. Sodium bicarbonate (0.16 g, 1.9 mmol) was added and stirred at 25° C. for 10 minutes. The reaction mixture was concentrated to obtain 2-fluorobenzenesulfonamide (0.2 g, 1.3 mmol, 98% yield).

Step-2:—N-((2-fluorophenyl)sulfonyl)-4-(5-(trifluoromethyl)-1,2,4-oxadiazol-3-yl)benzamide (compound no. 155)

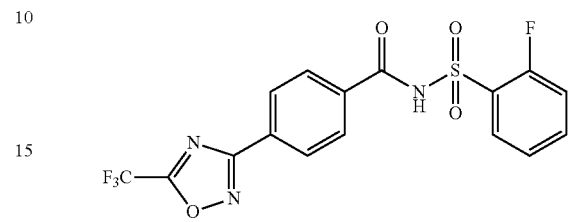

To a stirred solution of 4-(5-(trifluoromethyl)-1,2,4-oxadiazol-3-yl)benzoic acid (0.3 g, 1.0 mmol) in dry N,N-dimethylformamide (5 mL) under nitrogen atmosphere, 1-(3-Dimethylaminopropyl)-3-ethylcarbodiimide hydrochloride (0.4 g, 2.0 mmol) was added followed by the addition of 4-dimethylaminopyridine (0.2 g, 2.0 mmol) and 2-fluorobenzenesulfonamide (0.2 g, 1.0 mmol) at 25° C. The resulting reaction mixture was stirred for 12 h at 25° C. After completion of the reaction, the reaction mixture was diluted with dichloromethane (30 mL) and washed thrice with water (20 mL). Dichloromethane layer was dried over anhydrous sodium sulphate. The volatiles were evaporated under vacuum. Crude residue was purified by preparative HPLC to obtain N-((2-fluorophenyl)sulfonyl-4-(5-(trifluoromethyl)-1,2,4-oxadiazol-3-yl)benzamide (0.2 g, 35% yield).

TABLE NO. 4

The following compounds were prepared the procedure analogous to that of the Compound 155 using appropriate starting materials.

| Compound No. | IUPAC Name | Structure | Yield |
|---|---|---|---|
| 153 | N-tosyl-4-(5-(trifluoromethyl)-1,2,4-oxadiazol-3-yl)benzamide | 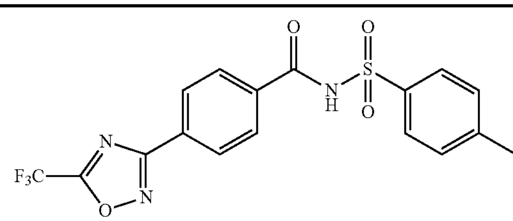 | 0.1 g, 24% yield |
| 154 | N-((5-chloro-2-methoxyphenyl)sulfonyl)-4-(5-(trifluoromethyl)-1,2,4-oxadiazol-3-yl)benzamide | 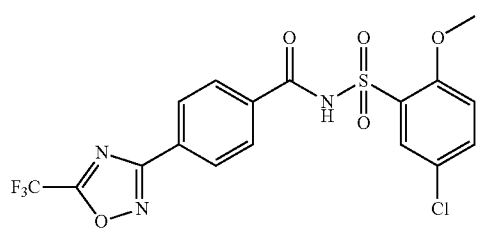 [SMILES: COc1ccc(Cl)cc1S(=O)(=O)NC(=O)c1ccc(-c2noc(C(F)(F)F)n2)cc1] | 0.2 g, 44% yield |
| 156 | N-((2,4-dichlorophenyl)sulfonyl)-4-(5-(trifluoromethyl)-1,2,4-oxadiazol-3-yl)benzamide | 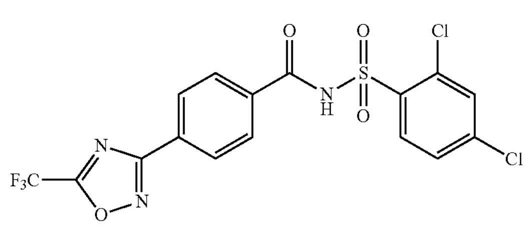 [SMILES: O=C(NS(=O)(=O)c1ccc(Cl)cc1Cl)c1ccc(-c2noc(C(F)(F)F)n2)cc1] | 0.3 g, 57% yield |

TABLE NO. 4-continued

The following compounds were prepared the procedure analogous to that of the Compound 155 using appropriate starting materials.

| Compound No. | IUPAC Name | Structure | Yield |
|---|---|---|---|
| 157 | N-((4-methoxyphenyl)sulfonyl)-4-(5-(trifluoromethyl)-1,2,4-oxadiazol-3-yl)benzamide | 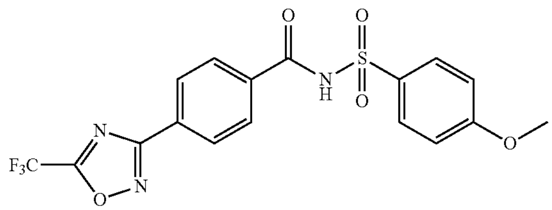 [SMILES: COc1ccc(S(=O)(=O)NC(=O)c2ccc(-c3noc(C(F)(F)F)n3)cc2)cc1] | 0.1 g, 16% yield |
| 158 | N-((3-methoxyphenyl)sulfonyl)-4-(5-(trifluoromethyl)-1,2,4-oxadiazol-3-yl)benzamide | 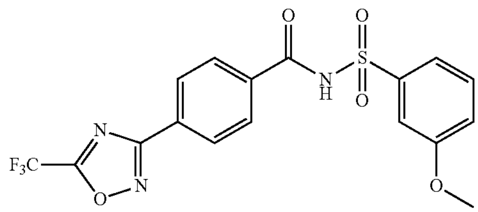 [SMILES: COc1cccc(S(=O)(=O)NC(=O)c2ccc(-c3noc(C(F)(F)F)n3)cc2)c1] | 0.1 g, 26% yield |
| 159 | 4-(5-(trifluoromethyl)-1,2,4-oxadiazol-3-yl)-N-((4-(trifluoromethyl)phenyl)sulfonyl)benzamide | 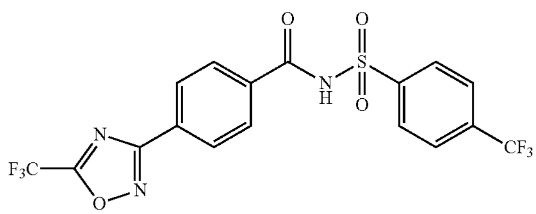 [SMILES: O=C(NS(=O)(=O)c1ccc(C(F)(F)F)cc1)c1ccc(-c2noc(C(F)(F)F)n2)cc1] | 0.3 g, 56% yield |
| 160 | N-(pyridin-3-ylsulfonyl)-4-(5-(trifluoromethyl)-1,2,4-oxadiazol-3-yl)benzamide | 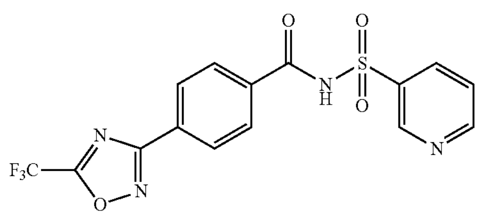 [SMILES: O=C(NS(=O)(=O)c1cccnc1)c1ccc(-c2noc(C(F)(F)F)n2)cc1] | 0.2 g, 29% yield |
| 161 | N-((2,5-difluorophenyl)sulfonyl)-4-(5-(trifluoromethyl)-1,2,4-oxadiazol-3-yl)benzamide | 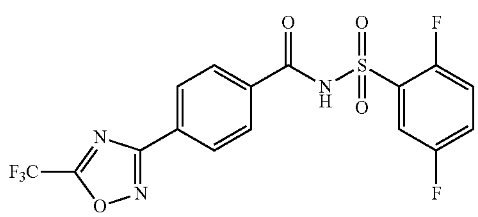 [SMILES: O=C(NS(=O)(=O)c1cc(F)ccc1F)c1ccc(-c2noc(C(F)(F)F)n2)cc1] | 0.2 g, 41% yield |
| 167 | N-((4-bromophenyl)sulfonyl)-4-(5-(trifluoromethyl)-1,2,4-oxadiazol-3-yl)benzamide | 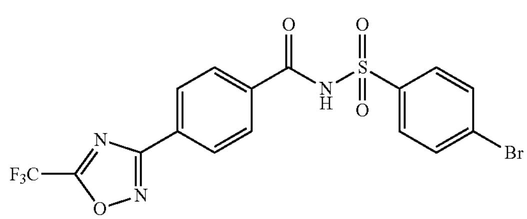 [SMILES: O=C(NS(=O)(=O)c1ccc(Br)cc1)c1ccc(-c2noc(C(F)(F)F)n2)cc1] | 0.2 g, 43% yield |
| 163 | N-((2,6-dichlorophenyl)sulfonyl)-4-(5-(trifluoromethyl)-1,2,4-oxadiazol-3-yl)benzamide | 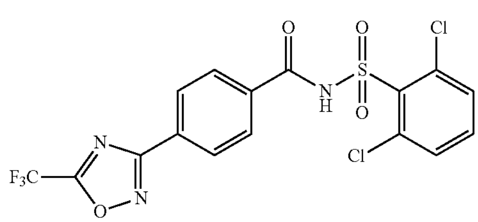 [SMILES: O=C(NS(=O)(=O)c1c(Cl)cccc1Cl)c1ccc(-c2noc(C(F)(F)F)n2)cc1] | 0.2 g, 47% yield |

TABLE NO. 4-continued

The following compounds were prepared the procedure analogous to that of the Compound 155 using appropriate starting materials.

| Compound No. | IUPAC Name | Structure | Yield |
|---|---|---|---|
| 164 | N-((3-fluorophenyl)sulfonyl)-4-(5-(trifluoromethyl)-1,2,4-oxadiazol-3-yl)benzamide | 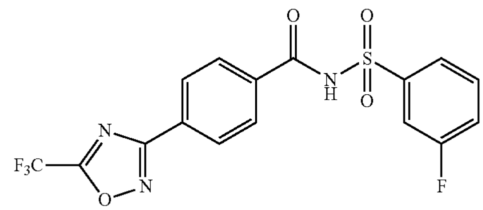 [SMILES: O=C(NS(=O)(=O)c1cccc(F)c1)c1ccc(-c2noc(C(F)(F)F)n2)cc1] | 0.3 g, 52% yield |

Example 5:—Preparation of ((2-fluoro-4(5(trifluromethyl)-1,2,4-oxadiazol-3-yl)phenyl)imino)(2-fluorphenyl)(methyl)-$\lambda^6$-sulfanone (Compound no. 165)

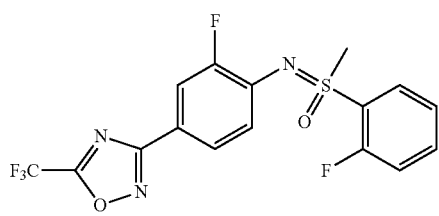 [SMILES: CS(=O)(=Nc1ccc(-c2noc(C(F)(F)F)n2)cc1F)c1ccccc1F]

Step 1:—3-Fluoro-4-(((2-fluorophenyl)(methyl)(oxo)-$\lambda^6$-sulfaneylidene)amino)benzonitrile

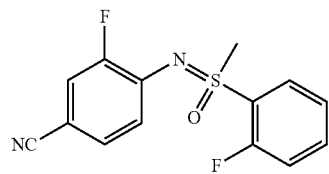 [SMILES: CS(=O)(=Nc1ccc(C#N)cc1F)c1ccccc1F]

To a stirred solution of (2-fluorophenyl)(imino)(methyl)-$\lambda^6$-sulfanone (0.4 g, 2.3 mmol) in N,N-dimethylformamide (8 mL), potassium tert-butoxide (0.3 g, 28 mmol) was added at 0° C. and allowed to stir at 25° C. for 10 minutes. The reaction mixture was cooled again to 0° C. and 3,4-difluorobenzonitrile (0.3 g, 2.3 mmol) was added. The stirring was continued at 25° C. for 4 h. The reaction mixture was diluted with ethyl acetate (60 mL) and washed twice with water (20 mL). The obtained crude product was purified by flash column chromatography on silica gel using hexane to 50% ethyl acetate in hexane as an eluent to obtain pure 3-fluoro-4-(((2-fluorophenyl)(methyl)(oxo)-$\lambda^6$-sulfanylidene)amino) benzonitrile (0.5 g, 1.6 mmol, 71% yield).

Step 2:—3-Fluoro-4-(((2-fluorophenyl)(methyl)(oxo)-$\lambda^6$-sulfanylidene)amino)-N'-hydroxybenzimidamide

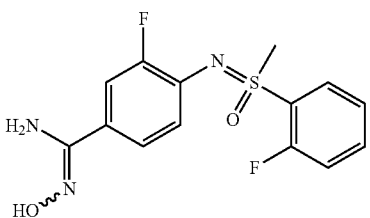 [SMILES: CS(=O)(=Nc1ccc(C(N)=NO)cc1F)c1ccccc1F]

To a stirred solution of 3-fluoro-4-(((2-fluorophenyl)(methyl)(oxo)-$\lambda^6$-sulfanylidene)amino)benzonitrile (0.5 g, 1.6 mmol) in ethanol (8 mL), sodium bicarbonate (0.3 g, 3.3 mmol) and hydroxylamine hydrochloride (0.2 g, 3.3 mmol) were added at 25° C. The resulting reaction mixture was stirred at 70° C. for 16 h. The reaction mixture was filtered and the filtrate was evaporated under vacuum to obtain 3-fluoro-4-(((2-fluorophenyl)(methyl)(oxo)-$\lambda^6$-sulfanylidene)amino)-N'-hydroxybenzimidamide (0.5 g, 1.5 mmol, 90% yield)

((2-Fluoro-4-(5-(trifluoromethyl)-1,2,4-oxadiazol-3-yl)phenyl)imino)(2-fluorophenyl)(methyl)-$\lambda^6$-sulfanone

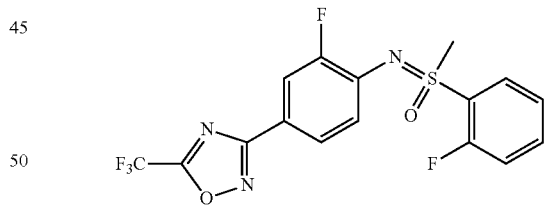

To a stirred solution of 3-fluoro-4-(((2-fluorophenyl)(methyl)(oxo)-$\lambda^6$-sulfanylidene)amino)-N'-hydroxybenzimidamide (0.5 g, 1.5 mmol) in tetrahydrofuran (8 mL), trifluoro acetic anhydride (0.3 mL, 2.2 mmol) was added slowly at 0° C. under nitrogen atmosphere and then stirred at 25° C. for 16 h. The resulting reaction mixture was diluted with ethyl acetate (50 mL). The ethyl acetate layer was washed twice with aqueous sodium bicarbonate solution (20 mL), dried over anhydrous sodium sulphate and evaporated under vacuum. Crude product was purified by flash column chromatography on silica gel using hexane to 50% ethyl acetate in hexane as an eluent to obtain ((2-fluoro-4-(5-(trifluoromethyl)-1,2,4-oxadiazol-3-yl)phenyl)imino)(2-fluorophenyl)(methyl)-$\lambda^6$-sulfanone (0.5 g, 1.2 mmol, 84% yield).

TABLE NO. 5

The following compounds were prepared by the procedure analogous to that of the Compound 165 using appropriate starting materials.

| Compound No. | IUPAC Name | Structure | Yield |
|---|---|---|---|
| 166 | ((2-fluoro-4-(5-(trifluoromethyl)-1,2,4-oxadiazol-3-yl)phenyl)imino)(2-fluorophenyl)(methyl)-$\lambda^6$-sulfanone | | 0.5 g, 84% yield |
| 166 | ((2-fluoro-4-(5-(trifluoromethyl)-1,2,4-oxadiazol-3-yl)phenyl)imino)(methyl)(phenyl)-$\lambda^6$-sulfanone | | 0.4 g, 60% yield |
| 167 | (4-chlorophenyl)((2-fluoro-4-(5-(trifluoromethyl)-1,2,4-oxadiazol-3-yl)phenyl)imino)(methyl)-$\lambda^6$-sulfanone | 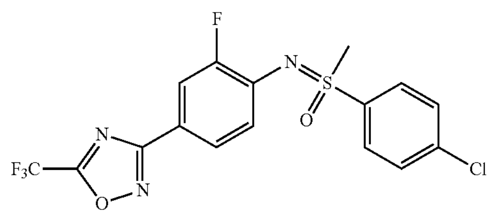 [SMILES: CS(=O)(=Nc1ccc(-c2noc(C(F)(F)F)n2)cc1F)c1ccc(Cl)cc1] | 0.4 g, 70% yield |
| 168 | ((2-fluoro-4-(5-(trifluoromethyl)-1,2,4-oxadiazol-3-yl)phenyl)imino)(methyl)(pyridin-2-yl)-$\lambda^6$-sulfanone | 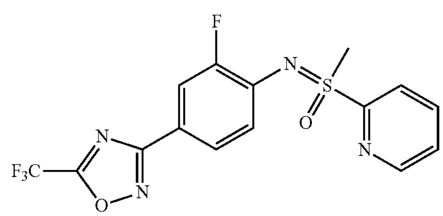 [SMILES: CS(=O)(=Nc1ccc(-c2noc(C(F)(F)F)n2)cc1F)c1ccccn1] | 0.2 g, 40% yield |
| 169 | ((2-fluoro-4-(5-(trifluoromethyl)-1,2,4-oxadiazol-3-yl)phenyl)imino)(3-fluorophenyl)(methyl)-$\lambda^6$-sulfanone | 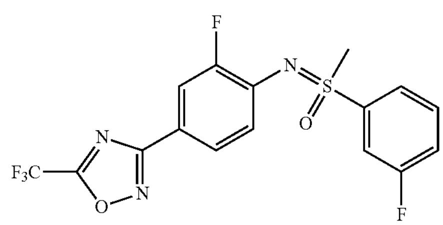 [SMILES: CS(=O)(=Nc1ccc(-c2noc(C(F)(F)F)n2)cc1F)c1cccc(F)c1] | 0.4 g, 63% yield |
| 170 | ((2-fluoro-4-(5-(trifluoromethyl)-1,2,4-oxadiazol-3-yl)phenyl)imino)(4-fluorophenyl)(methyl)-$\lambda^6$-sulfanone | 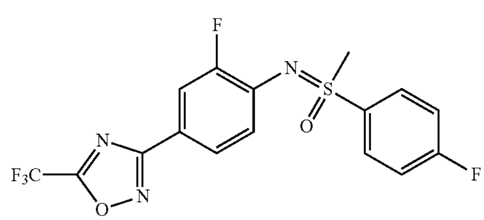 [SMILES: CS(=O)(=Nc1ccc(-c2noc(C(F)(F)F)n2)cc1F)c1ccc(F)cc1] | 0.4 g, 53% yield |
| 171 | ((2-fluoro-4-(5-(trifluoromethyl)-1,2,4-oxadiazol-3-yl)phenyl)imino)(4-methoxyphenyl)(methyl)-$\lambda^6$-sulfanone | 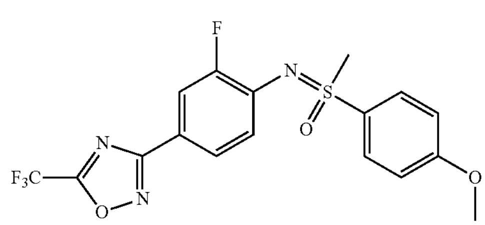 [SMILES: COc1ccc(S(C)(=O)=Nc2ccc(-c3noc(C(F)(F)F)n3)cc2F)cc1] | 0.3 g, 44% yield |

Example 6:—Preparation of 2-fluoro-N-(methyl (oxo)(4-(5-(trifluoromethyl)-1,2,4-oxadiazol-3-yl) phenyl)-λ⁶-sulfaneylidene)benzamide (compound no. 172)

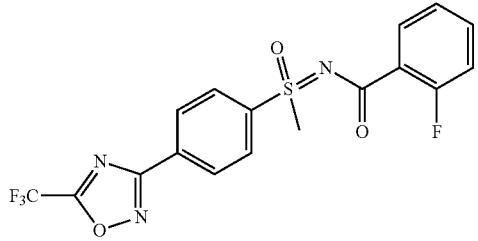 [SMILES: CS(=O)(=NC(=O)c1ccccc1F)c1ccc(-c2noc(C(F)(F)F)n2)cc1]

Step 1:—N'-hydroxy-4-(methylthio)benzimidamide

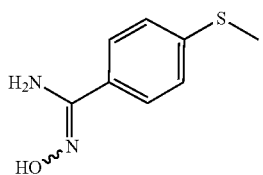

N'-hydroxy-4-(methylthio)benzimidamide (10.1 g) was prepared by the procedure described in step 2 of example 1.

Step 2:—3-(4-(methylthio)phenyl)-5-(trifluoromethyl)-1,2,4-oxadiazole

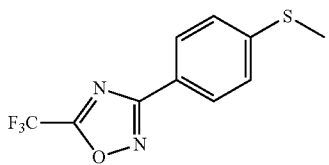 [SMILES: CSc1ccc(-c2noc(C(F)(F)F)n2)cc1]

3-(4-(Methylthio)phenyl)-5-(trifluoromethyl)-1,2,4-oxadiazole (12.3 g, 83% yield) was prepared by the procedure described in step-3 of example 1.

Step 3:—Synthesis of imino(methyl)(4-(5-(trifluoromethyl)-1,2,4-oxadiazol-3-yl)phenyl)-λ⁶-sulfanone

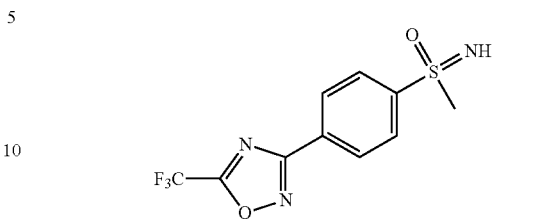

Imino(methyl)(4-(5-(trifluoromethyl)-1,2,4-oxadiazol-3-yl)phenyl)-λ⁶-sulfanone (10.5 g, 94% yield) was prepared by the procedure described in step-6 of example 1.

Step 4:—Synthesis of 2-fluoro-N-(methyl(oxo)(4-(5-(trifluoromethyl)-1,2,4-oxadiazol-3-yl)phenyl)-λ⁶-sulfaneylidene)benzamide

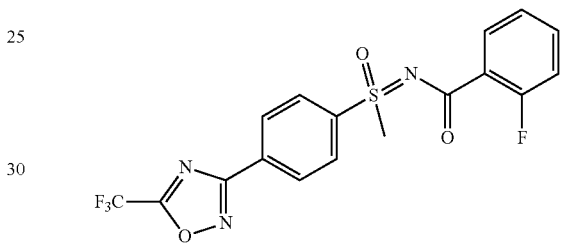

To a stirred solution of imino(methyl)(4-(5-(trifluoromethyl)-1,2,4-oxadiazol-3-yl)phenyl)-λ⁶-sulfanone (0.3 g, 1.0 mmol), 4-Dimethylaminopyridine (0.01 g, 0.1 mmol) and triethylamine (0.2 ml, 1.5 mmol) in dichloromethane (10 mL), 2-fluorobenzoyl chloride (0.163 g, 1.030 mmol) was added at 0° C. The resulting reaction mixture was stirred for 2 h at 25° C. The volatiles were evaporated and the residue was extracted by ethyl acetate (60 mL). Ethyl acetate layer was washed thrice with water (10 mL), dried over anhydrous sodium sulphate and concentrated under vacuum. Crude product was purified by flash column chromatography on silica gel using hexane to 60% ethyl acetate in hexane as an eluent to obtain pure 2-fluoro-N-(methyl(oxo)(4-(5-(trifluoromethyl)-1,2,4-oxadiazol-3-yl)phenyl)-λ⁶-sulfanylidene) benzamide (0.3 g, 0.8 mmol, 79% yield).

TABLE NO. 6

The following compounds were prepared by the procedure analogous to that of the compound 172 using appropriate starting materials.

| Compound No. | IUPAC Name | Structure | Yield |
| --- | --- | --- | --- |
| 172 | 2-fluoro-N-(methyl(oxo)(4-(5-(trifluoromethyl)-1,2,4-oxadiazol-3-yl)phenyl)-λ⁶-sulfaneylidene)benzamide | 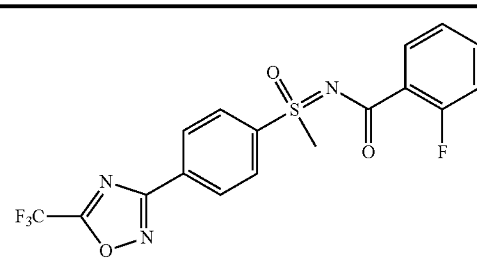 | 0.3 g, 79% yield |

TABLE NO. 6-continued

The following compounds were prepared by the procedure analogous to that of the compound 172 using appropriate starting materials.

| Compound No. | IUPAC Name | Structure | Yield |
|---|---|---|---|
| 173 | 3-methoxy-N-(methyl(oxo)(4-(5-(trifluoromethyl)-1,2,4-oxadiazol-3-yl)phenyl)-λ⁶-sulfaneylidene)benzamide | 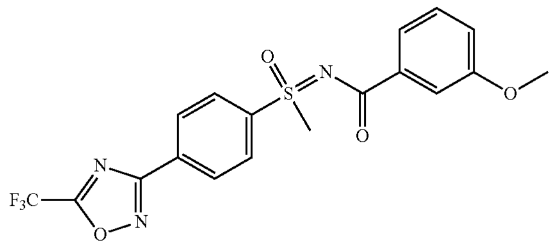 [SMILES: COc1cccc(C(=O)N=S(C)(=O)c2ccc(-c3noc(C(F)(F)F)n3)cc2)c1] | 0.3 g, 79% yield |
| 174 | 3-fluoro-N-(methyl(oxo)(4-(5-(trifluoromethyl)-1,2,4-oxadiazol-3-yl)phenyl)-λ⁶-sulfaneylidene)benzamide | 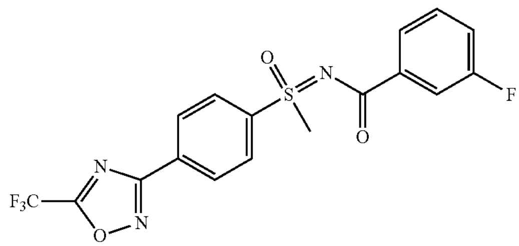 [SMILES: CS(=O)(=NC(=O)c1cccc(F)c1)c1ccc(-c2noc(C(F)(F)F)n2)cc1] | 0.2 g, 43% yield |
| 175 | 4-chloro-2-fluoro-N-(methyl(oxo)(4-(5-(trifluoromethyl)-1,2,4-oxadiazol-3-yl)phenyl)-λ⁶-sulfaneylidene)benzamide | 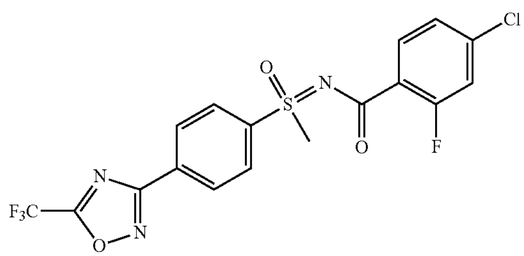 [SMILES: CS(=O)(=NC(=O)c1ccc(Cl)cc1F)c1ccc(-c2noc(C(F)(F)F)n2)cc1] | 0.3 g, 57% yield |
| 176 | 2-chloro-6-fluoro-N-(methyl(oxo)(4-(5-(trifluoromethyl)-1,2,4-oxadiazol-3-yl)phenyl)-λ⁶-sulfaneylidene)benzamide | 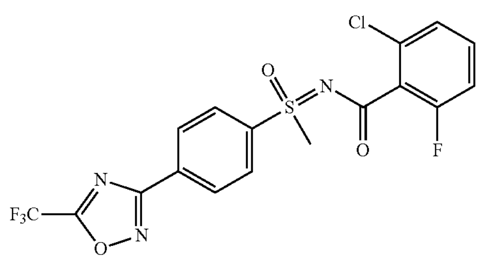 [SMILES: CS(=O)(=NC(=O)c1c(F)cccc1Cl)c1ccc(-c2noc(C(F)(F)F)n2)cc1] | 0.2 g, 36% yield |
| 177 | N-(methyhoxo)(4-(5-(trifluoromethyl)-1,2,4-oxadiazol-3-yl)phenyl)-λ⁶-sulfaneylidene)benzamide | 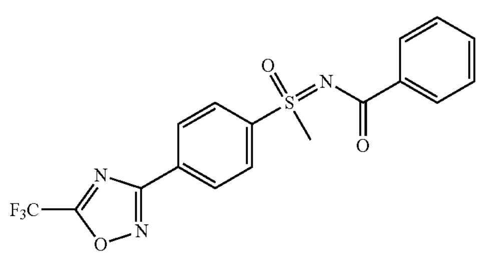 [SMILES: CS(=O)(=NC(=O)c1ccccc1)c1ccc(-c2noc(C(F)(F)F)n2)cc1] | 0.2 g, 41% yield |
| 178 | N-(methyl(oxo)(4-(5-(trifluoromethyl)-1,2,4-oxadiazol-3-yl)phenyl)-λ⁶-sulfaneylidene)-2-phenylacetamide | 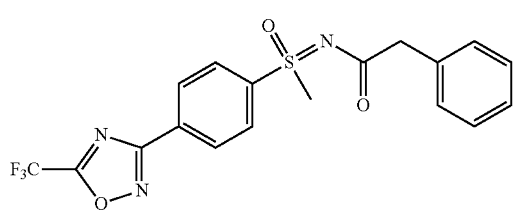 [SMILES: CS(=O)(=NC(=O)Cc1ccccc1)c1ccc(-c2noc(C(F)(F)F)n2)cc1] | 0.1 g, 30% yield |

TABLE NO. 6-continued

The following compounds were prepared by the procedure analogous to that of the compound 172 using appropriate starting materials.

| Compound No. | IUPAC Name | Structure | Yield |
|---|---|---|---|
| 179 | 4-chloro-N-(methyl(oxo)(4-(5-(trifluoromethyl)-1,2,4-oxadiazol-3-yl)phenyl)-$\lambda^6$-sulfaneylidene)benzamide | 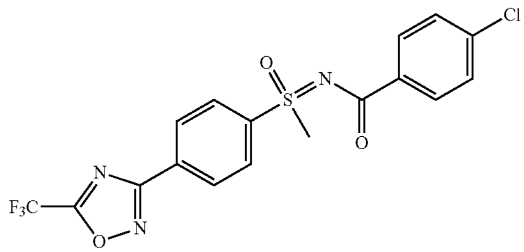 [SMILES: CS(=O)(=NC(=O)c1ccc(Cl)cc1)c1ccc(-c2noc(C(F)(F)F)n2)cc1] | 0.3 g, 64% yield |
| 180 | N-(methyl(oxo)(4-(5-(trifluoromethyl)-1,2,4-oxadiazol-3-yl)phenyl)-$\lambda^6$-sulfaneylidene)pivalamide | 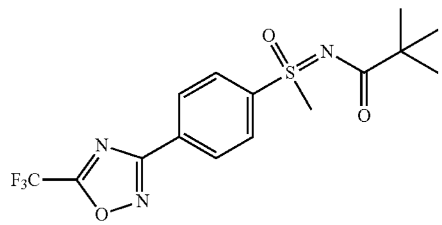 [SMILES: CC(C)(C)C(=O)N=S(C)(=O)c1ccc(-c2noc(C(F)(F)F)n2)cc1] | 0.3 g, 78% yield |
| 181 | N-(methyl(oxo)(4-(5-(trifluoromethyl)-1,2,4-oxadiazol-3-yl)phenyl)-$\lambda^6$-sulfaneylidene)cyclopropanecarboxamide | 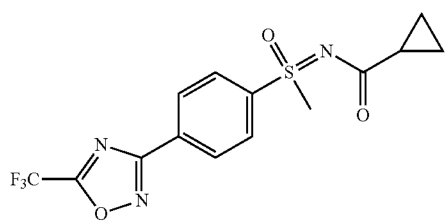 [SMILES: CS(=O)(=NC(=O)C1CC1)c1ccc(-c2noc(C(F)(F)F)n2)cc1] | 0.3 g, 77% yield |

Example 7:—Preparation of ((3-chlorobenzyl)imino)(methyl)(4-(5-(trifluoromethyl)-1,2,4-oxadiazol-3-yl)phenyl)-$\lambda^6$-sulfanone (Compound no. 182)

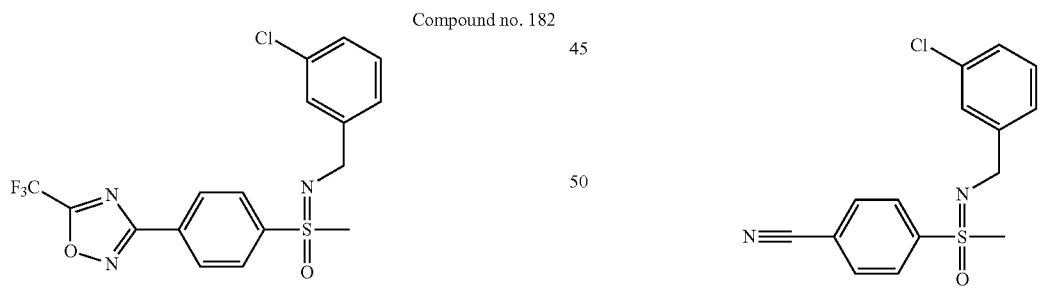

Compound no. 182

Step 1:—4-(S-methylsulfonimidoyl)benzonitrile

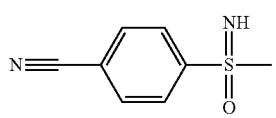

4-(S-methylsulfonimidoyl)benzonitrile (6 g, 83% yield) was prepared by the procedure described in step-6 of example 1.

Step 2:—4-(N-(3-chlorobenzyl)-S-methylsulfonimidoyl)benzonitrile 4-(S-methylsulfonimidoyl)benzonitrile (0.5 g, 2.8 mmol) was dissolved in N,N-dimethylformamide (5 mL), followed by addition of potassium-t-butoxide (0.4 g, 3.3 mmol) at 0° C. and stirred for 15 minutes at 0° C. 3-Chlorobenzyl bromide (0.5 mL, 4.2 mmol) was added and allowed to stir for 3 h. After completion of the reaction, ethyl acetate (25 mL) and saturated ammonium chloride solution (10 mL) were added to the reaction mixture. Ethyl acetate layer was isolated and washed twice with water (10 mL), dried over anhydrous sodium sulphate and concentrated under vacuum to obtain 4-(N-(3-chlorobenzyl)-S-methylsulfonimidoyl) benzonitrile (0.8 g).

Step 3:—4-(N-(3-chlorobenzyl)-S-methylsulfonimidoyl)-N'-hydroxybenzimidamide

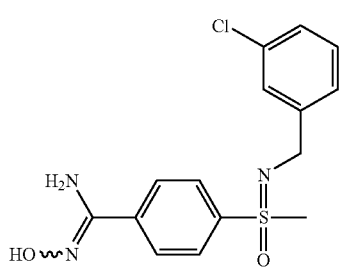 [SMILES: CS(=O)(=NCc1cccc(Cl)c1)c1ccc(C(N)=NO)cc1]

4-(N-(3-chlorobenzyl)-S-methylsulfonimidoyl)-N'-hydroxybenzimidamide (1.2 g) was prepared by procedure as described in step-2 of example 1.

Step 4:—((3-chlorobenzyl)imino)(methyl)(4-(5-(trifluoromethyl)-1,2,4-oxadiazol-3-yl)phenyl)-$\lambda^6$-sulfanone

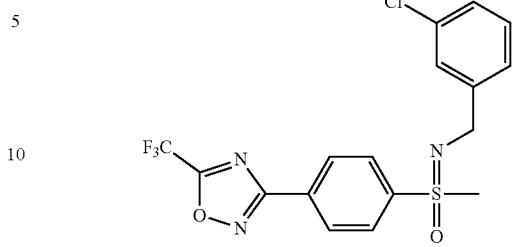

To a stirred solution of 4-(N-(3-chlorobenzyl)-S-methylsulfonimidoyl)-N'-hydroxybenzimidamide (1.2 g, 3.8 mmol) in tetrahydrofuran (6 mL), trifluoroacetic anhydride (0.6 mL, 4.5 mmol) was added slowly at 5° C. under nitrogen atmosphere. The resulting reaction mixture was stirred for 18 h at 25° C. After completion of the reaction, the reaction mixture was diluted with ethyl acetate (60 mL). The ethyl acetate layer was washed with saturated sodium bicarbonate solution (30 mL), dried over anhydrous sodium sulphate and concentrated under vacuum. The crude product was purified by column chromatography on silica gel using hexane to 50% ethyl acetate in hexane as an eluent to obtain ((3-chlorobenzyl)imino)(methyl)(4-(5-(trifluoromethyl)-1,2,4-oxadiazol-3-yl)phenyl)-$\lambda^6$-sulfanone (0.6 g, 1.2 mmol, 38% yield)

TABLE NO. 7

The following compounds were prepared by the procedure analogous to that of the compound 182 using appropriate strating materials.

| Compound No. | IUPAC Name | Structure | Yield |
|---|---|---|---|
| 183 | ((4-fluorobenzyl)imino)(methyl)(4-(5-(trifluoromethyl)-1,2,4-oxadiazol-3-yl)phenyl-$\lambda^6$-sulfanone | 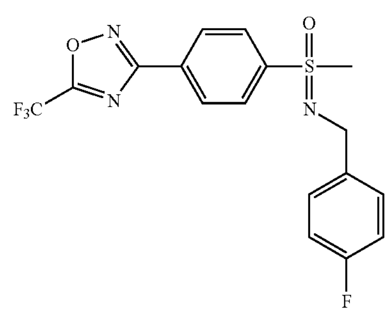 [SMILES: CS(=O)(=NCc1ccc(F)cc1)c1ccc(-c2noc(C(F)(F)F)n2)cc1] | 0.3 g, 26% yield |
| 184 | ((2,4-difluorobenzyl)imino)(methyl)(4-(5-(trifluoromethyl)-1,2,4-oxadiazol-3-yl)phenyl)-$\lambda^6$-sulfanone | 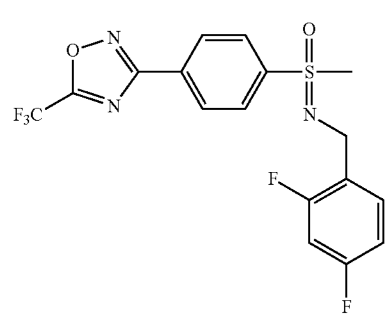 [SMILES: CS(=O)(=NCc1ccc(F)cc1F)c1ccc(-c2noc(C(F)(F)F)n2)cc1] | 0.3 g, 30% yield |

TABLE NO. 7-continued

The following compounds were prepared by the procedure analogous to that of the compound 182 using appropriate strating materials.

| Compound No. | IUPAC Name | Structure | Yield |
|---|---|---|---|
| 185 | ((3-fluorobenzyl)imino)(methyl)(4-(5-(trifluoromethyl)-1,2,4-oxadiazol-3-yl)phenyl)-λ⁶-sulfanone | 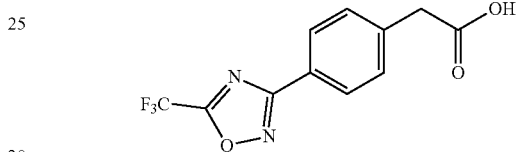 | 0.3 g, 19% yield |

Example 8: Preparation of N-((4-fluorophenyl)(methyl)(oxo)-λ⁶-sulfaneylidene)-2-(4-(5-(trifluoromethyl)-1,2,4-oxadiazol-3-yl)phenyl)acetamide (Compound no. 186)

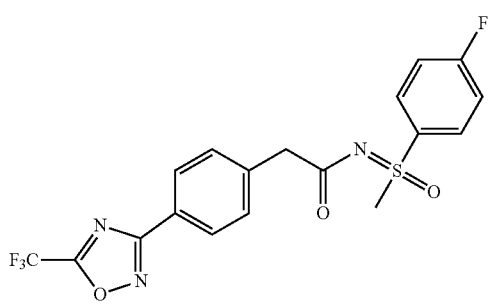

Compound 186

Step-1:—2-(4-(N'-hydroxycarbamimidoyl)phenyl) acetic acid

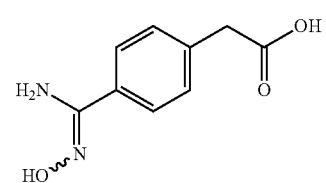 [SMILES: NC(=NO)c1ccc(CC(=O)O)cc1]

To a stirred solution of 2-(4-cyanophenyl)acetic acid (5.0 g, 31.0 mmol) in ethanol (120 mL), 50% of aqueous hydroxylamine solution (4.8 mL, 155 mmol) was added at 0° C. and stirred at 65° C. for 4 h. The reaction mixture was concentrated under vacuum to obtain 2-(4-(N'-hydroxycarbamimidoyl)phenyl)acetic acid (5.5 g).

Step-2:—Preparation of 2-(4-(5-(trifluoromethyl)-1,2,4-oxadiazol-3-yl)phenyl)acetic acid

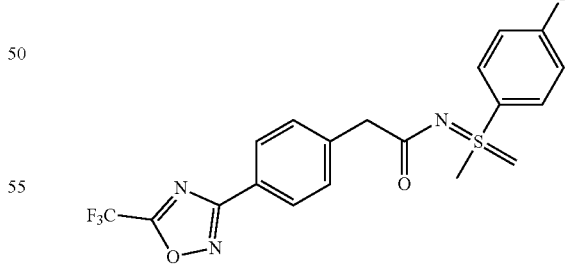

To a stirred solution of 2-(4-(N'-hydroxycarbamimidoyl) phenyl)acetic acid (5.5 g, 28.3 mmol) in tetrahydrofuran (100 mL), trifluoroacetic anhydride (8 mL, 56.6 mmol) was added at 0° C. under nitrogen atmosphere and stirred at 25° C. for 16 h. After completion of the reaction, the reaction mixture was concentrated and purified by column chromatography on silica gel using hexane to 60% ethyl acetate in hexane as an eluent to obtain pure 2-(4-(5-(trifluoromethyl)-1,2,4-oxadiazol-3-yl)phenyl)acetic acid (6.0 g, 78% yield).

Step-3:—Preparation of N-((4-fluorophenyl)(methyl)(oxo)-λ⁶-sulfaneylidene)-2-(4-(5-(trifluoromethyl)-1,2,4-oxadiazol-3-yl)phenyl)acetamide To a stirred solution of 2-(4-(5-(trifluoromethyl)-1,2,4-oxadiazol-3-yl)phenyl)acetic acid (0.4 g, 1.3 mmol) in dichloromethane (10 mL), 1-(3-dimethylaminopropyl)-3-ethylcarbodiimide hydrochloride (0.5 g, 2.6 mmol) and 4-dimethylaminopyridine (0.5 g, 3.9 mmol) were added at 0-5° C. under nitrogen atmosphere. (4-fluorophenyl)(imino)(methyl)-λ⁶-sulfanone (0.3 g, 1.4 mmol was added and stirred at 25° C. for 16 h. The resulting reaction mixture was diluted with dichloromethane (60 mL) and washed twice with water (20 mL). Dichloromethane layer was collected and dried over anhydrous sodium sulphate and concentrated under vacuum. Crude product was purified by preparative HPLC to obtain N-((4-fluorophenyl)(methyl)(oxo)-$\lambda^6$-sulfanylidene)-2-(4-(5-(trifluoromethyl)-1,2,4-oxadiazol-3-yl)phenyl)acetamide (0.3 g, 0.7 mmol, 54% yield).

TABLE NO. 8

The following compounds were prepared by the procedure analogous to that of the compound 186 using appropriate starting materials.

| Compound No. | IUPAC Name | Structure | Yield |
|---|---|---|---|
| 187 | N-((4-methoxyphenyl)(methyl)(oxo)-$\lambda^6$-sulfaneylidene)-2-(4-(5-(trifluoromethyl)-1,2,4-oxadiazol-3-yl)phenyl)acetamide | 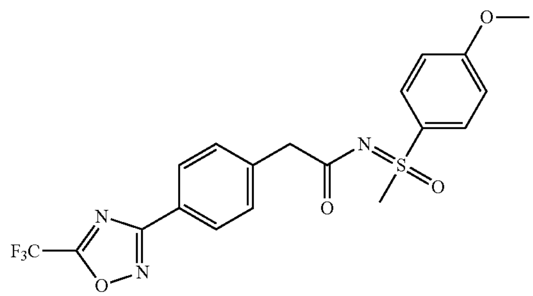 [SMILES: COc1ccc(S(C)(=O)=NC(=O)Cc2ccc(-c3noc(C(F)(F)F)n3)cc2)cc1] | 0.3 g, 54% yield |
| 188 | N-((2-fluorophenyl)(methyl)(oxo)-$\lambda^6$-sulfaneylidene)-2-(4-(5-(trifluoromethyl)-1,2,4-oxadiazol-3-yl)phenyl)acetamide | 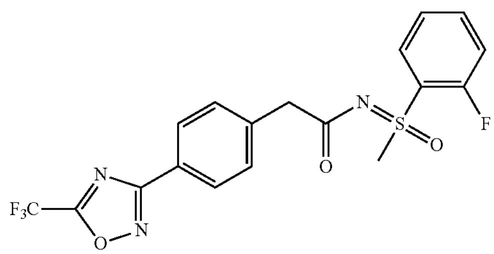 [SMILES: CS(=O)(=NC(=O)Cc1ccc(-c2noc(C(F)(F)F)n2)cc1)c1ccccc1F] | 0.2 g, 42% yield |
| 189 | N-((4-chlorophenyl)(methyl)(oxo)-$\lambda^6$-sulfaneylidene)-2-(4-(5-(trifluoromethyl)-1,2,4-oxadiazol-3-yl)phenyl)acetamide | 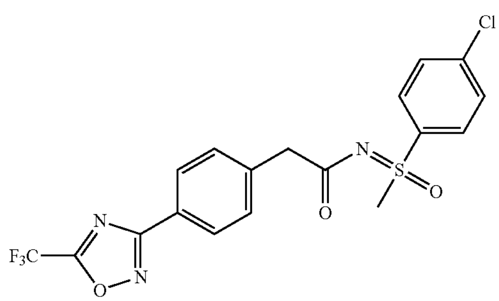 [SMILES: CS(=O)(=NC(=O)Cc1ccc(-c2noc(C(F)(F)F)n2)cc1)c1ccc(Cl)cc1] | 0.2 g, 49% yield |
| 190 | N-((3-fluorophenyl)(methyl)(oxo)-$\lambda^6$-sulfaneylidene)-2-(4-(5-(trifluoromethyl)-1,2,4-oxadiazol-3-yl)phenyl)acetamide | 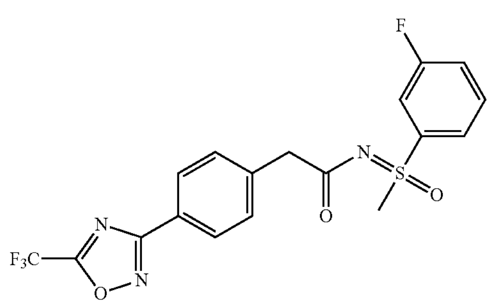 [SMILES: CS(=O)(=NC(=O)Cc1ccc(-c2noc(C(F)(F)F)n2)cc1)c1cccc(F)c1] | 0.2 g, 41% yield |

TABLE NO. 8-continued

The following compounds were prepared by the procedure analogous to that of the compound 186 using appropriate starting materials.

| Compound No. | IUPAC Name | Structure | Yield |
|---|---|---|---|
| 191 | N-(methyl(oxo)(thiazol-2-yl)-$\lambda^6$-sulfaneylidene)-2-(4-(5-(trifluoromethyl)-1,2,4-oxadiazol-3-yl)phenyl)acetamide | 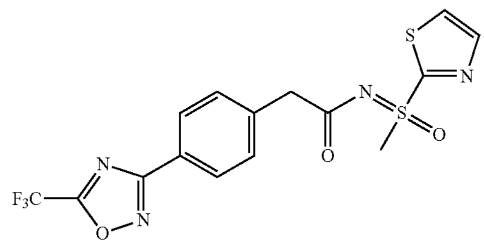 [SMILES: CS(=O)(=NC(=O)Cc1ccc(-c2noc(C(F)(F)F)n2)cc1)c1nccs1] | 0.1 g, 23% yield |
| 192 | N-((3-methoxyphenyl)(methyl)(oxo)-$\lambda^6$-sulfaneylidene)-2-(4-(5-(trifluoromethyl)-1,2,4-oxadiazol-3-yl)phenyl)acetamide | 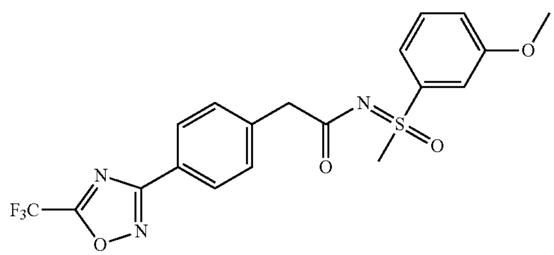 [SMILES: COc1cccc(S(C)(=O)=NC(=O)Cc2ccc(-c3noc(C(F)(F)F)n3)cc2)c1] | 0.3 g, 57% yield |
| 193 | N-((2,4-difluorobenzyl)(methyl)(oxo)-$\lambda^6$-sulfaneylidene)-2-(4-(5-(trifluoromethyl)-1,2,4-oxadiazol-3-yl)phenyl)acetamide | 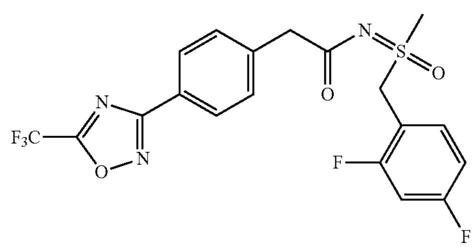 [SMILES: CS(=O)(Cc1ccc(F)cc1F)=NC(=O)Cc1ccc(-c2noc(C(F)(F)F)n2)cc1] | 0.2 g, 44% yield |
| 194 | N-(methyl(oxo)(phenyl)-$\lambda^6$-sulfaneylidene)-2-(4-(5-(trifluoromethyl)-1,2,4-oxadiazol-3-yl)phenyl)acetamide | 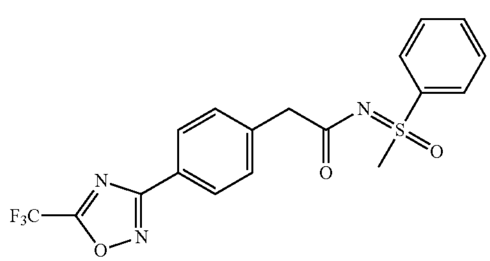 [SMILES: CS(=O)(=NC(=O)Cc1ccc(-c2noc(C(F)(F)F)n2)cc1)c1ccccc1] | 0.2 g, 36% yield |
| 195 | N-((2-fluorobenzyl)(methyl)(oxo)-$\lambda^6$-sulfaneylidene)-2-(4-(5-(trifluoromethyl)-1,2,4-oxadiazol-3-yl)phenyl)acetamide | 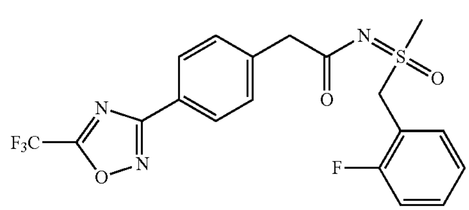 [SMILES: CS(=O)(Cc1ccccc1F)=NC(=O)Cc1ccc(-c2noc(C(F)(F)F)n2)cc1] | 0.2 g, 42% yield |

Example 9:—Preparation of N-((2-fluorophenyl)(methyl)(oxo)-λ⁶-sulfaneylidene)-5-(5-(trifluoromethyl)-1,2,4-oxadiazol-3-yl)picolinamide

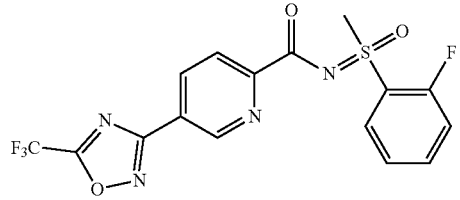 [SMILES: CS(=O)(=NC(=O)c1ccc(-c2noc(C(F)(F)F)n2)cn1)c1ccccc1F]

Step 1:—Synthesis of 5-(N'-hydroxycarbamimidoyl)picolinic acid

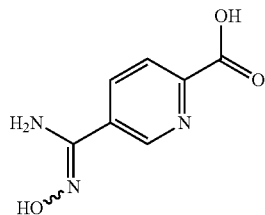 [SMILES: NC(=NO)c1ccc(C(=O)O)nc1]

To a stirred solution of 5-cyanopicolinic acid (0.5 g, 3.4 mmol) in ethanol (10 mL), 50% of aqueous hydroxylamine solution (0.52 mL, 16.9 mmol) was added. The resulting reaction mixture was stirred at 65° C. for 4 hours. After completion of the reaction, the volatiles were evaporated under vacuum to obtain 5-(N'-hydroxycarbamimidoyl)picolinic acid (0.6 g).

Step 2:—5-(5-(trifluoromethyl)-1,2,4-oxadiazol-3-yl)picolinic acid

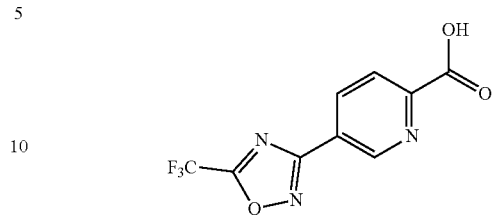

To a stirred solution of 5-(N'-hydroxycarbamimidoyl)picolinic acid (6 g, 33 mmol) in tetrahydrofuran (50 mL), trifluoroacetic anhydride (8.4 mL, 59.6 mmol) was added slowly at 0-5° C. under nitrogen atmosphere. The resulting reaction mixture was stirred for 18 h at 25° C. Solvent was removed under reduced pressure. Crude residue was stirred with water (20 mL) at 25° C. Obtained precipitate was filtered and solid was dried under vacuum to obtain 5-(5-(trifluoromethyl)-1,2,4-oxadiazol-3-yl)picolinic acid (7.5 g, 28.9 mmol).

Step 3:—Synthesis of N-((2-fluorophenyl)(methyl)(oxo)-λ⁶-sulfaneylidene)-5-(5-(trifluoromethyl)-1,2,4-oxadiazol-3-yl)picolinamide Compound 196

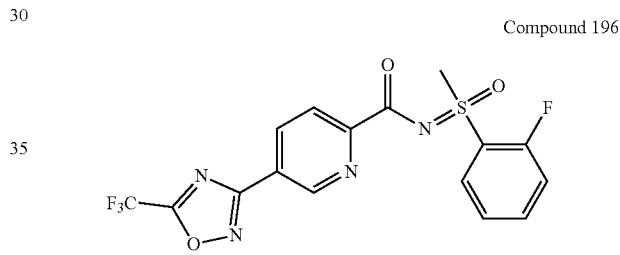

N-((2-fluorophenyl)(methyl)(oxo)-λ⁶-sulfaneylidene)-5-(5-(trifluoromethyl)-1,2,4-oxadiazol-3-yl)picolinamide (0.13 g, 23% yield) was synthesized by the procedure as described in step-3 of example 8.

TABLE NO. 9

The following compounds were prepared by the procedure analogous to that of the Compound 196 using appropriate starting materials.

| Compound No. | IUPAC Name | Structure | Yield |
|---|---|---|---|
| 197 | N-(methyl(oxo)(phenyl)-λ⁶-sulfaneylidene)-5-(5-(trifluoromethyl)-1,2,4-oxadiazol-3-yl)picolinamide | 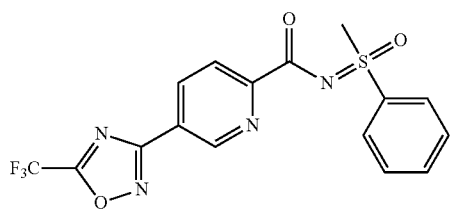 [SMILES: CS(=O)(=NC(=O)c1ccc(-c2noc(C(F)(F)F)n2)cn1)c1ccccc1] | 0.3 g 49% yield |

TABLE NO. 9-continued

The following compounds were prepared by the procedure analogous to that of the Compound 196 using appropriate starting materials.

| Compound No. | IUPAC Name | Structure | Yield |
|---|---|---|---|
| 198 | N-((4-methoxyphenyl)(methyl)(oxo)-$\lambda^6$-sulfaneylidene)-5-(5-(trifluoromethyl)-1,2,4-oxadiazol-3-yl)picolinamide | 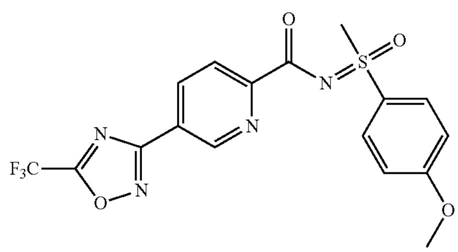 [SMILES: COc1ccc(S(C)(=O)=NC(=O)c2ccc(-c3noc(C(F)(F)F)n3)cn2)cc1] | 0.3 g, 52% yield |
| 199 | N-(methyl(oxo)(pyridin-2-yl)-$\lambda^6$-sulfaneylidene)-5-(5-(trifluoromethyl)-1,2,4-oxadiazol-3-yl)picolinamide | 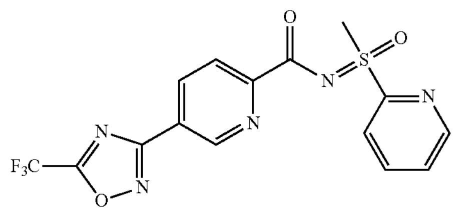 [SMILES: CS(=O)(=NC(=O)c1ccc(-c2noc(C(F)(F)F)n2)cn1)c1ccccn1] | 0.2 g, 38% yield |
| 200 | N-((2-methoxyethyl)(methyl)(oxo)-$\lambda^6$-sulfaneylidene)-5-(5-(trifluoromethyl)-1,2,4-oxadiazol-3-yl)picolinamide | 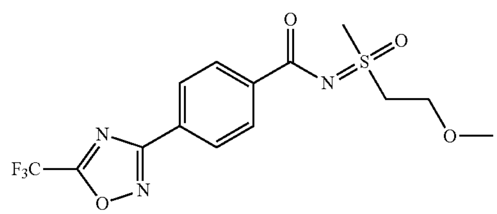 [SMILES: COCCS(C)(=O)=NC(=O)c1ccc(-c2noc(C(F)(F)F)n2)cc1] | 0.3 g, 65% yield |
| 201 | 2-fluoro-N-(methyl(oxo)(phenyl)-$\lambda^6$-sulfanylidene)-4-(5-(trifluoromethyl)-1,2,4-oxadiazol-3-yl)benzamide | 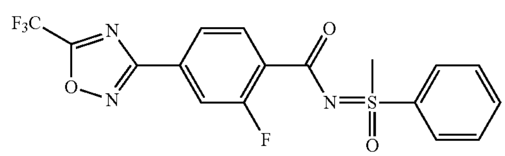 [SMILES: CS(=O)(=NC(=O)c1ccc(-c2noc(C(F)(F)F)n2)cc1F)c1ccccc1] | 0.2 g, 42% yield |
| 202 | 2-fluoro-N-((4-methoxyphenyl)(methyl)(oxo)-$\lambda^6$-sulfanylidene)-4-(5-(trifluoromethyl)-1,2,4-oxadiazol-3-yl)benzamide | 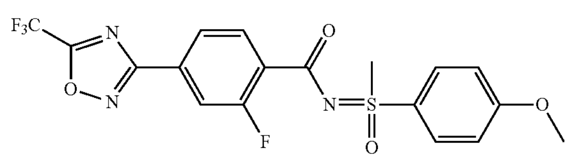 [SMILES: COc1ccc(S(C)(=O)=NC(=O)c2ccc(-c3noc(C(F)(F)F)n3)cc2F)cc1] | 0.2 g, 51% yield |
| 203 | 2-fluoro-N-((2-fluorophenyl)(methyl)(oxo)-$\lambda^6$-sulfanylidene)-4-(5-(trifluoromethyl)-1,2,4-oxadiazol-3-yl)benzamide | 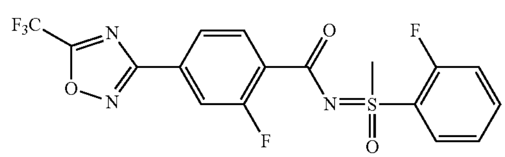 | 0.1 g, 18% yield |
| 204 | N-(ethyl(methyl)(oxo)-$\lambda^6$-sulfanylidene)-2-fluoro-4-(5-(trifluoromethyl)-1,2,4-oxadiazol-3-yl)benzamide | 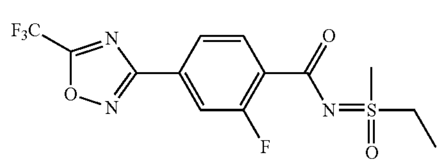 [SMILES: CCS(C)(=O)=NC(=O)c1ccc(-c2noc(C(F)(F)F)n2)cc1F] | 0.05 g, 16% yield |
| 205 | 2-fluoro-N-(methyl(oxo)(pyridin-2-yl)-$\lambda^6$-sulfanylidene)-4-(5-(trifluoromethyl)-1,2,4-oxadiazol-3-yl)benzamide | 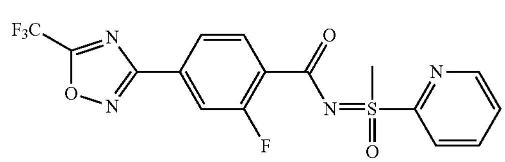 [SMILES: CS(=O)(=NC(=O)c1ccc(-c2noc(C(F)(F)F)n2)cc1F)c1ccccn1] | 0.1 g, 25% yield |

Example 10—Preparation of N-(methyl(oxo)(phenyl)-λ⁶-sulfaneylidene)-4-((5-(trifluoromethyl)-1,2,4-oxadiazol-3-yl)methyl)benzamide (compound no. 222)

compound no. 222

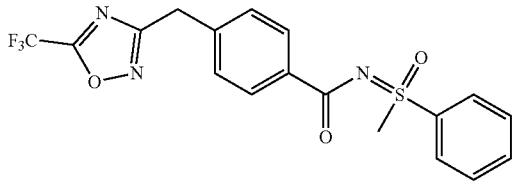

Step 1:—Preparation of methyl-4-(2-amino-2-(hydroxyimino)ethyl)benzoate

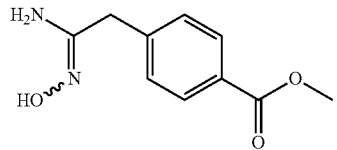

To a solution of methyl 4-(cyanomethyl)benzoate (9.5 g, 54.2 mmol) in ethanol (100 mL), hydroxylamine hydrochloride (6.78 g, 98 mmol) and sodium bicarbonate (8.20 g, 98 mmol) were added. The resulting reaction mixture was stirred at 65° C. for 18 h. The reaction mixture was filtered and the filtrate was concentrated under reduced pressure to obtain methyl-4-(2-amino-2-(hydroxyimino)ethyl)benzoate (11.2 g, 53.8 mmol, 99% yield).

Step 2:—Preparation of methyl 4-((5-(trifluoromethyl)-1,2,4-oxadiazol-3-yl)methyl)benzoate

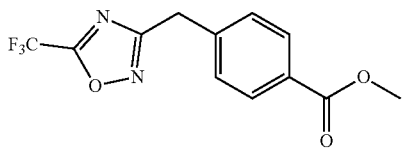 [SMILES: COC(=O)c1ccc(Cc2noc(C(F)(F)F)n2)cc1]

To a solution of methyl-4-(2-amino-2-(hydroxyimino)ethyl)benzoate (11.2 g, 53.8 mmol) in tetrahydrofuran (100 mL), trifluoroacetic anhydride (11.4 mL, 81 mmol) was added at 0-5° C. and stirred at 25° C. for 16 h. The resulting reaction mixture was poured into ice cold mixture of ethyl acetate (300 mL) and saturated sodium bicarbonate solution (200 mL) with stirring (caution—pH must remain basic). The ethyl acetate layer was separated, washed twice with saturated sodium bicarbonate solution (50 mL), dried over anhydrous sodium sulphate and concentrated. The crude product was purified by flash column chromatography on silica gel using 0-50% ethyl acetate in hexane as an eluent to obtain pure methyl 4-((5-(trifluoromethyl)-1,2,4-oxadiazol-3-yl)methyl)benzoate (15.4 g, 31.4 mmol, 58% yield).

Step-3:—N-(methyl(oxo)(phenyl)-λ⁶-sulfaneylidene)-4-((5-(trifluoromethyl)-1,2,4-oxadiazol-3-yl)methyl)benzamide (compound no. 222)

(compound no. 222)

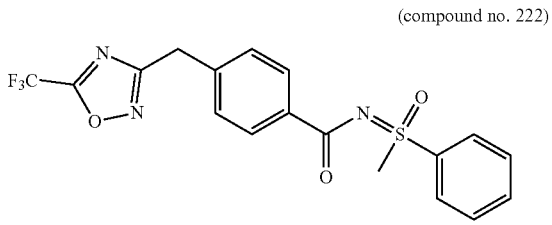 [SMILES: CS(=O)(=NC(=O)c1ccc(Cc2noc(C(F)(F)F)n2)cc1)c1ccccc1]

To a stirred solution of methyl 4-((5-(trifluoromethyl)-1,2,4-oxadiazol-3-yl)methyl)benzoate (0.4 g, 1.2 mmol), imino(methyl)(phenyl)-λ⁶-sulfanone (0.5 g, 3.1 mmol) and toluene (7 mL), trimethylaluminium 25% in hexane (1.529 ml, 3.06 mmol) was added at 0-5° C. and stirred at 65° C. for 16 h. The resulting reaction mixture was cooled to 25° C. and poured into a mixture of 5% aq. acetic acid (7 mL) and ethyl acetate (15 mL), stirred at 25° C. for 10 minutes, organic layer was isolated. Aqueous layer was again extracted into ethyl acetate (20 mL). Ethyl acetate layer was washed by water (20 mL), dried over anhydrous sodium sulphate and concentrated under reduced pressure. Purification was done by column chromatography on silica gel using hexane to 60% ethyl acetate in hexane as an eluent to obtain N-(methyl(oxo)(phenyl)-λ⁶-sulfanylidene)-4-((5-(trifluoromethyl)-1,2,4-oxadiazol-3-yl)methyl)benzamide (0.4 g, 1.0 mmol, 78% yield).

TABLE NO. 10

The following compound was prepared by the procedure analogous to that of the compound no. 222 using appropriate starting materials.

| Compound No. | IUPAC Name | Structure | Yield |
|---|---|---|---|
| 221 | N-(methyl(oxo)(propyl)-λ⁶-sulfaneylidene)-4-((5-(trifluoromethyl)-1,2,4-oxadiazol-3-yl)methyl)benzamide | 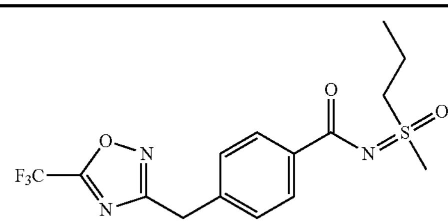 | 0.2 g, 40% yield |

BIOLOGY EXAMPLES

Biological Test Examples for Fungal Pathogens

Example 1: *Pyricularia oryzae* (Rice Blast)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification, each plate was seeded with 5 mm size mycelial disc taken form periphery of actively growing virulent culture plate. Plates were incubated in growth chambers at 25° C. temperature and 60% relative humidity for seven days and radial growth was measured.

| Compounds | 3 | 13 | 14 | 15 | 17 | 18 | 19 | 20 | 22 | 23 |
|---|---|---|---|---|---|---|---|---|---|---|
| 27 | 29 | 96 | 97 | 106 | 114 | 117 | 122 | 124 | 127 | 130 | 133 |
| 134 | 137 | 138 | 139 | 141 | 143 | 144 | 145 | 146 | 147 | 148 | 149 |
| 151 | 151 | 152 | 152 | 165 | 166 | 167 | 169 | 171 | 181 | 182 | 183 |
| 184 | & 185 | | | | | | | | | | at 300 ppm gave more than 70% control in these tests when compared to the untreated check which showed extensive disease development.

Example 2: *Rhizoctonia solani* (Rice Sheath Blight/Potato Black Scurf)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification, each plate was seeded with 5 mm size mycelial disc taken form periphery of actively growing virulent culture plate. Plates were incubated in growth chambers at 25° C. temperature and 60% relative humidity for seven days and radial growth was measured.

| Compounds | 15 | 50 | 90 | 128 | & | 133 |
|---|---|---|---|---|---|---| at 300 ppm gave more than 70% control in these tests when compared to the untreated check which showed extensive disease development.

Example 3: *Botrytis cinerea* (Gray Mold)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification, each plate was seeded with 5 mm size mycelial disc taken form periphery of actively growing virulent culture plate. Plates were incubated in growth chambers at 22° C. temperature and 90% relative humidity for seven days and radial growth was measured.

| Compounds | 14 | 15 | 17 | 23 | 48 | 90 | 108 | 109 | 133 |
|---|---|---|---|---|---|---|---|---|---|
| 138 | 139 | 140 | 153 | 156 | & | 157 | | | | at 300 ppm gave more than 70% in these tests when compared to the untreated check which showed extensive disease development.

Example 4: *Alternaria solani* (Early Blight of Tomato/Potato)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification each plate was seeded with 5 mm size mycelial disc taken form periphery of actively growing virulent culture plate. Plates were incubated in growth chambers at 25° C. temperature and 60% relative humidity for seven days and radial growth was measured.

| Compounds | 13 | 14 | 15 | 17 | 18 | 20 | 23 | 33 | 47 | 48 |
|---|---|---|---|---|---|---|---|---|---|---|
| 52 | 56 | 59 | 62 | 71 | 73 | 75 | 94 | 96 | 99 | 108 | 109 |
| 117 | 137 | 148 | 157 | 158 | 162 | & | 163 | | | | at 300 ppm gave more than 70% control in these tests when compared to the untreated check which showed extensive disease development.

Example 5: *Colletotrichum capsici* (Anthracnose)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification, each plate was seeded with 5 mm size mycelial disc taken form periphery of actively growing virulent culture plate. Plates were incubated in growth chambers at 25° C. temperature and 60% relative humidity for seven days and radial growth was measured.

| Compounds | 13 | 15 | 17 | 18 | 22 | 23 | 133 | 156 |
|---|---|---|---|---|---|---|---|---|
| & | 181 | | | | | | | | at 300 ppm gave more than 70% control in these tests when compared to the untreated check which showed extensive disease development.

Example 6: *Septoria lycopersici* (Leaf Spot of Tomato)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification, each plate was seeded with 5 mm size mycelial disc taken form periphery of actively growing virulent culture plate. Plates were incubated in growth chambers at 25° C. temperature and 70% relative humidity for seven days and radial growth was measured. Compound 134 at 300 ppm gave more than 70% control in these tests when compared to the untreated check which showed extensive disease development.

Example 7: *Fusarium culmorum* (Foot Rot of Cereals)

Compounds were dissolved in 0.3% DMSO & then added to Potato Dextrose Agar medium just prior to dispensing it into petri dishes. 5 mL medium with compound in the desired concentration was dispensed into 60 mm sterile petri-plates. After solidification, each plate was seeded with 5 mm size mycelial disc taken form periphery of actively growing virulent culture plate. Plates were incubated in growth chambers at 25° C. temperature and 60% relative humidity for seven days and radial growth was measured.

Example 8: *Phakopsora pachyrhizi* Test in Soybean

Compounds were dissolved in 2% DMSO/Acetone & then mixed with water to the calibrated spray volume of 50 mL and poured into the spray bottles for further applications.

To test the preventive activity of compounds, healthy young soybean plants raised in the greenhouse were sprayed with active compound preparation at the stated application rates inside the spray cabinets using hallowcone nozzles. One day after treatment, the plants were inoculated with spore suspension containing $2.1 \times 10^6$ *Phakopsora pachyrhizi* inoculum. The inoculated plants were then kept in greenhouse chamber at 25° C. temperature & 90% relative humidity for disease expression.

A visual assessment of compound's performance was carried out by rating the disease severity (0-100% scale) on treated plants on 3, 7, 10 & 15 days after application. Efficacy (% control) of the compounds was calculated by comparing the disease rating in the treatment with the one of the untreated control. The sprayed plants were also assessed for compound's plant compatibility by recording symptoms like necrosis, chlorosis & stunting.

| Compounds | 1 | 2 | 3 | 4 | 5 | 6 | 7 | 9 | 10 | 12 | 14 | 15 |
|---|---|---|---|---|---|---|---|---|---|---|---|---|
| | 16 | 17 | 18 | 19 | 20 | 21 | 22 | 23 | 25 | 26 | 27 | 28 |
| | 30 | 31 | 36 | 38 | 40 | 42 | 47 | 48 | 50 | 51 | 52 | 53 |
| | 54 | 56 | 57 | 58 | 59 | 62 | 71 | 75 | 85 | 89 | 91 | 92 |
| | 96 | 99 | 108 | 109 | 110 | | | | | | | | showed >90% at 500 ppm control in these tests when compared to the untreated check which showed extensive disease development.

The invention claimed is:

1. A compound of Formula I,

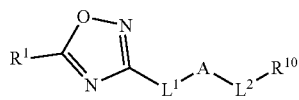

Formula I wherein:
$R^1$ is $C_1$-$C_2$-haloalkyl;
$L^1$ is a direct bond, —$CR^2R^3$—, —C(=O)—, —O—, —S(=O)$_{0-2}$—, —$NR^4$— or —$CR^2R^3$C(=O)—; wherein, an expression "-" at the start and the end of the group indicates the point of attachment to either oxadiazole ring or A;
A is an aromatic or non-aromatic 5- or 6-membered carbocyclic ring, wherein the ring members of the non-aromatic carbocyclic ring are selected from C, C(=O), C(=S), C(=$CR^{2a}R^{3a}$) and C=$NR^6$; or
A is an aromatic or non-aromatic 5- or 6-membered heterocyclic ring; wherein the heteroatom of the aromatic heterocyclic ring is selected from N, O and S; wherein heteroatom of the non-aromatic heterocyclic ring is selected from N, O, S(=O)$_{0-2}$, and S(=O)$_{0-1}$ (=$NR^6$) and one or more C atoms of the non-aromatic heterocyclic ring may be optionally replaced by C(=O), C(=S), C(=$CR^{2a}R^{3a}$) and C=$NR^6$; and
wherein, A is unsubstituted or is substituted with one or more identical or different $R^A$ groups, wherein, $R^A$ is selected from the group consisting of halogen, cyano, nitro, amino, hydroxy, $SF_5$, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxy-$C_1$-$C_4$-alkyl, $C_1$-$C_6$-hydroxyalkyl, $C_2$-$C_6$-haloalkenyl, $C_2$-$C_6$-haloalkynyl, $C_3$-$C_8$-halocycloalkyl, $C_1$-$C_6$-alkoxy, $C_1$-$C_6$-haloalkoxy, $C_1$-$C_6$-haloalkoxycarbonyl, $C_1$-$C_6$-alkylthio, $C_1$-$C_6$-haloalkylthio and $C_1$-$C_6$-haloalkylsulfinyl;

wherein, $R^A$ may be optionally substituted with one or more identical or different $R^a$ selected from halogen, cyano, nitro, $C_1$-$C_6$-alkyl, $C_1$-$C_6$-haloalkyl, $C_1$-$C_6$-alkoxy or $C_1$-$C_6$-haloalkoxy;

or two $R^A$ together with the atoms to which they are attached may form a 3- to 10-membered aromatic or non-aromatic carbocyclic ring or ring system, or aromatic or non-aromatic heterocyclic ring or ring system which may be optionally substituted with one or more identical or different $R^a$, $R^4$, $R^6$, and $R^{6b}$ are independently selected from the group of hydrogen, cyano, hydroxy, $NR^bR^c$, (C=O)—$R^d$, $S(O)_{0-2}R^e$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylamino, di-$C_1$-$C_6$-alkylamino, tri-$C_1$-$C_6$-alkylamino and $C_3$-$C_8$-cycloalkyl;

$R^b$ and $R^c$ are independently selected from the group of hydrogen, hydroxyl, cyano, $C_1$-$C_4$-alkyl, $C_1$-$C_4$-haloalkyl, $C_1$-$C_4$-alkoxy, $C_3$-$C_8$-cycloalkyl or $C_3$-$C_8$-halocycloalkyl, $R^d$ is selected from the group of hydrogen, hydroxy, halogen, $NR^bR^c$, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl and $C_3$-$C_8$-halocycloalkyl; and $R^e$ is selected from the group of hydrogen, halogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl and $C_3$-$C_8$-halocycloalkyl;

$L^2$ is a fragment selected from the group of

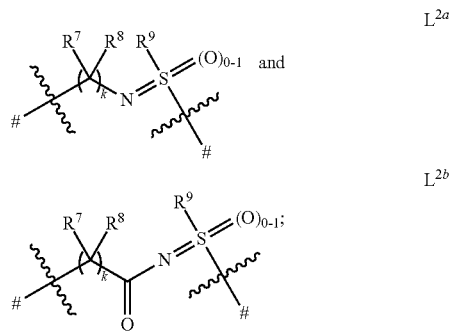

wherein, k is an integer ranging from 0 to 4; an expression "#" indicates the point of attachment;

wherein, in Formula I when $R^1$ is $CF_3$; A is phenyl ring or $C_3$-$C_7$ carbocyclic ring or 5- to 6-membered heterocyclic ring; $L^2$ is $L^{2a}$ wherein S atom of $L^{2a}$ is attached to A, and k=0 then $R^{10}$ is not hydrogen, cyano, nitro, $C_1$-$C_3$alkyl or $C_1$-$C_3$ haloalkyl;

wherein, in Formula I when $R^1$ is $CF_3$; A is phenyl ring or 5- to 6-membered heteroaromatic ring $L^2$ is $L^{2b}$ wherein S atom of $L^{2b}$ is attached to A, and k=0 to 4 then $R^{10}$ is not cyano, nitro, $R^{11}$ and $OR^{11}$; wherein, $R^{11}$ is hydrogen, $C_1$-$C_6$-alkyl optionally substituted with a group selected from halogen, cyano, nitro, $C_1$-$C_6$-alkoxy, $C_1$-$C_6$-haloalkoxy, $C_1$-$C_6$-alkylthio, $C_1$-$C_6$-haloalkylthio, and phenyl ring optionally substituted with $C_1$-$C_6$-alkyl, $C_1$-$C_6$-haloalkyl, $C_1$-$C_6$-alkoxy and $C_1$-$C_6$-haloalkoxy;

$R^2$, $R^3$, $R^{2a}$, $R^{3a}$, $R^{2b}$, $R^{2c}$, $R^{3c}$, $R^{2d}$, $R^{3d}$, $R^7$ and $R^8$ are independently selected from hydrogen, halogen, cyano, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_3$-$C_6$-halocycloalkyl, $C_1$-$C_4$-alkoxy and $C_1$-$C_4$-haloalkoxy; or $R^2$ and $R^3$; $R^{2a}$ and $R^{3a}$; $R^{2c}$ and $R^{3c}$; $R^{2d}$ and $R^{3d}$; and/or $R^7$ and $R^8$ together with the atoms to which they are attached may form 3- to 5-membered non-aromatic carbocylic ring or heterocyclic ring which may be optionally substituted with halogen, $C_1$-$C_2$-alkyl, $C_1$-$C_2$-haloalkyl or $C_1$-$C_2$-alkoxy;

$R^9$ is selected from the group consisting of hydrogen; $NR^gR^h$, wherein, $R^g$ and $R^h$ independently represent hydrogen, hydroxyl, cyano, $C_1$-$C_4$-alkyl, $C_1$-$C_4$-haloalkyl, $C_1$-$C_4$-alkoxy or $C_3$-$C_8$-cycloalkyl; (C=O)—$R^i$, wherein, $R^i$ represents hydrogen, halogen, cyano, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl, $C_3$-$C_6$-halocycloalkyl, $C_1$-$C_4$-alkoxy, and $C_1$-$C_4$-haloalkoxy; $C_{1-8}$-alkyl-$S(O)_{0-2}R^j$, wherein $R^j$ represents hydrogen, halogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl; $C_1$-$C_6$-alkyl-(C=O)—$R^i$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_6$-alkoxy, $C_1$-$C_6$-haloalkoxy, $C_3$-$C_8$-cycloalkyl, $C_4$-$C_8$-cycloalkenyl, $C_5$-$C_8$-cycloalkynyl, $C_7$-$C_{19}$-aralkyl;

wherein, $R^9$ may optionally be substituted with one or more identical or different substituents selected from the group consisting of halogen, cyano, nitro, hydroxy, $C_1$-$C_6$-alkyl, $C_2$-$C_6$-alkenyl, $C_2$-$C_6$-alkynyl, $C_3$-$C_8$-cycloalkyl, $C_3$-$C_8$-cycloalkylalkyl, $C_1$-$C_6$-haloalkyl, $C_1$-$C_6$-alkoxy-$C_1$-$C_4$-alkyl, $C_1$-$C_6$-hydroxyalkyl, $C_2$-$C_6$-haloalkenyl, $C_2$-$C_6$-haloalkynyl, $C_3$-$C_8$-halocycloalkyl, $C_1$-$C_6$-alkoxy, $C_1$-$C_6$-haloalkoxy, $C_1$-$C_6$-haloalkoxycarbonyl, $C_1$-$C_6$-alkylcarbonyl, $C_1$-$C_6$-alkoxycarbonyl, $C_1$-$C_6$-alkylaminocarbonyl and di-$C_1$-$C_6$-alkylaminocarbonyl;

$R^{10}$ is selected from the group consisting of halogen, hydroxy, cyano, —$OR^{12}$, —$NR^{13}R^{14}$, nitro, —SH, —SCN, —$COR^{15}$, —$C(=O)OR^{12}$, —$C(=O)NR^{13}R^{14}$, —$NR^{13}C(=O)R^{15}$, —$O(C=O)R^{15}$, —$O(C=O)NR^{13}R^{14}$, —$C(=NOR^{13})R^{15}$, —$NR^{13}SO_2R^{16}$, —$CSR^{16}$, —$C(=S)OR^{12}$, —$C(=S)NR^{13}R^{14}$, —$NR^{13}C(=S)R^{15}$, —$O(C=S)R^{15}$, —$O(C=S)NR^{13}R^{14}$, —$O(C=S)SR^{16}$, —$N=C(R^{15})_2$, —NHCN, —$SO_2NHCN$, —$C(=O)NHCN$, —$C(=S)NHCN$, —$C(=S(O))NHCN$, —$SO_2NR^{12}R^{13}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_3$-$C_8$-cycloalkyl-$C_1$-$C_6$-alkyl, $C_3$-$C_8$-cycloalkyl-$C_3$-$C_8$-cycloalkyl, $C_3$-$C_8$-halocycloalkyl-$C_1$-$C_6$-alkyl, $C_1$-$C_6$-alkyl-$C_3$-$C_8$-cycloalkyl-$C_1$-$C_6$-alkyl, $C_3$-$C_8$-cycloalkenyl, $C_3$-$C_8$-halocycloalkenyl, $C_1$-$C_6$-alkoxy-$C_1$-$C_6$-alkyl, $C_3$-$C_8$-cycloalkoxy-$C_1$-$C_6$-alkyl, $C_1$-$C_6$-alkoxy-$C_1$-$C_6$-alkoxy-$C_1$-$C_6$-alkyl, $C_1$-$C_6$-alkyl-$C_1$-$C_6$-thioalkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylamino, di-$C_1$-$C_6$-alkylamino, $C_1$-$C_6$-alkylamino-$C_1$-$C_6$-alkyl, di-$C_1$-$C_6$-alkylamino-$C_1$-$C_6$-alkyl, $C_1$-$C_6$-haloalkylamino-$C_1$-$C_6$-alkyl, $C_3$-$C_8$-cycloalkylamino, $C_3$-$C_8$-cycloalkylamino-$C_1$-$C_6$-alkyl, $C_1$-$C_6$-alkylcarbonyl, $C_1$-$C_6$-haloalkoxy-$C_1$-$C_6$-alkyl, $C_1$-$C_6$-hydroxyalkyl, $C_2$-$C_6$-hydroxyalkenyl, $C_2$-$C_6$-hydroxyalkynyl, $C_3$-$C_8$-halocycloalkoxy, $C_3$-$C_8$-cycloalkyl-$C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkoxy, $C_1$-$C_6$-alkylcarbonylalkoxy, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl, tri-$C_1$-$C_6$-alkylsilyl, $C_1$-$C_6$-alkylsulfonylamino, $C_1$-$C_6$-haloalkylsulfonylamino, $C_1$-$C_6$-alkylcarbonylthio, $C_1$-$C_6$-alkylsulfonyloxy, $C_1$-$C_6$-alkylsulfinyloxy, $C_6$-$C_{10}$-arylsulfonyloxy, $C_6$-$C_{10}$-arylsulfinyloxy, $C_6$-$C_{10}$-arylsulfonyl, $C_6$-$C_{10}$-arylsulfinyl, $C_6$-$C_{10}$-arylthio, $C_1$-$C_6$-cyanoalkyl, $C_2$-$C_6$-alkenylcarbonyloxy, $C_1$-$C_6$-alkoxy-$C_1$-$C_6$-alkylthio, $C_1$-$C_6$-alkylthio-$C_1$-$C_6$-alkoxy, $C_2$-$C_6$-haloalkenylcarbonyloxy, $C_1$-$C_6$-alkoxycarbonyl-$C_1$-$C_6$-alkyl, $C_1$-$C_6$-alkoxy-$C_2$-$C_6$-alkynyl, $C_2$-$C_6$-alkynylthio, $C_3$-$C_8$-halocycloalkyloxy, $C_2$-$C_6$-alkenylamino, $C_2$-$C_6$-alkynylamino, $C_1$-$C_6$-haloalkylamino, $C_3$-$C_8$-cycloalkyl-$C_1$-$C_6$-alkylamino, $C_1$-$C_6$-alkoxyamino, $C_1$-$C_6$-haloalkoxyamino, $C_1$-$C_6$-alkoxycarbonylamino, $C_1$-$C_6$-alkylcarbonyl-$C_1$-$C_6$-alkylamino, $C_1$-$C_6$-haloalkylcarbonyl-$C_1$-$C_6$-alkylamino, $C_1$-$C_6$-alkoxycarbonyl-$C_1$-$C_6$-alkylamino, $C_2$-$C_6$-alkenylthio, $C_1$-$C_6$-alkoxy-$C_1$-$C_6$-alkylcarbonyl, $C_1$-$C_6$-haloalkoxycarbonylamino, di($C_1$-$C_6$-haloalkyl)amino-$C_1$-$C_6$-alkyl, $C_3$-$C_8$-halocycloalkenyloxy-$C_1$-$C_6$-alkyl, $C_1$-$C_6$-alkoxy($C_1$-$C_6$-alkyl)aminocarbonyl, $C_1$-$C_6$-haloalkylsulfonylaminocarbonyl, $C_1$-$C_6$-alkylsulfonylaminocarbonyl, $C_1$-$C_6$-alkoxycarbonylalkoxy, $C_1$-$C_6$-alkylaminothiocarbonylamino, $C_3$-$C_8$-cycloalkyl-$C_1$-$C_6$-alkylamino-$C_1$-$C_6$-alkyl, $C_1$-$C_6$-alkylthiocarbonyl, $C_3$-$C_8$-cycloalkenyloxy-$C_1$-$C_6$-alkyl, $C_1$-$C_6$-alkoxy-$C_1$-$C_6$-alkoxycarbonyl, di-$C_1$-$C_6$-alkylaminothiocarbonylamino, $C_1$-$C_6$-haloalkoxy-$C_1$-$C_6$-haloalkoxy, $C_1$-$C_6$-alkoxy-$C_1$-$C_6$-haloalkoxy, $C_3$-$C_8$-halocycloalkoxy-$C_1$-$C_6$-alkyl, di-$C_1$-$C_6$-alkylaminocarbonylamino, $C_1$-$C_6$-alkoxy-$C_2$-$C_6$-alkenyl, $C_1$-$C_6$-alkylthiocarbonyloxy, $C_1$-$C_6$-haloalkoxy-$C_1$-$C_6$-alkoxy, $C_1$-$C_6$-haloalkylsulfonyloxy, $C_1$-$C_6$-alkoxy-$C_1$-$C_6$-haloalkyl, di($C_1$-$C_6$-haloalkyl)amino, di-$C_1$-$C_6$-alkoxy-$C_1$-$C_6$-alkyl, $C_1$-$C_6$-alkylaminocarbonylamino, $C_1$-$C_6$-haloalkoxy-$C_1$-$C_6$-haloalkyl, $C_1$-$C_6$-alkylaminocarbonyl-$C_1$-$C_6$-alkylamino, tri-$C_1$-$C_6$-alkylsilyl-$C_2$-$C_6$-alkynyloxy, tri-$C_1$-$C_6$-alkylsilyloxy, tri-$C_1$-$C_6$-alkylsilyl-$C_2$-$C_6$-alkynyl, cyano($C_1$-$C_6$-alkoxy)-$C_1$-$C_6$-alkyl, di-$C_1$-$C_6$-alkylthio-$C_1$-$C_6$-alkyl, $C_1$-$C_6$-alkoxysulfonyl, $C_3$-$C_8$-halocycloalkoxycarbonyl, $C_1$-$C_6$-alkyl-$C_3$-$C_8$-cycloalkylcarbonyl, $C_3$-$C_8$-halocycloalkylcarbonyl, $C_2$-$C_6$-alkenyloxycarbonyl, $C_2$-$C_6$-alkynyloxycarbonyl, $C_1$-$C_6$-cyanoalkoxycarbonyl, $C_1$-$C_6$-alkylthio-$C_1$-$C_6$-alkoxycarbonyl, $C_2$-$C_6$-alkynylcarbonyloxy, $C_2$-$C_6$-haloalkynylcarbonyloxy, cyanocarbonyloxy, $C_1$-$C_6$-cyanoalkylcarbonyloxy, $C_3$-$C_8$-cycloalkylsulphonyloxy, $C_3$-$C_8$-cycloalkyl-$C_1$-$C_6$-alkylsulphonyloxy, $C_3$-$C_8$-halocycloalkylsulphonyloxy, $C_2$-$C_6$-alkenylsulphonyloxy, $C_2$-$C_6$-alkynylsulphonyloxy, $C_1$-$C_6$-cyanoalkylsulphonyloxy, $C_2$-$C_6$-haloalkenylsulphonyloxy, $C_2$-$C_6$- haloalkynylsulphonyloxy, $C_2$-$C_6$-alkynylcycloalkyloxy, $C_2$-$C_6$-cyanoalkenyloxy, $C_2$-$C_6$-cyanoalkynyloxy, $C_1$-$C_6$-alkoxycarbonyloxy, $C_2$-$C_6$-alkenyloxycarbonyloxy, $C_2$-$C_6$-alkynyloxycarbonyloxy, $C_1$-$C_6$-alkoxy-$C_1$-$C_6$-alkylcarbonyloxy, sulfilimines, sulfoximines, SF$_5$ and $Z^1Q^1$;

$Z^1$ and $Z^2$ are independently a direct bond, $CR^{2d}R^{3d}$, N, O, C(O), C(S), C($=CR^{2d}R^{3d}$) or S(O)$_{0-2}$;

$Q^1$ is selected from phenyl, benzyl, naphthalenyl, a 5- or 6-membered aromatic ring, an 8- to 11-membered aromatic multi-cyclic ring system, an 8- to 11-membered aromatic fused ring system, a 5- or 6-membered heteroaromatic ring, an 8- to 11-membered heteroaromatic multi-cyclic ring system or an 8- to 11-membered heteroaromatic fused ring system; wherein the heteroatom of the heteroaromatic rings is selected from N, O or S, and each ring or ring system may be optionally substituted with one or more substituents independently selected from $R^{17}$; or $Q^1$ is selected from a 3- to 7-membered non-aromatic carbocyclic ring, a 4-, 5-, 6- or 7-membered non-aromatic heterocyclic ring, an 8- to 15-membered non-aromatic multi-cyclic ring system, an 5- to 15 membered spirocyclic ring system, or an 8- to 15-membered non-aromatic fused ring system, wherein, the heteroatom of the non-aromatic rings is selected from N, O or S(O)$_{0-2}$, and C ring member of the non-aromatic carbocylic or non-aromatic heterocyclic rings or ring systems may be replaced with C(O), C(S), C($=CR^{2c}R^{3c}$) or C($=NR^{6b}$) and each ring or ring system may be optionally substituted with one or more substituents independently selected from $R^{17}$;

wherein, $R^{17}$ is selected from the group consisting of hydrogen, halogen, hydroxy, cyano, —OR$^{12}$, —NR$^{13}$R$^{14}$, nitro, —SH, —SCN, —COR$^{15}$, —C(=O)OR$^{12}$, —C(=O)NR$^{13}$R$^{14}$, —NR$^{13}$C(=O)R$^{15}$, —O(C=O)R$^{15}$, —O(C=O)NR$^{13}$R$^{14}$, —C(=NOR$^{13}$)R$^{15}$, —NR$^{13}$SO$_2$R$^{16}$, —CSR$^{16}$, —C(=S)OR$^{12}$, —C(=S)NR$^{13}$R$^{14}$, —NR$^{13}$C(=S)R$^{15}$, —O(C=S)R$^{15}$, —O(C=S)NR$^{13}$R$^{14}$, —O(C=S)SR$^{16}$, —N=C(R$^{15}$)$_2$, —NHCN, —SO$_2$NHCN, —C(=O)NHCN, —C(=S(O))NHCN, —C(=S)NHCN, —SO$_2$NR$^{12}$R$^{13}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_3$-$C_8$-cycloalkyl-$C_1$-$C_6$-alkyl, $C_3$-$C_8$-cycloalkyl-$C_3$-$C_8$-cycloalkyl, $C_3$-$C_8$-halocycloalkyl-$C_1$-$C_6$-alkyl, $C_1$-$C_6$-alkyl-$C_3$-$C_8$-cycloalkyl-$C_1$-$C_6$-alkyl, $C_3$-$C_8$-cycloalkenyl, $C_3$-$C_8$-halocycloalkenyl, $C_1$-$C_6$-alkoxy-$C_1$-$C_6$-alkyl, $C_3$-$C_8$-cycloalkoxy-$C_1$-$C_6$-alkyl, $C_1$-$C_6$-alkoxy-$C_1$-$C_6$-alkoxy-$C_1$-$C_6$-alkyl, $C_1$-$C_6$-alkyl-$C_1$-$C_6$-thioalkyl, $C_1$-$C_6$-alkylsulfinyl-$C_1$-$C_6$-alkyl, $C_1$-$C_6$-alkylsulfonyl-$C_1$-$C_6$-alkyl, $C_1$-$C_6$-alkylamino, di-$C_1$-$C_6$-alkylamino, $C_1$-$C_6$-alkylamino-$C_1$-$C_6$-alkyl, di-$C_1$-$C_6$-alkylamino-$C_1$-$C_6$-alkyl, $C_1$-$C_6$-haloalkylamino-$C_1$-$C_6$-alkyl, $C_3$-$C_8$-cycloalkylamino, $C_3$-$C_8$-cycloalkylamino-$C_1$-$C_6$-alkyl, $C_1$-$C_6$-alkylcarbonyl, $C_1$-$C_6$-haloalkoxy-$C_1$-$C_6$-alkyl, $C_1$-$C_6$-hydroxyalkyl, $C_2$-$C_6$-hydroxyalkenyl, $C_2$-$C_6$-hydroxyalkynyl, $C_3$-$C_8$-halocycloalkoxy, $C_3$-$C_8$-cycloalkyl-$C_1$-$C_6$-alkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkoxy, $C_1$-$C_6$-alkylcarbonylalkoxy, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl, tri-$C_1$-$C_6$-alkylsilyl, $C_1$-$C_6$-alkylsulfonylamino, $C_1$-$C_6$-haloalkylsulfonylamino, $C_1$-$C_6$-alkylcarbonylthio, $C_1$-$C_6$-alkylsulfonyloxy, $C_1$-$C_6$-alkylsulfinyloxy, $C_6$-$C_{10}$-arylsulfonyloxy, $C_6$-$C_{10}$-arylsulfinyloxy, $C_6$-$C_{10}$-arylsulfonyl, $C_6$-$C_{10}$-arylsulfinyl, $C_6$-$C_{10}$-arylthio, $C_1$-$C_6$-cyanoalkyl, $C_2$-$C_6$-alkenylcarbonyloxy, $C_1$-$C_6$-alkoxy-$C_1$-$C_6$-alkylthio, $C_1$-$C_6$-alkylthio-$C_1$-$C_6$-alkoxy, $C_2$-$C_6$-haloalkenylcarbonyloxy, $C_1$-$C_6$-alkoxycarbonyl-$C_1$-$C_6$-alkyl, $C_1$-$C_6$-alkoxy-$C_2$-$C_6$-alkynyl, $C_2$-$C_6$-alkynylthio, $C_3$-$C_8$-halocycloalkylcarbonyloxy, $C_2$-$C_6$-alkenylamino, $C_2$-$C_6$-alkynylamino, $C_1$-$C_6$-haloalkylamino, $C_3$-$C_8$-cycloalkyl-$C_1$-$C_6$-alkylamino, $C_1$-$C_6$-alkoxyamino, $C_1$-$C_6$-haloalkoxyamino, $C_1$-$C_6$-alkoxycarbonylamino, $C_1$-$C_6$-alkylcarbonyl-$C_1$-$C_6$-alkylamino, $C_1$-$C_6$-haloalkylcarbonyl-$C_1$-$C_6$-alkylamino, $C_1$-$C_6$-alkoxycarbonyl-$C_1$-$C_6$-alkylamino, $C_2$-$C_6$-alkenylthio, $C_1$-$C_6$-alkoxy-$C_1$-$C_6$-alkylcarbonyl, $C_1$-$C_6$-haloalkoxycarbonylamino, di($C_1$-$C_6$-haloalkyl)amino-$C_1$-$C_6$-alkyl, $C_3$-$C_8$-halocycloalkenyloxy-$C_1$-$C_6$-alkyl, $C_1$-$C_6$-alkoxy($C_1$-$C_6$-alkyl)aminocarbonyl, $C_1$-$C_6$-haloalkylsulfonylaminocarbonyl, $C_1$-$C_6$-alkylsulfonylaminocarbonyl, $C_1$-$C_6$-alkoxycarbonylalkoxy, $C_1$-$C_6$-alkylaminothiocarbonylamino, $C_3$-$C_8$-cycloalkyl-$C_1$-$C_6$-alkylamino-$C_1$-$C_6$-alkyl, $C_1$-$C_6$-alkylthiocarbonyl, $C_3$-$C_8$-cycloalkenyloxy-$C_1$-$C_6$-alkyl, $C_1$-$C_6$-alkoxy-$C_1$-$C_6$-alkoxycarbonyl, di-$C_1$-$C_6$-alkylaminothiocarbonylamino, $C_1$-$C_6$-haloalkoxy-$C_1$-$C_6$-haloalkoxy, $C_1$-$C_6$-alkoxy-$C_1$-$C_6$-haloalkoxy, $C_3$-$C_8$-halocycloalkoxy-$C_1$-$C_6$-alkyl, di-$C_1$-$C_6$-alkylaminocarbonylamino, $C_1$-$C_6$-alkoxy-$C_2$-$C_6$-alkenyl, $C_1$-$C_6$-alkylthiocarbonyloxy, $C_1$-$C_6$-haloalkoxy-$C_1$-$C_6$-alkoxy, $C_1$-$C_6$-haloalkylsulfonyloxy, $C_1$-$C_6$-alkoxy-$C_1$-$C_6$-haloalkyl, di($C_1$-$C_6$-haloalkyl)amino, di-$C_1$-$C_6$-alkoxy-$C_1$-$C_6$-alkyl, $C_1$-$C_6$-alkylaminocarbonylamino, $C_1$-$C_6$-haloalkoxy-$C_1$-$C_6$-haloalkyl, $C_1$-$C_6$-alkylaminocarbonyl-$C_1$-$C_6$-alkylamino, tri-$C_1$-$C_6$-alkylsilyl-$C_2$-$C_6$-alkynyloxy, tri-$C_1$-$C_6$-alkylsilyloxy, tri-$C_1$-$C_6$-alkylsilyl-$C_2$-$C_6$-alkynyl, cyano($C_1$-$C_6$-alkoxy)-$C_1$-$C_6$-alkyl, di-$C_1$-$C_6$-alkylthio-$C_1$-$C_6$-alkyl, $C_1$-$C_6$-alkoxysulfonyl, $C_3$-$C_8$-halocycloalkoxycarbonyl, $C_1$-$C_6$-alkyl-$C_3$-$C_8$-cycloalkylcarbonyl, $C_3$-$C_8$-halocycloalkylcarbonyl, $C_2$-$C_6$-alkenyloxycarbonyl, $C_2$-$C_6$-alkynyloxycarbonyl, $C_1$-$C_6$-cyanoalkoxycarbonyl, $C_1$-$C_6$-alkylthio-$C_1$-$C_6$-alkoxycarbonyl, $C_2$-$C_6$-alkynylcarbonyloxy, $C_2$-$C_6$-haloalkynylcarbonyloxy, cyanocarbonyloxy, $C_1$-$C_6$-cyanoalkylcarbonyloxy, $C_3$-$C_8$-cycloalkylsulphonyloxy, $C_3$-$C_8$-cycloalkyl-$C_1$-$C_6$-alkylsulphonyloxy, $C_3$-$C_8$-halocycloalkylsulphonyloxy, $C_2$-$C_6$-alkenylsulphonyloxy, $C_2$-$C_6$-alkynylsulphonyloxy, $C_1$-$C_6$-cyanoalkylsulphonyloxy, $C_2$-$C_6$-haloalkenylsulphonyloxy, $C_2$-$C_6$-haloalkynylsulphonyloxy, $C_2$-$C_6$-alkynylcycloalkyloxy, $C_2$-$C_6$-cyanoalkenyloxy, $C_2$-$C_6$-cyanoalkynyloxy, $C_1$-$C_6$-alkoxycarbonyloxy, $C_2$-$C_6$-alkenyloxycarbonyloxy, $C_2$-$C_6$-alkynyloxycarbonyloxy, $C_1$-$C_6$-alkoxy-$C_1$-$C_6$-alkylcarbonyloxy, sulfilimines, sulfoximines, SF$_5$ and $Z^2Q^2$;

$Q^2$ is selected from phenyl, benzyl, naphthalenyl, a 5- or 6-membered aromatic ring, an 8- to 11-membered aromatic multi-cyclic ring system, an 8- to 11-membered aromatic fused ring system, a 5- or 6-membered heteroaromatic ring, an 8- to 11-membered heteroaromatic multi-cyclic ring system or an 8- to 11-membered heteroaromatic fused ring system; wherein the heteroatom of the heteroaromatic rings is selected from N, O or S, and each ring or ring system may be optionally substituted with one or more substituents independently selected from hydrogen, halogen, cyano, $-OR^{12}$, $-NR^{13}R^{14}$, $C_1$-$C_6$-alkyl, $C_1$-$C_6$-haloalkyl, $C_1$-$C_6$-alkoxy, $C_1$-$C_6$-alkoxy-$C_1$-$C_6$-alkyl, $C_1$-$C_6$-haloalkoxy, $C_3$-$C_8$-cycloalkyl, $C_1$-$C_6$-alkyl-$C_3$-$C_8$-cycloalkyl, $C_3$-$C_8$-cycloalkoxy-$C_1$-$C_6$-alkyl, $C_3$-$C_8$-halocycloalkyl, $C_1$-$C_6$-alkylsulfonyl-$C_1$-$C_6$-alkyl, $C_1$-$C_6$-alkylamino-$C_1$-$C_6$-alkyl, $C_3$-$C_8$-cycloalkylamino-$C_1$-$C_6$-alkyl, $C_1$-$C_6$-haloalkoxy-$C_1$-$C_6$-alkyl, $C_3$-$C_8$-halocycloalkoxy, $C_1$-$C_6$-alkylsulfonyl, $C_3$-$C_8$-cycloalkylsulfonyl and $C_1$-$C_6$-alkylsulfonylamino; or $Q^2$ is selected from a 3- to 7-membered non-aromatic carbocyclic ring, a 4-, 5-, 6- or 7-membered non-aromatic heterocyclic ring, an 8- to 15-membered non-aromatic multi-cyclic ring system, an 5- to 15 membered spirocyclic ring system, or an 8- to 15-membered non-aromatic fused ring system, wherein, the heteroatom of the non-aromatic rings is selected from N, O or $S(O)_{0-2}$, and C ring member of the non-aromatic carbocyclic or non-aromatic heterocyclic rings or ring systems may be replaced with C(O), C(S), C(=$CR^{2c}R^{3c}$) or C(=$NR^{6b}$), and each ring or ring system may be optionally substituted with one or more substituents independently selected from hydrogen, halogen, cyano, $-OR^{12}$, $-NR^{13}R^{14}$, $C_1$-$C_6$-alkyl, $C_1$-$C_6$-haloalkyl, $C_1$-$C_6$-alkoxy, $C_1$-$C_6$-alkoxy-$C_1$-$C_6$-alkyl, $C_1$-$C_6$-haloalkoxy, $C_3$-$C_8$-cycloalkyl, $C_1$-$C_6$-alkyl-$C_3$-$C_8$-cycloalkyl, $C_3$-$C_8$-cycloalkoxy-$C_1$-$C_6$-alkyl, $C_3$-$C_8$-halocycloalkyl, $C_1$-$C_6$-alkylsulfonyl-$C_1$-$C_6$-alkyl, $C_1$-$C_6$-alkylamino-$C_1$-$C_6$-alkyl, $C_3$-$C_8$-cycloalkylamino-$C_1$-$C_6$-alkyl, $C_1$-$C_6$-haloalkoxy-$C_1$-$C_6$-alkyl, $C_3$-$C_8$-halocycloalkoxy, $C_1$-$C_6$-alkylsulfonyl, $C_3$-$C_8$-cycloalkylsulfonyl and $C_1$-$C_6$-alkylsulfonylamino:

$R^9$ and $R^{10}$; and/or $R^9$ and $R^4$ together with the atoms to which they are attached may form a 3- to 10-membered carbocyclic ring or ring system, or heterocyclic ring or ring system which may be optionally substituted with $R^{17}$;
wherein,
$R^{12}$ is selected from the group consisting of $C_1$-$C_6$-alkyl, $C_1$-$C_6$-haloalkyl, $C_3$-$C_8$-cycloalkyl and $C_3$-$C_8$-halocycloalkyl,
$R^{13}$ and $R^{14}$ are independently selected from the group consisting of hydrogen, hydroxyl, cyano, $C_1$-$C_6$-alkyl, $C_1$-$C_6$-haloalkyl, $C_1$-$C_6$-alkoxy, $C_3$-$C_8$-cycloalkyl and $C_3$-$C_8$-halocycloalkyl,
$R^{15}$ is selected from the group consisting of hydrogen, hydroxy, halogen, $NR^bR^c$, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl and $C_3$-$C_8$-cycloalkyl, and
$R^{16}$ is selected from the group consisting of hydrogen, halogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl and $C_3$-$C_8$-cycloalkyl;

or N-oxides, metal complexes, isomers, polymorphs or the agriculturally acceptable salts thereof.

2. The compound of claim 1, wherein; α carbon atom of $R^1$ from the oxadiazole ring bears at least two fluorine atoms; and the β carbon atom of $R^1$ from the oxadiazole ring in case of $C_2$-haloalkyl bears at least one fluorine atom.

3. The compound of claim 1,
wherein:
$R^1$ is trifluoroalkyl;
$L^1$ is a direct bond;
A is a phenyl ring or pyridyl ring; wherein phenyl or pyridyl ring is unsubstituted or substituted with one or more identical or different $R^A$ groups,
wherein, $R^A$ is halogen, cyano, $C_1$-$C_6$-alkyl and $C_1$-$C_6$-alkoxy,
wherein $R^A$ may be optionally substituted with one or more identical or different $R^a$ selected from halogen, cyano, and amino;
$L^2$ is a fragment selected from the group of

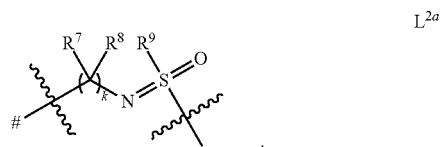

$L^{2a}$

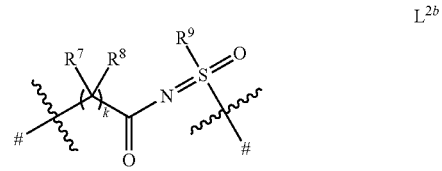

$L^{2b}$ wherein, k is an integer ranging from 0 to 1; an expression "#" indicates the point of attachment;
$R^7$ and $R^8$ are independently selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl and $C_1$-$C_4$-alkoxy;
$R^9$ is selected from the group consisting of $C_1$-$C_6$-alkyl, $C_2$-$C_6$-alkenyl, $C_1$-$C_6$-haloalkyl, $C_1$-$C_6$-alkoxy, $C_1$-$C_6$-haloalkoxy and $C_3$-$C_8$-cycloalkyl;
$R^{10}$ is selected from the group consisting of $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_3$-$C_8$-cycloalkyl-$C_1$-$C_6$-alkyl, $C_3$-$C_8$-cycloalkyl-$C_3$-$C_8$-cycloalkyl, $C_3$-$C_8$-halocycloalkyl-$C_1$-$C_6$-alkyl, $C_1$-$C_6$-alkyl-$C_3$-$C_8$-cycloalkyl-$C_1$-$C_6$-alkyl, $C_1$-$C_6$-alkoxy-$C_1$-$C_6$-alkyl, $C_3$-$C_8$-cycloalkoxy-$C_1$-$C_6$-alkyl, $C_1$-$C_6$-alkoxy-$C_1$-$C_6$-alkoxy-$C_1$-$C_6$-alkyl, $C_1$-$C_6$-haloalkoxy-$C_1$-$C_6$-alkyl, $C_1$-$C_6$-hydroxyalkyl, $C_3$-$C_8$-halocycloalkoxy, $C_3$-$C_8$-cycloalkyl-$C_1$-$C_6$-alkoxy, $C_1$-$C_6$-alkoxy-$C_1$-$C_6$-alkoxy, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl or $Z^1Q^1$;
$Z^1$ and $Z^2$ are independently represents a direct bond, $CR^{2d}R^{3d}$ and O;
$Q^1$ represents phenyl, benzyl, 5- or 6-membered aromatic ring, a 5- or 6-membered heteroaromatic ring; wherein the heteroatom of the heteroaromatic ring is selected from N, O and S; and each ring may be optionally substituted with one or more substituents independently selected from $R^{17}$; or wherein, $R^{17}$ is selected from the group consisting of halogen, cyano, —$OR^{12}$;

wherein $R^{12}$ represents $C_1$-$C_6$-alkyl, $C_1$-$C_6$-haloalkyl, $C_3$-$C_8$-cycloalkyl and $C_3$-$C_8$-halocycloalkyl; $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_1$-$C_6$-alkyl-$C_3$-$C_8$-cycloalkyl, $C_1$-$C_6$-alkylthio, $C_1$-$C_6$-haloalkylthio, $C_3$-$C_8$-cycloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkylsulfonyl, $C_3$-$C_8$-cycloalkylsulfinyl and $Z^2Q^2$;

$Q^2$ represents phenyl, benzyl, 5- or 6-membered aromatic ring, a 5- or 6-membered heteroaromatic ring; wherein the heteroatom of the heteroaromatic ring is selected from N, O and S; and each ring may be optionally substituted with one or more substituents independently selected from hydrogen, halogen, cyano, —$OR^{12}$, —$NR^{13}R^{14}$, $C_1$-$C_6$-alkyl, $C_1$-$C_6$-haloalkyl, $C_1$-$C_6$-alkoxy, $C_1$-$C_6$-alkoxy-$C_1$-$C_6$-alkyl, $C_1$-$C_6$-haloalkoxy, $C_3$-$C_8$-cycloalkyl, $C_1$-$C_6$-alkyl-$C_3$-$C_8$-cycloalkyl, $C_3$-$C_8$-cycloalkoxy-$C_1$-$C_6$-alkyl, $C_3$-$C_8$-halocycloalkyl, $C_1$-$C_6$-alkylsulfonyl-$C_1$-$C_6$-alkyl, $C_1$-$C_6$-alkylamino-$C_1$-$C_6$-alkyl, $C_3$-$C_8$-cycloalkylamino-$C_1$-$C_6$-alkyl, $C_1$-$C_6$-haloalkoxy-$C_1$-$C_6$-alkyl, $C_3$-$C_8$-halocycloalkoxy, $C_1$-$C_6$-alkylsulfonyl, $C_3$-$C_8$-cycloalkylsulfonyl and $C_1$-$C_6$-alkylsulfonylamino or $R^9$ and $R^{10}$ together with the atoms to which they are attached may form a 3- to 10-membered heterocyclic ring or ring system which may be optionally substituted with $R^{17}$; wherein the heteroatom of the heterocyclic ring or ring system is selected from N, O and $S(O)_{0-2}$.

4. The compound of claim 1, wherein said compound of formula (I) is selected from the group consisting of N-(methyl(oxo)(p-tolyl)-$\lambda^6$-sulfaneylidene)-4-(5-(trifluoromethyl)-1,2,4-oxadiazol-3-yl)benzamide; N-((4-cyanobenzyl)(methyl)(oxo)-$\lambda^6$-sulfaneylidene)-4-(5-(trifluoromethyl)-1,2,4-oxadiazol-3-yl)benzamide; N-((2,6-difluorobenzyl)(methyl)(oxo)-$\lambda^6$-sulfaneylidene)-4-(5-(trifluoromethyl)-1,2,4-oxadiazol-3-yl)benzamide; N-((2,3-difluorobenzyl)(methyl)(oxo)-$\lambda^6$-sulfaneylidene)-4-(5-(trifluoromethyl)-1,2,4-oxadiazol-3-yl)benzamide; N-((4-methoxybenzyl)(methyl)(oxo)-$\lambda^6$-sulfaneylidene)-4-(5-(trifluoromethyl)-1,2,4-oxadiazol-3-yl)benzamide; N-((4-bromobenzyl)(methyl)(oxo)-$\lambda^6$-sulfaneylidene)-4-(5-(trifluoromethyl)-1,2,4-oxadiazol-3-yl)benzamide; N-((2,6-difluorophenyl)(methyl)(oxo)-$\lambda^6$-sulfaneylidene)-4-(5-(trifluoromethyl)-1,2,4-oxadiazol-3-yl)benzamide; N-((2,4-difluorobenzyl)(methyl)(oxo)-$\lambda^6$-sulfaneylidene)-4-(5-(trifluoromethyl)-1,2,4-oxadiazol-3-yl)benzamide; N-((2-fluorobenzyl)(methyl)(oxo)-$\lambda^6$-sulfaneylidene)-4-(5-(trifluoromethyl)-1,2,4-oxadiazol-3-yl)benzamide; N-((3-fluorobenzyl)(methyl)(oxo)-$\lambda^6$-sulfaneylidene)-4-(5-(trifluoromethyl)-1,2,4-oxadiazol-3-yl)benzamide; N-(methyl(2-methylbenzyl)(oxo)-$\lambda^6$-sulfaneylidene)-4-(5-(trifluoromethyl)-1,2,4-oxadiazol-3-yl)benzamide; N-((3,5-dimethylphenyl)(methyl)(oxo)-$\lambda^6$-sulfaneylidene)-4-(5-(trifluoromethyl)-1,2,4-oxadiazol-3-yl)benzamide; N-((4-cyanophenyl)(methyl)(oxo)-$\lambda^6$-sulfaneylidene)-4-(5-(trifluoromethyl)-1,2,4-oxadiazol-3-yl)benzamide; N-(1-oxidotetrahydro-2H-1$\lambda^6$-thiopyran-1-ylidene)-4-(5-(trifluoromethyl)-1,2,4-oxadiazol-3-yl)benzamide; N-(methyl(oxo)(m-tolyl)-$\lambda^6$-sulfaneylidene)-4-(5-(trifluoromethyl)-1,2,4-oxadiazol-3-yl)benzamide; N-(methyl(3-methylbenzyl)(oxo)-$\lambda^6$-sulfaneylidene)-4-(5-(trifluoromethyl)-1,2,4-oxadiazol-3-yl)benzamide; N-((3-methoxyphenyl)(methyl)(oxo)-$\lambda^6$-sulfaneylidene)-4-(5-(trifluoromethyl)-1,2,4-oxadiazol-3-yl)benzamide; N-((2,4-difluorophenyl)(methyl)(oxo)-$\lambda^6$-sulfaneylidene)-4-(5-(trifluoromethyl)-1,2,4-oxadiazol-3-yl)benzamide; N-(methyl(oxo)(thiazol-2-yl)-$\lambda^6$-sulfaneylidene)-4-(5-(trifluoromethyl)-1,2,4-oxadiazol-3-yl)benzamide; N-((4-fluorobenzyl)(methyl)(oxo)-$\lambda^6$-sulfaneylidene)-4-(5-(trifluoromethyl)-1,2,4-oxadiazol-3-yl)benzamide; N-(methyl(oxo)(4-(trifluoromethyl)benzyl)-$\lambda^6$-sulfaneylidene)-4-(5-(trifluoromethyl)-1,2,4-oxadiazol-3-yl)benzamide; N-((2,6-dichlorobenzyl)(methyl)(oxo)-$\lambda^6$-sulfaneylidene)-4-(5-(trifluoromethyl)-1,2,4-oxadiazol-3-yl)benzamide; N-(methyl(oxo)(pyridin-2-ylmethyl)-$\lambda^6$-sulfaneylidene)-4-(5-(trifluoromethyl)-1,2,4-oxadiazol-3-yl)benzamide; N-(methyl(4-methylthiazol-2-yl)(oxo)-$\lambda^6$-sulfaneylidene)-4-(5-(trifluoromethyl)-1,2,4-oxadiazol-3-yl)benzamide; N-(methyl(5-methyl-1,3,4-thiadiazol-2-yl)(oxo)-$\lambda^6$-sulfaneylidene)-4-(5-(trifluoromethyl)-1,2,4-oxadiazol-3-yl)benzamide; N-((2,5-dichlorophenyl)(methyl)(oxo)-$\lambda^6$-sulfaneylidene)-4-(5-(trifluoromethyl)-1,2,4-oxadiazol-3-yl)benzamide; N-((2,4-dimethoxyphenyl)(methyl)(oxo)-$\lambda^6$-sulfaneylidene)-4-(5-(trifluoromethyl)-1,2,4-oxadiazol-3-yl)benzamide; N-((3,4-difluorophenyl)(methyl)(oxo)-$\lambda^6$-sulfaneylidene)-4-(5-(trifluoromethyl)-1,2,4-oxadiazol-3-yl)benzamide; N-(4-oxido-1,4$\lambda^6$-oxathian-4-ylidene)-4-(5-(trifluoromethyl)-1,2,4-oxadiazol-3-yl)benzamide; N-((2-fluorophenyl)(methyl)(oxo)-$\lambda^6$-sulfaneylidene)-4-(3-(trifluoromethyl)-1,2,4-oxadiazol-5-yl)benzamide; N-(methyl(oxo)(pyridin-4-ylmethyl)-$\lambda^6$-sulfaneylidene)-4-(5-(trifluoromethyl)-1,2,4-oxadiazol-3-yl)benzamide; N-((4-chlorobenzyl)(methyl)(oxo)-$\lambda^6$-sulfaneylidene)-4-(5-(trifluoromethyl)-1,2,4-oxadiazol-3-yl)benzamide; N-((4-chloro-3-fluorobenzyl)(methyl)(oxo)-$\lambda^6$-sulfaneylidene)-4-(5-(trifluoromethyl)-1,2,4-oxadiazol-3-yl)benzamide; N-((2,5-difluorobenzyl)(methyl)(oxo)-$\lambda^6$-sulfaneylidene)-4-(5-(trifluoromethyl)-1,2,4-oxadiazol-3-yl)benzamide; N-((2-fluorophenyl)(methyl)(oxo)-$\lambda^6$-sulfaneylidene)-3-(5-(trifluoromethyl)-1,2,4-oxadiazol-3-yl)benzamide; N-(methyl(oxo)(4-(trifluoromethyl)phenyl)-$\lambda^6$-sulfaneylidene)-3-(5-(trifluoromethyl)-1,2,4-oxadiazol-3-yl)benzamide; N-((4-fluorophenyl)(methyl)(oxo)-$\lambda^6$-sulfaneylidene)-3-(5-(trifluoromethyl)-1,2,4-oxadiazol-3-yl)benzamide; N-(methyl(oxo)(pyridin-2-yl)-$\lambda^6$-sulfaneylidene)-3-(5-(trifluoromethyl)-1,2,4-oxadiazol-3-yl)benzamide; N-(methyl(oxo)(phenyl)-$\lambda^6$-sulfaneylidene)-3-(5-(trifluoromethyl)-1,2,4-oxadiazol-3-yl)benzamide; N-((2,6-difluorobenzyl)(methyl)(oxo)-$\lambda^6$-sulfaneylidene)-3-(5-(trifluoromethyl)-1,2,4-oxadiazol-3-yl)benzamide; N-((2,4-difluorobenzyl)(methyl)(oxo)-$\lambda^6$-sulfaneylidene)-3-(5-(trifluoromethyl)-1,2,4-oxadiazol-3-yl)benzamide; N-((4-methoxybenzyl)(methyl)(oxo)-$\lambda^6$-sulfaneylidene)-3-(5-(trifluoromethyl)-1,2,4-oxadiazol-3-yl)benzamide; N-((4-methoxyphenyl)(methyl)(oxo)-$\lambda^6$-sulfaneylidene)-3-(5-(trifluoromethyl)-1,2,4-oxadiazol-3-yl)benzamide; N-((2,6-difluorophenyl)(methyl)(oxo)-$\lambda^6$-sulfaneylidene)-3-(5-(trifluoromethyl)-1,2,4-oxadiazol-3-yl)benzamide; N-(methyl(oxo)(thiazol-2-yl)-$\lambda^6$-sulfaneylidene)-3-(5-(trifluoromethyl)-1,2,4-oxadiazol-3-yl)benzamide; N-(1-oxidotetrahydro-2H-1$\lambda^6$-thiopyran-1-ylidene)-3-(5-(trifluoromethyl)-1,2,4-oxadiazol-3-yl)benzamide; N-((4-cyanobenzyl)(methyl)(oxo)-$\lambda^6$-sulfaneylidene)-3-(5-(trifluoromethyl)-1,2,4-oxadiazol-3-yl)benzamide; N-((4-fluorophenyl)(isopropyl)(oxo)-$\lambda^6$-sulfaneylidene)-4-(5-(trifluoromethyl)-1,2,4-oxadiazol-3-yl)benzamide; N-(isopropyl(4-methoxyphenyl)(oxo)-$\lambda^6$-sulfaneylidene)-4-(5-(trifluoromethyl)-1,2,4-oxadiazol-3-yl)benzamide; N-((4- chlorophenyl)(isopropyl)(oxo)-λ$^6$-sulfaneylidene)-4-(5-(trifluoromethyl)-1,2,4-oxadiazol-3-yl)benzamide; N-(isopropyl(oxo)(pyridin-2-yl)-λ$^6$-sulfaneylidene)-4-(5-(trifluoromethyl)-1,2,4-oxadiazol-3-yl)benzamide; N-(isopropyl(oxo)(phenyl)-λ$^6$-sulfaneylidene)-4-(5-(trifluoromethyl)-1,2,4-oxadiazol-3-yl)benzamide; 3-fluoro-N-((4-methoxyphenyl)(methyl)(oxo)-λ$^6$-sulfaneylidene)-4-(5-(trifluoromethyl)-1,2,4-oxadiazol-3-yl)benzamide; N-((3-bromophenyl)(ethyl)(oxo)-λ$^6$-sulfaneylidene)-4-(5-(trifluoromethyl)-1,2,4-oxadiazol-3-yl)benzamide; N-(methyl(oxo)(2-phenoxyethyl)-λ$^6$-sulfaneylidene)-4-(5-(trifluoromethyl)-1,2,4-oxadiazol-3-yl)benzamide; (2,6-difluorophenyl)(methyl)((4-(5-(trifluoromethyl)-1,2,4-oxadiazol-3-yl)phenyl)imino)-λ$^6$-sulfanone; (2,6-difluorobenzyl)(methyl)((4-(5-(trifluoromethyl)-1,2,4-oxadiazol-3-yl)phenyl)imino)-λ$^6$-sulfanone; (2,4-difluorobenzyl)(methyl)((4-(5-(trifluoromethyl)-1,2,4-oxadiazol-3-yl)phenyl)imino)-λ$^6$-sulfanone; (2,3-difluorobenzyl)(methyl)((4-(5-(trifluoromethyl)-1,2,4-oxadiazol-3-yl)phenyl)imino)-λ$^6$-sulfanone; methyl(2-methylbenzyl)((4-(5-(trifluoromethyl)-1,2,4-oxadiazol-3-yl)phenyl)imino)-λ$^6$-sulfanone; (4-fluorobenzyl)(methyl)((4-(5-(trifluoromethyl)-1,2,4-oxadiazol-3-yl)phenyl)imino)-λ$^6$-sulfanone; methyl((4-(5-(trifluoromethyl)-1,2,4-oxadiazol-3-yl)phenyl)imino)(4-(trifluoromethyl)benzyl)benzyl)-λ$^6$-sulfanone; (2,6-dichlorobenzyl)(methyl)((4-(5-(trifluoromethyl)-1,2,4-oxadiazol-3-yl)phenyl)imino)-λ$^6$-sulfanone; (4-bromobenzyl)(methyl)((4-(5-(trifluoromethyl)-1,2,4-oxadiazol-3-yl)phenyl)imino)-λ$^6$-sulfanone; methyl(pyridin-2-ylmethyl)((4-(5-(trifluoromethyl)-1,2,4-oxadiazol-3-yl)phenyl)imino)-λ$^6$-sulfanone; (2-fluorobenzyl)(methyl)((4-(5-(trifluoromethyl)-1,2,4-oxadiazol-3-yl)phenyl)imino)-λ$^6$-sulfanone; (3-fluorobenzyl)(methyl)((4-(5-(trifluoromethyl)-1,2,4-oxadiazol-3-yl)phenyl)imino)-λ$^6$-sulfanone; (2,4-dimethoxyphenyl)(methyl)((4-(5-(trifluoromethyl)-1,2,4-oxadiazol-3-yl)phenyl)imino)-λ$^6$-sulfanone; (3,4-difluorophenyl)(methyl)((4-(5-(trifluoromethyl)-1,2,4-oxadiazol-3-yl)phenyl)imino)-λ$^6$-sulfanone; (4-chlorobenzyl)(methyl)((4-(5-(trifluoromethyl)-1,2,4-oxadiazol-3-yl)phenyl)imino)-λ$^6$-sulfanone; (4-chloro-3-fluorobenzyl)(methyl)((4-(5-(trifluoromethyl)-1,2,4-oxadiazol-3-yl)phenyl)imino)-λ$^6$-sulfanone; (4-methoxyphenyl)(methyl)((3-(5-(trifluoromethyl)-1,2,4-oxadiazol-3-yl)phenyl)imino)-λ$^6$-sulfanone; (3-methoxyphenyl)(methyl)((3-(5-(trifluoromethyl)-1,2,4-oxadiazol-3-yl)phenyl)imino)-λ$^6$-sulfanone; 1-((3-(5-(trifluoromethyl)-1,2,4-oxadiazol-3-yl)phenyl)imino)hexahydro-1λ$^6$-thiopyran 1-oxide; (2,4-dimethoxyphenyl)(methyl)((3-(5-(trifluoromethyl)-1,2,4-oxadiazol-3-yl)phenyl)imino)-λ$^6$-sulfanone; (4-fluorophenyl)(methyl)((3-(5-(trifluoromethyl)-1,2,4-oxadiazol-3-yl)phenyl)imino)-λ$^6$-sulfanone; (2-fluorophenyl)(methyl)((3-(5-(trifluoromethyl)-1,2,4-oxadiazol-3-yl)phenyl)imino)-λ$^6$-sulfanone; (3-methoxyphenyl)(methyl)((4-(5-(trifluoromethyl)-1,2,4-oxadiazol-3-yl)phenyl)imino)-λ$^6$-sulfanone; (2,5-dichlorophenyl)(methyl)((4-(5-(trifluoromethyl)-1,2,4-oxadiazol-3-yl)phenyl)imino)-λ$^6$-sulfanone; (4-methoxyphenyl)(methyl)((6-(5-(trifluoromethyl)-1,2,4-oxadiazol-3-yl)pyridin-3-yl)imino)-λ$^6$-sulfanone; methyl(phenyl)((6-(5-(trifluoromethyl)-1,2,4-oxadiazol-3-yl)pyridin-3-yl)imino)-λ$^6$-sulfanone; methyl(pyridin-2-yl)((6-(5-(trifluoromethyl)-1,2,4-oxadiazol-3-yl)pyridin-3-yl)imino)-λ$^6$-sulfanone; (2,6-difluorobenzyl)(methyl)((6-(5-(trifluoromethyl)-1,2,4-oxadiazol-3-yl)pyridin-3-yl)imino)-λ$^6$-sulfanone; (4-chlorophenyl)(methyl)((3-(5-(trifluoromethyl)-1,2,4-oxadiazol-3-yl)phenyl)imino)-λ$^6$-sulfanone; methyl(pyridin-2-yl)((3-(5-(trifluoromethyl)-1,2,4-oxadiazol-3-yl)phenyl)imino)-λ$^6$-sulfanone; methyl(m-tolyl)((3-(5-(trifluoromethyl)-1,2,4-oxadiazol-3-yl)phenyl)imino)-λ$^6$-sulfanone; methyl(thiazol-2-yl)((3-(5-(trifluoromethyl)-1,2,4-oxadiazol-3-yl)phenyl)imino)-λ$^6$-sulfanone; methyl((4-(5-(trifluoromethyl)-1,2,4-oxadiazol-3-yl)phenyl)imino)(4-(trifluoromethyl)pyridin-2-yl)-λ$^6$-sulfanone; methyl(4-methylthiazol-2-yl)((4-(5-(trifluoromethyl)-1,2,4-oxadiazol-3-yl)phenyl)imino)-λ$^6$-sulfanone; methyl(thiazol-2-yl)((4-(5-(trifluoromethyl)-1,2,4-oxadiazol-3-yl)phenyl)imino)-λ$^6$-sulfanone; (4-chlorophenyl)(methyl)((6-(5-(trifluoromethyl)-1,2,4-oxadiazol-3-yl)pyridin-3-yl)imino)-λ$^6$-sulfanone; (2,6-difluorophenyl)(methyl)((6-(5-(trifluoromethyl)-1,2,4-oxadiazol-3-yl)pyridin-3-yl)imino)-λ$^6$-sulfanone; (3,4-difluorophenyl)(methyl)((3-(5-(trifluoromethyl)-1,2,4-oxadiazol-3-yl)phenyl)imino)-λ$^6$-sulfanone; methyl(phenyl)((3-(5-(trifluoromethyl)-1,2,4-oxadiazol-3-yl)phenyl)imino)-λ$^6$-sulfanone; (4-fluorophenyl)(methyl)((6-(5-(trifluoromethyl)-1,2,4-oxadiazol-3-yl)pyridin-3-yl)imino)-λ$^6$-sulfanone; methyl((6-(5-(trifluoromethyl)-1,2,4-oxadiazol-3-yl)pyridin-3-yl)imino)(4-(trifluoromethyl)phenyl)-λ$^6$-sulfanone; (2-fluorophenyl)(methyl)((6-(5-(trifluoromethyl)-1,2,4-oxadiazol-3-yl)pyridin-3-yl)imino)-λ$^6$-sulfanone; (4-fluorobenzyl)(methyl)((6-(5-(trifluoromethyl)-1,2,4-oxadiazol-3-yl)pyridin-3-yl)imino)-λ$^6$-sulfanone; (3-methoxyphenyl)(methyl)((6-(5-(trifluoromethyl)-1,2,4-oxadiazol-3-yl)pyridin-3-yl)imino)-λ$^6$-sulfanone; 1-((6-(5-(trifluoromethyl)-1,2,4-oxadiazol-3-yl)pyridin-3-yl)imino)hexahydro-1λ$^6$-thiopyran 1-oxide; 4-((6-(5-(trifluoromethyl)-1,2,4-oxadiazol-3-yl)pyridin-3-yl)imino)-1,4λ$^6$-oxathiane 4-oxide; methyl(p-tolyl)((4-(5-(trifluoromethyl)-1,2,4-oxadiazol-3-yl)phenyl)imino)-λ$^6$-sulfanone; (2,4-difluorophenyl)(methyl)((4-(5-(trifluoromethyl)-1,2,4-oxadiazol-3-yl)phenyl)imino)-λ$^6$-sulfanone; methyl((4-(5-(trifluoromethyl)-1,2,4-oxadiazol-3-yl)phenyl)imino)(5-(trifluoromethyl)pyridin-2-yl)-λ$^6$-sulfanone; 4-((4-(5-(trifluoromethyl)-1,2,4-oxadiazol-3-yl)phenyl)imino)-1,4λ$^6$-oxathiane 4-oxide; 1-((4-(5-(trifluoromethyl)-1,2,4-oxadiazol-3-yl)phenyl)imino)hexahydro-1λ$^6$-thiopyran 1-oxide; methyl(4-(5-(trifluoromethyl)-1,2,4-oxadiazol-3-yl)phenyl)((4-(5-(trifluoromethyl)-1,2,4-oxadiazol-3-yl)phenyl)imino)-λ$^6$-sulfanone; methyl(4-(5-(trifluoromethyl)-1,2,4-oxadiazol-3-yl)phenyl)((3-(5-(trifluoromethyl)-1,2,4-oxadiazol-3-yl)phenyl)imino)-λ$^6$-sulfanone; methyl(p-tolyl)((4-(5-(trifluoromethyl)-1,2,4-oxadiazol-3-yl)benzyl)imino)-λ$^6$-sulfanone; methyl(phenyl)((3-(5-(trifluoromethyl)-1,2,4-oxadiazol-3-yl)benzyl)imino)-λ$^6$-sulfanone; (4-methoxyphenyl)(methyl)((3-(5-(trifluoromethyl)-1,2,4-oxadiazol-3-yl)benzyl)imino)-λ$^6$-sulfanone; (2,4-dimethoxyphenyl)(methyl)((3-(5-(trifluoromethyl)-1,2,4-oxadiazol-3-yl)benzyl)imino)-λ$^6$-sulfanone; (3,4-difluorophenyl)(methyl)((3-(5-(trifluoromethyl)-1,2,4-oxadiazol-3-yl)benzyl)imino)-λ$^6$-sulfanone; methyl((3-(5-(trifluoromethyl)-1,2,4-oxadiazol-3-yl)benzyl)imino)(4-((4-(trifluoromethyl)pyridin-2-yl)oxy)phenyl)-λ$^6$-sulfanone; (4-chlorophenyl)(methyl)((3-(5-(trifluoromethyl)-1,2,4-oxadiazol-3-yl)benzyl)imino)-λ$^6$-sulfanone; methyl(thiazol-2-yl)((3-(5-(trifluoromethyl)-1,2,4-oxadiazol-3-yl)benzyl)imino)-λ$^6$-sulfanone; (4-fluorophenyl)(methyl)((3-(5-(trifluoromethyl)-1,2,4-oxadiazol-3-yl)benzyl)imino)-λ$^6$-sulfanone; (2-bromo-5-fluorophenyl)(methyl)((3-(5-(trifluoromethyl)-1,2,4-oxadiazol-3-yl)benzyl)imino)-λ$^6$-sulfanone; 4-fluoro-N-(3-(5-(trifluoromethyl)-1,2,4-oxadiazol-3-yl)benzyl)benzenesulfonamide; (4-bromo-2-fluorophenyl)(methyl)((3-(5-(trifluoromethyl)-1,2,4-oxadiazol-3-yl)benzyl)imino)-λ$^6$-sulfanone;

(2-fluorophenyl)(methyl)((3-(5-(trifluoromethyl)-1,2,4-oxadiazol-3-yl)benzyl)imino)-$\lambda^6$-sulfanone; 4-((3-(5-(trifluoromethyl)-1,2,4-oxadiazol-3-yl)benzyl)imino)-1,4$\lambda^6$-oxathiane 4-oxide; isopropyl(4-methoxyphenyl)((4-(5-(trifluoromethyl)-1,2,4-oxadiazol-3-yl)benzyl)imino)-$\lambda^6$-sulfanone; isopropyl(phenyl)((4-(5-(trifluoromethyl)-1,2,4-oxadiazol-3-yl)benzyl)imino)-$\lambda^6$-sulfanone; (4-chlorophenyl)(isopropyl)((4-(5-(trifluoromethyl)-1,2,4-oxadiazol-3-yl)benzyl)imino)-$\lambda^6$-sulfanone; N-tosyl-4-(5-(trifluoromethyl)-1,2,4-oxadiazol-3-yl)benzamide; N-((5-chloro-2-methoxyphenyl)sulfonyl)-4-(5-(trifluoromethyl)-1,2,4-oxadiazol-3-yl)benzamide; N-((2-fluorophenyl)sulfonyl)-4-(5-(trifluoromethyl)-1,2,4-oxadiazol-3-yl)benzamide; N-((2,4-dichlorophenyl)sulfonyl)-4-(5-(trifluoromethyl)-1,2,4-oxadiazol-3-yl)benzamide; N-((4-methoxyphenyl)sulfonyl)-4-(5-(trifluoromethyl)-1,2,4-oxadiazol-3-yl)benzamide; N-((3-methoxyphenyl)sulfonyl)-4-(5-(trifluoromethyl)-1,2,4-oxadiazol-3-yl)benzamide; 4-(5-(trifluoromethyl)-1,2,4-oxadiazol-3-yl)-N-((4-(trifluoromethyl)phenyl)sulfonyl)benzamide; N-(pyridin-3-ylsulfonyl)-4-(5-(trifluoromethyl)-1,2,4-oxadiazol-3-yl)benzamide; N-((2,5-difluorophenyl)sulfonyl)-4-(5-(trifluoromethyl)-1,2,4-oxadiazol-3-yl)benzamide; N-((4-bromophenyl)sulfonyl)-4-(5-(trifluoromethyl)-1,2,4-oxadiazol-3-yl)benzamide; N-((2,6-dichlorophenyl)sulfonyl)-4-(5-(trifluoromethyl)-1,2,4-oxadiazol-3-yl)benzamide; N-((3-fluorophenyl)sulfonyl)-4-(5-(trifluoromethyl)-1,2,4-oxadiazol-3-yl)benzamide; ((2-fluoro-4-(5-(trifluoromethyl)-1,2,4-oxadiazol-3-yl)phenyl)imino)(2-fluorophenyl)(methyl)-$\lambda^6$-sulfanone; ((2-fluoro-4-(5-(trifluoromethyl)-1,2,4-oxadiazol-3-yl)phenyl)imino)(methyl)(phenyl)-$\lambda^6$-sulfanone; (4-chlorophenyl)((2-fluoro-4-(5-(trifluoromethyl)-1,2,4-oxadiazol-3-yl)phenyl)imino)(methyl)-$\lambda^6$-sulfanone; ((2-fluoro-4-(5-(trifluoromethyl)-1,2,4-oxadiazol-3-yl)phenyl)imino)(methyl)(pyridin-2-yl)-$\lambda^6$-sulfanone; ((2-fluoro-4-(5-(trifluoromethyl)-1,2,4-oxadiazol-3-yl)phenyl)imino)(3-fluorophenyl)(methyl)-$\lambda^6$-sulfanone; ((2-fluoro-4-(5-(trifluoromethyl)-1,2,4-oxadiazol-3-yl)phenyl)imino)(4-fluorophenyl)(methyl)-$\lambda^6$-sulfanone; ((2-fluoro-4-(5-(trifluoromethyl)-1,2,4-oxadiazol-3-yl)phenyl)imino)(4-methoxyphenyl)(methyl)-$\lambda^6$-sulfanone; 2-fluoro-N-(methyl(oxo)(4-(5-(trifluoromethyl)-1,2,4-oxadiazol-3-yl)phenyl)-$\lambda^6$-sulfaneylidene)benzamide; 3-methoxy-N-(methyl(oxo)(4-(5-(trifluoromethyl)-1,2,4-oxadiazol-3-yl)phenyl)-$\lambda^6$-sulfaneylidene)benzamide; 3-fluoro-N-(methyl(oxo)(4-(5-(trifluoromethyl)-1,2,4-oxadiazol-3-yl)phenyl)-$\lambda^6$-sulfaneylidene)benzamide; 4-chloro-2-fluoro-N-(methyl(oxo)(4-(5-(trifluoromethyl)-1,2,4-oxadiazol-3-yl)phenyl)-$\lambda^6$-sulfaneylidene)benzamide; 2-chloro-6-fluoro-N-(methyl(oxo)(4-(5-(trifluoromethyl)-1,2,4-oxadiazol-3-yl)phenyl)-$\lambda^6$-sulfaneylidene)benzamide; N-(methyl(oxo)(4-(5-(trifluoromethyl)-1,2,4-oxadiazol-3-yl)phenyl)-$\lambda^6$-sulfaneylidene)benzamide; N-(methyl(oxo)(4-(5-(trifluoromethyl)-1,2,4-oxadiazol-3-yl)phenyl)-$\lambda^6$-sulfaneylidene)-2-phenylacetamide; 4-chloro-N-(methyl(oxo)(4-(5-(trifluoromethyl)-1,2,4-oxadiazol-3-yl)phenyl)-$\lambda^6$-sulfaneylidene)benzamide; N-(methyl(oxo)(4-(5-(trifluoromethyl)-1,2,4-oxadiazol-3-yl)phenyl)-$\lambda^6$-sulfaneylidene)pivalamide; N-(methyl(oxo)(4-(5-(trifluoromethyl)-1,2,4-oxadiazol-3-yl)phenyl)-$\lambda^6$-sulfaneylidene)cyclopropanecarboxamide; ((3-chlorobenzyl)imino)(methyl)(4-(5-(trifluoromethyl)-1,2,4-oxadiazol-3-yl)phenyl)-$\lambda^6$-sulfanone; ((4-bromobenzyl)imino)(methyl)(4-(5-(trifluoromethyl)-1,2,4-oxadiazol-3-yl)phenyl)-$\lambda^6$-sulfanone; ((2,4-difluorobenzyl)imino)(methyl)(4-(5-(trifluoromethyl)-1,2,4-oxadiazol-3-yl)phenyl)-$\lambda^6$-sulfanone; ((3-fluorobenzyl)imino)(methyl)(4-(5-(trifluoromethyl)-1,2,4-oxadiazol-3-yl)phenyl)-$\lambda^6$-sulfanone; N-((4-fluorophenyl)(methyl)(oxo)-$\lambda^6$-sulfaneylidene)-2-(4-(5-(trifluoromethyl)-1,2,4-oxadiazol-3-yl)phenyl)acetamide; ((2,4-difluorophenyl)imino)(methyl)(4-(5-(trifluoromethyl)-1,2,4-oxadiazol-3-yl)phenyl)-$\lambda^6$-sulfanone; ((2-fluoro-4-methoxyphenyl)imino)(methyl)(4-(5-(trifluoromethyl)-1,2,4-oxadiazol-3-yl)phenyl)-$\lambda^6$-sulfanone; ((2-fluorophenyl)imino)(methyl)(4-(5-(trifluoromethyl)-1,2,4-oxadiazol-3-yl)phenyl)-$\lambda^6$-sulfanone; ((2-methoxy-4-(5-(trifluoromethyl)-1,2,4-oxadiazol-3-yl)phenyl)imino)(4-methoxyphenyl)(methyl)-$\lambda^6$-sulfanone; ((2-methoxy-4-(5-(trifluoromethyl)-1,2,4-oxadiazol-3-yl)phenyl)imino)(methyl)(phenyl)-$\lambda^6$-sulfanone; ((2-methoxy-4-(5-(trifluoromethyl)-1,2,4-oxadiazol-3-yl)phenyl)imino)(methyl)(pyridin-2-yl)-$\lambda^6$-sulfanone; ((2-methoxyphenyl)imino)(methyl)(4-(5-(trifluoromethyl)-1,2,4-oxadiazol-3-yl)phenyl)-$\lambda^6$-sulfanone; ((3-fluoro-4-(5-(trifluoromethyl)-1,2,4-oxadiazol-3-yl)phenyl)imino)(2-fluorobenzyl)(trifluoromethyl)-$\lambda^6$-sulfanone; ((3-fluoro-4-(5-(trifluoromethyl)-1,2,4-oxadiazol-3-yl)phenyl)imino)(2-fluorophenyl)(trifluoromethyl)-$\lambda^6$-sulfanone; ((3-fluoro-4-(5-(trifluoromethyl)-1,2,4-oxadiazol-3-yl)phenyl)imino)(4-methoxyphenyl)(trifluoromethyl)-$\lambda^6$-sulfanone; ((3-fluoro-4-(5-(trifluoromethyl)-1,2,4-oxadiazol-3-yl)phenyl)imino)(phenyl)(trifluoromethyl)-$\lambda^6$-sulfanone; ((3-fluoro-4-(5-(trifluoromethyl)-1,2,4-oxadiazol-3-yl)phenyl)imino)(pyridin-2-yl)(trifluoromethyl)-$\lambda^6$-sulfanone; ((3-fluorophenyl)imino)(methyl)(4-(5-(trifluoromethyl)-1,2,4-oxadiazol-3-yl)phenyl)-$\lambda^6$-sulfanone; ((4-fluorophenyl)imino)(methyl)(4-(5-(trifluoromethyl)-1,2,4-oxadiazol-3-yl)phenyl)-$\lambda^6$-sulfanone; ((4-methoxyphenyl)imino)(methyl)(4-(5-(trifluoromethyl)-1,2,4-oxadiazol-3-yl)phenyl)-$\lambda^6$-sulfanone; ((5-methoxypyridin-2-yl)imino)(methyl)(4-(5-(trifluoromethyl)-1,2,4-oxadiazol-3-yl)phenyl)-$\lambda^6$-sulfanone; (2-(dimethylamino)ethyl)(methyl)((4-((5-(trifluoromethyl)-1,2,4-oxadiazol-3-yl)methyl)phenyl)imino)-$\lambda^6$-sulfanone; (2-(dimethylamino)ethyl)(methyl)((4-(5-(trifluoromethyl)-1,2,4-oxadiazol-3-yl)benzyl)imino)-$\lambda^6$-sulfanone; (2,4-difluorophenyl)(methyl)((4-((5-(trifluoromethyl)-1,2,4-oxadiazol-3-yl)methyl)phenyl)imino)-$\lambda^6$-sulfanone; (2-fluoro-4-methoxyphenyl)(methyl)((4-((5-(trifluoromethyl)-1,2,4-oxadiazol-3-yl)methyl)phenyl)imino)-$\lambda^6$-sulfanone; (2-fluoro-4-methoxyphenyl)(methyl)((4-(5-(trifluoromethyl)-1,2,4-oxadiazol-3-yl)benzyl)imino)-$\lambda^6$-sulfanone; (2-fluorobenzyl)((2-methoxy-4-(5-(trifluoromethyl)-1,2,4-oxadiazol-3-yl)phenyl)imino)(methyl)-$\lambda^6$-sulfanone; (2-fluorobenzyl)((3-methoxy-4-(5-(trifluoromethyl)-1,2,4-oxadiazol-3-yl)phenyl)imino)(methyl)-$\lambda^6$-sulfanone; (2-fluorobenzyl)(isopropyl)((4-(5-(trifluoromethyl)-1,2,4-oxadiazol-3-yl)phenyl)imino)-$\lambda^6$-sulfanone; (2-fluorobenzyl)(methyl)((5-(5-(trifluoromethyl)-1,2,4-oxadiazol-3-yl)pyridin-2-yl)imino)-$\lambda^6$-sulfanone; (2-fluorobenzyl)(methyl)((5-(5-(trifluoromethyl)-1,2,4-oxadiazol-3-yl)pyrimidin-2-yl)imino)-$\lambda^6$-sulfanone; (2-fluorobenzyl)(trifluoromethyl)((4-(5-(trifluoromethyl)-1,2,4-oxadiazol-3-yl)phenyl)imino)-$\lambda^6$-sulfanone; (2-fluorophenyl)((2-methoxy-4-(5-(trifluoromethyl)-1,2,4-oxadiazol-3-yl)phenyl)imino)(methyl)-$\lambda^6$-sulfanone; (2-fluorophenyl)(isopropyl)((4-(5-(trifluoromethyl)-1,2,4-oxadiazol-3-yl)phenyl)imino)-$\lambda^6$-sulfanone; (2-fluorophenyl)(methyl)((4-((5-(trifluoromethyl)-1,2,4-oxadiazol-3-yl)methyl)phenyl)imino)-$\lambda^6$-sulfanone; (2-fluorophenyl)(methyl)((5-(5-(trifluoromethyl)-1,2,4-oxadiazol-3-yl)pyridin-2-yl)imino)-$\lambda^6$-sulfanone; (2-fluorophenyl)(methyl)((5-(5-

(trifluoromethyl)-1,2,4-oxadiazol-3-yl)pyrimidin-2-yl)imino)-$\lambda^6$-sulfanone; (2-fluorophenyl)(trifluoromethyl)((4-(5-(trifluoromethyl)-1,2,4-oxadiazol-3-yl)phenyl)imino)-$\lambda^6$-sulfanone; (2-methoxyethyl)(methyl)((4-(5-(trifluoromethyl)-1,2,4-oxadiazol-3-yl)methyl)phenyl)imino)-$\lambda^6$-sulfanone; (2-methoxyethyl)(methyl)((4-(5-(trifluoromethyl)-1,2,4-oxadiazol-3-yl)benzyl)imino)-$\lambda^6$-sulfanone; (2-methoxyphenyl)(methyl)((4-((5-(trifluoromethyl)-1,2,4-oxadiazol-3-yl)methyl)phenyl)imino)-$\lambda^6$-sulfanone; (3-fluorophenyl)(methyl)((4-((5-(trifluoromethyl)-1,2,4-oxadiazol-3-yl)methyl)phenyl)imino)-$\lambda^6$-sulfanone; (3-fluoropyridin-4-yl)(methyl)((4-((5-(trifluoromethyl)-1,2,4-oxadiazol-3-yl)methyl)phenyl)imino)-$\lambda^6$-sulfanone; (3-methoxyphenyl)(methyl)((4-((5-(trifluoromethyl)-1,2,4-oxadiazol-3-yl)methyl)phenyl)imino)-$\lambda^6$-sulfanone; (3-methoxypyridin-4-yl)(methyl)((4-((5-(trifluoromethyl)-1,2,4-oxadiazol-3-yl)methyl)phenyl)imino)-$\lambda^6$-sulfanone; (3-methoxypyridin-4-yl)(methyl)((4-(5-(trifluoromethyl)-1,2,4-oxadiazol-3-yl)benzyl)imino)-$\lambda^6$-sulfanone; (4-(difluoromethyl)phenyl)(methyl)((4-(5-(trifluoromethyl)-1,2,4-oxadiazol-3-yl)phenyl)imino)-$\lambda^6$-sulfanone; (4-fluoro-2-methoxyphenyl)(methyl)((4-((5-(trifluoromethyl)-1,2,4-oxadiazol-3-yl)methyl)phenyl)imino)-$\lambda^6$-sulfanone; (4-fluoro-2-methoxyphenyl)(methyl)((4-(5-(trifluoromethyl)-1,2,4-oxadiazol-3-yl)benzyl)imino)-$\lambda^6$-sulfanone; (4-fluorophenyl)(methyl)((4-((5-(trifluoromethyl)-1,2,4-oxadiazol-3-yl)methyl)phenyl)imino)-$\lambda^6$-sulfanone; (4-methoxyphenyl)(methyl)((4-((5-(trifluoromethyl)-1,2,4-oxadiazol-3-yl)methyl)phenyl)imino)-$\lambda^6$-sulfanone; (4-methoxyphenyl)(methyl)((5-(5-(trifluoromethyl)-1,2,4-oxadiazol-3-yl)pyridin-2-yl)imino)-$\lambda^6$-sulfanone; (4-methoxyphenyl)(methyl)((5-(5-(trifluoromethyl)-1,2,4-oxadiazol-3-yl)pyrimidin-2-yl)imino)-$\lambda^6$-sulfanone; (4-methoxyphenyl)(trifluoromethyl)((4-(5-(trifluoromethyl)-1,2,4-oxadiazol-3-yl)phenyl)imino)-$\lambda^6$-sulfanone; (cyclobutylimino)(methyl)(4-(5-(trifluoromethyl)-1,2,4-oxadiazol-3-yl)phenyl)-$\lambda^6$-sulfanone; (cyclobutylmethyl)(methyl)((4-((5-(trifluoromethyl)-1,2,4-oxadiazol-3-yl)methyl)phenyl)imino)-$\lambda^6$-sulfanone; (cyclobutylmethyl)(methyl)((4-(5-(trifluoromethyl)-1,2,4-oxadiazol-3-yl)benzyl)imino)-$\lambda^6$-sulfanone; (cyclohexylimino)(methyl)(4-(5-(trifluoromethyl)-1,2,4-oxadiazol-3-yl)phenyl)-$\lambda^6$-sulfanone; (cyclopentylimino)(methyl)(4-(5-(trifluoromethyl)-1,2,4-oxadiazol-3-yl)phenyl)-A-sulfanone; (cyclopentylmethyl)(methyl)((4-((5-(trifluoromethyl)-1,2,4-oxadiazol-3-yl)methyl)phenyl)imino)-$\lambda^6$-sulfanone; (cyclopentylmethyl)(methyl)((4-(5-(trifluoromethyl)-1,2,4-oxadiazol-3-yl)benzyl)imino)-$\lambda^6$-sulfanone; (cyclopropylimino)(methyl)(4-(5-(trifluoromethyl)-1,2,4-oxadiazol-3-yl)phenyl)-$\lambda^6$-sulfanone; (cyclopropylmethyl)(2-fluorobenzyl)((4-(5-(trifluoromethyl)-1,2,4-oxadiazol-3-yl)phenyl)imino)-$\lambda^6$-sulfanone; (cyclopropylmethyl)(2-fluorophenyl)((4-(5-(trifluoromethyl)-1,2,4-oxadiazol-3-yl)phenyl)imino)-$\lambda^6$-sulfanone; (cyclopropylmethyl)(4-methoxyphenyl)((4-(5-(trifluoromethyl)-1,2,4-oxadiazol-3-yl)phenyl)imino)-$\lambda^6$-sulfanone; (cyclopropylmethyl)(methyl)((4-((5-(trifluoromethyl)-1,2,4-oxadiazol-3-yl)methyl)phenyl)imino)-$\lambda^6$-sulfanone; (cyclopropylmethyl)(methyl)((4-(5-(trifluoromethyl)-1,2,4-oxadiazol-3-yl)benzyl)imino)-$\lambda^6$-sulfanone; (cyclopropylmethyl)(phenyl)((4-(5-(trifluoromethyl)-1,2,4-oxadiazol-3-yl)phenyl)imino)-$\lambda^6$-sulfanone; (cyclopropylmethyl)(pyridin-2-yl)((4-(5-(trifluoromethyl)-1,2,4-oxadiazol-3-yl)phenyl)imino)-$\lambda^6$-sulfanone; (furan-3-ylimino)(methyl)(4-(5-(trifluoromethyl)-1,2,4-oxadiazol-3-yl)phenyl)-$\lambda^6$-sulfanone; 1-methyl-N-(methyl(oxo)(4-(5-(trifluoromethyl)-1,2,4-oxadiazol-3-yl)phenyl)-$\lambda^6$-sulfaneylidene)-1H-imidazole-4-carboxamide; 1-methyl-N-(methyl(oxo)(4-(5-(trifluoromethyl)-1,2,4-oxadiazol-3-yl)phenyl)-$\lambda^6$-sulfaneylidene)-1H-imidazole-5-carboxamide; 2,4-difluoro-N-(methyl(oxo)(4-(5-(trifluoromethyl)-1,2,4-oxadiazol-3-yl)phenyl)-$\lambda^6$-sulfaneylidene)benzamide; 2-fluoro-4-methoxy-N-(methyl(oxo)(4-(5-(trifluoromethyl)-1,2,4-oxadiazol-3-yl)phenyl)-$\lambda^6$-sulfaneylidene)benzamide; 2-fluoro-N-((2-fluorobenzyl)(methyl)(oxo)-$\lambda^6$-sulfaneylidene)-4-(5-(trifluoromethyl)-1,2,4-oxadiazol-3-yl)benzamide; 2-fluoro-N-((2-fluorophenyl)(methyl)(oxo)-$\lambda^6$-sulfaneylidene)-4-(5-(trifluoromethyl)-1,2,4-oxadiazol-3-yl)benzamide; 2-fluoro-N-((4-methoxyphenyl)(methyl)(oxo)-$\lambda^6$-sulfaneylidene)-4-(5-(trifluoromethyl)-1,2,4-oxadiazol-3-yl)benzamide; 2-fluoro-N-(4-oxido-1,4$\lambda^6$-oxathian-4-ylidene)-4-(5-(trifluoromethyl)-1,2,4-oxadiazol-3-yl)benzamide; 2-fluoro-N-(methyl(oxo)(pyridin-2-yl)-$\lambda^6$-sulfaneylidene)-4-(5-(trifluoromethyl)-1,2,4-oxadiazol-3-yl)benzamide; 2-fluoro-N-(methyl(oxo)(pyridin-4-yl)-$\lambda^6$-sulfaneylidene)-4-(5-(trifluoromethyl)-1,2,4-oxadiazol-3-yl)benzamide; 2-methoxy-N-((4-methoxyphenyl)(methyl)(oxo)-$\lambda^6$-sulfaneylidene)-4-(5-(trifluoromethyl)-1,2,4-oxadiazol-3-yl)benzamide; 2-methoxy-N-(4-oxido-1,4$\lambda^6$-oxathian-4-ylidene)-4-(5-(trifluoromethyl)-1,2,4-oxadiazol-3-yl)benzamide; 2-methoxy-N-(methyl(oxo)(4-(5-(trifluoromethyl)-1,2,4-oxadiazol-3-yl)phenyl)-$\lambda^6$-sulfaneylidene)benzamide; 2-methoxy-N-(methyl(oxo)(pyridin-2-yl)-$\lambda^6$-sulfaneylidene)-4-(5-(trifluoromethyl)-1,2,4-oxadiazol-3-yl)benzamide; 2-methoxy-N-(methyl(oxo)(pyridin-4-yl)-$\lambda^6$-sulfaneylidene)-4-(5-(trifluoromethyl)-1,2,4-oxadiazol-3-yl)benzamide; 3-fluoro-N-((2-fluorobenzyl)(methyl)(oxo)-$\lambda^6$-sulfaneylidene)-4-(5-(trifluoromethyl)-1,2,4-oxadiazol-3-yl)benzamide; 3-fluoro-N-((2-fluorophenyl)(methyl)(oxo)-$\lambda^6$-sulfaneylidene)-4-(5-(trifluoromethyl)-1,2,4-oxadiazol-3-yl)benzamide; 3-fluoro-N-(4-oxido-1,4$\lambda^6$-oxathian-4-ylidene)-4-(5-(trifluoromethyl)-1,2,4-oxadiazol-3-yl)benzamide; 3-fluoro-N-(methyl(oxo)(pyridin-2-yl)-$\lambda^6$-sulfaneylidene)-4-(5-(trifluoromethyl)-1,2,4-oxadiazol-3-yl)benzamide; 3-fluoro-N-(methyl(oxo)(pyridin-4-yl)-$\lambda^6$-sulfaneylidene)-4-(5-(trifluoromethyl)-1,2,4-oxadiazol-3-yl)benzamide; 3-methoxy-N-((4-methoxyphenyl)(methyl)(oxo)-$\lambda^6$-sulfaneylidene)-4-(5-(trifluoromethyl)-1,2,4-oxadiazol-3-yl)benzamide; 3-methoxy-N-(4-oxido-1,4$\lambda^6$-oxathian-4-ylidene)-4-(5-(trifluoromethyl)-1,2,4-oxadiazol-3-yl)benzamide; 3-methoxy-N-(methyl(oxo)(pyridin-2-yl)-$\lambda^6$-sulfaneylidene)-4-(5-(trifluoromethyl)-1,2,4-oxadiazol-3-yl)benzamide; 3-methoxy-N-(methyl(oxo)(pyridin-4-yl)-$\lambda^6$-sulfaneylidene)-4-(5-(trifluoromethyl)-1,2,4-oxadiazol-3-yl)benzamide; 4-(5-(trifluoromethyl)-1,2,4-oxadiazol-3-yl)-N-((trifluoromethyl)sulfonyl)benzamide; 4-fluoro-N-(methyl(oxo)(4-(5-(trifluoromethyl)-1,2,4-oxadiazol-3-yl)phenyl)-$\lambda^6$-sulfaneylidene)benzamide; 4-methoxy-N-(methyl(oxo)(4-(5-(trifluoromethyl)-1,2,4-oxadiazol-3-yl)phenyl)-$\lambda^6$-sulfaneylidene)benzamide; 5-methoxy-N-(methyl(oxo)(4-(5-(trifluoromethyl)-1,2,4-oxadiazol-3-yl)phenyl)-$\lambda^6$-sulfaneylidene)picolinamide; allyl(methyl)((4-((5-(trifluoromethyl)-1,2,4-oxadiazol-3-yl)methyl)phenyl)imino)-$\lambda^6$-sulfanone; allyl(methyl)((4-(5-(trifluoromethyl)-1,2,4-oxadiazol-3-yl)benzyl)imino)-$\lambda^6$-sulfanone; allyl(methyl)((4-(5-(trifluoromethyl)-1,2,4-oxadiazol-3-yl)phenyl)imino)-$\lambda^6$-sulfanone; cyclopentyl(methyl)((4-(5-(trifluoromethyl)-1,2,4-oxadiazol-3-yl)phenyl)imino)-$\lambda^6$-sulfanone; cyclopropyl(methyl)((4-((5-(trifluoromethyl)-1,2,4-oxadiazol-3-yl)methyl)phenyl)imino)-$\lambda^6$-sulfanone; cyclopropyl(methyl)((4-(5-(trifluoromethyl)-1,2,4-oxadiazol-3-yl)benzyl)imino)-$\lambda^6$-sulfanone; cyclopropyl(methyl)((4-(5-(trifluoromethyl)-1,2,4-oxadiazol-3-yl)phenyl)imino)-$\lambda^6$-sulfanone; isobutyl(methyl)((4-((5-(trifluoromethyl)-1,2,4-oxadiazol-3-yl)methyl)phenyl)imino)-$\lambda^6$-sulfanone; isobutyl(methyl)((4-(5-(trifluoromethyl)-1,2,4-oxadiazol-3-yl)benzyl)imino)-$\lambda^6$-sulfanone; isobutyl(methyl)((4-(5-(trifluoromethyl)-1,2,4-oxadiazol-3-yl)phenyl)imino)-$\lambda^6$-sulfanone; isopropyl(4-methoxyphenyl)((4-(5-(trifluoromethyl)-1,2,4-oxadiazol-3-yl)phenyl)imino)-$\lambda^6$-sulfanone; isopropyl(phenyl)((4-(5-(trifluoromethyl)-1,2,4-oxadiazol-3-yl)phenyl)imino)-$\lambda^6$-sulfanone; isopropyl(pyridin-2-yl)((4-(5-(trifluoromethyl)-1,2,4-oxadiazol-3-yl)phenyl)imino)-$\lambda^6$-sulfanone; methyl((1-methyl-1H-imidazol-4-yl)imino)(4-(5-(trifluoromethyl)-1,2,4-oxadiazol-3-yl)phenyl)-$\lambda^6$-sulfanone; methyl((1-methyl-1H-imidazol-5-yl)imino)(4-(5-(trifluoromethyl)-1,2,4-oxadiazol-3-yl)phenyl)-$\lambda^6$-sulfanone; methyl(oxazol-4-yl)((4-((5-(trifluoromethyl)-1,2,4-oxadiazol-3-yl)methyl)phenyl)imino)-$\lambda^6$-sulfanone; methyl(oxazol-4-yl)((4-(5-(trifluoromethyl)-1,2,4-oxadiazol-3-yl)benzyl)imino)-$\lambda^6$-sulfanone; methyl(oxazol-5-yl)((4-((5-(trifluoromethyl)-1,2,4-oxadiazol-3-yl)methyl)phenyl)imino)-$\lambda^6$-sulfanone; methyl(oxazol-5-yl)((4-(5-(trifluoromethyl)-1,2,4-oxadiazol-3-yl)benzyl)imino)-$\lambda^6$-sulfanone; methyl(oxazol-5-ylimino)(4-(5-(trifluoromethyl)-1,2,4-oxadiazol-3-yl)phenyl)-$\lambda^6$-sulfanone; methyl(perfluoroethyl)((4-((5-(trifluoromethyl)-1,2,4-oxadiazol-3-yl)methyl)phenyl)imino)-$\lambda^6$-sulfanone; methyl(perfluoroethyl)((4-(5-(trifluoromethyl)-1,2,4-oxadiazol-3-yl)benzyl)imino)-$\lambda^6$-sulfanone; methyl(phenyl)((4-((5-(trifluoromethyl)-1,2,4-oxadiazol-3-yl)methyl)phenyl)imino)-$\lambda^6$-sulfanone; methyl(phenyl)((5-(5-(trifluoromethyl)-1,2,4-oxadiazol-3-yl)pyridin-2-yl)imino)-$\lambda^6$-sulfanone; methyl(phenyl)((5-(5-(trifluoromethyl)-1,2,4-oxadiazol-3-yl)pyrimidin-2-yl)imino)-$\lambda^6$-sulfanone; methyl(phenylimino)(4-(5-(trifluoromethyl)-1,2,4-oxadiazol-3-yl)phenyl)-$\lambda^6$-sulfanone; methyl(prop-2-yn-1-yl)((4-((5-(trifluoromethyl)-1,2,4-oxadiazol-3-yl)methyl)phenyl)imino)-$\lambda^6$-sulfanone; methyl(prop-2-yn-1-yl)((4-(5-(trifluoromethyl)-1,2,4-oxadiazol-3-yl)benzyl)imino)-$\lambda^6$-sulfanone; methyl(prop-2-yn-1-yl)((4-(5-(trifluoromethyl)-1,2,4-oxadiazol-3-yl)phenyl)imino)-$\lambda^6$-sulfanone; methyl(pyridin-2-yl)((4-((5-(trifluoromethyl)-1,2,4-oxadiazol-3-yl)methyl)phenyl)imino)-$\lambda^6$-sulfanone; methyl(pyridin-2-yl)((5-(5-(trifluoromethyl)-1,2,4-oxadiazol-3-yl)pyridin-2-yl)imino)-$\lambda^6$-sulfanone; methyl(pyridin-2-yl)((5-(5-(trifluoromethyl)-1,2,4-oxadiazol-3-yl)pyrimidin-2-yl)imino)-$\lambda^6$-sulfanone; methyl(pyridin-2-ylimino)(4-(5-(trifluoromethyl)-1,2,4-oxadiazol-3-yl)phenyl)-$\lambda^6$-sulfanone; methyl(pyridin-3-yl)((4-((5-(trifluoromethyl)-1,2,4-oxadiazol-3-yl)methyl)phenyl)imino)-$\lambda^6$-sulfanone; methyl(pyridin-4-yl)((4-((5-(trifluoromethyl)-1,2,4-oxadiazol-3-yl)methyl)phenyl)imino)-$\lambda^6$-sulfanone; methyl(pyrimidin-2-yl)((4-((5-(trifluoromethyl)-1,2,4-oxadiazol-3-yl)methyl)phenyl)imino)-$\lambda^6$-sulfanone; methyl(pyrimidin-2-yl)((4-(5-(trifluoromethyl)-1,2,4-oxadiazol-3-yl)benzyl)imino)-$\lambda^6$-sulfanone; methyl(pyrimidin-2-ylimino)(4-(5-(trifluoromethyl)-1,2,4-oxadiazol-3-yl)phenyl)-$\lambda^6$-sulfanone; methyl(pyrimidin-4-yl)((4-((5-(trifluoromethyl)-1,2,4-oxadiazol-3-yl)methyl)phenyl)imino)-$\lambda^6$-sulfanone; methyl(pyrimidin-4-yl)((4-(5-(trifluoromethyl)-1,2,4-oxadiazol-3-yl)benzyl)imino)-$\lambda^6$-sulfanone; methyl(pyrimidin-4-ylimino)(4-(5-(trifluoromethyl)-1,2,4-oxadiazol-3-yl)phenyl)-$\lambda^6$-sulfanone; methyl(thiazol-4-yl)((4-((5-(trifluoromethyl)-1,2,4-oxadiazol-3-yl)methyl)phenyl)imino)-$\lambda^6$-sulfanone; methyl(thiazol-4-yl)((4-(5-(trifluoromethyl)-1,2,4-oxadiazol-3-yl)benzyl)imino)-$\lambda^6$-sulfanone; methyl(thiazol-5-yl)((4-((5-(trifluoromethyl)-1,2,4-oxadiazol-3-yl)methyl)phenyl)imino)-$\lambda^6$-sulfanone; methyl(thiazol-5-yl)((4-(5-(trifluoromethyl)-1,2,4-oxadiazol-3-yl)benzyl)imino)-$\lambda^6$-sulfanone; methyl(thiazol-5-ylimino)(4-(5-(trifluoromethyl)-1,2,4-oxadiazol-3-yl)phenyl)-$\lambda^6$-sulfanone; methyl(thiophen-2-yl)((4-((5-(trifluoromethyl)-1,2,4-oxadiazol-3-yl)methyl)phenyl)imino)-$\lambda^6$-sulfanone; methyl(thiophen-2-yl)((4-(5-(trifluoromethyl)-1,2,4-oxadiazol-3-yl)benzyl)imino)-$\lambda^6$-sulfanone; methyl(thiophen-2-ylimino)(4-(5-(trifluoromethyl)-1,2,4-oxadiazol-3-yl)phenyl)-$\lambda^6$-sulfanone; methyl(thiophen-3-yl)((4-((5-(trifluoromethyl)-1,2,4-oxadiazol-3-yl)methyl)phenyl)imino)-$\lambda^6$-sulfanone; methyl(thiophen-3-yl)((4-(5-(trifluoromethyl)-1,2,4-oxadiazol-3-yl)benzyl)imino)-$\lambda^6$-sulfanone; methyl(thiophen-3-ylimino)(4-(5-(trifluoromethyl)-1,2,4-oxadiazol-3-yl)phenyl)-$\lambda^6$-sulfanone; methyl(trifluoromethyl)((4-((5-(trifluoromethyl)-1,2,4-oxadiazol-3-yl)methyl)phenyl)imino)-$\lambda^6$-sulfanone; methyl(trifluoromethyl)((4-(5-(trifluoromethyl)-1,2,4-oxadiazol-3-yl)benzyl)imino)-$\lambda^6$-sulfanone; N-(((1-methylazetidin-3-yl)methyl)sulfonyl)-4-(5-(trifluoromethyl)-1,2,4-oxadiazol-3-yl)benzamide; N-((2-(dimethylamino)ethyl)(methyl)(oxo)-$\lambda^6$-sulfaneylidene)-4-((5-(trifluoromethyl)-1,2,4-oxadiazol-3-yl)methyl)benzamide; N-((2-(dimethylamino)ethyl)sulfonyl)-4-(5-(trifluoromethyl)-1,2,4-oxadiazol-3-yl)benzamide; N-((2-(dimethylamino)ethyl)sulfonyl)-N-methyl-4-(5-(trifluoromethyl)-1,2,4-oxadiazol-3-yl)benzamide; N-((2,4-difluorophenyl)(methyl)(oxo)-$\lambda^6$-sulfaneylidene)-4-((5-(trifluoromethyl)-1,2,4-oxadiazol-3-yl)methyl)benzamide; N-((2-fluoro-4-methoxyphenyl)(methyl)(oxo)-$\lambda^6$-sulfaneylidene)-4-((5-(trifluoromethyl)-1,2,4-oxadiazol-3-yl)methyl)benzamide; N-((2-fluorobenzyl)(methyl)(oxo)-$\lambda^6$-sulfaneylidene)-2-methoxy-4-(5-(trifluoromethyl)-1,2,4-oxadiazol-3-yl)benzamide; N-((2-fluorobenzyl)(methyl)(oxo)-$\lambda^6$-sulfaneylidene)-3-methoxy-4-(5-(trifluoromethyl)-1,2,4-oxadiazol-3-yl)benzamide; N-((2-fluorobenzyl)(methyl)(oxo)-$\lambda^6$-sulfaneylidene)-5-(5-(trifluoromethyl)-1,2,4-oxadiazol-3-yl)picolinamide; N-((2-fluorobenzyl)(methyl)(oxo)-$\lambda^6$-sulfaneylidene)-5-(5-(trifluoromethyl)-1,2,4-oxadiazol-3-yl)pyrazine-2-carboxamide; N-((2-fluorobenzyl)(methyl)(oxo)-$\lambda^6$-sulfaneylidene)-5-(5-(trifluoromethyl)-1,2,4-oxadiazol-3-yl)pyrimidine-2-carboxamide; N-((2-fluorobenzyl)(methyl)(oxo)-$\lambda^6$-sulfaneylidene)-6-(5-(trifluoromethyl)-1,2,4-oxadiazol-3-yl)nicotinamide; N-((2-fluorobenzyl)(oxo)(trifluoromethyl)-$\lambda^6$-sulfaneylidene)-4-(5-(trifluoromethyl)-1,2,4-oxadiazol-3-yl)benzamide; N-((2-fluorophenyl)(methyl)(oxo)-$\lambda^6$-sulfaneylidene)-2-methoxy-4-(5-(trifluoromethyl)-1,2,4-oxadiazol-3-yl)benzamide; N-((2-fluorophenyl)(methyl)(oxo)-$\lambda^6$-sulfaneylidene)-3-methoxy-4-(5-(trifluoromethyl)-1,2,4-oxadiazol-3-yl)benzamide; N-((2-fluorophenyl)(methyl)(oxo)-$\lambda^6$-sulfaneylidene)-4-((5-(trifluoromethyl)-1,2,4-oxadiazol-3-yl)methyl)benzamide; N-((2-fluorophenyl)(methyl)(oxo)-$\lambda^6$-sulfaneylidene)-5-(5-(trifluoromethyl)-1,2,4-oxadiazol-3-yl)pyrazine-2-carboxamide; N-((2-fluorophenyl)(methyl)(oxo)-$\lambda^6$-sulfaneylidene)-5-(5-(trifluoromethyl)-1,2,4-oxadiazol-3-yl)pyrimidine-2-carboxamide; N-((2-fluorophenyl)(methyl)(oxo)-$\lambda^6$-sulfaneylidene)-6-(5-(trifluoromethyl)-1,2,4-oxadiazol-3-yl)nicotinamide; N-((2-fluorophenyl)(oxo)(trifluoromethyl)-$\lambda^6$-sulfaneylidene)-4-(5-(trifluoromethyl)-1,2,4-oxadiazol-3-yl)benzamide; N-((2-methoxyethyl)(methyl)(oxo)-$\lambda^6$-sulfaneylidene)-4-((5-(trifluoromethyl)-1,2,4-oxadiazol-3-yl)methyl)benzamide; N-((2-methoxyethyl)sulfonyl)-4-(5-(trifluoromethyl)-1,2,4-oxadiazol-3-yl)benzamide; N-((2- methoxyethyl)sulfonyl)-N-methyl-4-(5-(trifluoromethyl)-1,2,4-oxadiazol-3-yl)benzamide; N-((2-methoxyphenyl)(methyl)(oxo)-$\lambda^6$-sulfaneylidene)-4-((5-(trifluoromethyl)-1,2,4-oxadiazol-3-yl)methyl)benzamide; N-((3-fluorophenyl)(methyl)(oxo)-$\lambda^6$-sulfaneylidene)-4-((5-(trifluoromethyl)-1,2,4-oxadiazol-3-yl)methyl)benzamide; N-((3-fluoropyridin-4-yl)(methyl)(oxo)-$\lambda^6$-sulfaneylidene)-4-((5-(trifluoromethyl)-1,2,4-oxadiazol-3-yl)methyl)benzamide; N-((3-methoxyphenyl)(methyl)(oxo)-$\lambda^6$-sulfaneylidene)-4-((5-(trifluoromethyl)-1,2,4-oxadiazol-3-yl)methyl)benzamide; N-((3-methoxypyridin-4-yl)(methyl)(oxo)-$\lambda^6$-sulfaneylidene)-4-((5-(trifluoromethyl)-1,2,4-oxadiazol-3-yl)methyl)benzamide; N-((4-(difluoromethyl)phenyl)(methyl)(oxo)-$\lambda^6$-sulfaneylidene)-4-(5-(trifluoromethyl)-1,2,4-oxadiazol-3-yl)benzamide; N-((4-chlorophenyl)(cyclopropylmethyl)(oxo)-$\lambda^6$-sulfaneylidene)-4-(5-(trifluoromethyl)-1,2,4-oxadiazol-3-yl)benzamide; N-((4-chlorophenyl)(methyl)(oxo)-$\lambda^6$-sulfaneylidene)-2-fluoro-4-(5-(trifluoromethyl)-1,2,4-oxadiazol-3-yl)benzamide; N-((4-chlorophenyl)(methyl)(oxo)-$\lambda^6$-sulfaneylidene)-2-methoxy-4-(5-(trifluoromethyl)-1,2,4-oxadiazol-3-yl)benzamide; N-((4-chlorophenyl)(methyl)(oxo)-$\lambda^6$-sulfaneylidene)-3-fluoro-4-(5-(trifluoromethyl)-1,2,4-oxadiazol-3-yl)benzamide; N-((4-chlorophenyl)(methyl)(oxo)-$\lambda^6$-sulfaneylidene)-3-methoxy-4-(5-(trifluoromethyl)-1,2,4-oxadiazol-3-yl)benzamide; N-((4-chlorophenyl)(methyl)(oxo)-$\lambda^6$-sulfaneylidene)-5-(5-(trifluoromethyl)-1,2,4-oxadiazol-3-yl)picolinamide; N-((4-chlorophenyl)(methyl)(oxo)-$\lambda^6$-sulfaneylidene)-5-(5-(trifluoromethyl)-1,2,4-oxadiazol-3-yl)pyrazine-2-carboxamide; N-((4-chlorophenyl)(methyl)(oxo)-$\lambda^6$-sulfaneylidene)-5-(5-(trifluoromethyl)-1,2,4-oxadiazol-3-yl)pyrimidine-2-carboxamide; N-((4-chlorophenyl)(methyl)(oxo)-$\lambda^6$-sulfaneylidene)-6-(5-(trifluoromethyl)-1,2,4-oxadiazol-3-yl)nicotinamide; N-((4-chlorophenyl)(oxo)(trifluoromethyl)-$\lambda^6$-sulfaneylidene)-4-(5-(trifluoromethyl)-1,2,4-oxadiazol-3-yl)benzamide; N-((4-fluoro-2-methoxyphenyl)(methyl)(oxo)-$\lambda^6$-sulfaneylidene)-4-((5-(trifluoromethyl)-1,2,4-oxadiazol-3-yl)methyl)benzamide; N-((4-fluorophenyl)(methyl)(oxo)-$\lambda^6$-sulfaneylidene)-4-((5-(trifluoromethyl)-1,2,4-oxadiazol-3-yl)methyl)benzamide; N-((4-fluorophenyl)(methyl)(oxo)-$\lambda^6$-sulfaneylidene)-5-(5-(trifluoromethyl)-1,2,4-oxadiazol-3-yl)pyrimidine-2-carboxamide; N-((4-methoxyphenyl)(methyl)(oxo)-$\lambda^6$-sulfaneylidene)-4-((5-(trifluoromethyl)-1,2,4-oxadiazol-3-yl)methyl)benzamide; N-((4-methoxyphenyl)(methyl)(oxo)-$\lambda^6$-sulfaneylidene)-5-(5-(trifluoromethyl)-1,2,4-oxadiazol-3-yl)pyrazine-2-carboxamide; N-((4-methoxyphenyl)(methyl)(oxo)-$\lambda^6$-sulfaneylidene)-5-(5-(trifluoromethyl)-1,2,4-oxadiazol-3-yl)pyrimidine-2-carboxamide; N-((4-methoxyphenyl)(methyl)(oxo)-$\lambda^6$-sulfaneylidene)-6-(5-(trifluoromethyl)-1,2,4-oxadiazol-3-yl)nicotinamide; N-((4-methoxyphenyl)(oxo)(trifluoromethyl)-$\lambda^6$-sulfaneylidene)-4-(5-(trifluoromethyl)-1,2,4-oxadiazol-3-yl)benzamide; N-((cyclobutylmethyl)(methyl)(oxo)-$\lambda^6$-sulfaneylidene)-4-((5-(trifluoromethyl)-1,2,4-oxadiazol-3-yl)methyl)benzamide; N-((cyclobutylmethyl)sulfonyl)-4-(5-(trifluoromethyl)-1,2,4-oxadiazol-3-yl)benzamide; N-((cyclobutylmethyl)sulfonyl)-N-methyl-4-(5-(trifluoromethyl)-1,2,4-oxadiazol-3-yl)benzamide; N-((cyclopentyl)(methyl)(oxo)-$\lambda^6$-sulfaneylidene)-4-((5-(trifluoromethyl)-1,2,4-oxadiazol-3-yl)methyl)benzamide; N-((cyclopropylmethyl)(2-fluorobenzyl)(oxo)-$\lambda^6$-sulfaneylidene)-4-(5-(trifluoromethyl)-1,2,4-oxadiazol-3-yl)benzamide; N-((cyclopropylmethyl)(2-fluorophenyl)(oxo)-$\lambda^6$-sulfaneylidene)-4-(5-(trifluoromethyl)-1,2,4-oxadiazol-3-yl)benzamide; N-((cyclopropylmethyl)(4-methoxyphenyl)(oxo)-$\lambda^6$-sulfaneylidene)-4-(5-(trifluoromethyl)-1,2,4-oxadiazol-3-yl)benzamide; N-((cyclopropylmethyl)(methyl)(oxo)-$\lambda^6$-sulfaneylidene)-4-((5-(trifluoromethyl)-1,2,4-oxadiazol-3-yl)methyl)benzamide; N-((cyclopropylmethyl)(oxo)(pyridin-2-yl)-$\lambda^6$-sulfaneylidene)-4-(5-(trifluoromethyl)-1,2,4-oxadiazol-3-yl)benzamide; N-((cyclopropylmethyl)(oxo)(pyridin-4-yl)-$\lambda^6$-sulfaneylidene)-4-(5-(trifluoromethyl)-1,2,4-oxadiazol-3-yl)benzamide; N-((oxetan-3-ylmethyl)sulfonyl)-4-(5-(trifluoromethyl)-1,2,4-oxadiazol-3-yl)benzamide; N-((perfluoroethyl)sulfonyl)-4-(5-(trifluoromethyl)-1,2,4-oxadiazol-3-yl)benzamide; N-(1-oxido-1$\lambda^6$-thietan-1-ylidene)-4-((5-(trifluoromethyl)-1,2,4-oxadiazol-3-yl)methyl)benzamide; N-(1-oxidotetrahydro-1$\lambda^6$-thiophen-1-ylidene)-4-((5-(trifluoromethyl)-1,2,4-oxadiazol-3-yl)methyl)benzamide; N-(1-oxidotetrahydro-2H-1$\lambda^6$-thiopyran-1-ylidene)-4-((5-(trifluoromethyl)-1,2,4-oxadiazol-3-yl)methyl)benzamide; N-(4-oxido-1,4$\lambda^6$-oxathian-4-ylidene)-4-((5-(trifluoromethyl)-1,2,4-oxadiazol-3-yl)methyl)benzamide; N-(4-oxido-1,4$\lambda^6$-oxathian-4-ylidene)-5-(5-(trifluoromethyl)-1,2,4-oxadiazol-3-yl)pyrazine-2-carboxamide; N-(4-oxido-1,4$\lambda^6$-oxathian-4-ylidene)-5-(5-(trifluoromethyl)-1,2,4-oxadiazol-3-yl)pyrimidine-2-carboxamide; N-(4-oxido-1,4$\lambda^6$-oxathian-4-ylidene)-6-(5-(trifluoromethyl)-1,2,4-oxadiazol-3-yl)nicotinamide; N-(allyl(methyl)(oxo)-$\lambda^6$-sulfaneylidene)-4-((5-(trifluoromethyl)-1,2,4-oxadiazol-3-yl)methyl)benzamide; N-(allylsulfonyl)-4-(5-(trifluoromethyl)-1,2,4-oxadiazol-3-yl)benzamide; N-(allylsulfonyl)-N-methyl-4-(5-(trifluoromethyl)-1,2,4-oxadiazol-3-yl)benzamide; N-(cyclopentyl(methyl)(oxo)-$\lambda^6$-sulfaneylidene)-4-(5-(trifluoromethyl)-1,2,4-oxadiazol-3-yl)benzamide; N-(cyclopropyl(methyl)(oxo)-$\lambda^6$-sulfaneylidene)-4-((5-(trifluoromethyl)-1,2,4-oxadiazol-3-yl)methyl)benzamide; N-(cyclopropyl(methyl)(oxo)-$\lambda^6$-sulfaneylidene)-4-(5-(trifluoromethyl)-1,2,4-oxadiazol-3-yl)benzamide; N-(cyclopropylsulfonyl)-4-(5-(trifluoromethyl)-1,2,4-oxadiazol-3-yl)benzamide; N-(ethylsulfonyl)-4-(5-(trifluoromethyl)-1,2,4-oxadiazol-3-yl)benzamide; N-(isobutyl(methyl)(oxo)-$\lambda^6$-sulfaneylidene)-4-((5-(trifluoromethyl)-1,2,4-oxadiazol-3-yl)methyl)benzamide; N-(isobutyl(methyl)(oxo)-$\lambda^6$-sulfaneylidene)-4-(5-(trifluoromethyl)-1,2,4-oxadiazol-3-yl)benzamide; N-(isobutylsulfonyl)-4-(5-(trifluoromethyl)-1,2,4-oxadiazol-3-yl)benzamide; N-(isobutylsulfonyl)-N-methyl-4-(5-(trifluoromethyl)-1,2,4-oxadiazol-3-yl)benzamide; N-(isopropyl(methyl)(oxo)-$\lambda^6$-sulfaneylidene)-4-(5-(trifluoromethyl)-1,2,4-oxadiazol-3-yl)benzamide; N-(isopropylsulfonyl)-4-(5-(trifluoromethyl)-1,2,4-oxadiazol-3-yl)benzamide; N-(methyl(oxo)(4-(5-(trifluoromethyl)-1,2,4-oxadiazol-3-yl)phenyl)-$\lambda^6$-sulfaneylidene)cyclobutanecarboxamide; N-(methyl(oxo)(4-(5-(trifluoromethyl)-1,2,4-oxadiazol-3-yl)phenyl)-$\lambda^6$-sulfaneylidene)cyclohexanecarboxamide; N-(methyl(oxo)(4-(5-(trifluoromethyl)-1,2,4-oxadiazol-3-yl)phenyl)-$\lambda^6$-sulfaneylidene)cycloheptanecarboxamide; N-(methyl(oxo)(4-(5-(trifluoromethyl)-1,2,4-oxadiazol-3-yl)phenyl)-$\lambda^6$-sulfaneylidene)furan-3-carboxamide; N-(methyl(oxo)(4-(5-(trifluoromethyl)-1,2,4-oxadiazol-3-yl)phenyl)-$\lambda^6$-sulfaneylidene)oxazole-5-carboxamide; N-(methyl(oxo)(4-(5-(trifluoromethyl)-1,2,4-oxadiazol-3-yl)phenyl)-$\lambda^6$-sulfaneylidene)picolinamide; N-(methyl(oxo)(4-(5-(trifluoromethyl)-1,2,4-oxadiazol-3-yl)phenyl)-$\lambda^6$-sulfaneylidene)pyrimidine-2-carboxamide; N-(methyl(oxo)(4-(5-(trifluoromethyl)-1,2,4-oxadiazol-3-yl)phenyl)-$\lambda^6$-sulfaneylidene)pyrimidine-4-carboxamide; N-(methyl(oxo)(4-(5-(trifluoromethyl)-1,2,4-oxadiazol-3-yl)phenyl)-$\lambda^6$-sulfaneylidene)thiazole-5-carboxamide; N-(methyl(oxo)(4-

(5-(trifluoromethyl)-1,2,4-oxadiazol-3-yl)phenyl)-$\lambda^6$-sulfaneylidene)thiophene-2-carboxamide; N-(methyl(oxo) (4-(5-(trifluoromethyl)-1,2,4-oxadiazol-3-yl)phenyl)-$\lambda^6$-sulfaneylidene)thiophene-3-carboxamide; N-(methyl(oxo) (perfluoroethyl)-$\lambda^6$-sulfaneylidene)-4-((5-(trifluoromethyl)-1,2,4-oxadiazol-3-yl)methyl)benzamide; N-(methyl(oxo) (phenyl)-$\lambda^6$-sulfaneylidene)-5-(5-(trifluoromethyl)-1,2,4-oxadiazol-3-yl)pyrimidine-2-carboxamide; N-(methyl(oxo) (prop-2-yn-1-yl)-$\lambda^6$-sulfaneylidene)-4-((5-(trifluoromethyl)-1,2,4-oxadiazol-3-yl)methyl)benzamide; N-(methyl(oxo)(prop-2-yn-1-yl)-$\lambda^6$-sulfaneylidene)-4-(5-(trifluoromethyl)-1,2,4-oxadiazol-3-yl)benzamide; N-(methyl(oxo)(propyl)-$\lambda^6$-sulfaneylidene)-4-(5-(trifluoromethyl)-1,2,4-oxadiazol-3-yl)benzamide; N-(methyl(oxo) (pyridin-2-yl)-$\lambda^6$-sulfaneylidene)-4-((5-(trifluoromethyl)-1,2,4-oxadiazol-3-yl)methyl)benzamide; N-(methyl(oxo) (pyridin-2-yl)-$\lambda^6$-sulfaneylidene)-5-(5-(trifluoromethyl)-1,2,4-oxadiazol-3-yl)pyrazine-2-carboxamide; N-(methyl (oxo)(pyridin-2-yl)-$\lambda^6$-sulfaneylidene)-5-(5-(trifluoromethyl)-1,2,4-oxadiazol-3-yl)pyrimidine-2-carboxamide; N-(methyl(oxo)(pyridin-2-yl)-$\lambda^6$-sulfaneylidene)-6-(5-(trifluoromethyl)-1,2,4-oxadiazol-3-yl)nicotinamide; N-(methyl(oxo)(pyridin-3-yl)-$\lambda^6$-sulfaneylidene)-4-((5-(trifluoromethyl)-1,2,4-oxadiazol-3-yl)methyl)benzamide; N-(methyl(oxo)(pyridin-4-yl)-$\lambda^6$-sulfaneylidene)-4-((5-(trifluoromethyl)-1,2,4-oxadiazol-3-yl)methyl)benzamide; N-(methyl(oxo)(pyridin-4-yl)-$\lambda^6$-sulfaneylidene)-5-(5-(trifluoromethyl)-1,2,4-oxadiazol-3-yl)picolinamide; N-(methyl(oxo)(pyridin-4-yl)-$\lambda^6$-sulfaneylidene)-5-(5-(trifluoromethyl)-1,2,4-oxadiazol-3-yl)pyrazine-2-carboxamide; N-(methyl(oxo)(pyridin-4-yl)-$\lambda^6$-sulfaneylidene)-5-(5-(trifluoromethyl)-1,2,4-oxadiazol-3-yl)pyrimidine-2-carboxamide; N-(methyl(oxo)(pyridin-4-yl)-$\lambda^6$-sulfaneylidene)-6-(5-(trifluoromethyl)-1,2,4-oxadiazol-3-yl)nicotinamide; N-(methyl(oxo)(pyrimidin-2-yl)-$\lambda^6$-sulfaneylidene)-4-((5-(trifluoromethyl)-1,2,4-oxadiazol-3-yl)methyl)benzamide; N-(methyl(oxo) (pyrimidin-4-yl)-$\lambda^6$-sulfaneylidene)-4-((5-(trifluoromethyl)-1,2,4-oxadiazol-3-yl)methyl)benzamide; N-(methyl(oxo)(trifluoromethyl)-$\lambda^6$-sulfaneylidene)-4-((5-(trifluoromethyl)-1,2,4-oxadiazol-3-yl)methyl)benzamide; N-(oxo(pyridin-2-yl)(trifluoromethyl)-$\lambda^6$-sulfaneylidene)-4-(5-(trifluoromethyl)-1,2,4-oxadiazol-3-yl)benzamide; N-(oxo(pyridin-4-yl)(trifluoromethyl)-$\lambda^6$-sulfaneylidene)-4-(5-(trifluoromethyl)-1,2,4-oxadiazol-3-yl)benzamide; N-(prop-2-yn-1-ylsulfonyl)-4-(5-(trifluoromethyl)-1,2,4-oxadiazol-3-yl)benzamide; N-(propylsulfonyl)-4-(5-(trifluoromethyl)-1,2,4-oxadiazol-3-yl)benzamide; N-methyl-4-(5-(trifluoromethyl)-1,2,4-oxadiazol-3-yl)-N-((trifluoromethyl)sulfonyl)benzamide; N-methyl-N-(((1-methylazetidin-3-yl)methyl)sulfonyl)-4-(5-(trifluoromethyl)-1,2,4-oxadiazol-3-yl)benzamide; N-methyl-N-((oxetan-3-ylmethyl)sulfonyl)-4-(5-(trifluoromethyl)-1,2,4-oxadiazol-3-yl)benzamide; N-methyl-N-((perfluoroethyl)sulfonyl)-4-(5-(trifluoromethyl)-1,2,4-oxadiazol-3-yl)benzamide; N-methyl-N-(prop-2-yn-1-ylsulfonyl)-4-(5-(trifluoromethyl)-1,2,4-oxadiazol-3-yl) benzamide; phenyl(trifluoromethyl)((4-(5-(trifluoromethyl)-1,2,4-oxadiazol-3-yl)phenyl)imino)-$\lambda^6$-sulfanone; and pyridin-2-yl(trifluoromethyl)((4-(5-(trifluoromethyl)-1,2,4-oxadiazol-3-yl)phenyl)imino)-$\lambda^6$-sulfanone.

5. A combination comprising the compound of claim 1 and at least one further pesticidally active substance selected from the group consisting of fungicides, insecticides, nematicides, acaricides, biopesticides, herbicides, safeners, plant growth regulators, antibiotics, fertilizers and nutrients.

6. A composition comprising at least one compound of claim 1 and at least one agrochemically acceptable auxiliary.

7. The composition of claim 6, further comprising at least one pesticidally active substance selected from the group consisting of fungicides, insecticides, nematicides, acaricides, biopesticides, herbicides, safeners, plant growth regulators, antibiotics, fertilizers and nutrients.

8. A composition comprising at least one compound of claim 1 and seed, wherein the amount of the at least one compound is from 0.1 gai to 10 kgai per 100 kg of seeds.

9. A method for controlling or preventing phytopathogenic fungi, wherein the method comprises treating the fungi or the materials, plants, plant parts, locus thereof, soil or seeds to be protected against fungal attack, with an effective amount of the compound of claim 1.

10. A method for controlling or preventing infestation of plants by phytopathogenic micro-organisms in agricultural crops, floricultural crops and or horticultural crops wherein an effective amount of the compound of claim 1 is applied to the seeds of plants.

11. A method for controlling or preventing plant diseases, the method comprising
    applying an effective amount of the compound of claim 1 to a plant or a seed.

12. The method of claim 11, wherein the plant diseases are selected from *Puccinia* spp. (rusts), comprising *P. triticina* (brown or leaf rust), *P. striiformis* (stripe or yellow rust), *P. hordei* (dwarf rust), *P. graminis* (stem or black rust) and *P. recondita* (brown or leaf rust) on cereals viz., wheat, barley or rye, and *Phakopsora* spp. comprising *Phakopsora pachyrhizi* and *P. meibomiae* on soybeans, *Hemileia vastatrix* (Coffee rust), *Uromyces* spp., comprising *U fabae* (rust of beans).

13. A process for preparing the compound of claim 1, wherein said process comprising at the steps from a to p:
    a. esterifying a compound of formula 1 into a compound of formula 2 using suitable esterifying reactant and reagent:

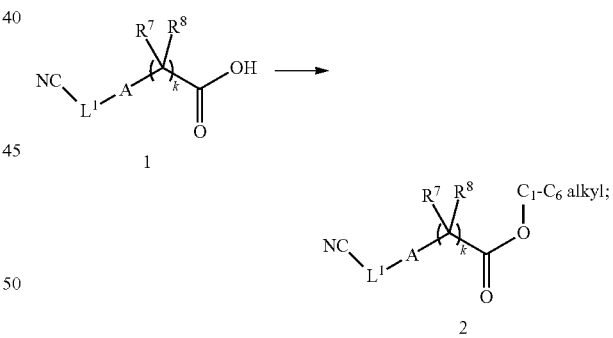

b. converting the compound of formula 2 by reacting with hydroxyl amine hydrochloride in the presence of suitable base into a compound of formula 3 or converting the compound of formula 1 by reacting with hydroxyl amine into a compound of formula 3':

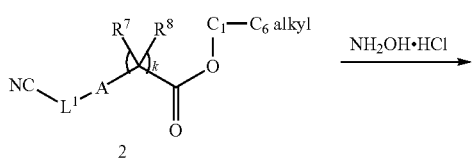

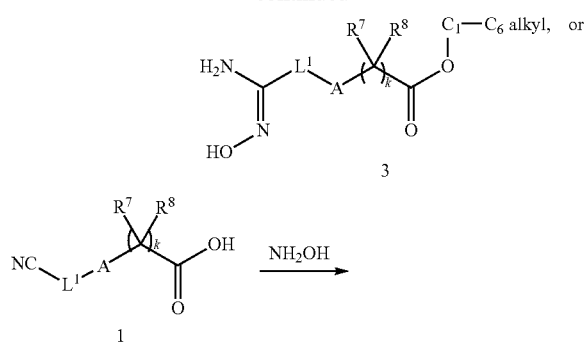
c. cyclizing the compound of formula 3 and a compound of formula 8 to obtain a compound of formula 4 or cyclizing the compound of formula 3' and a compound of formula 8 to obtain a compound of formula 5:
d. hydrolyzing the compound of formula 4 into a compound of formula 5:
e. reacting the compound of formula 5 and a compound of formula 6 to obtain the compound of formula I:

wherein, $L^2$ is

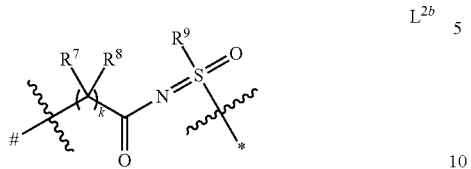

an expression "#" on the left side indicates the point of attachment to A, and an expression "*" on the right side indicates the point of attachment to $R^{10}$; or f. reacting a compound of formula 6 with a compound of formula 7 to obtain a compound of formula Ia:

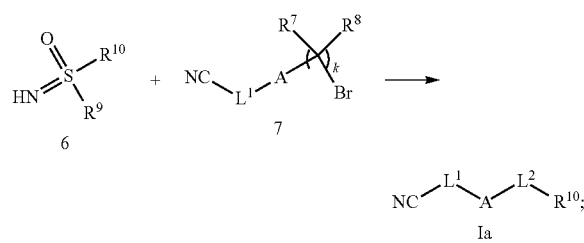

wherein, $L^2$ is

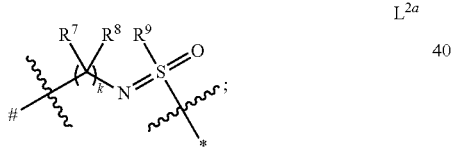

an expression "#" on the left side indicates the point of attachment to A, and an expression "*" on the right side indicates the point of attachment to $R^{10}$;

g. converting the compound of formula Ia by reacting with hydroxyl amine hydrochloride into a compound of formula Ib:

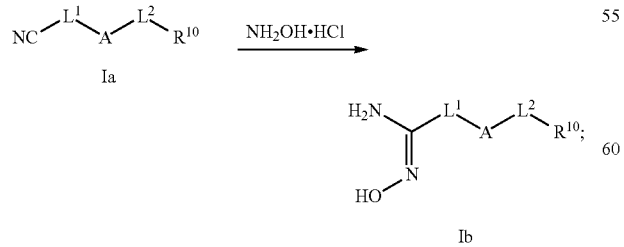

wherein, $L^2$ steps f to is

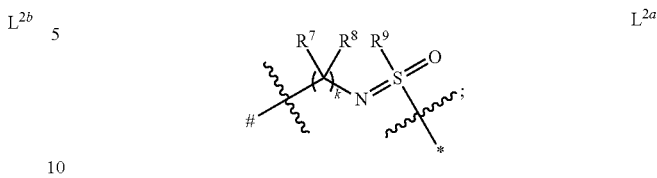

an expression "#" on the left side indicates the point of attachment to A, and an expression "*" on the right side indicates the point of attachment to $R^{10}$; and h. cyclizing the compound of formula Ib and a compound of formula 8 to obtain a compound of formula I:

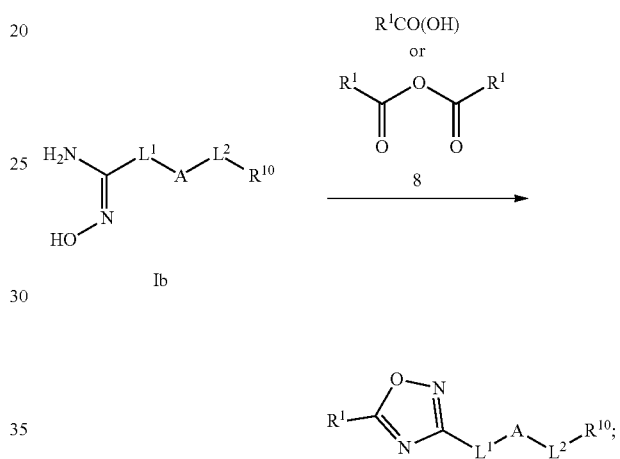

wherein, $L^2$ is

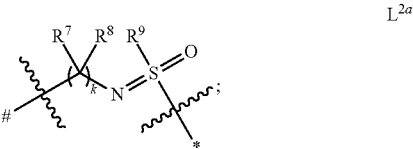

an expression "#" on the left side indicates the point of attachment to A, and an expression "*" on the right side indicates the point of attachment to $R^{10}$; or i. reacting a compound of formula 9 with ammonium carbamate to obtain a compound of formula 10:

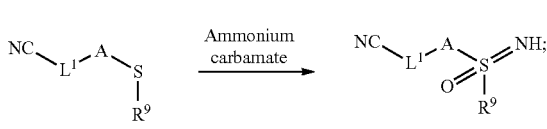

j. reacting the compound of formula 10 with a compound of formula 11 to obtain a compound of formula Ia:

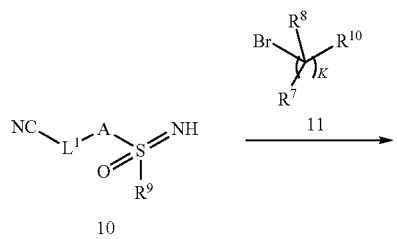

wherein, $L^2$ is $L^{2a}$ an expression "#" on the left side indicates the point of attachment to A, and an expression "*" on the right side indicates the point of attachment to $R^{10}$;

k. reacting the compound of formula Ia with hydroxyl amine hydrochloride to obtain a compound of formula Ib:

wherein, $L^2$ is $L^{2a}$ an expression "#" on the left side indicates the point of attachment to A, and an expression "*" on the right side indicates the point of attachment to $R^{10}$; and l. cyclizing the compound of formula Ib and the compound of formula 8 to obtain the compound of formula I:

wherein, $L^2$ is $L^{2a}$ an expression "#" on the left side indicates the point of attachment to A, and an expression "*" on the right side indicates the point of attachment to $R^{10}$;

or m. imidizing the compound of formula 9 to obtain a compound of formula 11:

n. cyclizing the compound of formula 11 with the compound of formula 8 to obtain a compound of formula 12:

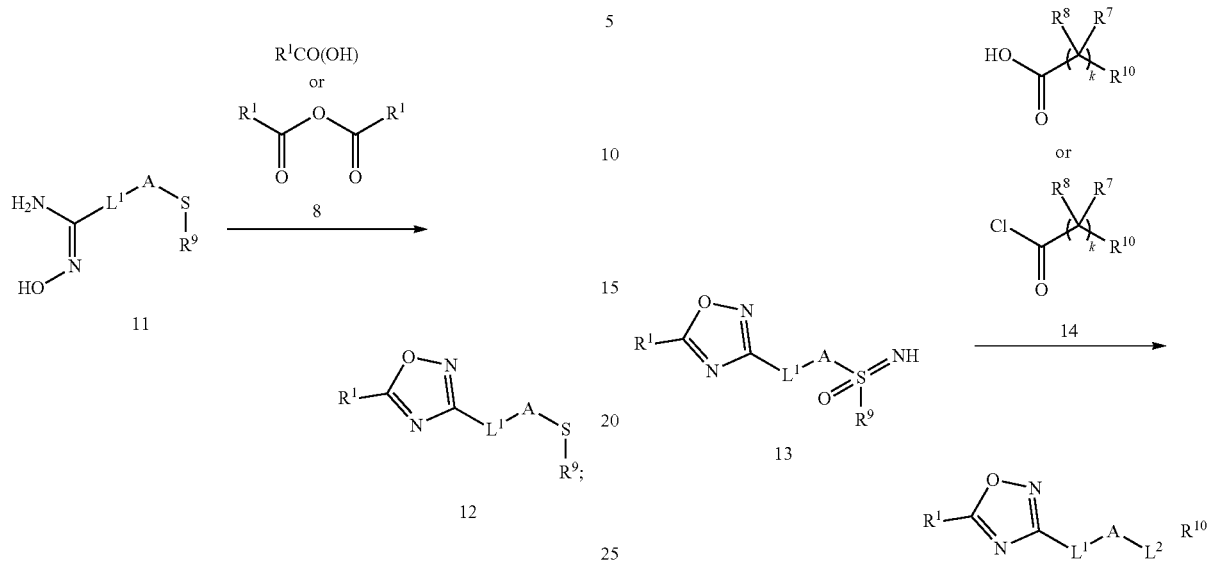

o. reacting the compound of formula 12 with ammonium carbamate to obtain a compound of formula 13:

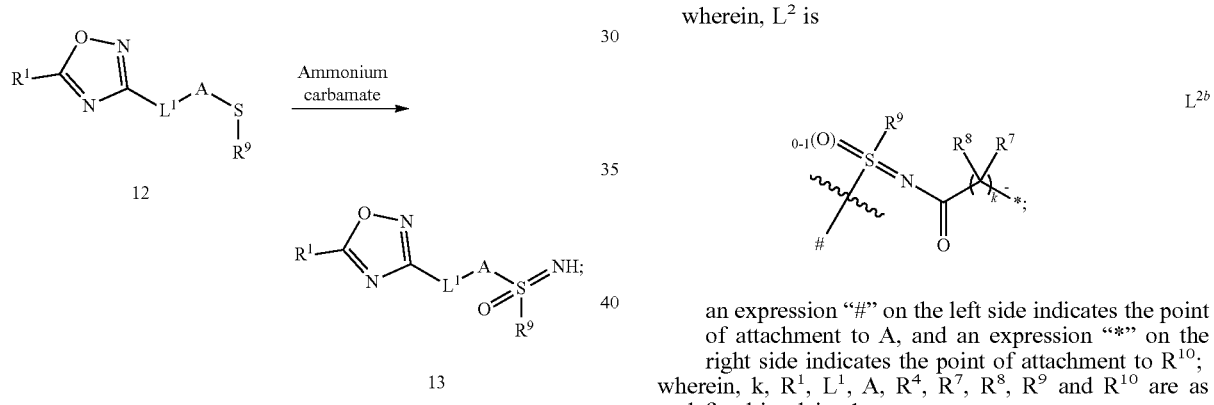

p. reacting the compound of formula 13 with a compound of formula 14 to obtain the compound of formula I:

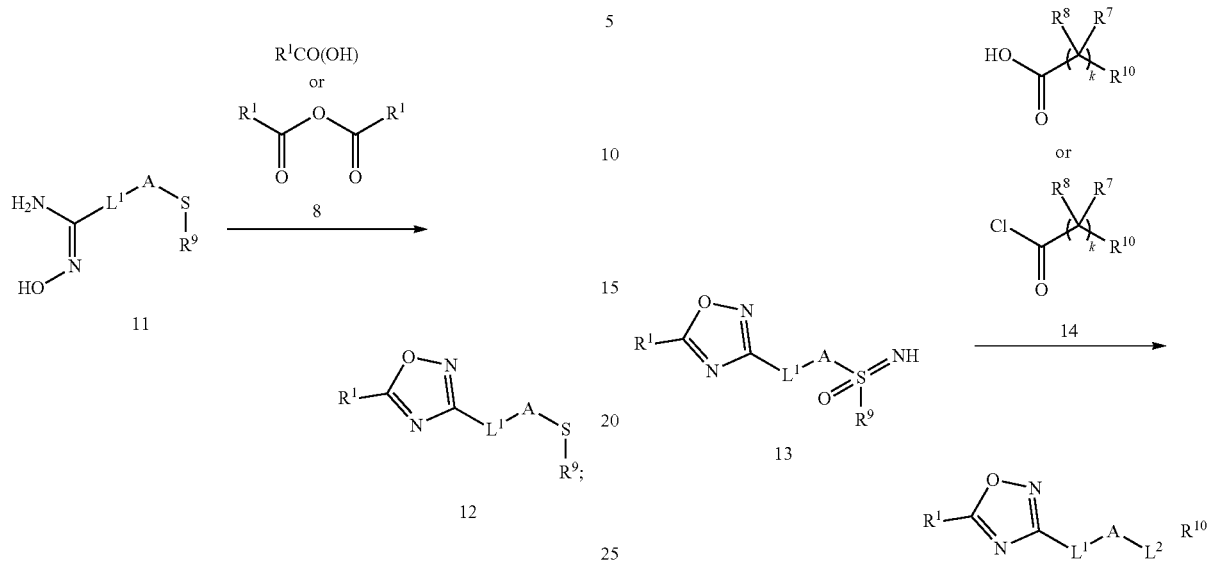

wherein, $L^2$ is $L^{2b}$ an expression "#" on the left side indicates the point of attachment to A, and an expression "*" on the right side indicates the point of attachment to $R^{10}$;
wherein, k, $R^1$, $L^1$, A, $R^4$, $R^7$, $R^8$, $R^9$ and $R^{10}$ are as defined in claim 1.

* * * * *